United States Patent
Manoharan et al.

(10) Patent No.: US 9,814,777 B2
(45) Date of Patent: Nov. 14, 2017

(54) TARGETING LIPIDS

(71) Applicant: Arbutus Biopharma Corporation, Burnaby, BC (CA)

(72) Inventors: Muthiah Manoharan, Cambridge, MA (US); Kallanthottathil G. Rajeev, Cambridge, MA (US); Jayaprakash K. Nair, Cambridge, MA (US); Muthusamy Jayaraman, Cambridge, MA (US)

(73) Assignee: Arbutus Biopharma Corporation, Burnaby, British Columbia (CA)

( * ) Notice: Subject to any disclaimer, the term of this patent is extended or adjusted under 35 U.S.C. 154(b) by 0 days.

(21) Appl. No.: 14/060,353

(22) Filed: Oct. 22, 2013

(65) Prior Publication Data

US 2014/0179761 A1 Jun. 26, 2014
US 2016/0375137 A9 Dec. 29, 2016

Related U.S. Application Data

(63) Continuation of application No. 12/328,669, filed on Dec. 4, 2008, now abandoned.

(60) Provisional application No. 60/992,309, filed on Dec. 4, 2007, provisional application No. 61/013,597, filed on Dec. 13, 2007, provisional application No. 61/127,751, filed on May 14, 2008, provisional application No. 61/091,093, filed on Aug. 22, 2008, provisional application No. 61/097,261, filed on Sep. 16, 2008.

(51) Int. Cl.

| A61K 31/7088 | (2006.01) |
|---|---|
| A61K 31/713 | (2006.01) |
| A61K 47/16 | (2006.01) |
| A61K 47/22 | (2006.01) |
| A61K 47/28 | (2006.01) |
| A61K 31/7004 | (2006.01) |
| A61K 31/7052 | (2006.01) |
| A61K 31/70 | (2006.01) |
| A61K 47/48 | (2006.01) |
| C07H 21/02 | (2006.01) |
| A61K 48/00 | (2006.01) |

(52) U.S. Cl.
CPC .............. *A61K 47/28* (2013.01); *A61K 31/70* (2013.01); *A61K 31/7004* (2013.01); *A61K 31/7052* (2013.01); *A61K 31/7088* (2013.01); *A61K 31/713* (2013.01); *A61K 47/16* (2013.01); *A61K 47/22* (2013.01); *A61K 47/48046* (2013.01); *A61K 47/48092* (2013.01); *A61K 47/48215* (2013.01); *C07H 21/02* (2013.01); *A61K 48/00* (2013.01); *Y02P 20/55* (2015.11)

(58) Field of Classification Search
CPC .. A61K 31/7088; A61K 31/713; A61K 47/16; A61K 47/22; A61K 47/28; A61K 47/48092; A61K 47/48215; C07H 21/02
USPC ...... 514/44, 777, 784; 536/17.9, 5; 544/258; 552/502; 560/159
See application file for complete search history.

(56) References Cited

U.S. PATENT DOCUMENTS

| 5,994,517 | A | 11/1999 | Ts'o et al. |
|---|---|---|---|
| 6,906,182 | B2 | 6/2005 | Ts'o et al. |
| 7,109,165 | B2 | 9/2006 | Matulic-Adamic et al. |
| 7,491,805 | B2 | 2/2009 | Vargeese et al. |
| 7,803,397 | B2 * | 9/2010 | Heyes et al. ............. 424/450 |
| 2002/0086356 | A1 | 7/2002 | Tuschl et al. |
| 2003/0148928 | A1 | 8/2003 | Beigelman et al. |
| 2004/0110296 | A1 | 6/2004 | Vargeese et al. |
| 2004/0259247 | A1 | 12/2004 | Tuschl et al. |
| 2006/0148740 | A1 | 7/2006 | Platenburg |
| 2009/0325297 | A1 | 12/2009 | Tian et al. |
| 2012/0101148 | A1 | 4/2012 | Aking et al. |

FOREIGN PATENT DOCUMENTS

| EP | 0957107 | 11/1999 |
|---|---|---|
| WO | WO 90/12096 | 10/1990 |
| WO | 1997043296 A1 | 11/1997 |
| WO | WO 99/52932 | 10/1999 |
| WO | WO 99/65925 | 12/1999 |
| WO | WO 00/44914 | 8/2000 |
| WO | WO 02/085908 | 10/2002 |
| WO | WO 02/094185 | 11/2002 |
| WO | WO 2004/024757 | 3/2004 |
| WO | WO 2004/080406 | 9/2004 |
| WO | WO 2004/090108 | 10/2004 |

(Continued)

OTHER PUBLICATIONS

Nunez et al. Journal of Carbohydrate Chemistry, vol. 22, No. 6, pp. 395-406, 2003.*

(Continued)

*Primary Examiner* — Janet Epps-Smith
(74) *Attorney, Agent, or Firm* — Viksnins Harris Padys Malen LLP

(57) ABSTRACT

The present invention provides targeting lipids of structure $$L^{100}\text{-linker-}L^{101} \quad (CI),$$

where $L^{100}$ is a lipid, lipophile, alkyl, alkenyl or alkynyl, $L^{101}$ is a ligand or —$CH_2CH_2(OCH_2CH_2)_pO(CH_2)_qCH_2$-ligand, p is 1-1000, and q is 1-20. In addition, the invention provides compositions and methods for the delivery of therapeutic agents to cells. In particular, these include novel lipids and nucleic acid-lipid particles that provide efficient encapsulation of nucleic acids and efficient delivery of the encapsulated nucleic acid to cells in vivo.

11 Claims, 20 Drawing Sheets

(56) References Cited

FOREIGN PATENT DOCUMENTS

| WO | WO 2004/094595 | 11/2004 |
|---|---|---|
| WO | WO 2006/020768 | 2/2006 |
| WO | WO 2006/078278 | 7/2006 |

OTHER PUBLICATIONS

Rensen et al. J. Med. Chem. 2004, 47, 5798-5808.*
Sliedregt et al. Journal of Medicinal Chemistry, vol. 42, No. 4, Feb. 25, 1999, pp. 609-618.*
Zimmermann et al. Nature Publishing Group, vol. 441, No. 7089, pp. 111-114.*
Akinc et al., "Targeted Delivery of RNAi Therapeutics with Endogenous and Exogenous Ligand-Based Mechanisms", *Molecular Therapy* vol. 18 (7), 1357-1364 (2010).
Biessen, et al., "The Cholesterol Derivative of a Triantennary Galactoside with High Affinity for Hepatic Asialoglycoprotein Receptor: A Potent Cholesterol Lowering Agent", *Journal of Medicinal Chemistry*, vol. 38(11), 1846-1852 (1995).
Biessen et al., "Synthesis of Cluster Galactosides with High Affinity for the Hepatic Asialoglycoprotein Receptor", *Journal of Medicinal Chemistry*, vol. 38(9), 1538-1546.
Chiu et al., "RNAi in Human Cells: Basic Structural and Functional Features of Small Interfering RNA", *Molecular Cell*, vol. 10, 549-561 (2002).
Choi et al., "Targeting Cancer Cells with DNA-Assembled Dendrimers: A Mix and Match Strategy for Cancer", *Cell Cycle*, vol. 4(5), 669-671 (2005).
Connolly et al., "Binding and Endocytosis of Cluster Glycosides by Rabbit Hepatocytes", *The Journal of Biological Chemistry*, vol. 257 (2), 939-645 (1982).
Crossman et al., "Synthesis of Some Second-Generation Substrate Analogues of Early Intermediates in the Biosynthetic Pathway of Glycosylphosphatidylinositol Membrane Anchors", *Carbohydrate Research*, vol. 321(1-2), 2-51 (1999).
Dubber et al., "Solid-Phase Synthesis of Multivalent Glycoconjugates on a DNA Synthesizer", *Bioconjugate Chemistry*, vol. 14(1), 239-246 (2003).
Guo et al., "Construction of Folate-Conjugated pRNA of Bateriophase phi29 DNA Packaging Motor for Delivery of Chimeric siRNA to Nasopharyngeal Carcinoma Cells", *Gene Therapy*, vol. 13(10), 814-820 (2006).
Hamzavi et al., "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers", *Bioconjugate Chemistry, ACS* vol. 14 (1), Washington, DC, US, 941-954, XP002270930; ISSN: 1043-1802 (Jan. 2003).
Ikeda et al., "Ligand-Targeted Delivery of Therapeutic siRNA", Pharmaceutical Research, vol. 23(8), 1631-1640 (2006).
Karskela et al., "Synthesis and Cellular Uptake of Fluorescently Labeled Multivalent Hyaluronan Disaccharide Conjugates of Oligonucleotide Phosphorothioates", *Bioconjugate Chemistry*, vol. 19(12), (2008).
Katajisto et al., "An Aminooxy-Functionalized Non-Nucleosidic Phosphoramidite for the Construction of Multiantennary Oligonucleotide Glycoconjugates on a Solid Support", *Current Protocols in Nucleic Acid Chemistry*, pp. 4.26.1-4.26.16 (2005).
Katajisto et al., "Solid-Phase Synthesis of Oligonucleotide Glycoconjugates Bearing Three Different Glycosyl Groups: Orthoganally Protected Bis (Hydroxymethyl)-N, N'-bis(3-Hydroxyproply)Malondiamide Phosphoramidite as Key Building Block", *Journal of Organic Chemistry*, vol. 69(22), 7609-7615 (2004).
Katajisto et al., "Solid-Phase Synthesis of Multiantennary Oligonucleotide Glycoconjugates Utilizing On-Support Oximation", Bioconjugate Chemistry, vol. 15(4), 890-896 (2004).
Krapcho et al., "Mono-Protected Diamines. N-tert-Butoxycarbonyl-a,f3-Alkanediamines from-O-Alkanediamines", *Synthetic Communications*, 2559-2564 (1990).
Li et al., "Folate-Mediated Targeting of Antisense Oligodeoxynucleotides to Ovarian Cancer Cells", *Pharmaceutical Research*, vol. 15(10), 1540-1545 (1998).
Liu et al., "Targeted Drug Delivery to Chemoresistant Cells: Folic Acid Derivatization of FdUMP [10] Enhances Cytotoxicity Toward 5-FU-Resistant Human Colorector Tumor Cells", *Journal of Organic Chemistry*, vol. 66(17), 5655-5663 (2001).
Mahato, R.I. et al., "Physicochemical and Disposition Characteristics of Antisense Oligonucleotides Complexed with Glycosylated Poly(L-lysine)", *Biochemical Pharmacology*, vol. 53, Pergamon, Oxford, GB, vol. 53, 887-895, XP000197861, ISSN: 0006-2952 (Jan. 1997).
Mahato et al., "Modulation of Gene Expression by Antisense and Antigene Oligodeoxynucleotides and Small Interfering RNA", *Expert Opinion on Drug Delivery*, vol. 2(1), 3-28 (2005).
Maier et al., "Synthesis of Antisense Oligonucleotides Conjugated to a Multivalent Carbohydrate Cluster for Cellular Targeting", *Bioconjugate Chemistry*, vol. 14, 18-29, XP002510288 (2003).
Murata et al., "Design of Quaternary Chitosan Conjugate Having Antennary Galactose Residues as a Gene Delivery Tool", *Carbohydrate Polymers*, vol. 32(2), 105-109 (1997).
Nunez et al., *Journal of Carbohydrate Chemistry*, vol. 22, No. 6, 395-406 (2003).
Rensen et al., "Design and Synthesis of Novel N-Acetylgalactosamine-Terminated Glycolipids for Targeting of Lipoproteins to the Hepatic Asialoglycoprotein Receptor", *Journal of Medicinal Chemistry*, vol. 47(23), 5798-5808 (2004).
Sioud, "On the Delivery of Small Interfering RNAs into Mammalian Cells", *Expert Opinion on Drug Delivery*, vol. 2(4), 639-651 (2005).
Six et al., "An Efficient and Stereoselective Synthesis of 1, 2-0-Dialkyl 3 0 Beta D Glycosyl-SN-Glycerols", *Tetrahedron Letters*, vol. 24(12), 1229-1232 (1983).
Six et al., "Influence of Carbohydrate Moities on Monolayer Properties of Dialkylglycerylletherglycosides, Simple Model Compounds of the Glycolipids of Halophilic Bacteria", *Journal of Colloid and Interface Science*, vol. 93(1), 109-114.
Sliedregt et al., "Design and Synthesis of Novel Amphiphilic Dendritic Galactosides for Selective Targeting of Liposomes to the Hepatic Asialoglycoprotein Receptor", *Journal of Medicinal Chemistry*, vol. 42, No. 4, 609-618 (1999).
Vaino et al., "Synthesis of a D-Lactosyl Cluster-Nucleoside Conjugate", *Chemical Communications*, 19, 1871-1872 (1997).
Wolfrum et al., "Mechanisms and optimization of in vivo delivery of lipophilic siRNAs", *Nature Biotechnology* 25(10), 1149-1157 (2007).
Wong et al., "Lipid, Sugar and Liposaccharide Based Delivery Systems", *Current Medicinal Chemistry*, vol. 8(9), 1123-1136 (2001).
Zatsepin et al., "Synthesis and Applications of Oligonucleotide-Carbohydrate Conjugates", *Chemistry & Biodiversity*, vol. 1(10), 1401-1417 (2004).
Zheng et al., "Distribution and anti-HBV effects of antisense oligodeoxynucleotides conjugated to galactosylated poly-L-lysine", *World Journal of Gastroenterology*, vol. 9, No. 6, 1251-1255, XP002510287 (2003).
Zimmermann et al., "RNAi-Mediated Gene Silencing in Non-Human Primates", *Nature Publishing Group*, vol. 441, No. 7089, 111-114 (2006).
Hashida, "Lipid carrier systems for targeted drug and gene delivery", *Chemical and Pharmaceutical Bulletin* 53 (11), 871-880 (2005).
Medina, "Targeted liposomal drug delivery in cancer", *Current Pharmaceutical Design* 10 (24), 2981-2989 (2004).
Noble, "Development of ligand-targeted liposomes for cancer therapy", *Expert Opinions on Therapeutic Targets* 8 (4), 335-353 (2004).
Pan, "Tumour-selective drug delivery via folate receptor-targeted liposomes", *Expert Opinions on Drug Delivery* 1 (1), 7-17 (2004).

(56) References Cited

OTHER PUBLICATIONS

Sapra, "Ligand-targeted liposomal anticancer drugs", *Progress in Lipid Research* 42(5), 439-462 (2003).
Sapra, "Ligand-targeted liposomes for cancer treatment", *Current Drug Delivery* 2(4), 369-381 (2005).
Endo et al., "Physical Properties and Barrier Functions of Synthetic Glyceroglycolipids", J Biochem, 92, 953-960 (1982).

\* cited by examiner

Figure 1.
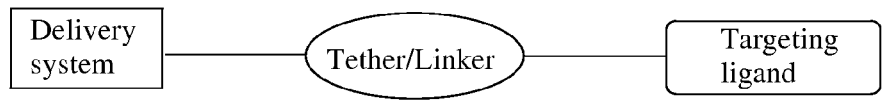
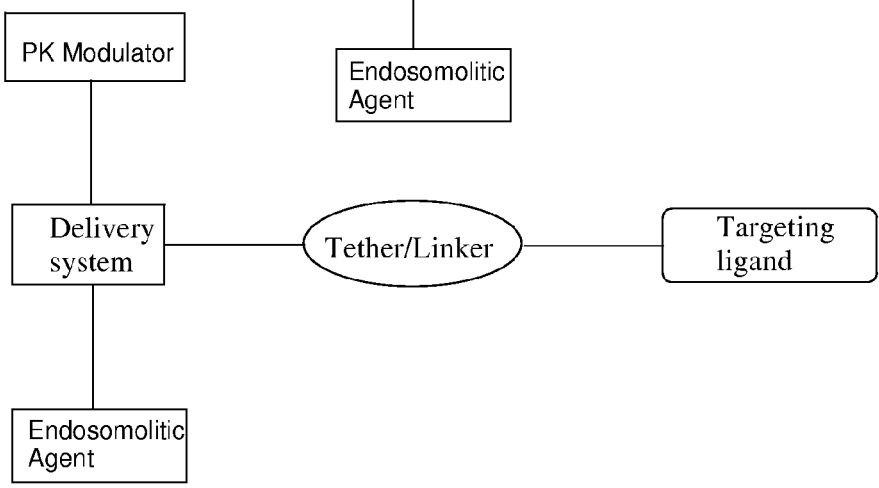
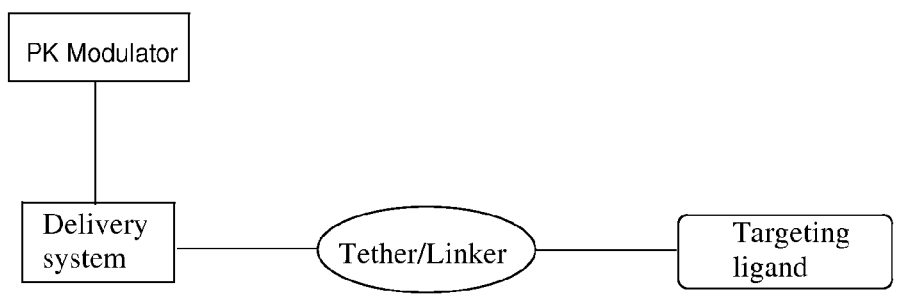

Figure 3. (a)
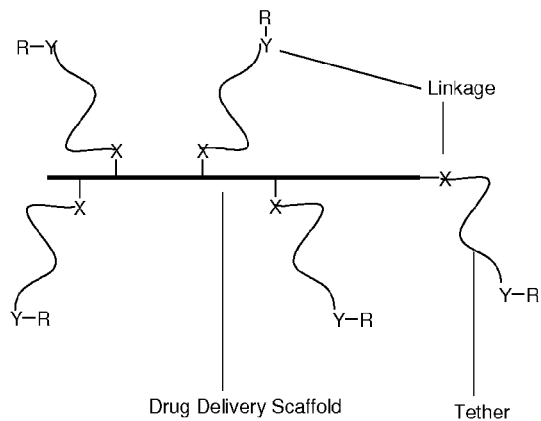
(b)
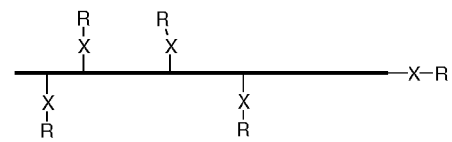
(c)
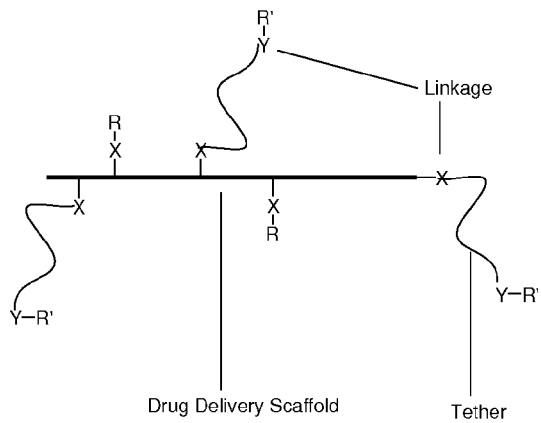
(d)
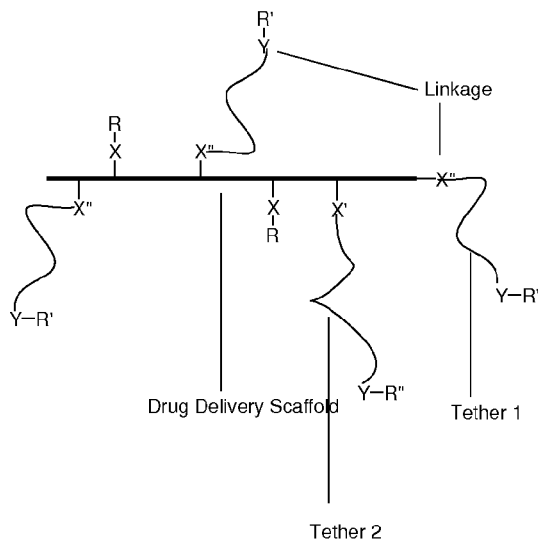

Figure 4. (a)
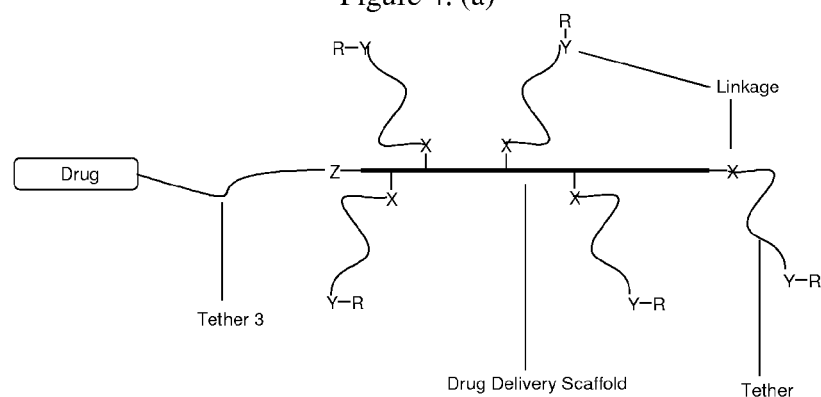
(b)
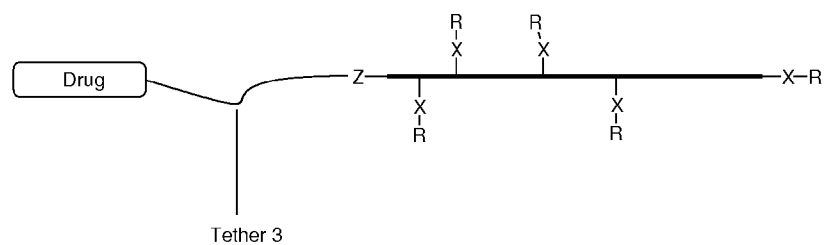
(c)
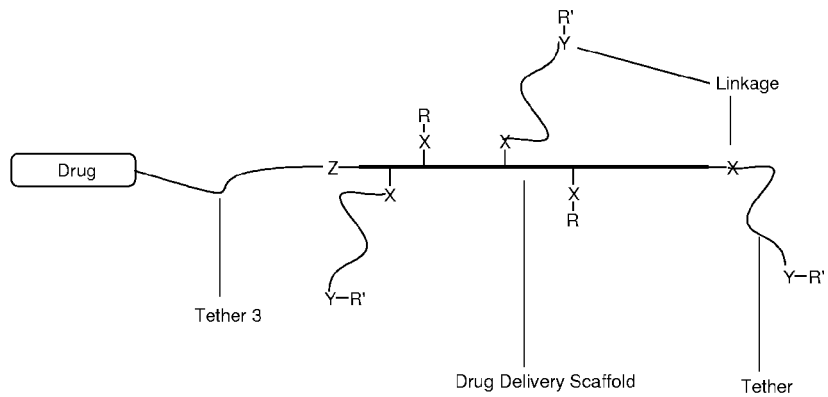
(d)
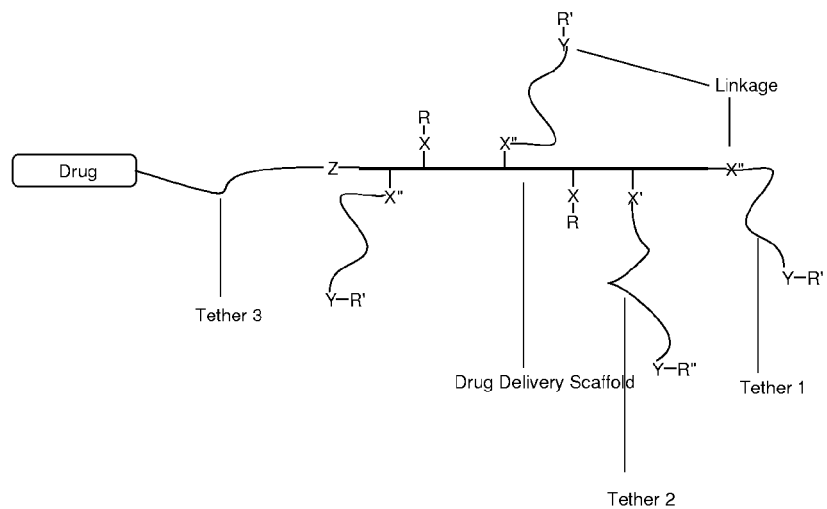

Figure 10

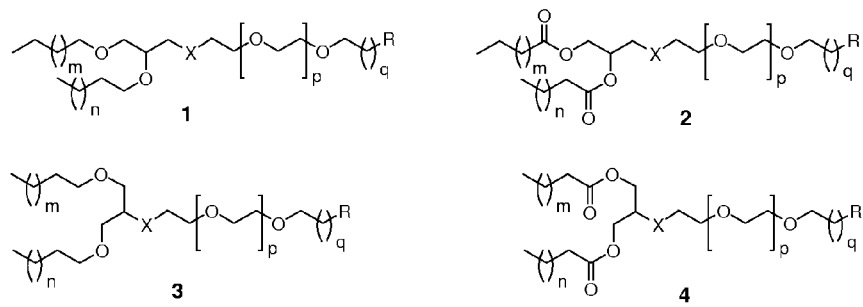

R = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L

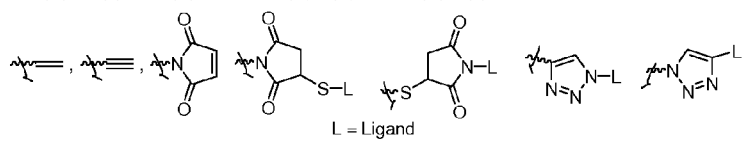

L = Ligand

X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;

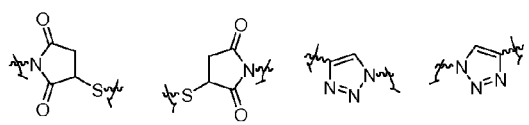

Glycerol backbone with *R* or *S* configuration or a racemic mixture of both. m = 5-29; n = 6-28, p = 1-1000 and q = 1-20

Figure 11

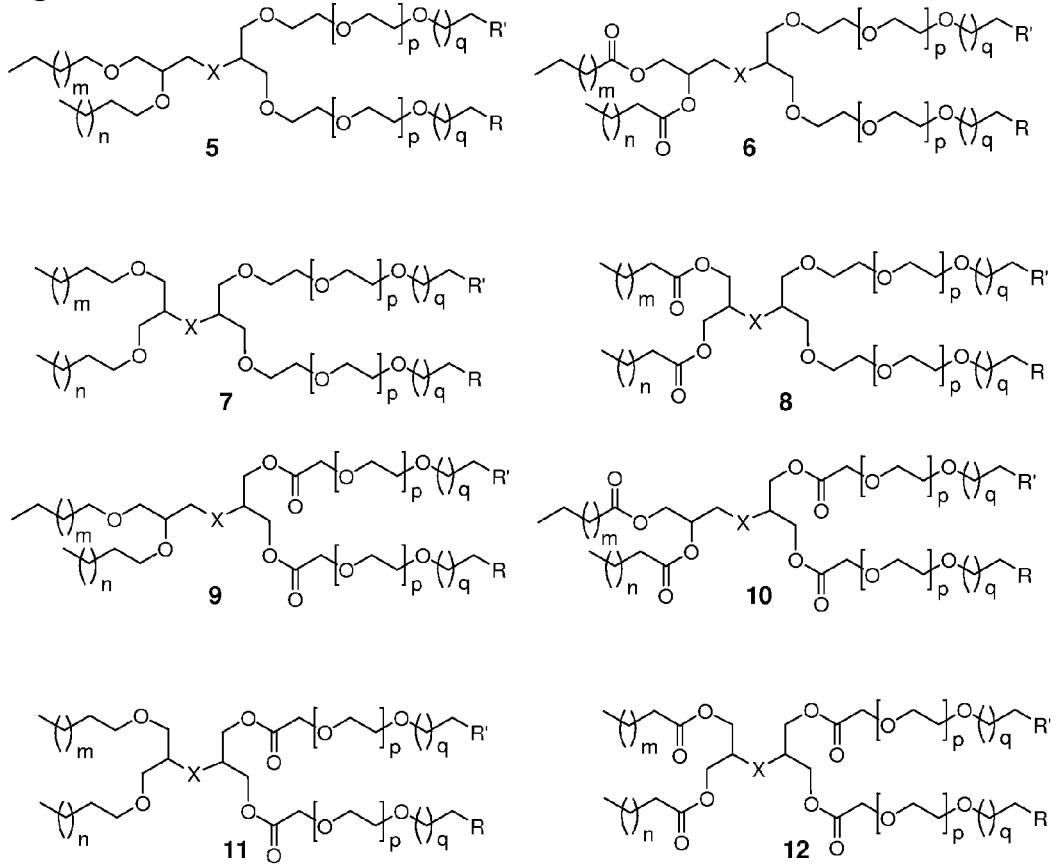

R, R' = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L

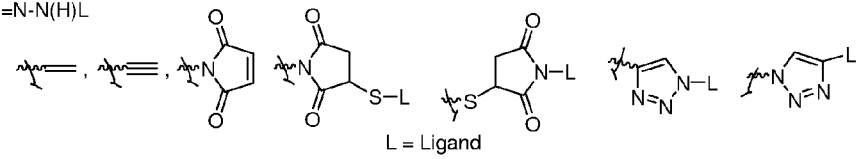

L = Ligand

X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;

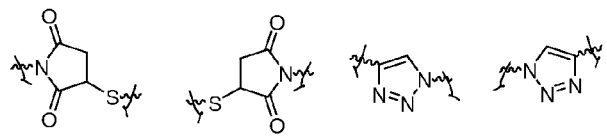

Glycerol backbone with *R* or *S* configuration or a racemic mixture of both. m = 5-29; n = 6-28, p = 1-1000 and q = 1-20

Figure 12
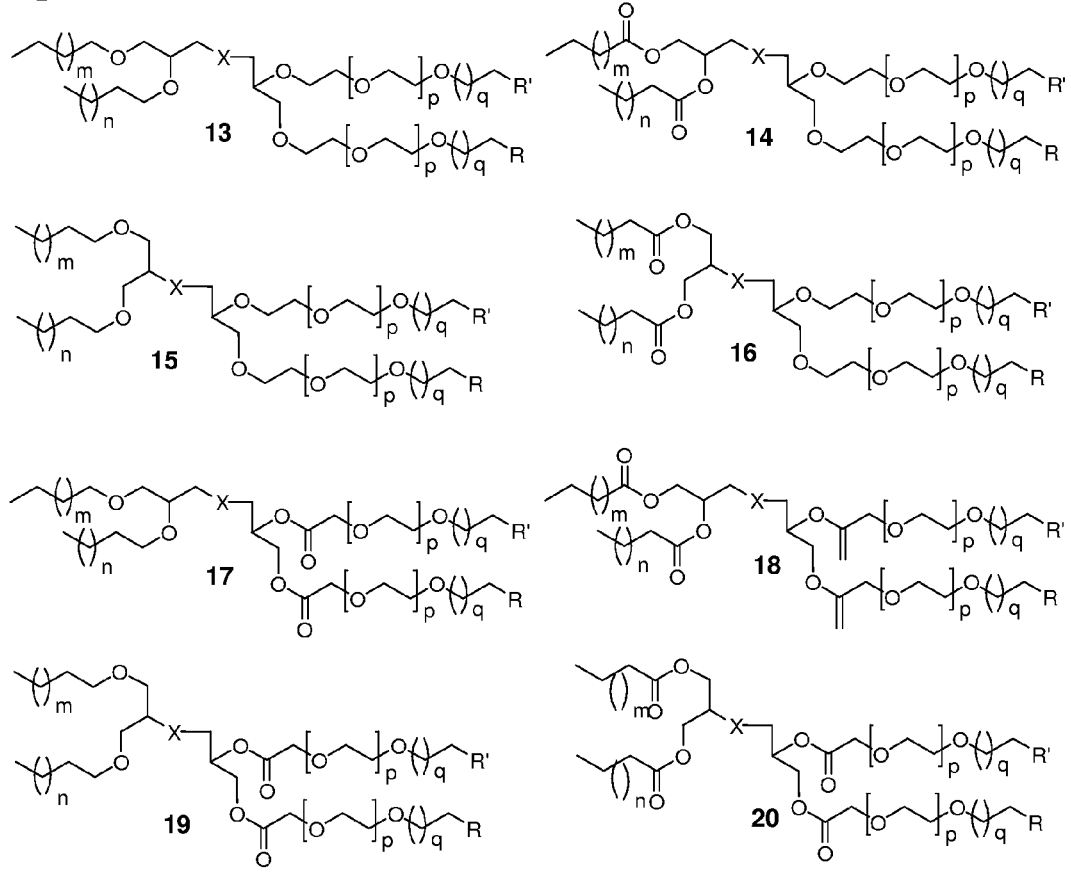
R, R' = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
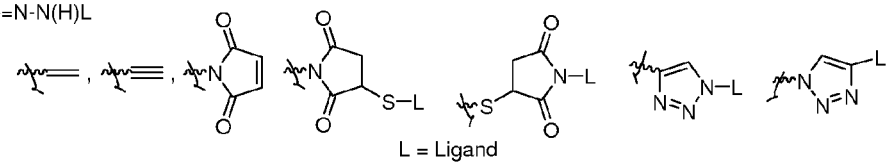
L = Ligand
X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;
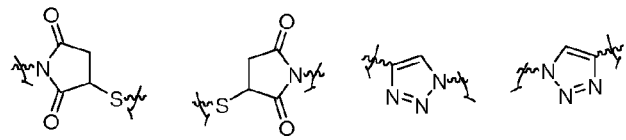

Figure 13
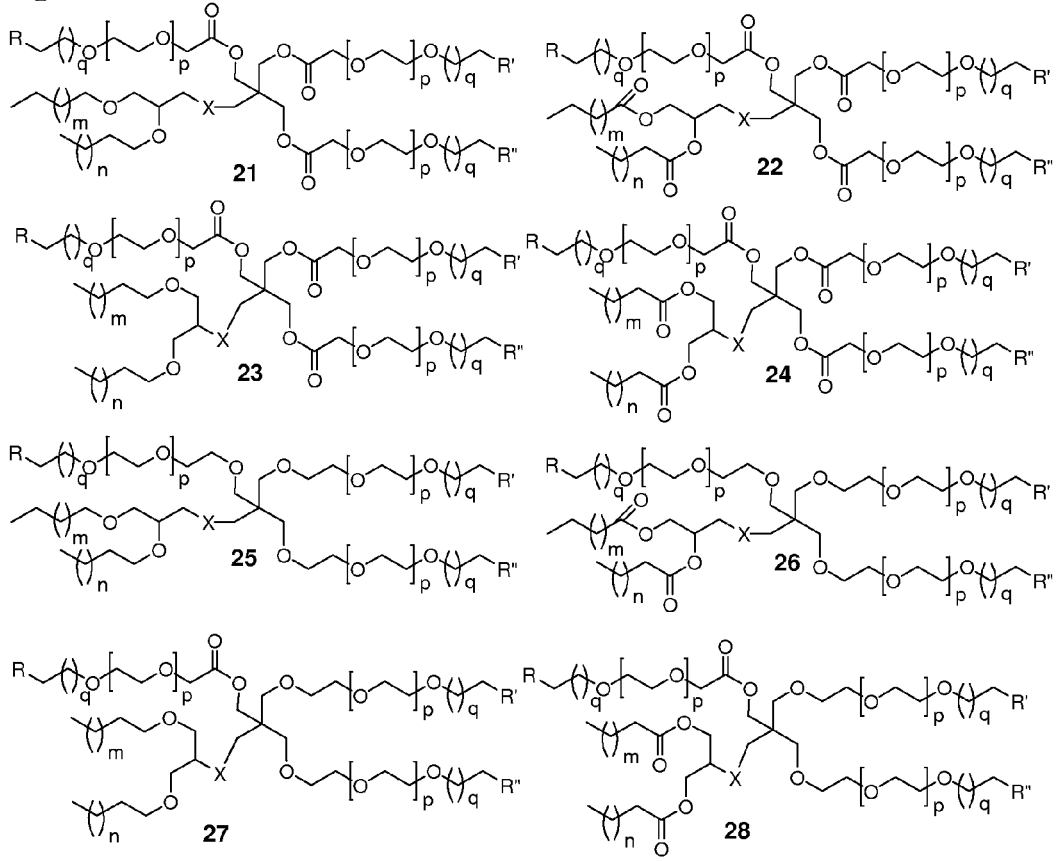
R, R', R" = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
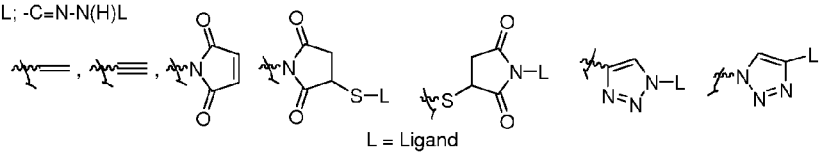
L = Ligand
X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;
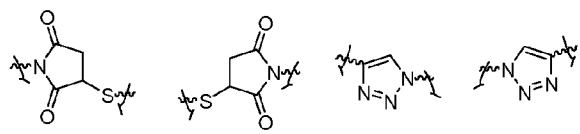

Figure 14

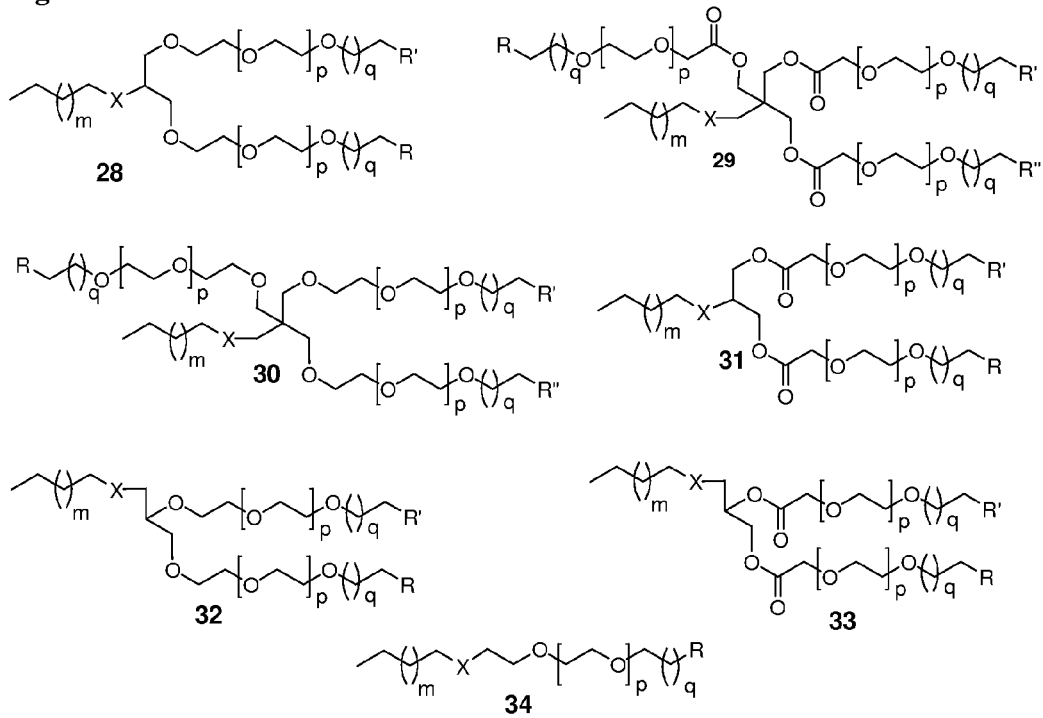

R, R', R" = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L

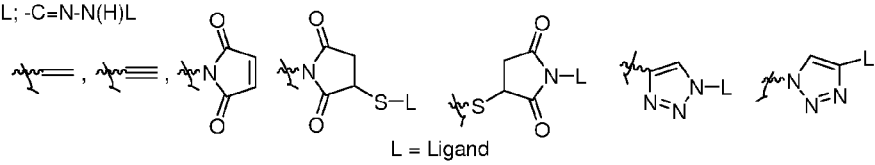

L = Ligand

X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;

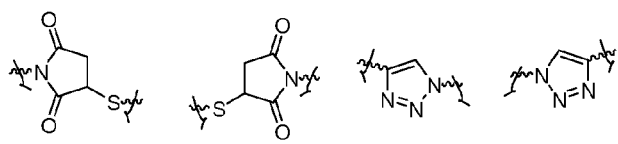

Glycerol backbone with *R* or *S* configuration or a racemic mixture of both. m = 5-29; n = 6-28, p = 1-1000 and q = 1-20

Figure 15
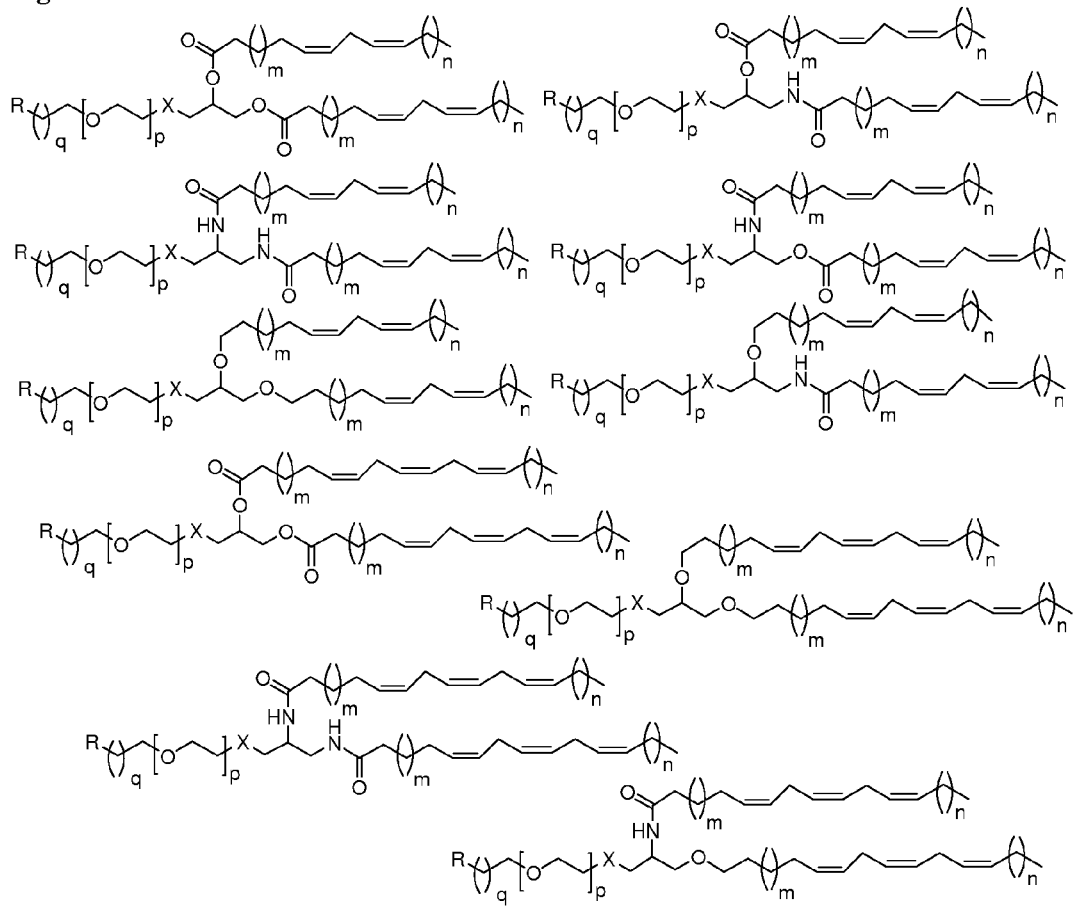
R = -OH; -OCH$_3$; -NH$_2$; -NHCH$_3$; -N(CH$_3$)$_2$; -SH; -SCH$_3$; -N$_3$; -COOH; -CONH$_2$; -CONHNH$_2$; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
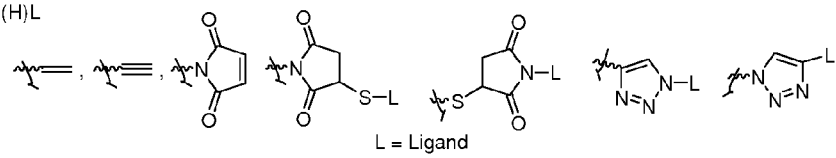
L = Ligand
X = O; NH; NCH$_3$; S, CH$_2$; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;
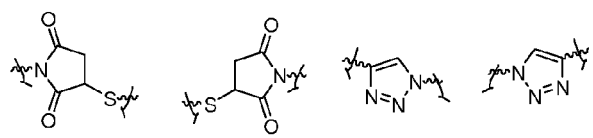

Figure 16
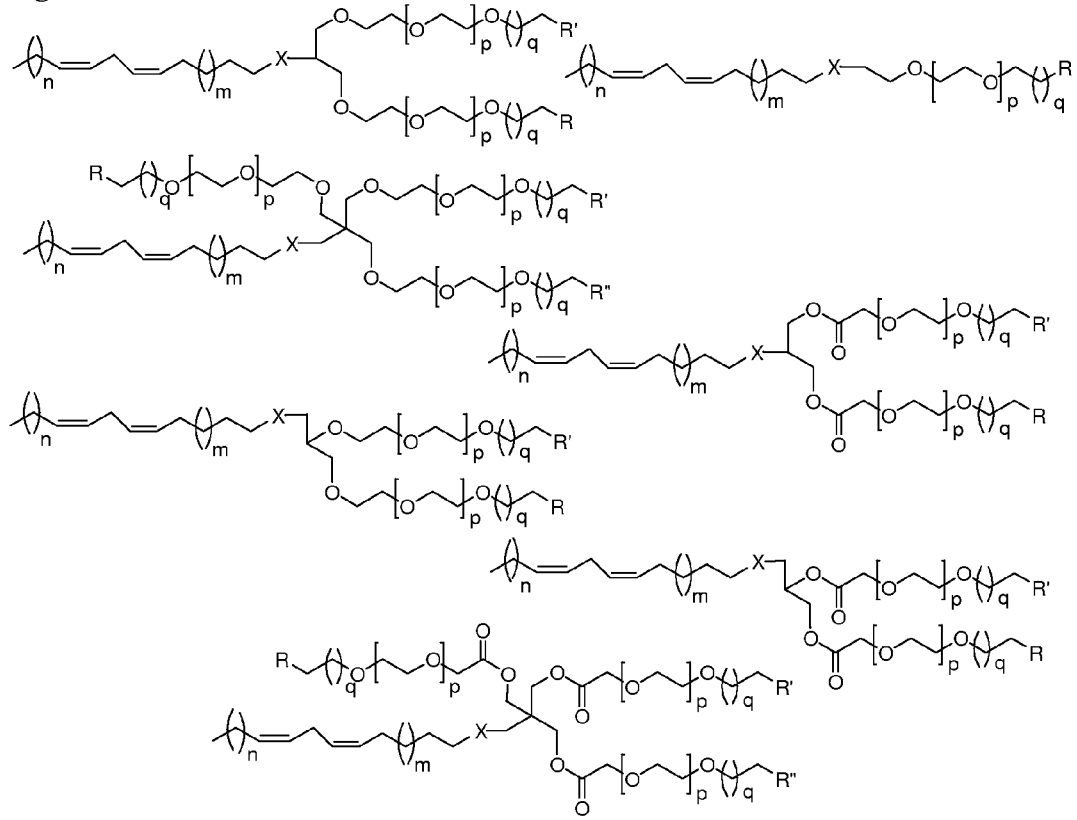
R, R', R" = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
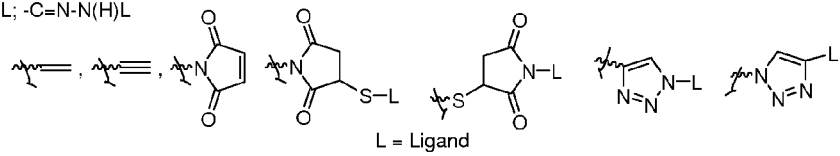
L = Ligand
X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;
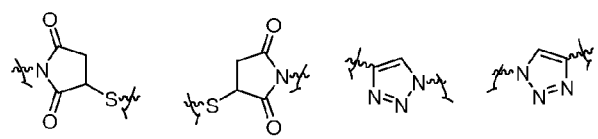

Figure 17
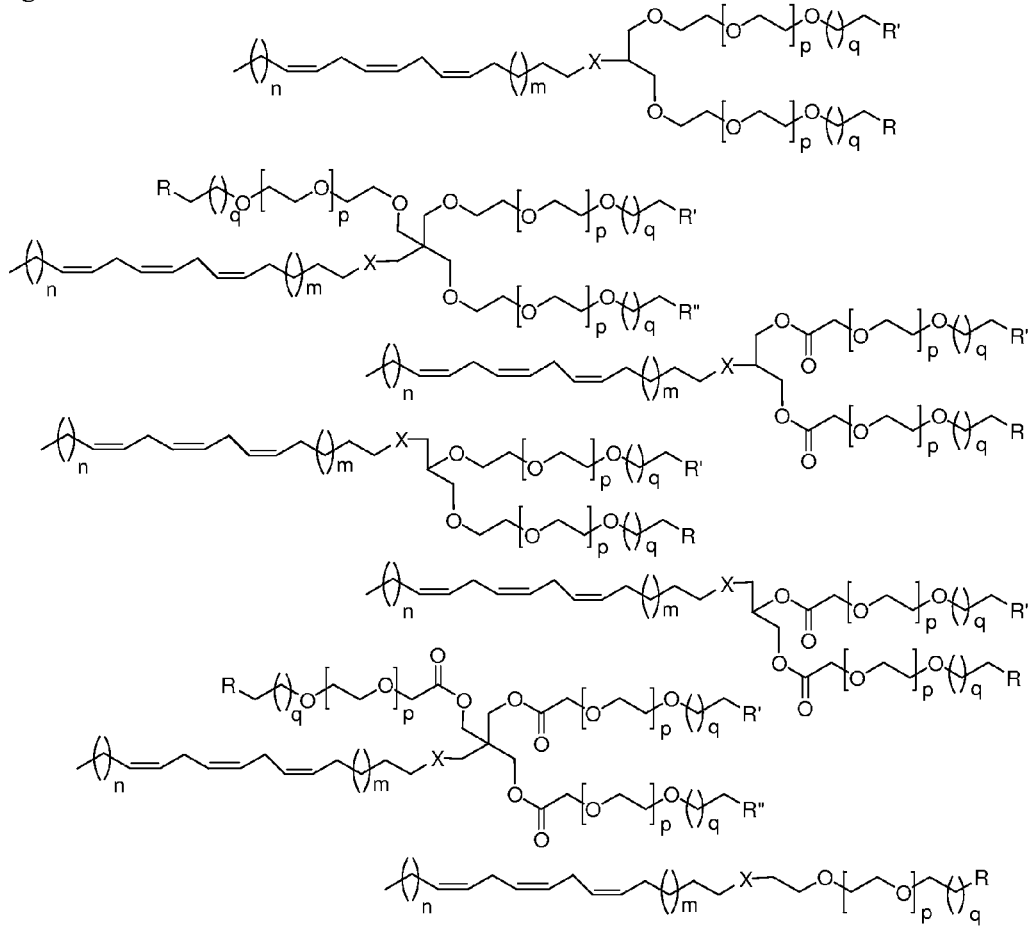
R, R', R" = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
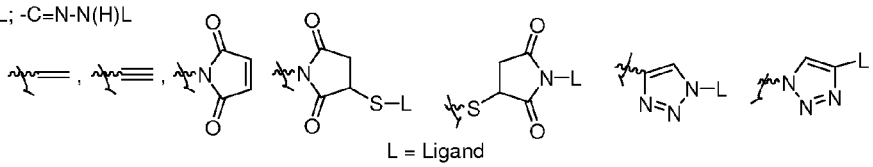
L = Ligand
X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; C(O)-O-; -C(O)-N(H)-; -C(O)-N(Me)-; -O-C(O)-; -NH-C(O)-; -N(Me)-C(O)-; -C=N-; -N=C-;
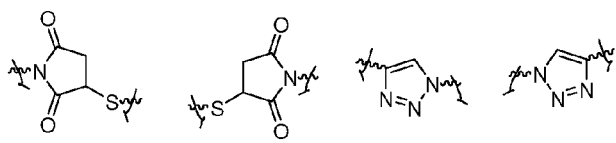

Figure 18
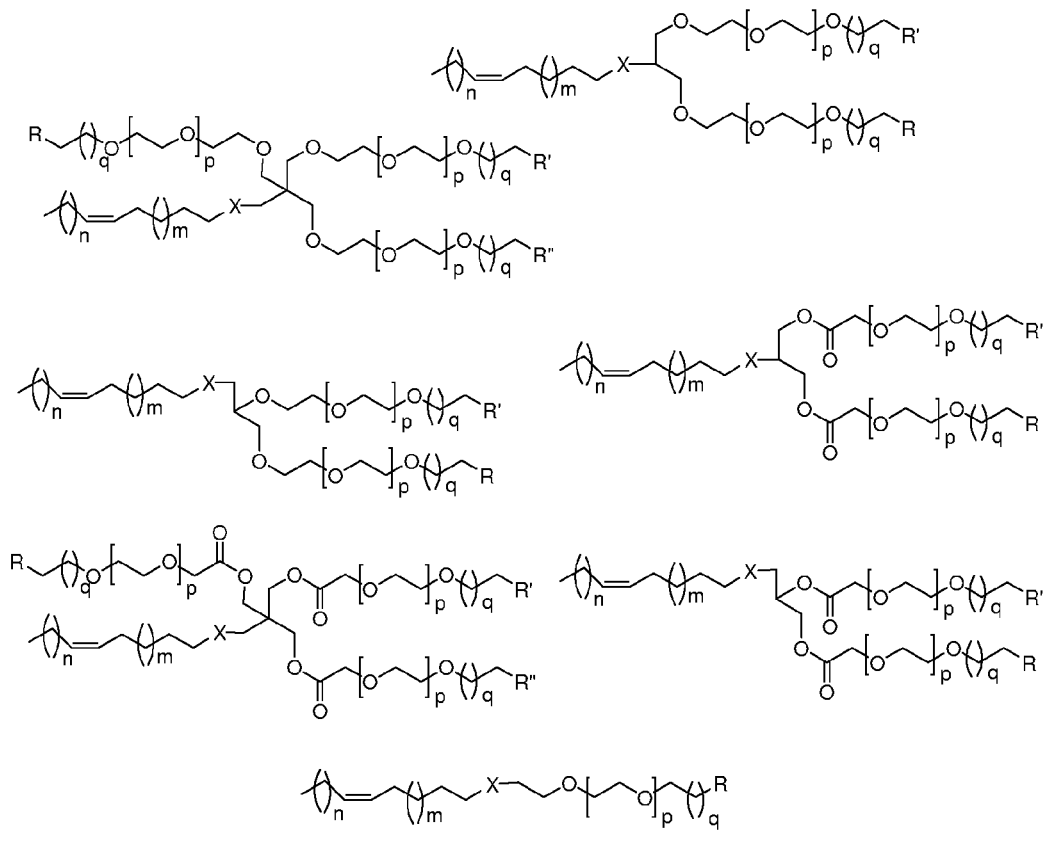
R, R', R" = -OH; -OCH₃; -NH₂; -NHCH₃; -N(CH₃)₂; -SH; -SCH₃; -N₃; -COOH; -CONH₂; -CONHNH₂; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
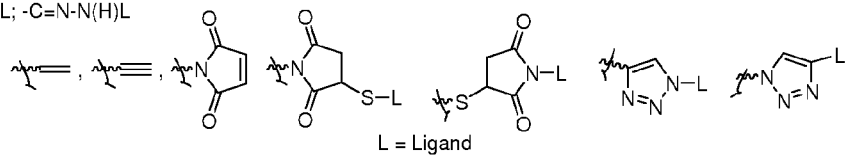
L = Ligand
X = O; NH; NCH₃; S, CH₂; S-S, -O-N=C-; -C(O)-N(H)-N=C-; -C=N-O-; -C=N-N(H)-C(O)-; -C(O)_N(Me)-N=C-; -C=N-N(Me)-C(O)-; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;
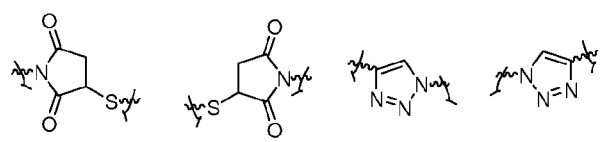

Figure 19
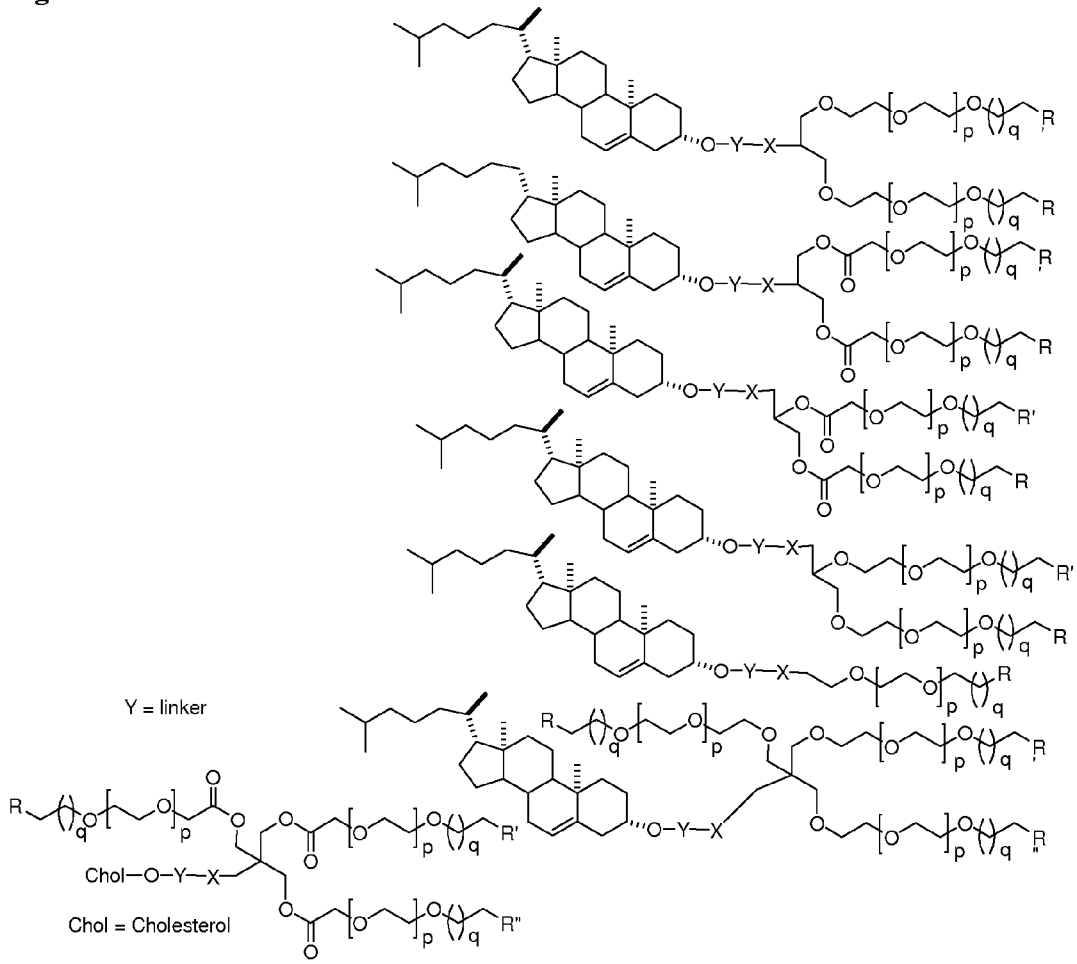
R, R', R" = -OH; -OCH$_3$; -NH$_2$; -NHCH$_3$; -N(CH$_3$)$_2$; -SH; -SCH$_3$; -N$_3$; -COOH; -CONH$_2$; -CONHNH$_2$; -C(O)L; -OL; -N(H)L; -O-C(O)-NH(L); -O-C(O)-OL; -NH-C(O)-N(H)L; NH-C(O)-O(L); -S-SL; -O-N=CL; -NH-N=CL; -C=N-OL; -C=N-N(H)L
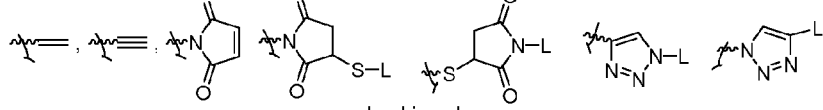
L = Ligand
X = O; NH; NCH$_3$; S, CH$_2$; S-S, -O-N=C-; -C(O)-N(H)-N=C-; -C=N-O-; -C=N-N(H)-C(O)-; -C(O)_N(Me)-N=C-; -C=N-N(Me)-C(O)- ; -O-C(O)-O-; -O-C(O)-NH-; -NH-C(O)-O-; -NH-C(O)-NH-; -N(Me)-C(O)-N(Me)-; -N(H)-C(O)-N(Me)-; -N(Me)-C(O)-N(H)-; -C(O)-O-; -C(O)-N(H)-; -C(O)-N(Me)-; -O-C(O)-; -NH-C(O)-; -N(Me)-C(O)-; -C=N-; -N=C-;
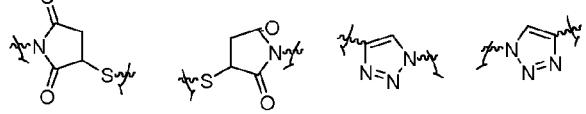

TARGETING LIPIDS

RELATED APPLICATIONS

This application is a continuation application of U.S. patent application Ser. No. 12/328,669, filed Dec. 4, 2008, and claims the benefit of priority of U.S. Provisional Application No. 60/992,309, filed Dec. 4, 2007, U.S. Provisional Application No. 61/013,597, filed Dec. 13, 2007, U.S. Provisional Application No. 61/127,751, filed May 14, 2008, U.S. Provisional Application No. 61/091,093, filed Aug. 22, 2008, and U.S. Provisional Application No. 61/097,261, filed Sep. 16, 2008. The entire content of each of these applications is hereby incorporated herein by reference.

GOVERNMENT SUPPORT

The work described herein was carried out, at least in part, using funds from the United States government under contract number HHSN266200600012C from the National Institute of Allergy and Infectious Diseases/National Institutes of Health/Department of Health and Human Services (NIAID/NIH/DHHS) and contract number HDTRA-1-07-C-0082, from the Department of Defense and Defense Threat Reduction Agency (DOD/DTRA). The government may therefore have certain rights in the invention.

TECHNICAL FIELD

The present invention relates to the field of therapeutic agent delivery using lipid particles. In particular, the present invention provides targeting lipids and lipid particles comprising these lipids, which are advantageous for the in vivo delivery of nucleic acids, as well as nucleic acid-lipid particle compositions suitable for in vivo therapeutic use. Additionally, the present invention provides methods of making these compositions, as well as methods of introducing nucleic acids into cells using these compositions, e.g., for the treatment of various disease conditions.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing. RNA interference or "RNAi" is a term initially coined by Fire and co-workers to describe the observation that double-stranded RNA (dsRNA) can block gene expression when it is introduced into worms (Fire et al. (1998) Nature 391, 806-811). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

siRNA has been shown to be extremely effective as a potential anti-viral therapeutic with numerous published examples appearing recently. siRNA molecules directed against targets in the viral genome dramatically reduce viral titers by orders of magnitude in animal models of influenza (Ge et. al., Proc. Natl. Acd. Sci. USA, 101:8676-8681 (2004); Tompkins et. al., Proc. Natl. Acd. Sci. USA, 101:8682-8686 (2004); Thomas et. al., Expert Opin. Biol. Ther. 5:495-505 (2005)), respiratory synctial virus (RSV) (Bitko et. al., Nat. Med. 11:50-55 (2005)), hepatitis B virus (HBV) (Morrissey et. al., Nat. Biotechnol. 23:1002-1007 (2005)), hepatitis C virus (Kapadia, Proc. Natl. Acad. Sci. USA, 100:2014-2018 (2003); Wilson et. al., Proc. Natl. Acad. Sci. USA, 100:2783-2788 (2003)) and SARS coronavirus (Li et. al., Nat. Med. 11:944-951 (2005)).

Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally-occurring events that alter the expression level of the target sequence, discussed by Cohen (Oligonucleotides: Antisense Inhibitors of Gene Expression, CRC Press, Inc., 1989, Boca Raton, Fla.) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid.

Another means by which antisense oligonucleotides alter the expression level of target sequences is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

The opportunity to use these and other nucleic1 acid based therapies holds significant promise, providing solutions to medical problems that could not be addressed with current, traditional medicines. The location and sequences of an increasing number of disease-related genes are being identified, and clinical testing of nucleic acid-based therapeutics for a variety of diseases is now underway.

Despite the advances in application of oligonucleotides and oligonucleotide analogs as therapeutics, the need exists for oligonucleotides having improved pharmacologic properties. Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport.

To attempt to improve efficacy, investigators have also employed lipid-based carrier systems to deliver chemically modified or unmodified therapeutic nucleic acids. In Zelphati, O and Szoka, F. C., *J. Contr. Rel.* 41:99-119 (1996), the authors refer to the use of anionic (conventional) liposomes, pH sensitive liposomes, immunoliposomes, fusogenic liposomes, and cationic lipid/antisense aggregates. Similarly siRNA has been administered systemically in cationic liposomes, and these nucleic acid-lipid particles have been reported to provide improved down-regulation of target proteins in mammals including non-human primates (Zimmermann et al., *Nature* 441: 111-114 (2006)).

In spite of this progress, there remains a need in the art for improved lipid-therapeutic nucleic acid compositions that are suitable for general therapeutic use. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these lipid-nucleic acid particles should be well-tolerated and provide an adequate therapeutic index, such that patient treatment at an effective dose of the nucleic acid is not associated with significant toxicity and/or risk to the patient. The present invention provides such compositions, methods of making the compositions, and methods of using the compositions to introduce nucleic acids into cells, including for the treatment of diseases.

BRIEF SUMMARY

The present invention provides targeting lipids having the structure shown in formula (I):

$$L_A[-P-Q-R-]T_q-L^B \quad \text{Formula (I)}$$

wherein:

$L^A$ is a ligand chosen from a carbohydrate, glucose, mannose, galactose, N-acetyl-galactosamine, fucose, glucosamine, lactose, maltose, folate, peptide, or has the structure shown in formula II-V:

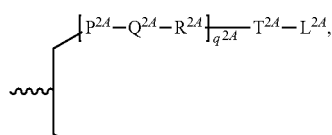

Formula (II)

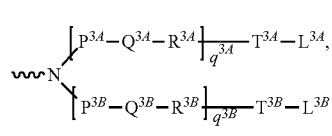

Formula (III)

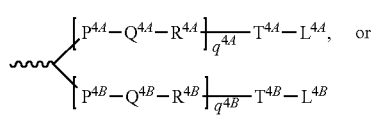

Formula (IV)

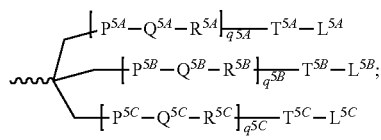

Formula (V)

q, $q^{2A}$, $q^{2B}$, $q^{3A}$, $q^{3B}$, $q^{4A}$, $q^{4B}$, $q^{5A}$, $q^{5B}$ and $q^{5C}$ and represent independently for each occurrence 0-20;

P, $P^{2A}$, $P^{2B}$, $P^{3A}$, $P^{3B}$, $P^{4A}$, $P^{4B}$, $P^{5A}$, $P^{5B}$, $P^{5C}$, T, $T^{2A}$, $T^{2B}$, $T^{3a}$, $T^{3B}$, $T^{4A}$, $T^{4B}$, $T_{4A}$, $T^{5B}$ and $T^{5C}$ are each independently for each occurrence absent, NR', O, S, C(O), OC(O), C(O)O, NHC(O), C(O)NH, NHCH$_2$, CH$_2$, CH$_2$NH or CH$_2$O, NHCH(R$^a$)C(O), —C(O)—CH(R$^a$)—NH—, CO, CH=N—O, CH$_2$S, urea, heterocycle, heteroaryl,

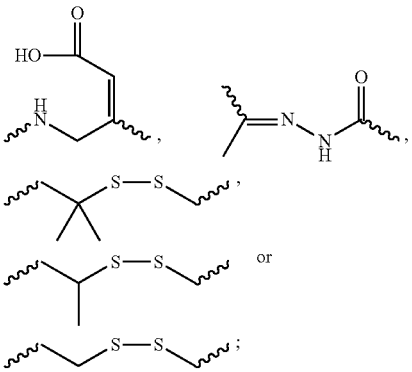

Q, $Q^{2A}$, $Q^{2B}$, $Q^{3A}$, $Q^{3B}$, $Q^{4A}$, $Q^{4B}$, $Q^{5A}$, $Q^{5B}$ and $Q^{5C}$ are independently for each occurrence absent, —(CH$_2$)$_n$—, —C(R')(R")(CH$_2$)$_n$—, —(CH$_2$)$_m$C(R')(R")—, —(CH$_2$CH$_2$O)$_p$CH$_2$CH$_2$—, or —(CH$_2$CH$_2$O)$_p$CH$_2$CH$_2$NH—;

$L^B$ is a ligand selected from a group consisting of lipophile, steroid (e.g., uvaol, hecigenin, diosgenin), terpene (e.g., triterpene, e.g., sarsasapogenin, Friedelin, epifriedelanol derivatized lithocholic acid), vitamin (e.g., folate, vitamin A, biotin, pyridoxal), ceramide or has the structure of formula (VI):

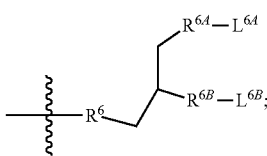

Formula (VI)

R, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^6$, $R^{6A}$ and $R^{6B}$ are each independently for each occurrence absent, CO, NH, NR', O, S, C(O), OC(O), C(O)O, NHC(O), C(O)NH, NHCH$_2$, CH$_2$, CH$_2$NH or CH$_2$O, NHCH(R$^a$)C(O), —C(O)—CH(R$^a$)—NH—, CO, CH=N—O,

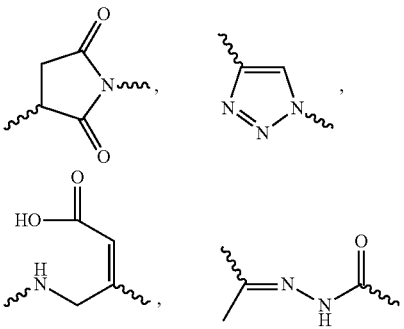

-continued

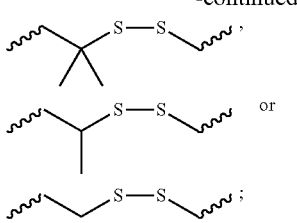

$L^{2A}$, $L^{2B}$, $L^{3A}$, $L^{3B}$, $L^{4A}$, $L^{4B}$, $L^{5A}$, $L^{5B}$ and $L^{5C}$ are each independently for each occurrence a carbohydrate, glucose, mannose, galactose, N-acetyl-galactosamine, fucose, glucosamine, lactose, maltose, folate or a peptide;

R' and R" are each independently H, $CH_3$, OH, SH, $NH_2$, $NR^{10}R^{20}$, alkyl, alkenyl or alkynyl; alternatively, R' and R" are each independently halogen;

$R^a$ is H or amino acid side chain;

$R^{10}$ and $R^{20}$ are each independently alkyl, alkenyl or alkynyl;

$L^{6A}$ and $L^{6B}$ are each independently alkyl, alkenyl or alkynyl, each of which is optionally substituted with one or more substituents;

m represent independently for each occurrence 0-50;
n represent independently for each occurrence 1-20; and
p represent independently for each occurrence 0-50.

When any of q, $q^{2A}$, $q^{2B}$, $q^{3A}$, $q^{3B}$, $q^{4A}$, $q^{4B}$, $q^{5A}$, $q^{5B}$ and $q^{5C}$ is greater than 1, the repeating unit can be the same or different from each other, for example when q is 3 the unit —[P-Q-R]$_q$— is expanded to —[P-Q-R]—[P-Q-R]—[P-Q-R]— and all of the —[P-Q-R]— units can be the same, completely different from each other or a mixture thereof.

The present invention further includes methods of preparing lipid particles and pharmaceutical compositions, as well as kits useful in the preparation of these lipid particle and pharmaceutical compositions. The method includes providing a composition that includes an agent, e.g. an oligonucleotide based construct that targets a selected target gene, e.g. a gene expressed in the liver, and the targeting lipid; and administering the composition to a test subject, e.g. an animal; thereby evaluating the agent and the targeting lipid, e.g. by evaluating the expression of the target gene.

BRIEF DESCRIPTION OF DRAWINGS

FIG. 1. Schematics of targeted delivery using targeting ligands.

FIG. 3. Schematic representation of polymer drug delivery systems with one or more targeting moiety (moieties) R separated by a tether. X and Y indicate chemical linkages between the scaffold/tether and tether/ligand. R' and/or R" is either targeting, fusogenic, endosomal releasing groups, hydrophobic/hydrophilic balancer such as saturated or unsaturated alkyls with varying length or PEG with varying length or circulation enhancer like PEGs, PK modulators.

FIG. 4. Schematics of polymer drug delivery systems with therapeutic agent conjugate conjugated to the polymer back bone via a tether and linkage Z (biocleavable or stable).

FIGS. 10-19. Schematic representation of some PEG-lipids of the invention.

DETAILED DESCRIPTION

Figure 2:
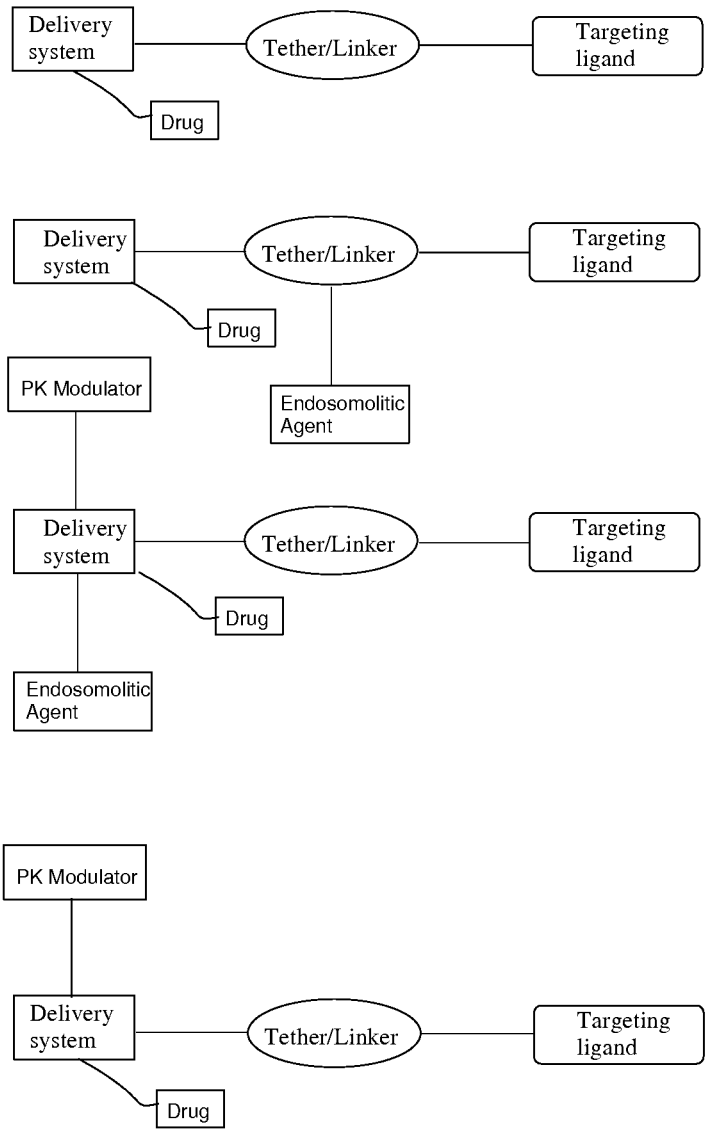
FIG. 2. Schematics of targeted delivery using targeting ligands with conjugated therapeutic agent.
Figure 5:
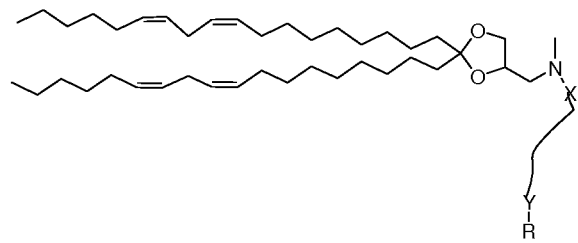
FIG. 5. pH sensitive lipid with targeting moiety.
Figure 6:
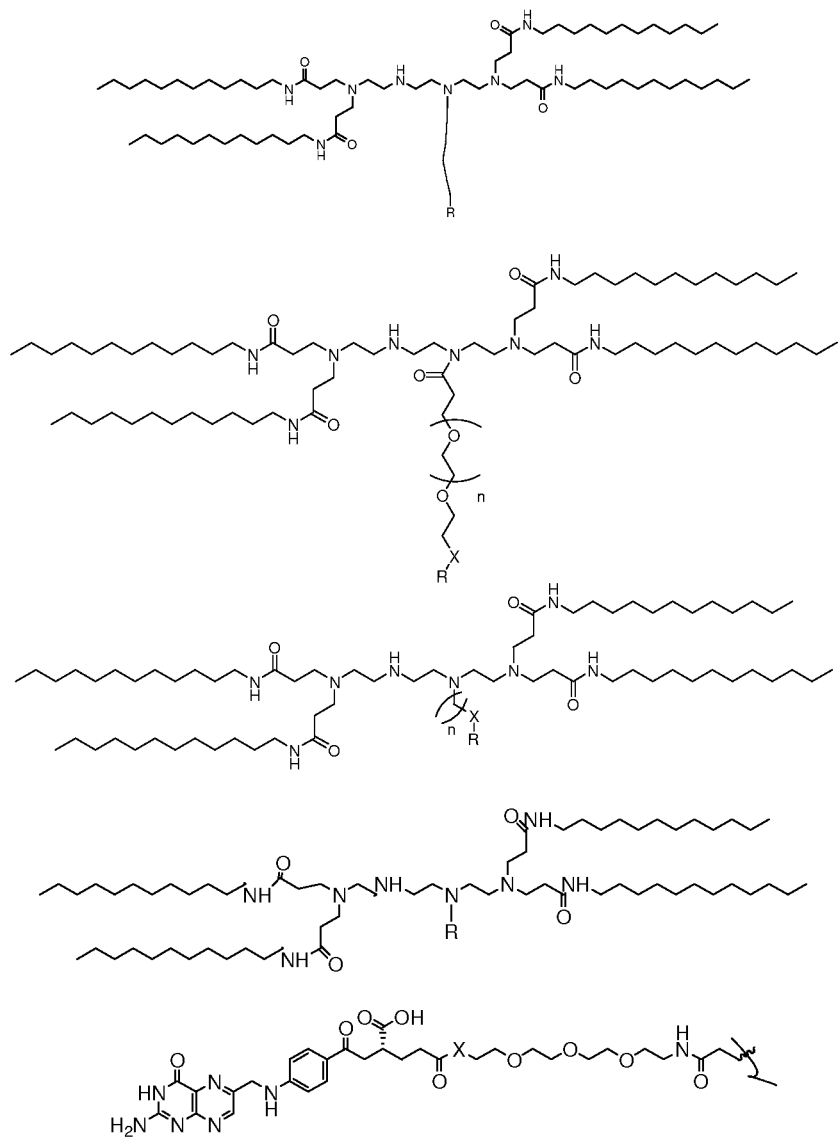
FIG. 6. Cationic lipid-folate conjugates.
Figure 7:
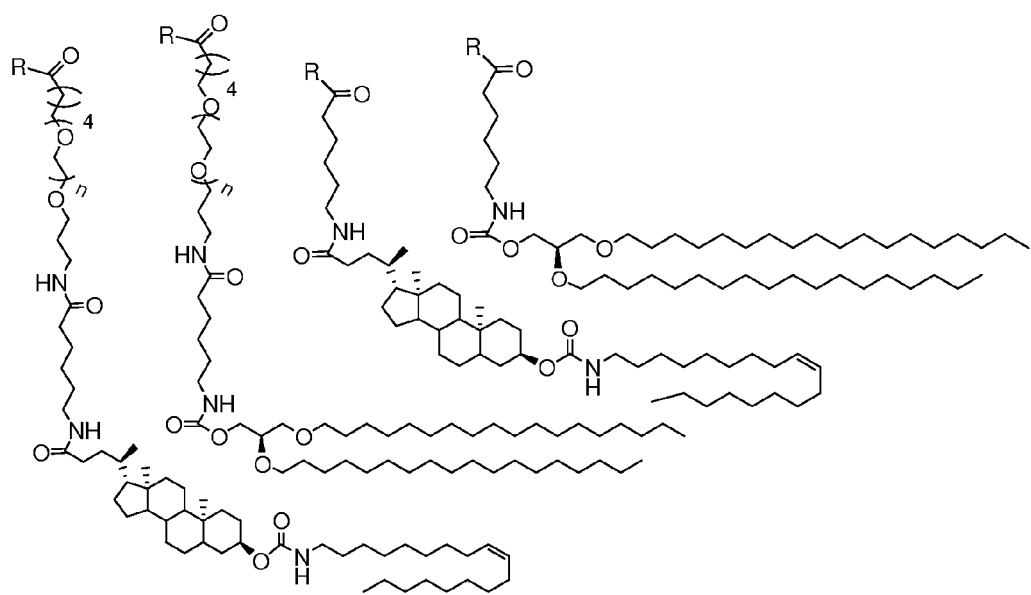
FIG. 7. Lipid-folate conjugates.

In one aspect the invention provides a targeting lipid monomer having the structure shown in formula (CI)

$L^{100}$-linker-$L_{101}$     (CI)

wherein:
$L^{100}$ is independently for each occurrence lipid, lipophile, alkyl, alkenyl or alkynyl, each of which is optionally substituted with one or more substituents;
$L^{101}$ is independently for each occurrence a ligand or —$CH_2CH_2(OCH_2CH_2)_pO(CH_2)_qCH_2$-ligand;
p is 1-1000; and
q is 1-20.

In one embodiment, the targeting lipid monomer has the structure shown in formula (CII)

$L^{100}$-linker-A-linker-$L^{101}$     (CII)

wherein:
A is O, NH, NCH3, S, CH2, S—S, —C(CH$_3$)$_2$—S—S—, —CH(CH$_3$)—S—S—, —O—N=C—, —C(O)—N(H)—N=C—, —C=N—O—, —C=N—N(H)—C(O)—, —C(O)N(Me)-N=C—, —C=N—N(Me)-C(O)—, —O—C(O)—O—, —O—C(O)—NH—, —NH—C(O)—O—, —NH—C(O)—NH—, —N(Me)-C(O)—N(Me)-, —N(H)—C(O)—N(Me)-, —N(Me)-C(O)—N(H)—, —C(O)—O—, —C(O)—N(H)—, —C(O)—N(Me)-, —O—C(O)—, —NH—C(O)—, —N(Me)-C(O)—, —C=N—, —N=C—,

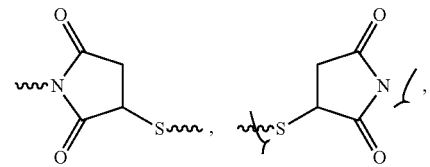

heterocycle or heteroaryl;
$L^{100}$ is independently for each occurrence lipid, lipophile, alkyl, alkenyl or alkynyl, each of which is optionally substituted with one or more substituents;
$L^{101}$ is independently for each occurrence a ligand or —$CH_2CH_2(OCH_2CH_2)_pO(CH_2)_qCH_2$-ligand;
p is 1-1000; and
q is 1-20.

In one embodiment, the targeting lipid monomer has the structure shown in formula (CIII)

$L^{110}$-A-$L^{111}$     (CIII)

$L^{110}$ is $L^{112}$,

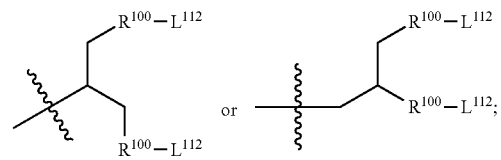

$R^{100}$ is independently for each occurrence absent, CO, NH, O, S, S—S, —C(CH$_3$)$_2$—S—S—, —CH(CH$_3$)—S—S—, C(O), OC(O), C(O)O, NHC(O), C(O)NH, NHCH$_2$, CH$_2$, CH$_2$NH, CH$_2$O, CH=N—O, heteroaryl, heterocycle,

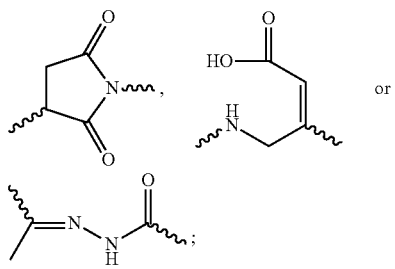

$L^{111}$ is $L^{113}$, $L^{114}$,

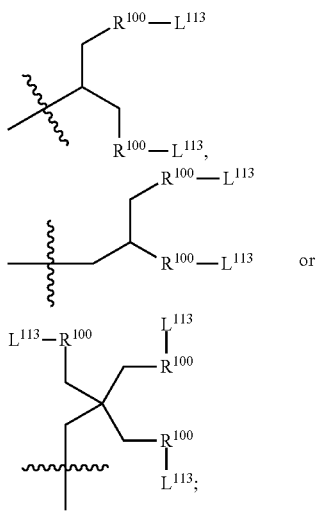

$L^{112}$ is independently for each occurrence lipid, lipophile, alkyl, alkenyl or alkynyl, each of which is optionally substituted with one or more substituents;

$L^{113}$ is independently for each occurrence —CH$_2$CH$_2$(OCH$_2$CH$_2$)$_p$O(CH$_2$)$_q$CH$_2$-$L^{114}$;

$L^{114}$ is independently for each occurrence a ligand, —C(O)-ligand, —O—C(O)-ligand, —N(H)-ligand, —O—C(O)—N(H)-ligand, —O—C(O)—O-ligand, —NH—C(O)—N(H)-ligand, —NH—C(O)—O-ligand, —S—S-ligand, —O—N=C-ligand, —NH—N=C-ligand, —C=N—O-ligand, —C=N—N(H)—ligand, heterocycle-ligand, heteroaryl-ligand,

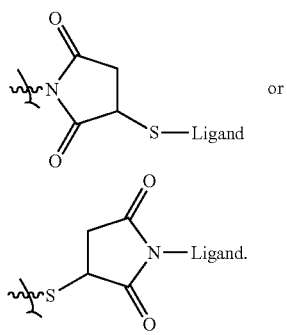

p is 1-1000; and
q is 1-20.

In one embodiment, $L^{110}$ is chosen from a group consisting of

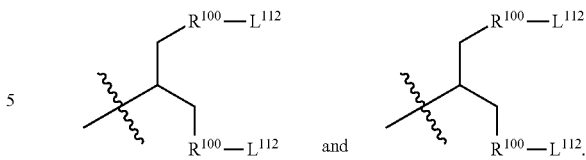

In one embodiment, $L^{111}$ is chosen from a group consisting of

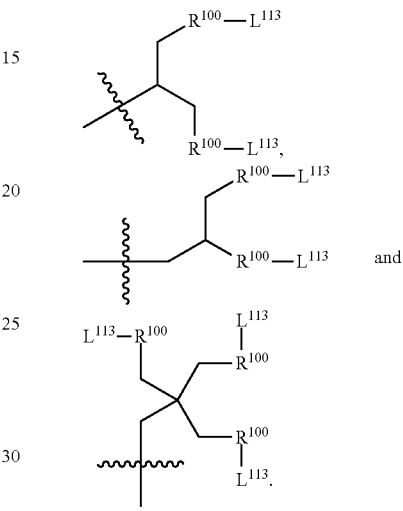

In one embodiment, $L^{112}$ is alkyl, for example $C_5$-$C_{31}$ alkyl, e.g., $C_{10}$-$C_{18}$ alkyl, e.g., $C_{14}$ alkyl, $C_{15}$ alkyl, $C_{16}$ alkyl, $C_{17}$ alkyl, $C_{18}$ alkyl.

In one embodiment, $L^{112}$ is alkenyl, for example $C_5$-$C_{31}$ alkenyl, e.g., $C_{10}$-$C_{18}$ alkenyl, e.g., $C_{14}$ alkenyl, $C_{15}$ alkenyl, $C_{16}$ alkenyl, $C_{17}$ alkenyl, $C_{18}$ alkenyl. In one embodiment $L^{112}$ comprises at least one double bond.

In one embodiment, $L^{112}$ is alkynyl, for example $C_5$-$C_{31}$ alkynyl, e.g., $C_{10}$-$C_{18}$ alkynyl, e.g., $C_{14}$ alkynyl, $C_{15}$ alkynyl, $C_{16}$ alkynyl, $C_{17}$ alkynyl, $C_{18}$ alkynyl. In one embodiment $L^{112}$ comprises at least one triple bond. In one embodiment, $L^{112}$ comprises at least one double bond and at least one triple bond.

In one embodiment, $L^{112}$ includes one double bond, for example a double bond in E or Z configuration.

In one embodiment, $L^{112}$ comprises two double bonds. In one embodiment, at least one double bond has a Z configuration. In one embodiment, both double bonds have a Z configuration. In one embodiment, at least one double bond has an E configuration. In one embodiment, both double bonds have an E configuration.

In one embodiment, $L^{112}$ comprises three double bonds. In one embodiment, at least one double bond has a Z configuration. In one embodiment, two double bonds have a Z configuration. In one embodiment all three double bonds have a Z configuration. In one embodiment, at least one double bond has an E configuration. In one embodiment, two double bonds have an E configuration. In one embodiment all three double bonds have an E configuration.

In one embodiment, $L^{112}$ is cholesterol. In one embodiment, $L^{112}$ is

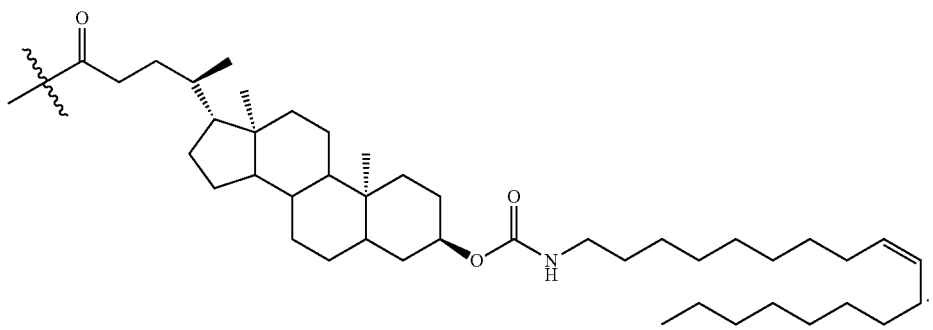 [SMILES: *C(=O)CC[C@@H](C)[C@H]1CCC2C3CCC4C[C@H](OC(=O)NCCCCCCCC/C=C\CCCCCCCC)CC[C@]4(C)C3CC[C@@]21C]
15
In one embodiment, $L^{114}$ is a targeting ligand, e.g. folate, carbohydrate.
In one embodiment, $L^{114}$ has the structure shown in formula (II)-(V).
In one embodiment, $L^{114}$ is chosen from group shown in FIG. 8.
In one embodiment, $L^{114}$ is chosen from group consisting of
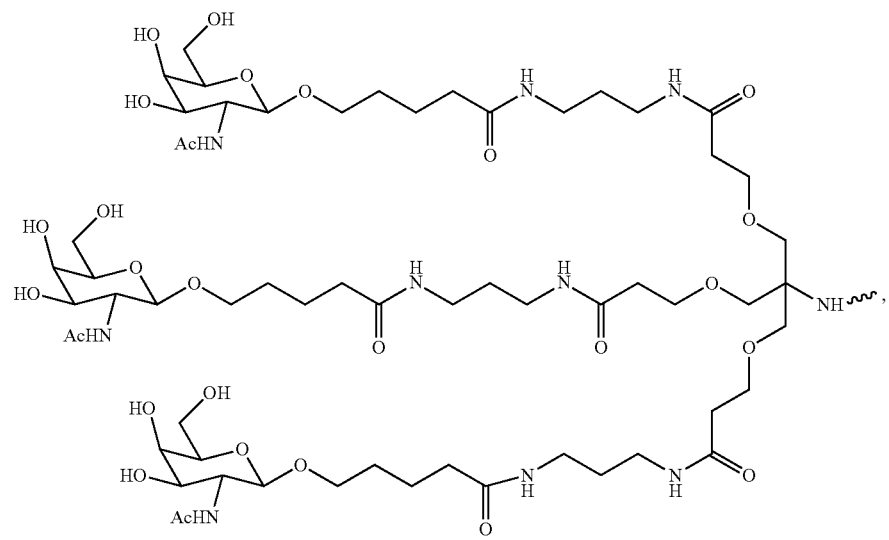
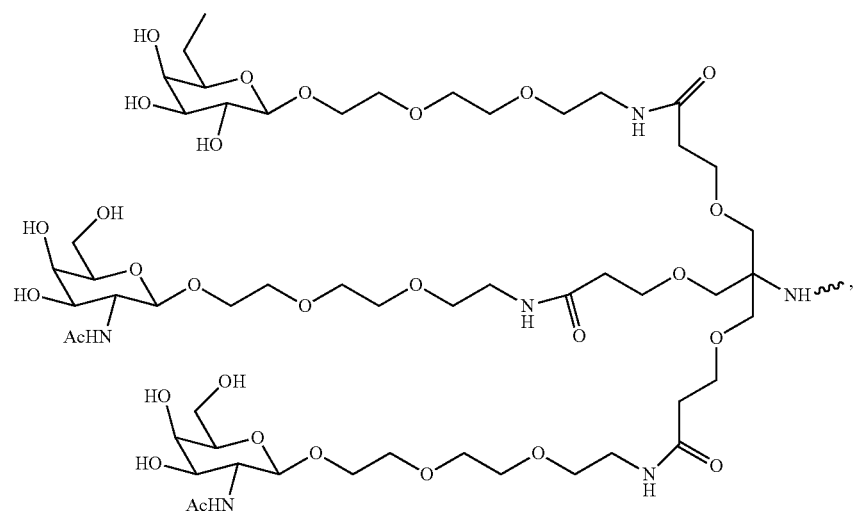

-continued
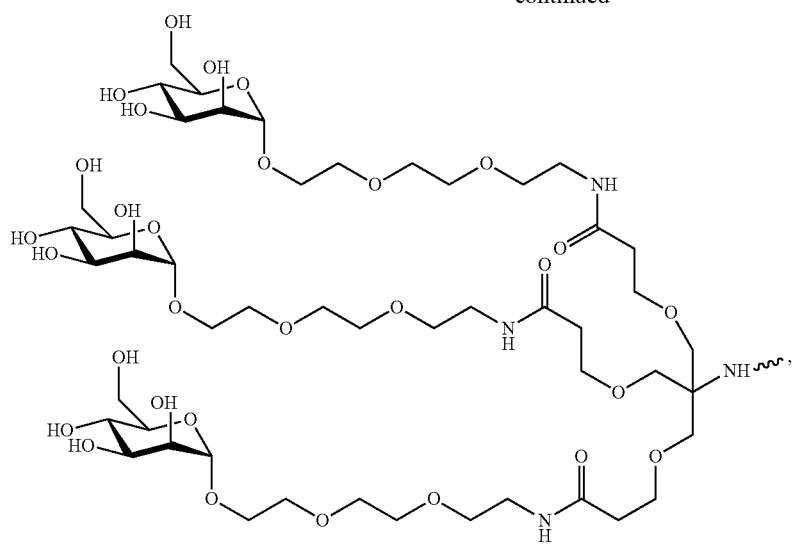
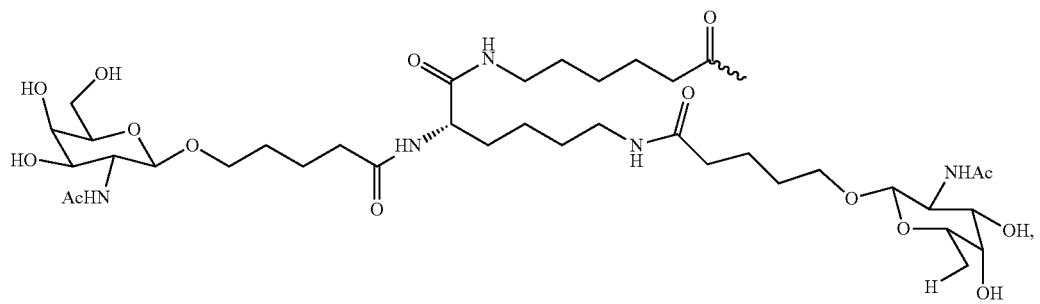
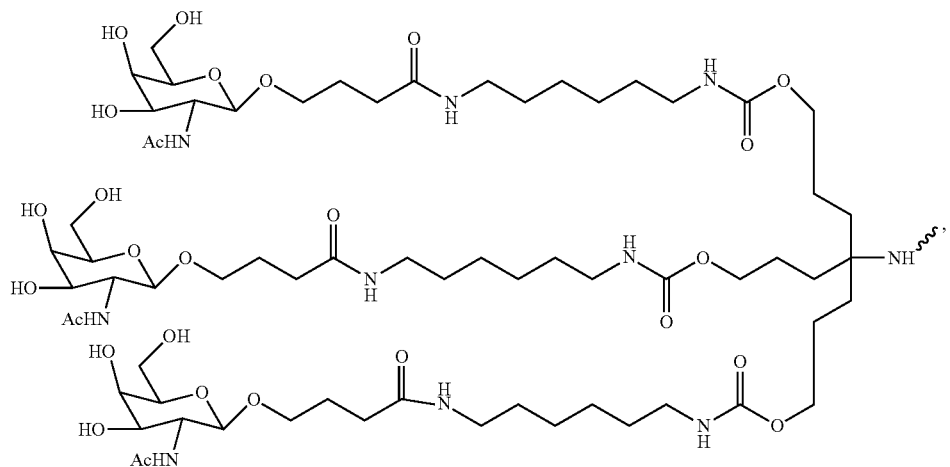
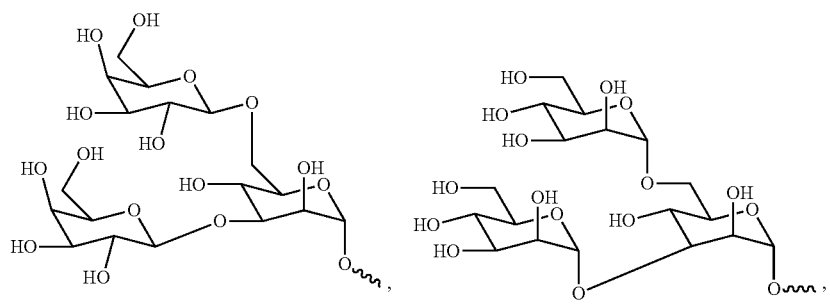

-continued

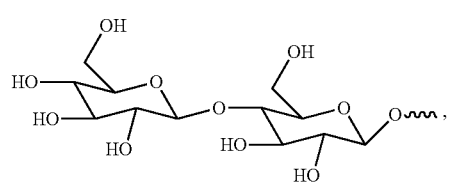
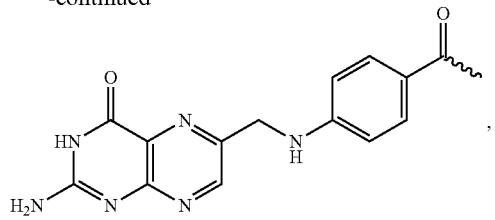
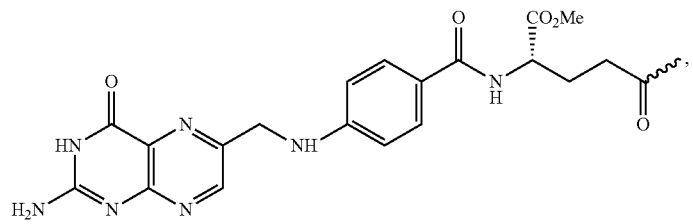
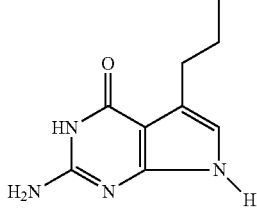
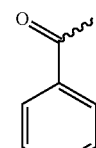

and

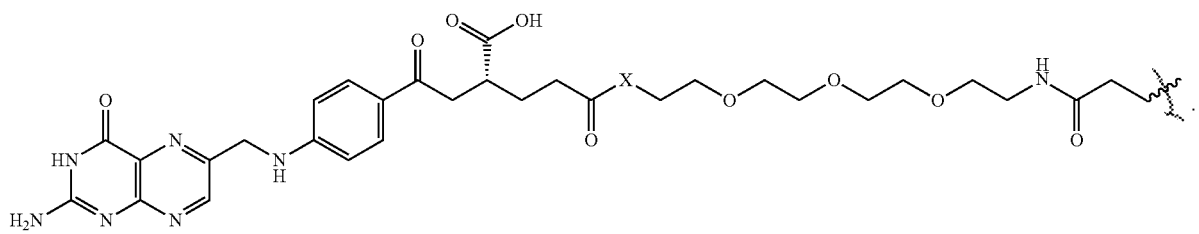

In one embodiment, when $L^{110}$ is chosen from a group consisting of

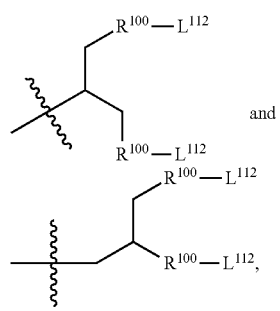

$L^{110}$ is a racemic mixture.

In one embodiment, when $L^{110}$ is chosen from a group consisting of

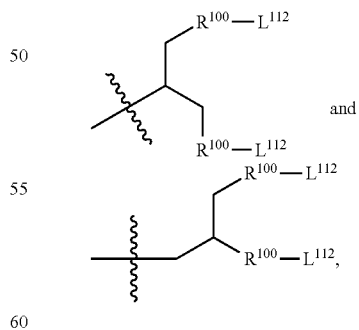

$L^{110}$ has an enantiomeric excess of the R isomer, e.g., at least about 65%, 70%, 75%, 80%, 85%, 90%, 95%, 97%, 98%, or 99%. In one embodiment the $L^{110}$ is an enantiomerically pure 'R' isomer.

In one embodiment, when $L^{110}$ is chosen from a group consisting of

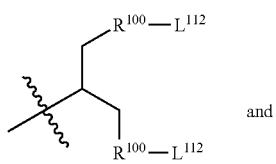

and

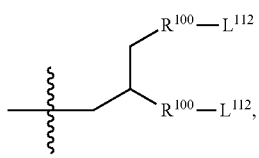

$L^{110}$ has an enantiomeric excess of the S isomer, e.g., at least about 65%, 70%, 75%, 80%, 85%, 90%, 95%, 97%, 98%, or 99%. In one embodiment $L^{110}$ is an enantiomerically pure 'S' isomer.

In one embodiment. when $L^{111}$ is chosen from a group consisting of

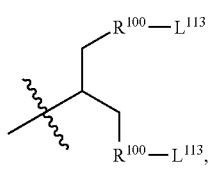

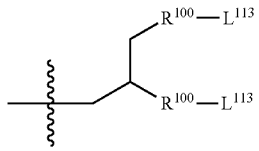

and

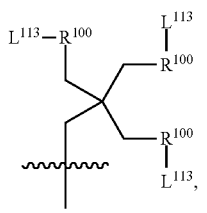

$L^{111}$ is a racemic mixture.

In one embodiment, when $L^{111}$ is chosen from a group consisting of

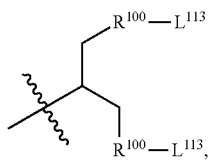

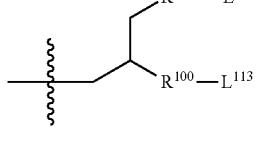

and

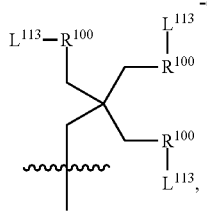

$L^{111}$ has an enantiomeric excess of the R isomer, e.g., at least about 65%, 70%, 75%, 80%, 85%, 90%, 95%, 97%, 98%, or 99%. In one embodiment the $L^{111}$ is an enantiomerically pure 'R' isomer.

In one embodiment, when $L^{111}$ is chosen from a group consisting of

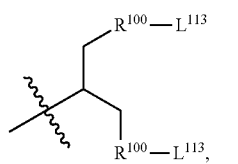

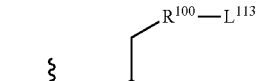

and

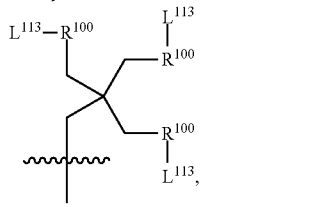

$L^{111}$ has an enantiomeric excess of the S isomer, e.g., at least about 65%, 70%, 75%, 80%, 85%, 90%, 95%, 97%, 98%, or 99%. In one embodiment $L^{111}$ is an enantiomerically pure 'S' isomer.

In one aspect the invention provides a lipid monomer having the structure shown in formula (CIV)

$$L^{210}\text{-A-}L^{211} \quad \text{(CIV)}$$

$L^{210}$ is $L^{212}$,

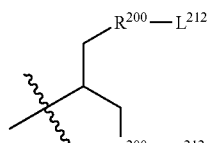

or

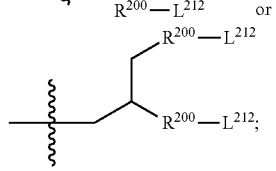

$R^{200}$ is independently for each occurrence absent, CO, NH, O, S, S—S, —C(CH$_3$)$_2$—S—S—, —CH(CH$_3$)—S—S—, C(O), OC(O), C(O)O, NHC(O), C(O)NH, NHCH$_2$, CH$_2$, CH$_2$NH, CH$_2$O, CH=N—O, heteroaryl, heterocycle,

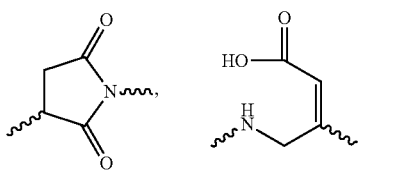

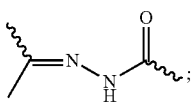

L²¹¹ is L²¹³,

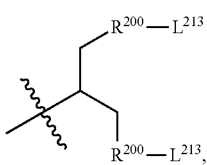

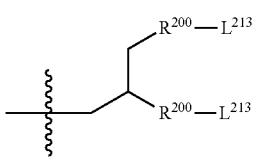

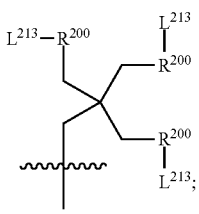

L²¹² is independently for each occurrence lipid, lipophile, alkyl, alkenyl or alkynyl, each of which is optionally substituted with one or more substituents;

L²¹³ is independently for each occurrence —CH₂CH₂(OCH₂CH₂)$_p$O(CH₂)$_q$CH₂-L²¹⁴;

L²¹⁴ is independently for each occurrence H, —OH, —OCH₃, —NH₂, N(H)CH₃, N(CH₃)₂, —SH, —SCH₃, —N₃, —COOH, —C(O)NH₂, —C(O)NHNH₂, —CH═CH₂, —C≡CH or

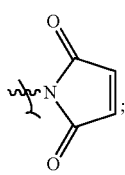

p is 1-1000; and
q is 1-20.

In one embodiment, L²¹⁰ is chosen from a group consisting of

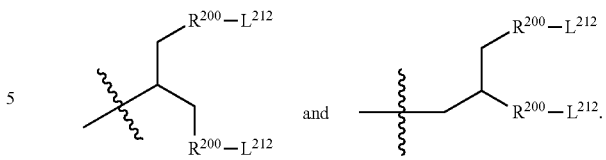

In one embodiment, L²¹¹ is chosen from a group consisting of

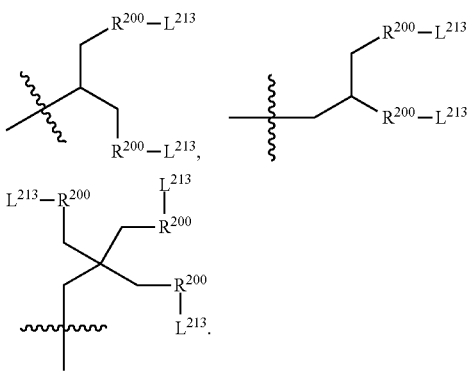

In one aspect the present invention provides targeting lipids having the structure shown in formula (I):

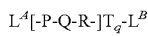

Formula (I)

wherein:

L$^A$ is a ligand chosen from a carbohydrate, glucose, mannose, galactose, N-acetyl-galactosamine, fucose, glucosamine, lactose, maltose, folate, peptide, or has the structure shown in formula II-V:

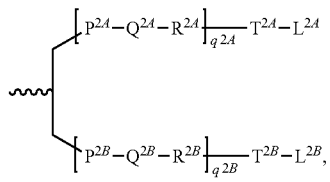

Formula (II)

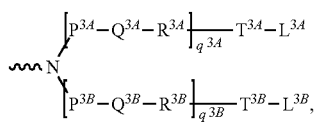

Formula (III)

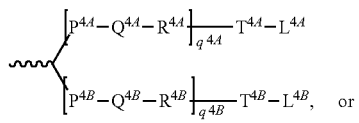

Formula (IV)

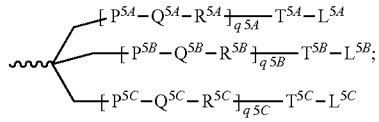

Formula (V)

q, $q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20;

P, $P^{2A}$, $P^{2B}$, $P^{3A}$, $P^{3B}$, $P^{4A}$, $P^{4B}$, $P^{5A}$, $P^{5B}$, $P^{5C}$, T, $T^{2A}$, $T^{2B}$, $T^{3a}$, $T^{3B}$, $T^{4A}$, $T^{4B}$, $T^{4A}$, $T^{5B}$ and $T^{5C}$ are each independently for each occurrence absent, NR', O, S, C(O), OC(O), C(O)O, NHC(O), C(O)NH, NHCH$_2$, CH$_2$, CH$_2$NH or CH$_2$O, NHCH(R$^a$)C(O), —C(O)—CH(R$^a$)—NH—, CO, CH=N—O, CH$_2$S, urea, heterocycle, heteroaryl,

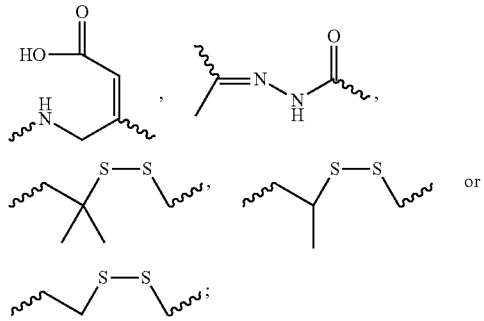

Q, $Q^{2A}$, $Q^{2B}$, $Q^{3A}$, $Q^{3B}$, $Q^{4A}$, $Q^{4B}$, $Q^{5A}$, $Q^{5B}$ and $Q^{5C}$ are independently for each occurrence absent, —(CH$_2$)$_n$—, —C(R')(R")(CH$_2$)$_n$—, —(CH$_2$)$_m$C(R')(R")—, —(CH$_2$CH$_2$O)$_p$CH$_2$CH$_2$—, or —(CH$_2$CH$_2$O)$_p$CH$_2$CH$_2$NH—;

$L^B$ is a ligand selected from a group consisting of lipophile, steroid (e.g., uvaol, hecigenin, diosgenin), terpene (e.g., triterpene, e.g., sarsasapogenin, Friedelin, epifriedelanol derivatized lithocholic acid), vitamin (e.g., folate, vitamin A, biotin, pyridoxal), ceramide or has the structure of formula (VI):

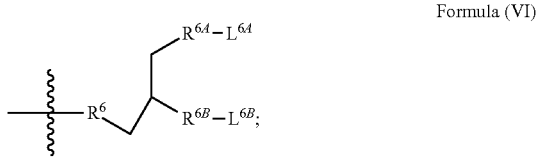

Formula (VI)

R, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^6$, $R^{6A}$ and $R^{6B}$ are each independently for each occurrence absent, CO, NH, NR', O, S, C(O), OC(O), C(O)O, NHC(O), C(O)NH, NHCH$_2$, CH$_2$, CH$_2$NH or CH$_2$O, NHCH(R')C(O), —C(O)—CH(R')—NH—, CO, CH=N—,

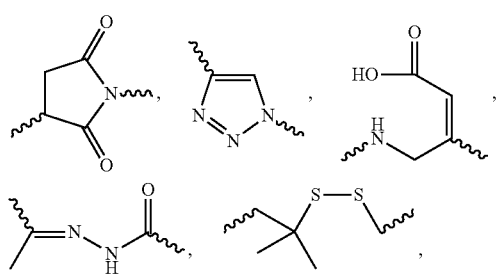

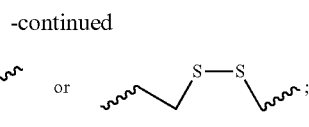

$L^{2A}$, $L^{2B}$, $L^{3A}$, $L^{3B}$, $L^{4A}$, $L^{4B}$, $L^{5A}$, $L^{5B}$ and $L^{5C}$ are each independently for each occurrence a carbohydrate, glucose, mannose, galactose, N-acetyl-galactosamine, fucose, glucosamine, lactose, maltose, folate or a peptide;

R' and R" are each independently H, CH$_3$, OH, SH, NH$_2$, NR$^{10}$R$^{20}$, alkyl, alkenyl or alkynyl;

R$^a$ is H or amino acid side chain;

R$^{10}$ and R$^{20}$ are each independently alkyl, alkenyl or alkynyl;

$L^{6A}$ and $L^{6B}$ are each independently alkyl, alkenyl or alkynyl, each of which is optionally substituted with one or more substituents;

m represent independently for each occurrence 0-50;

n represent independently for each occurrence 1-20; and p represent independently for each occurrence 0-50.

When any of q, $q^{2A}$, $q^{2B}$, $q^{3A}$, $q^{3B}$, $q^{4A}$, $q^{4B}$, $q^{5A}$, $q^{5B}$ and $q^{5C}$ is greater than 1, the repeating unit can be the same or different from each other, for example when q is 3 the unit —[P-Q-R]$_q$— is expanded to —[P-Q-R]—[P-Q-R]—[P-Q-R]— and all of the —[P-Q-R]— units can be the same, completely different from each other or a mixture thereof.

The lipophilic moiety can be chosen, for example, from the group consisting of a lipid, cholesterol, oleyl, linoleoyl, lauroyl, docosnyl, stearoyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, phenoxazine or a bile acid. A preferred lipophilic moiety is cholesterol.

In one embodiment, $L^A$ is mannose, galactose, N-acetylgalactosamine or has the structure shown in formula V. In a preferred embodiment, $L^A$ is mannose. In one embodiment $L^A$ has the structure shown in formula V.

In one embodiment, $L^A$ is

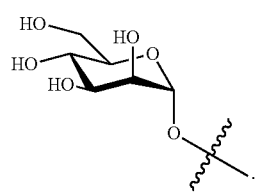

In one embodiment, $L^A$ is

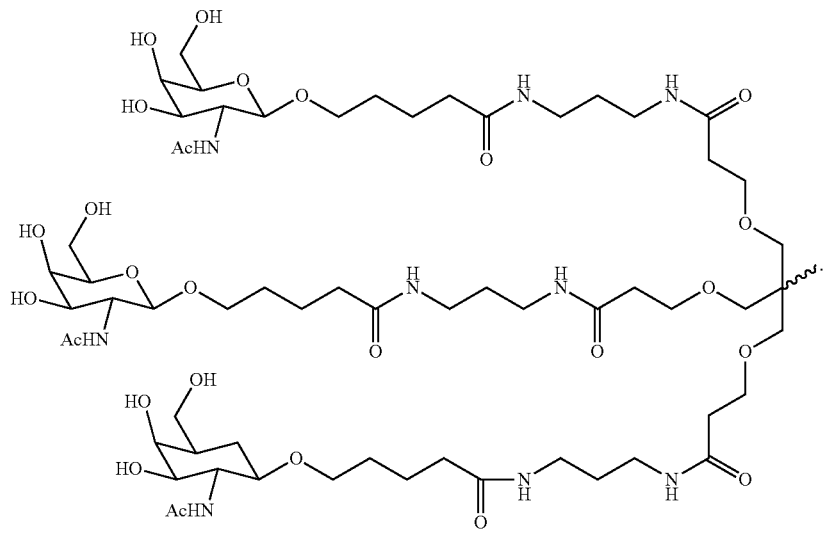 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)CC(CO)C(O)C1O]

In one embodiment both $L^{2A}$ and $L^{2B}$ are the same.
In one embodiment both $L^{2A}$ and $L^{2B}$ are different.
In one embodiment both $L^{3A}$ and $L^{3B}$ are the same.
In one embodiment both $L^{3A}$ and $L^{3B}$ are different.
In one embodiment both $L^{4A}$ and $L^{4B}$ are the same.
In one embodiment both $L^{4A}$ and $L^{4B}$ are different.
In one embodiment all of $L^{5A}$, $L^{5B}$ and $L^{5C}$ are the same.
In one embodiment two of $L^{5A}$, $L^{5B}$ and $L^{5C}$ are the same.
In one embodiment $L^{5A}$ and $L^{5B}$ are the same and $L^{5C}$ is different.
In one embodiment $L^{5A}$ and $L^{5C}$ are the same and $L^{5B}$ is different.
In one embodiment $L^{5B}$ and $L^{5C}$ are the same and $L^{5A}$ is different.
In one embodiment $L^{6A}$ and $L^{6B}$ are the same.
In one embodiment $L^{6A}$ and $L^{6B}$ are different.
In one embodiment, each of $R^{6A}$ and $R^{6B}$ are O, C(O), NH or NR'.
In one embodiment, each of $L^{6A}$ and $L^{6B}$ are independently alkyl, for example $C_6$-$C_{28}$ alkyl, e.g., $C_{10}$-$C_{18}$ alkyl, e.g., $C_{14}$ alkyl. In one embodiment, both $R^2$ and $R^3$ are alkyl, e.g., straight chain alkyl having the same length, e.g., $C_6$-$C_{28}$ alkyl, e.g., $C_{10}$-$C_{18}$ alkyl, e.g., $C_{14}$ alkyl or $C_{16}$ alkyl. In one embodiment, both $R^2$ and $R^3$ are $C_{14}$ alkyl.
In one embodiment, the formula VI represents a racemic mixture
In one embodiment, the compound of formula VI has an enantiomeric excess of the R isomer, e.g., at least about 65%, 70%, 75%, 80%, 85%, 90%, 95%, 97%, 98%, or 99%. In one embodiment the formula VI represents enantiomerically pure 'R' isomer.
In one embodiment, the compound of formula VI has an enantiomeric excess of the S isomer, e.g., at least about 65%, 70%, 75%, 80%, 85%, 90%, 95%, 97%, 98%, or 99%. In one embodiment the formula VI represents enantiomerically pure 'S' isomer.
In one embodiment, each of $L^{6A}$ and $L^{6B}$ are independently alkenyl, for example, each of $L^{6A}$ and $L^{6B}$ are independently $C_6$-$C_{30}$ alkenyl or each of $L^{6A}$ and $L^{6B}$ are the same alkenyl moiety. In one embodiment, each of $L^{6A}$ and $L^{6B}$ includes one double bond, for example a double bond in the E or Z configuration.

In one embodiment, each of $L^{6A}$ and $L^{6B}$ includes two double bond moieties. In one embodiment, at least one of the double bonds has a Z configuration. In one embodiment, both of the double bonds have a Z configuration. In one embodiment, at least one of $R^2$ and $R^3$ is provided in formula (VII) below

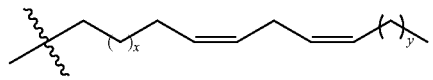

formula (VII)

wherein:
x is an integer from 1 to 8; and
y is an integer from 1-10.

In one embodiment, both of $L^{6A}$ and $L^{6B}$ are of the formula (VII). In one embodiment, at least one of the double bonds has an E configuration, e.g., both of the double bonds have an E configuration. In one embodiment, at least one of $L^{6A}$ and $L^{6B}$ is provided in formula (VIII) below

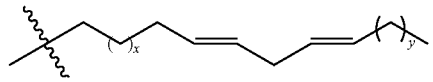

formula (VIII)

wherein:
x is an integer from 1 to 8; and
y is an integer from 1-10.

In one embodiment, each of $L^{6A}$ and $L^{6B}$ includes three double bond moieties. In one embodiment, at least one of the double bonds has a Z configuration. In one embodiment, at least two of the double bonds have a Z configuration. In one embodiment, all three of the double bonds have a Z configuration. In one embodiment, at least one of $L^{6A}$ and $L^{6B}$ is provided in formula (IX) below

IX)

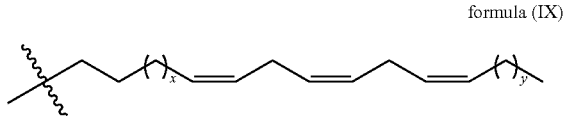

formula (IX)

wherein:
x is an integer from 1 to 8; and
y is an integer from 1-10.

In one embodiment, both of $L^{6A}$ and $L^{6B}$ are as provided in formula (IX). In one embodiment, at least one of the double bonds has an E configuration. In one embodiment, at least two of the double bonds have an E configuration. In one embodiment, all three of the double bonds have an E configuration. In one embodiment, at least one of $L^{6A}$ and $L^{6B}$ is provided in formula (X) below

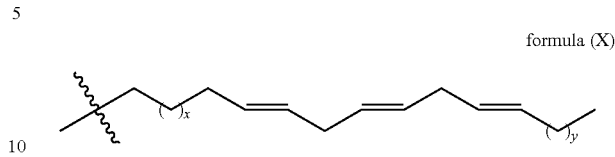

formula (X)

wherein:
x is an integer from 1 to 8; and
y is an integer from 1-10.

In one embodiment, $L^B$ is

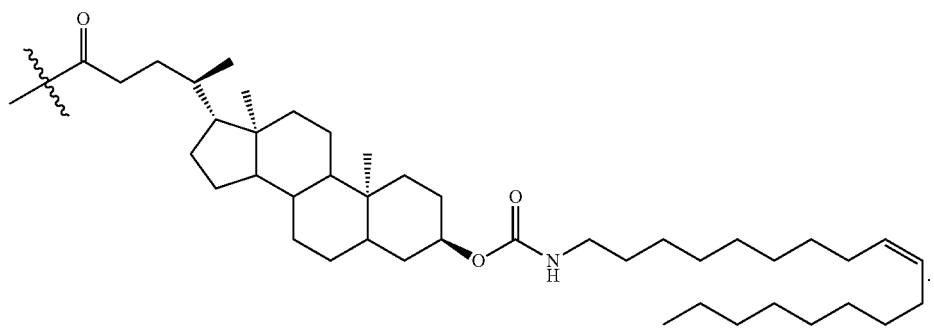 [SMILES: *C(=O)CC[C@@H](C)[C@H]1CCC2C3CCC4C[C@H](OC(=O)NCCCCCCCC/C=C\CCCCCCCC)CC[C@]4(C)C3CC[C@@]21C]

In one embodiment, $L^B$ is chosen from a group consisting of diacyl glycerol, distearylglycerol, dipalmitoylglycerol, dimyristoyl glycerol, dioleoyl glycerol, or other diacyl/steryl hydrophobic groups.

In one embodiments, $L^B$ is

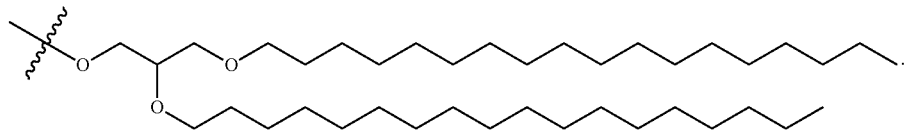

In one preferred embodiment, $L^B$ is

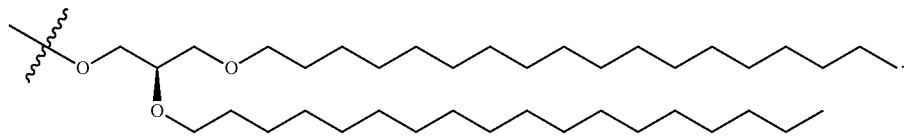 [SMILES: *OC[C@@H](COCCCCCCCCCCCCCCCCCC)OCCCCCCCCCCCCCCCCCC]

In another preferred embodiment, $L^B$ is

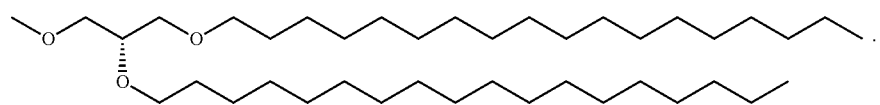 [SMILES: CCCCCCCCCCCCCCCCCCOC[C@@H](COC)OCCCCCCCCCCCCCCCCCC]

In one preferred embodiment formula I has the structure
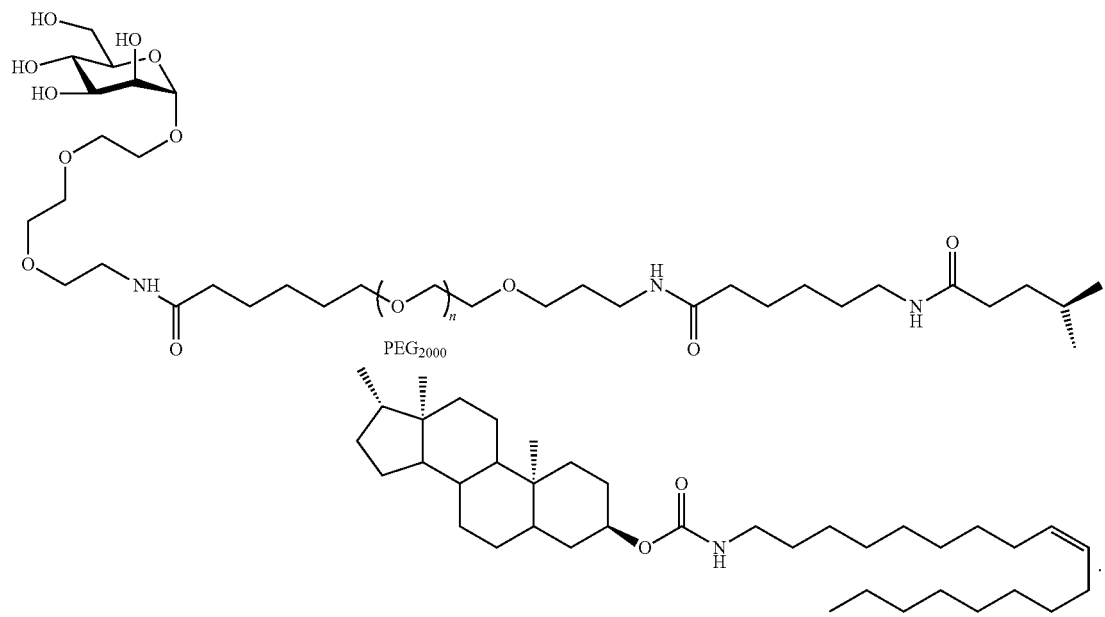
In another preferred embodiment formula I has the
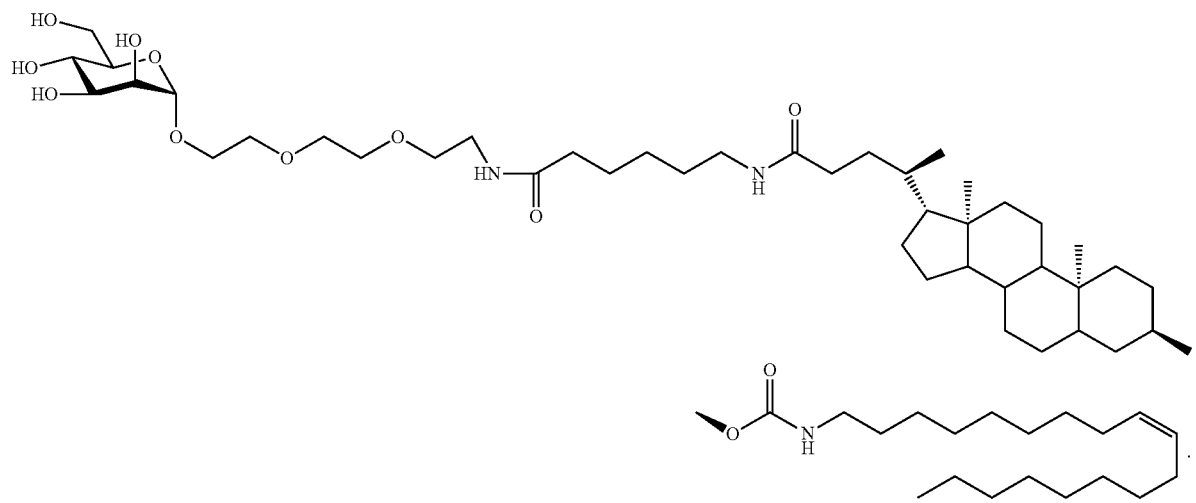
In one preferred embodiment formula I has the structure
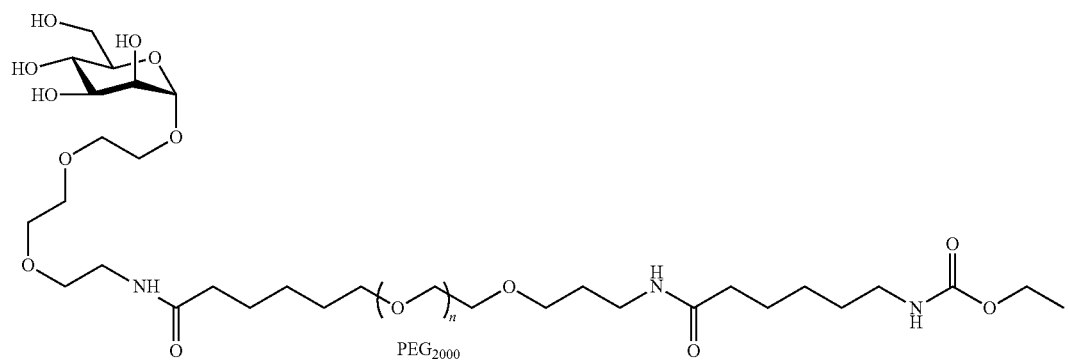

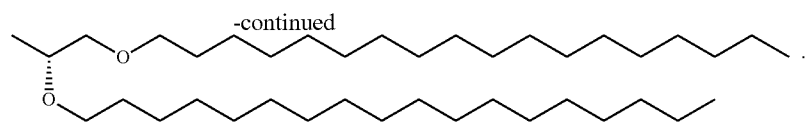
In another preferred embodiment formula I has the structure
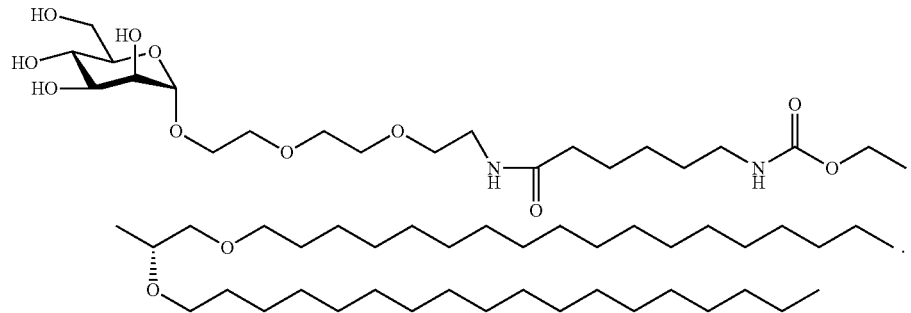
In one preferred embodiment formula I has the structure
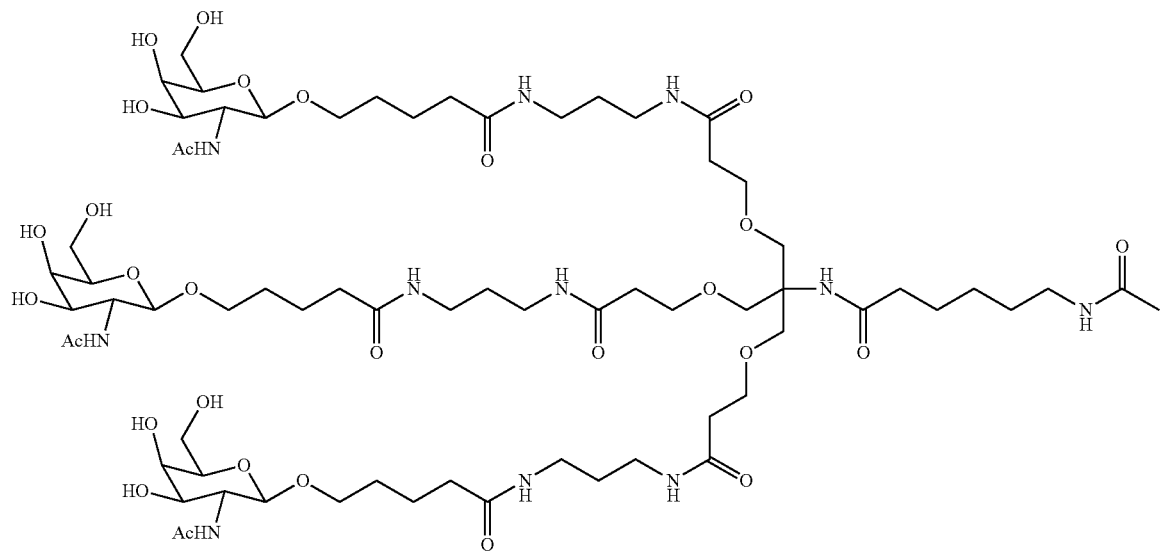
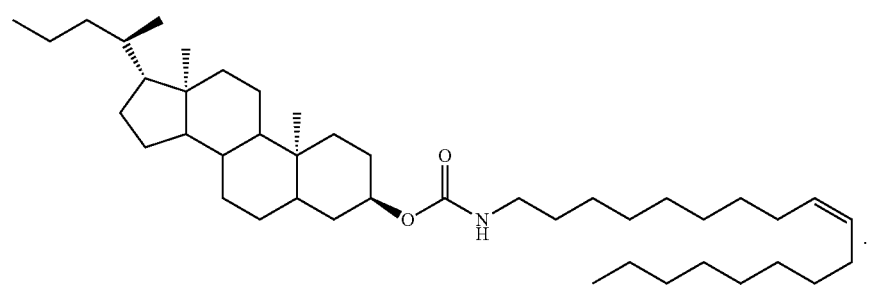

In another preferred embodiment formula I has the structure
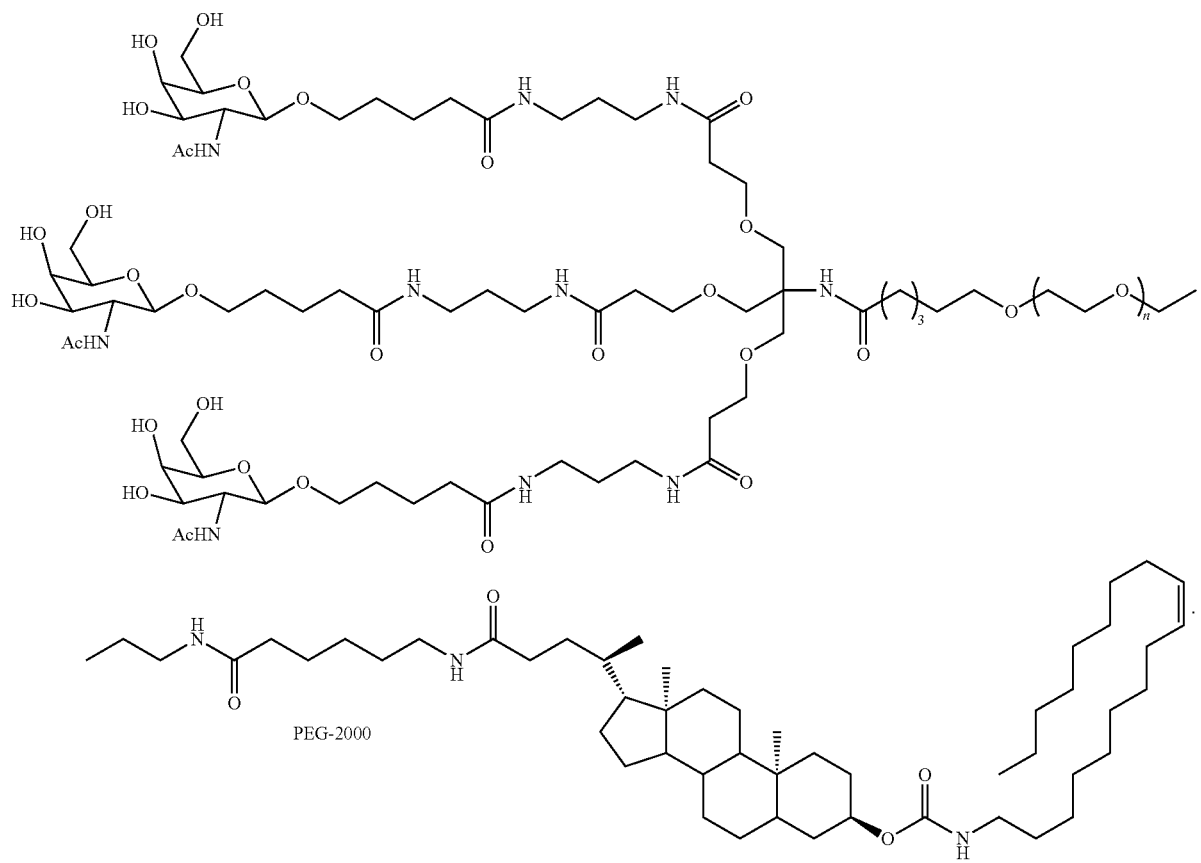
In one preferred embodiment formula I has the structure
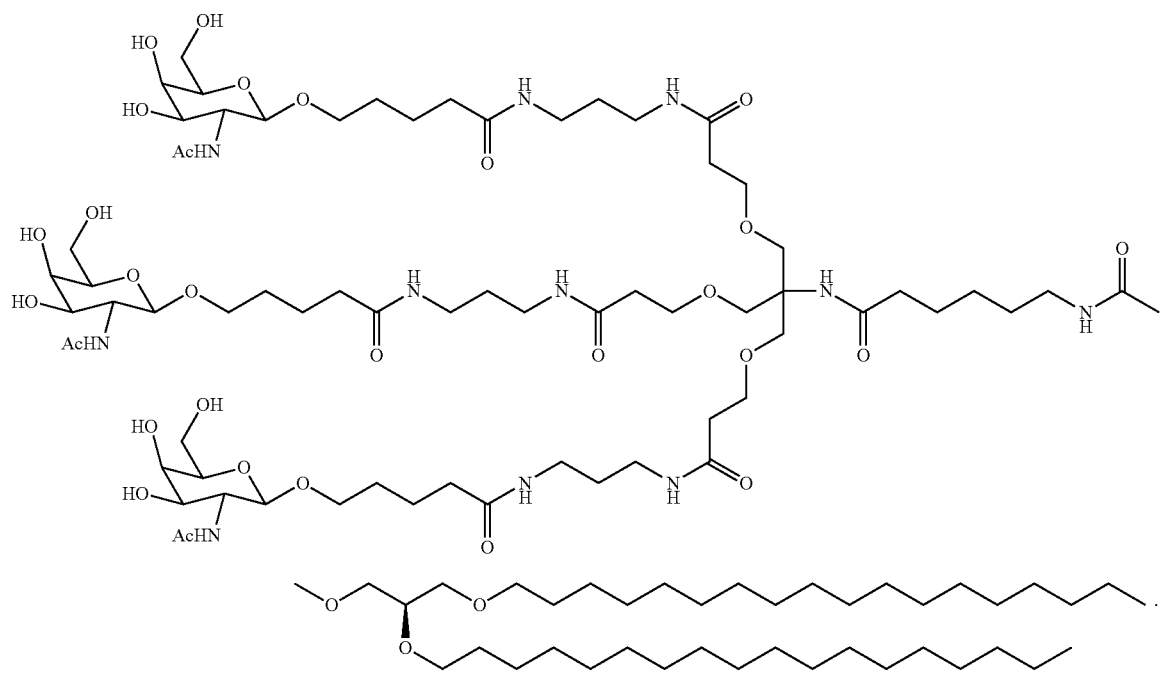

In another preferred embodiment formula I has the structure
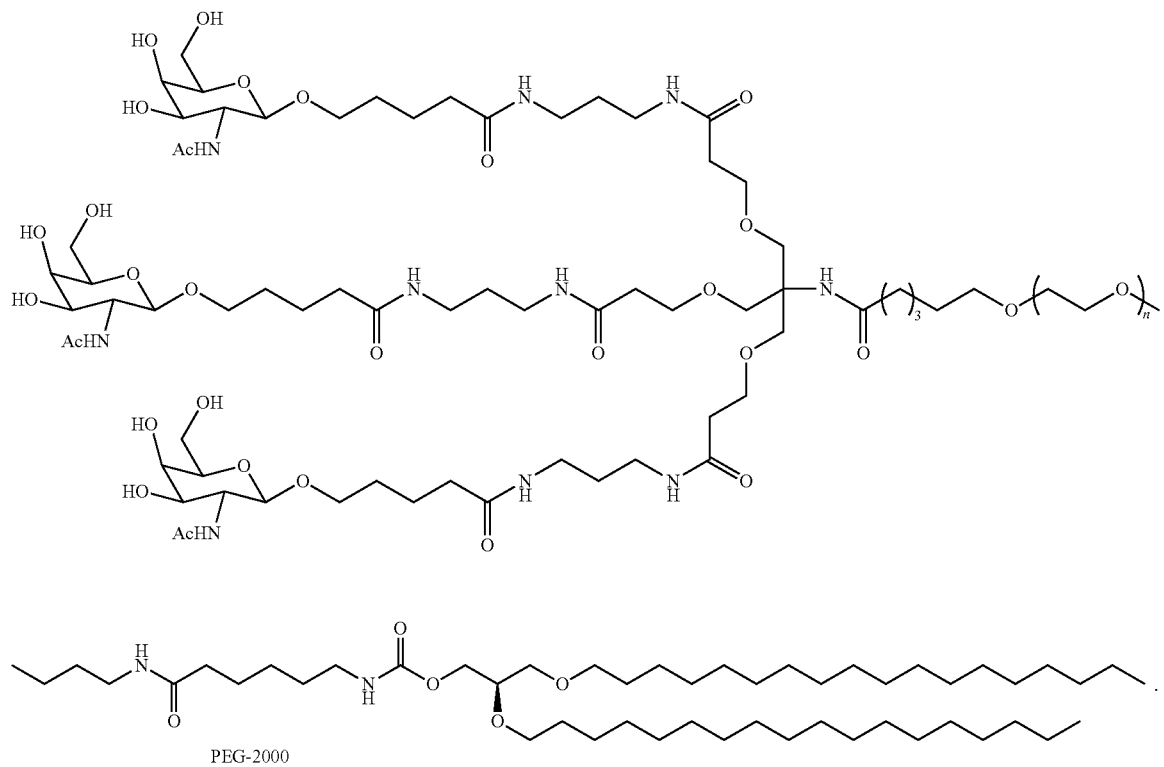
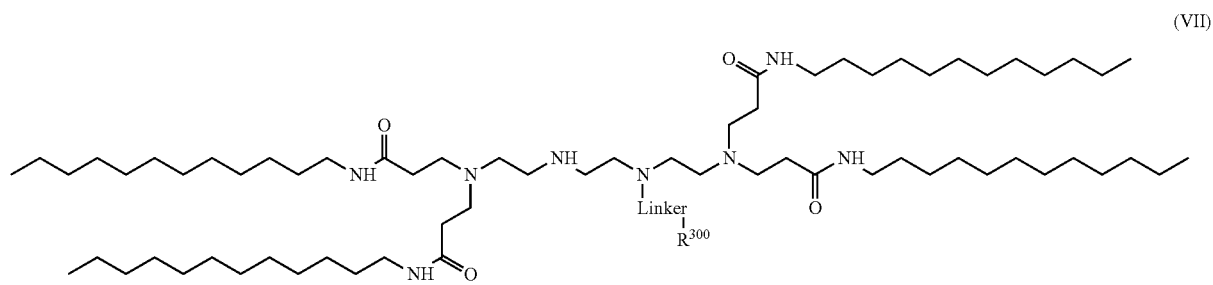
In one aspect the invention features targeting lipid monomer having the structure shown in formula (VII)
(VII)
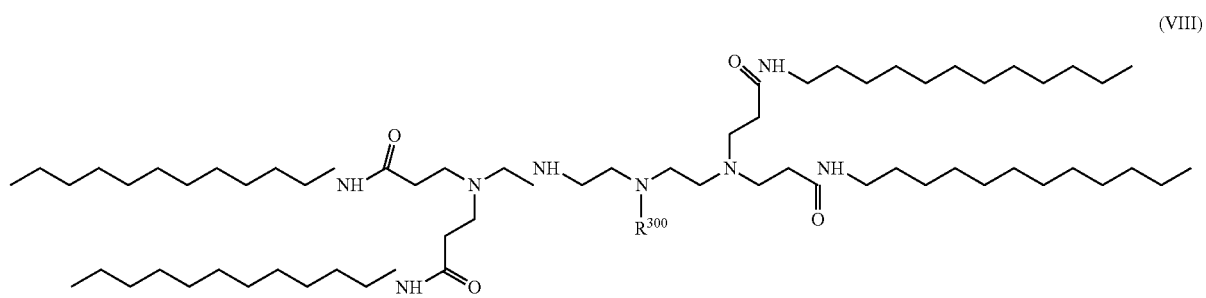
wherein $R^{300}$ is a ligand.
In one aspect, the invention features targeting lipids of the formula (VIII-XV):
(VIII)

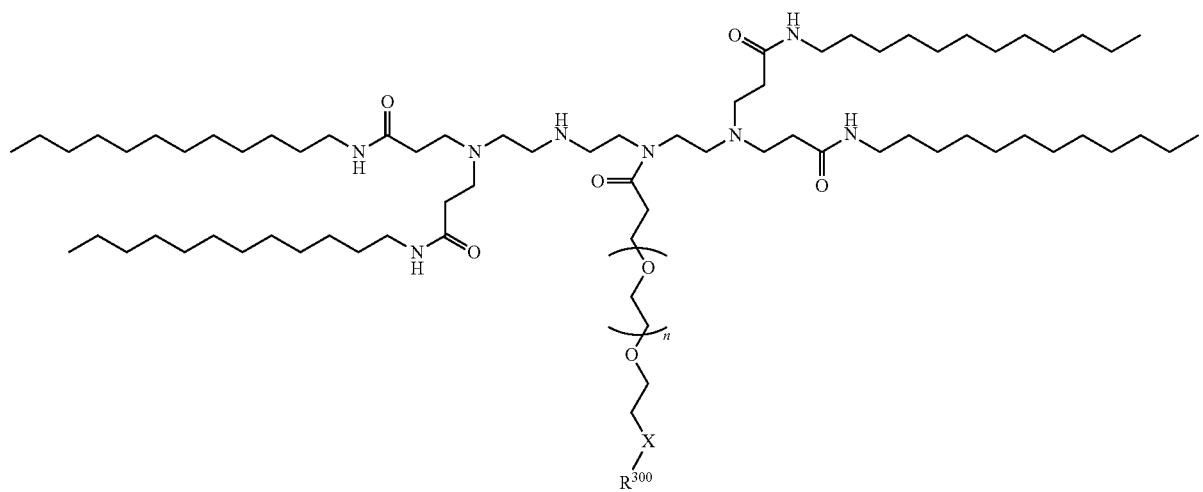
(IX)
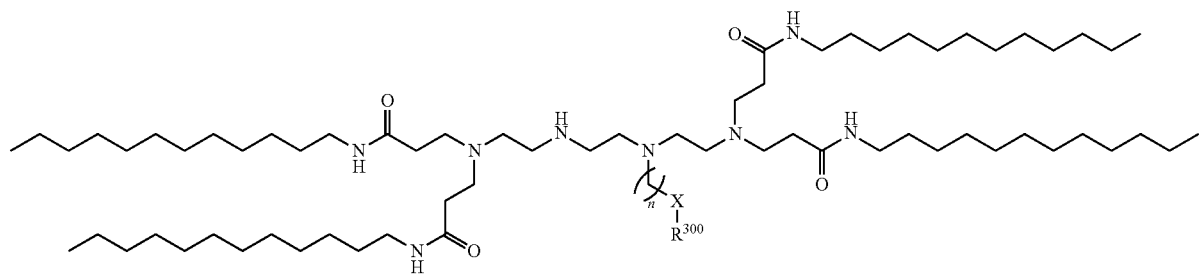
(X)
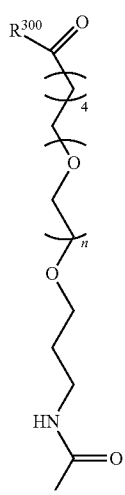
(XI)

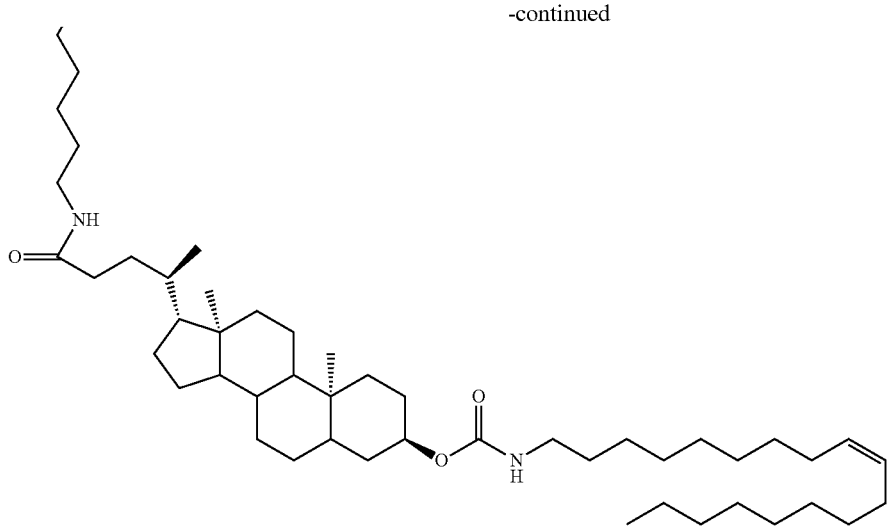
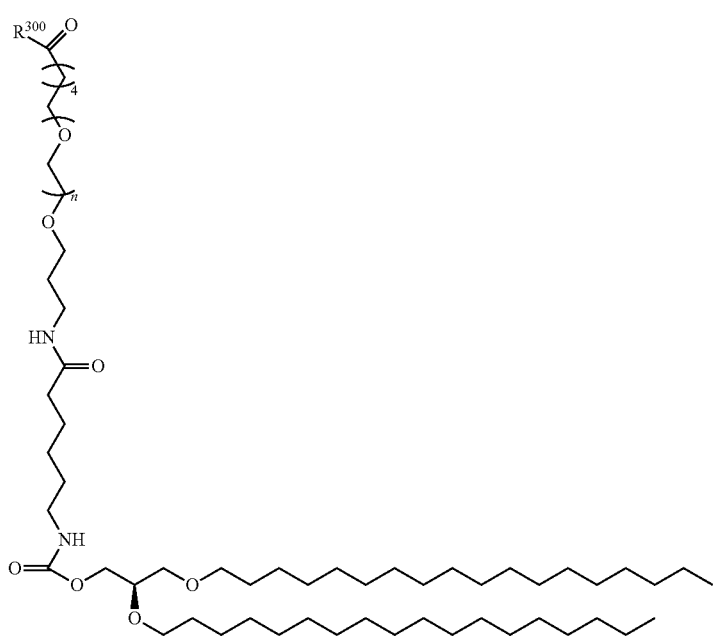
(XII)

(XIII)

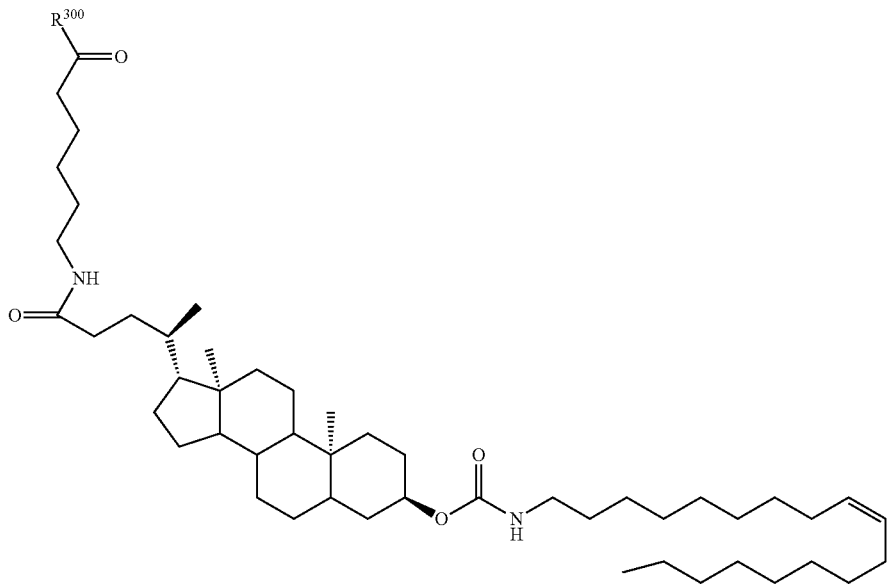

(XIV)

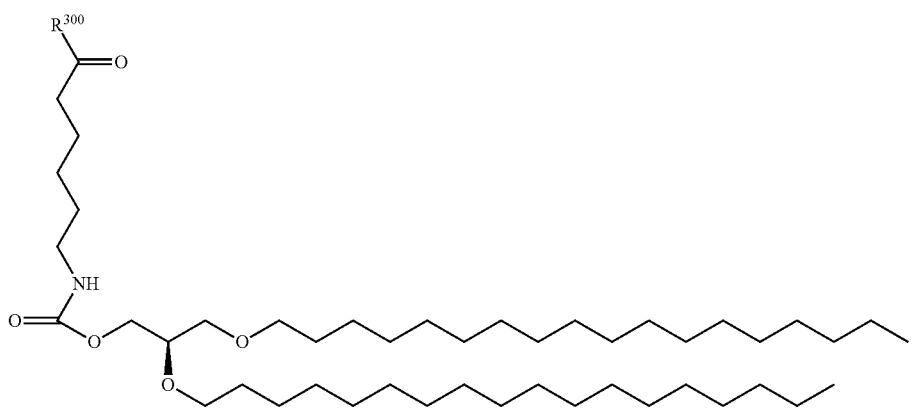

(XV)

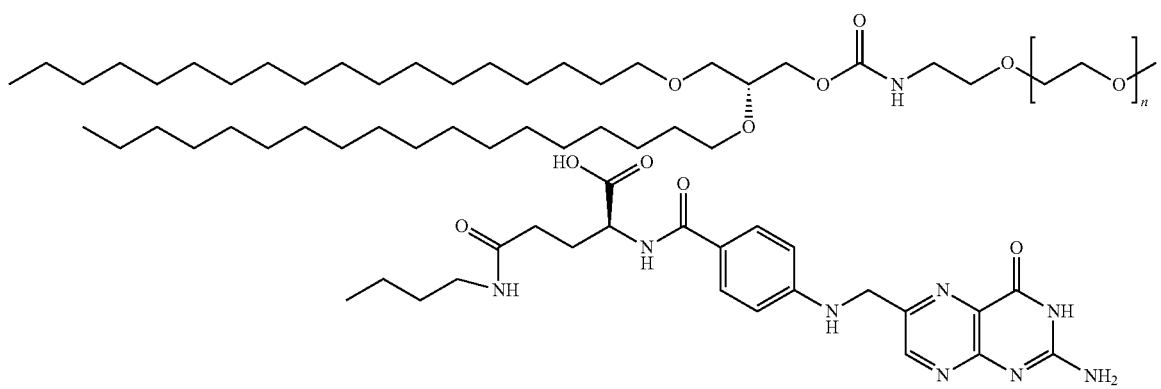

wherein R³⁰⁰ is a ligand; n is 0-20; and x is an ether linkage, a thioether linkage, a carbamate linkage, a urethane linkage, a biocleavable linker (such as disulfides, esters, amides), pH sensitive linker (such as hydrazones, oximes, acetals/ketal, orthoesters, CDM (Ref: Proc. Natl. Acad. Sci. USA 2007, 104(32), 12982-12987)), peptidase sensitive peptides, phosphates, triazole linkage derived from azide and alkyne, and/or a combination of these.

In one embodiment, R has the structure shown in formula (II)-(V).

Figure 8:
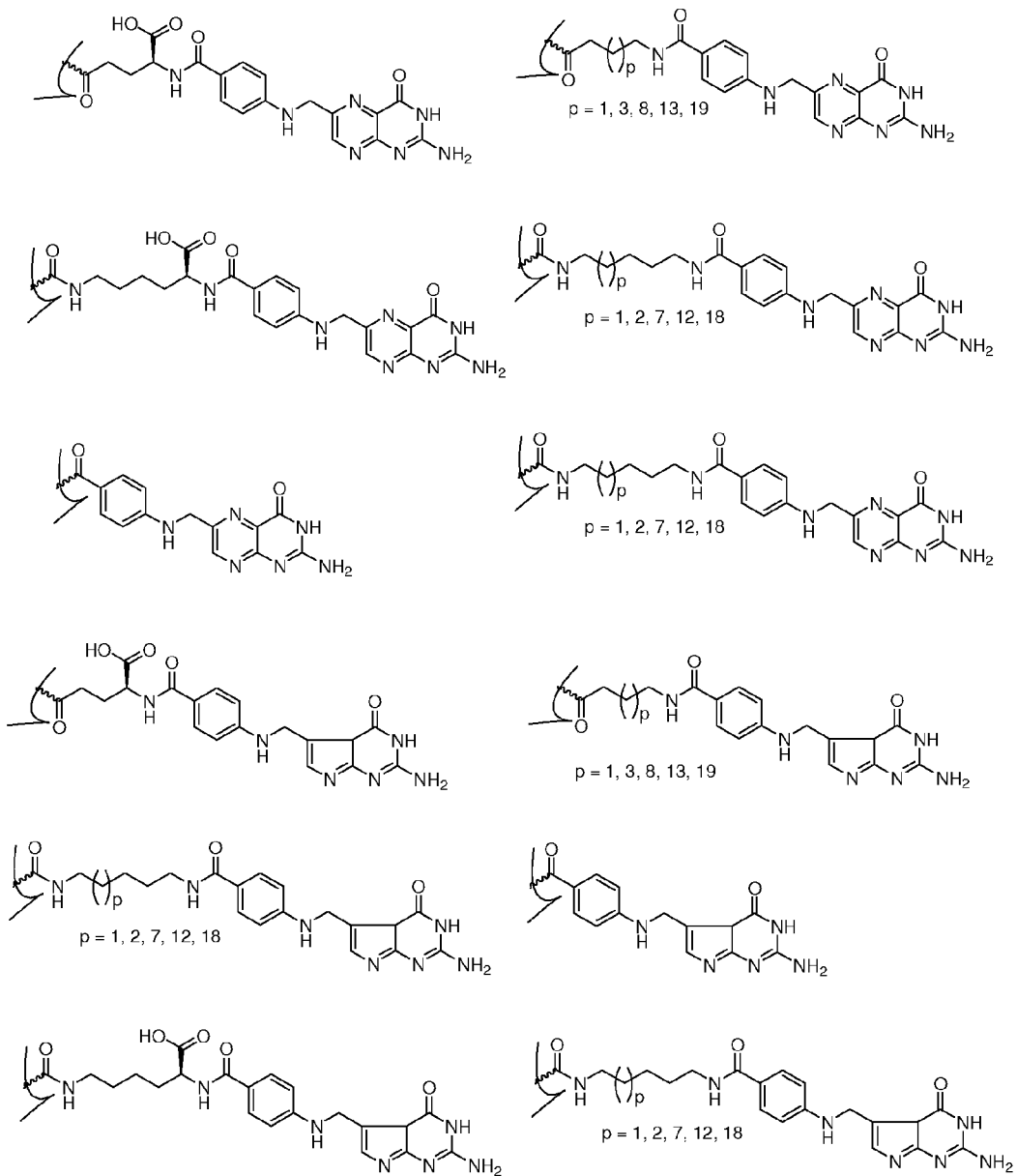
FIG. 8. Folate conjugated lipids, PEG-lipids and delivery systems for targeted delivery.
Figure 8:
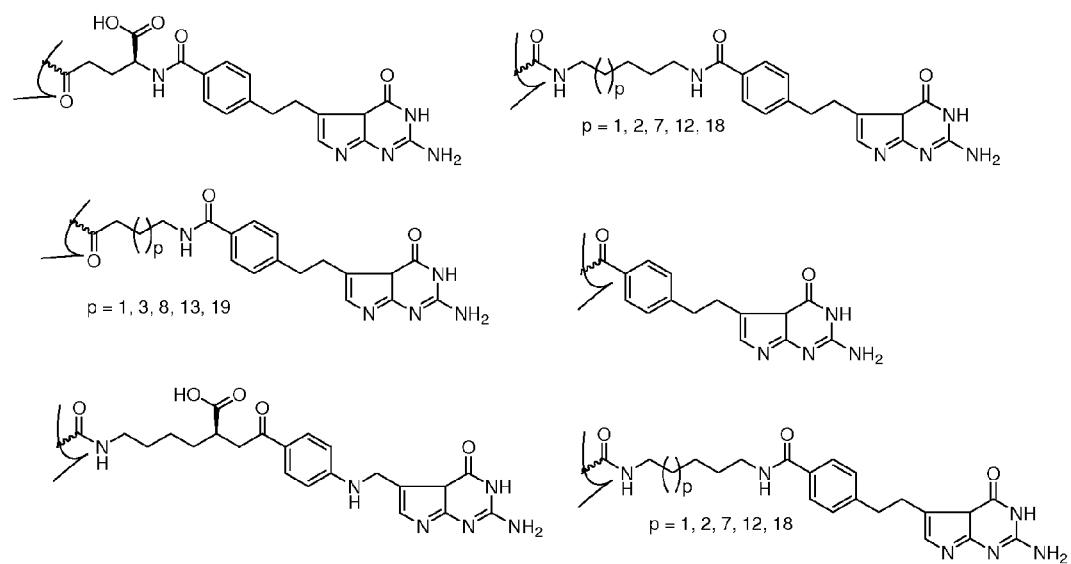
Figure 9:
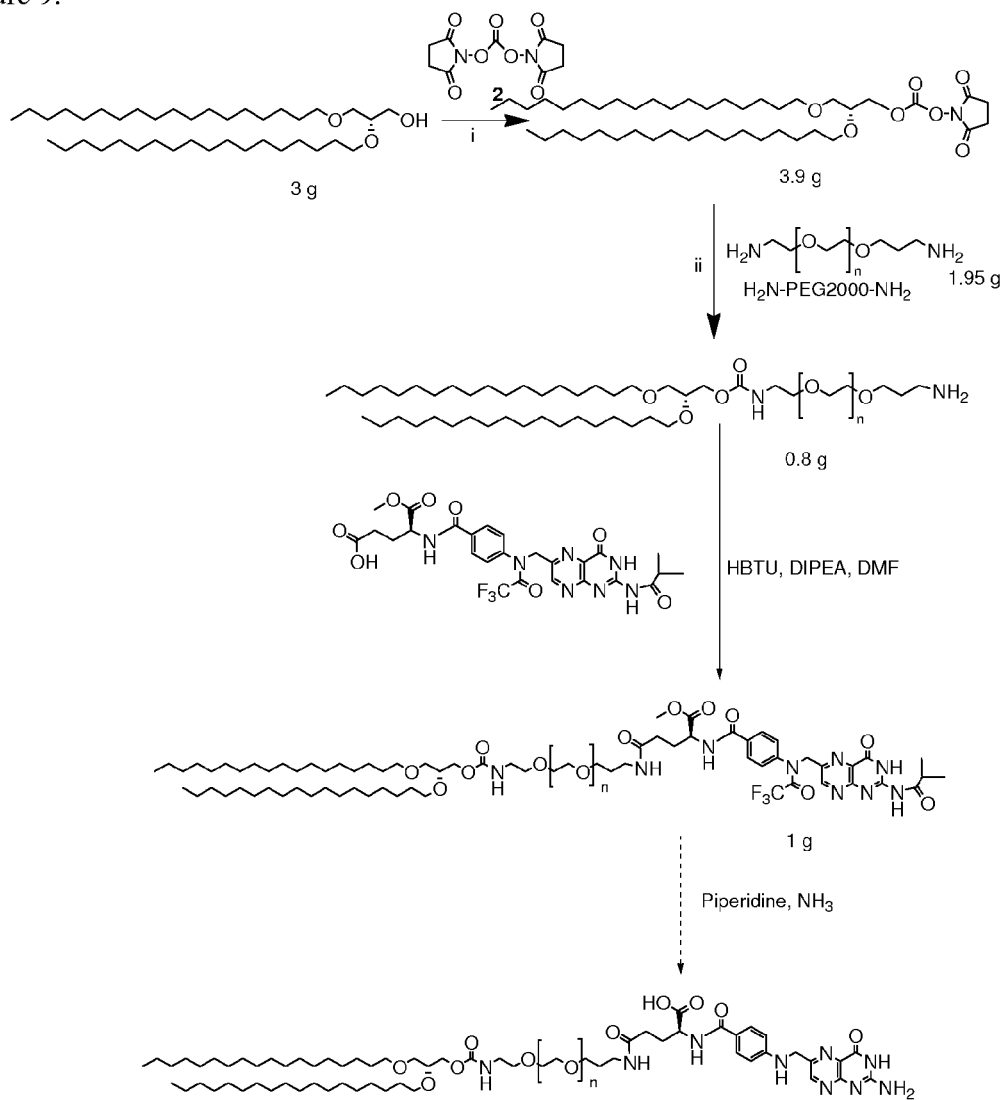
FIG. 9. Synthesis of folate conjugate.

In one embodiment, R is chosen from group shown in FIG. 8.

In one embodiment, R is chosen from group consisting of
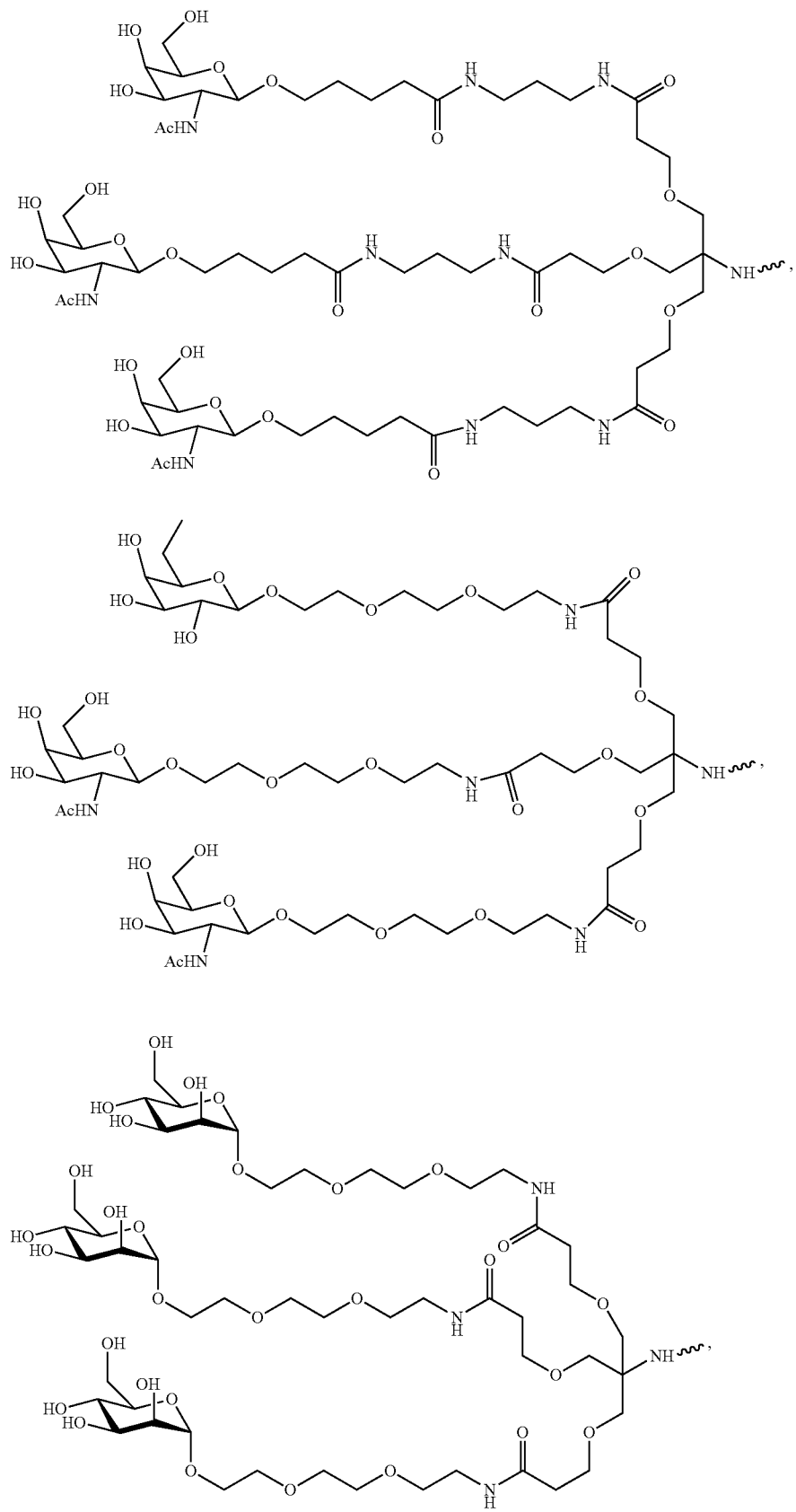

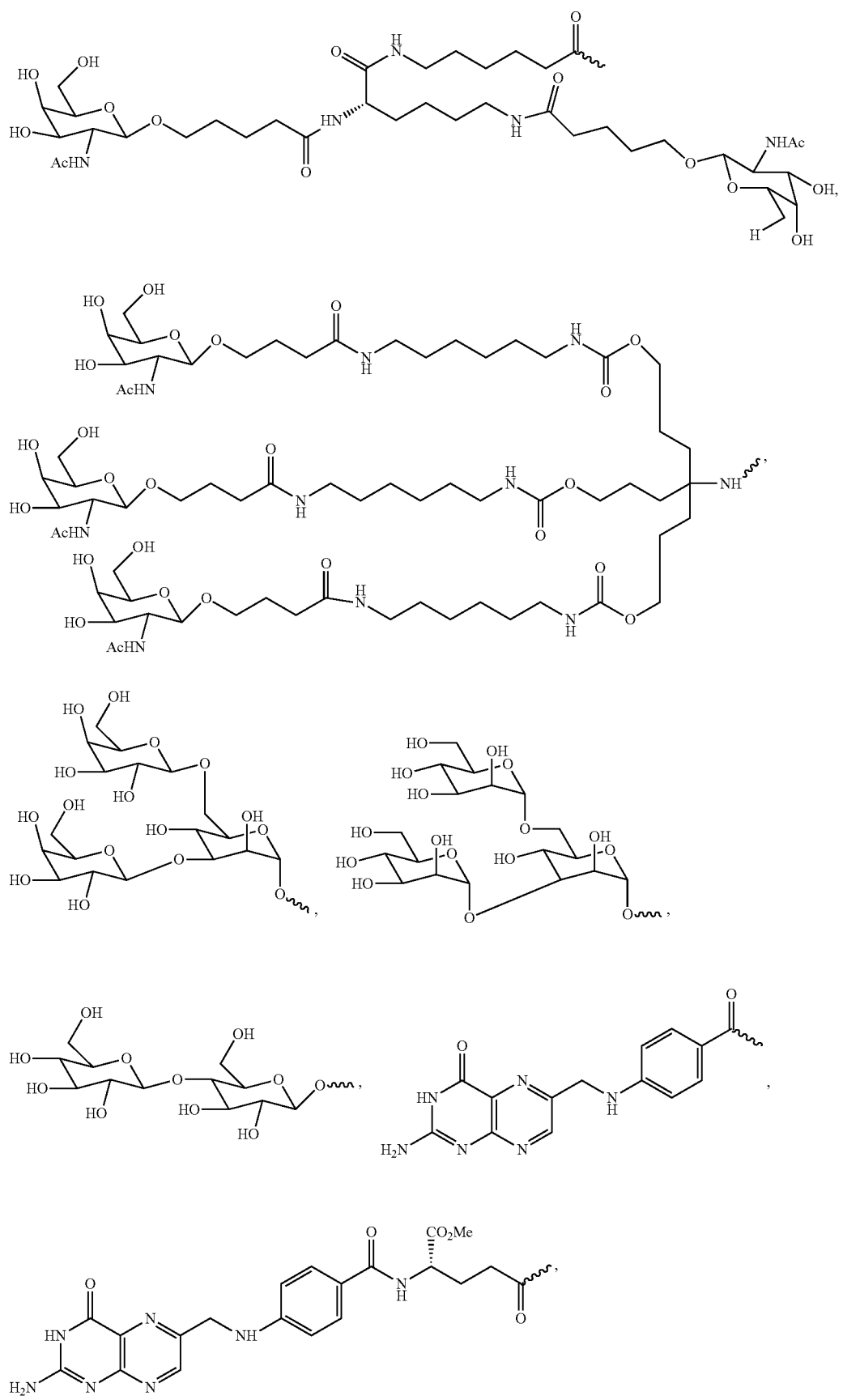

-continued

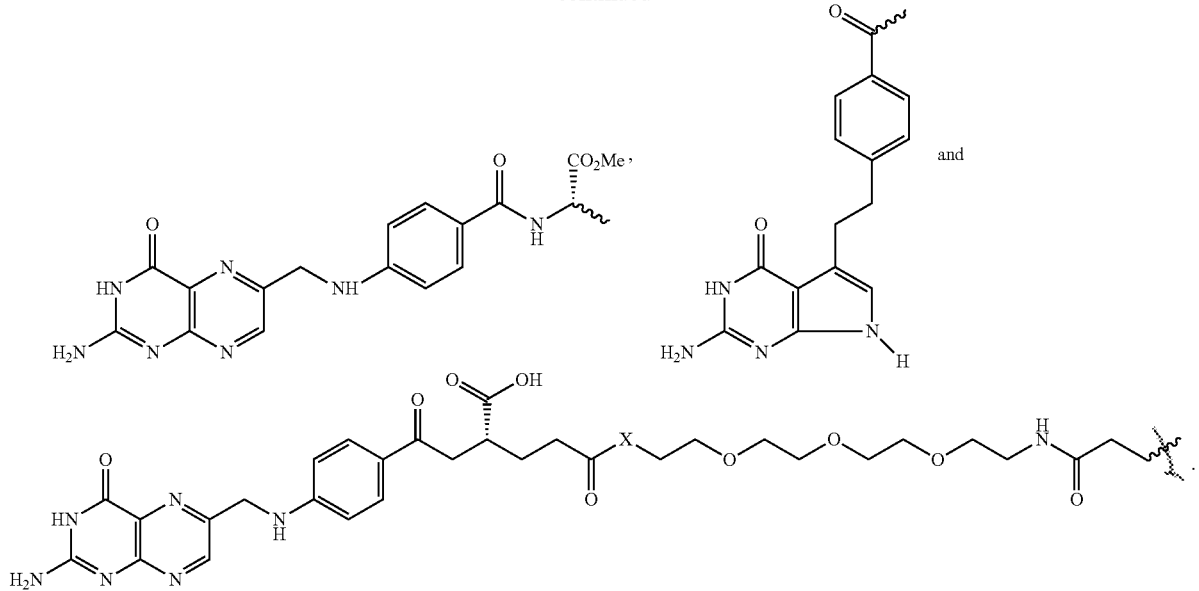

wherein x is an ether linkage, a thioether linkage, a carbamate linkage, a urethane linkage, a biocleavable linker (such as disulfides, esters, amides), pH sensitive linker (such as hydrazones, oximes, acetals/ketal, orthoesters, CDM (Ref: Proc. Natl. Acad. Sci. USA 2007, 104(32), 12982-12987)), peptidase sensitive peptides, phosphates, triazole linkage derived from azide and alkyne, and/or a combination of these.

In some embodiments, the present invention provides compounds of Table 1.

TABLE 1

Some preferred embodiments.

| | | |
|---|---|---|
| 1 | (structure) | Folate: stable hydrophobic alkyl tether |
| 2 | (structure) | Folate: stable hydrophilic tether |
| 3 | (structure) | Pteroate: stable hydrophobic alkyl tether |
| 4 | (structure) | Pteroate: stable hydrophilic tether |
| 5 | (structure) | Folate: disulfide linkage |

TABLE 1-continued

Some preferred embodiments.

| 6 | [structure: pterin-CH2-NH-C6H4-C(O)-NH-CH(COOH)-CH2-S-S-C(CH3)2-CH2CH2-C(O)-X—Lipid/PEG-Lipid] | Folate: gem-dimethyldisulfide linkage |
| --- | --- | --- |
| 7 | [structure: pterin-CH2-NH-C6H4-C(O)-NH-CH(COOH)-CH2CH2-C(O)-NH-(CH2)n-X—Drug Delivery Scaffold] | Folate: stable hydrophobic alkyl tether |
| 8 | [structure: pterin-CH2-NH-C6H4-C(O)-NH-CH(COOH)-CH2CH2-C(O)-NH-CH2CH2-(OCH2CH2)n-O-X—Drug Delivery Scaffold] | Folate: stable hydrophilic tether |
| 9 | [structure: pterin-CH2-NH-C6H4-C(O)-NH-(CH2)n-X—Drug Delivery Scaffold] | Pteroate: stable hydrophobic alkyl tether |
| 10 | [structure: pterin-CH2-NH-C6H4-C(O)-NH-CH2CH2-(OCH2CH2)n-O-X—Drug Delivery Scaffold] | Pteroate: stable hydrophilic tether |
| 11 | [structure: pterin-CH2-NH-C6H4-C(O)-NH-CH(COOH)-CH2-S-S-CH2CH2-C(O)-X—Drug Delivery Scaffold] | Folate: disulfide linkage |
| 12 | [structure: pterin-CH2-NH-C6H4-C(O)-NH-CH(COOH)-CH2-S-S-C(CH3)2-CH2CH2-C(O)-X—Drug Delivery Scaffold] | Folate: gem-dimethyldisulfide linkage | n is 0-20; x is an ether linage, a thioether linkage, a carbamate linkage, a urethane linkage, a biocleavable linker (such as disulfides, esters, amides), pH sensitive linker (such as hydrazones, oximes, acetals/ketal, orthoesters, CDM (Ref: Proc. Natl. Acad. Sci. USA 2007, 104(32), 12982-12987)), peptidase sensitive peptides, phosphates, triazole linkage derived from azide and alkyne, and/or a combination of these.

In one aspect the present invention provides drug delivery systems conjugated with targeting ligands.

Drug delivery system (also to referred to as "drug delivery scaffold" herein) can be based on a polymeric scaffold. Polymeric delivery systems include linear or branched polymers, dendrimers, water soluble, biocompatible, biodegradable, pH sensitive, cationic, anionic, neutral, hydrophilic, hydrophobic with or without endosomal release agent. Polymers also include pH sensitive masking of polyanionic or polycationic polymers, peptides, polysaccharides, oligosaccharides, polyglycidols. Tethers and linkages between the polymer and targeting moiety are same or similar to that of the lipid-ligand conjugates described herein.

In one embodiment, the drug delivery system is conjugated or associated with a moiety that can modulate the PK properties of the delivery system.

In one embodiment, the drug delivery system is conjugated or associated with an endosomal release agent.

In one embodiment, the drug delivery system is conjugated or associated with an endosomal release agent and a moiety that can modulate the PK properties of the delivery system.

In one embodiment, tether/linker that links the drug delivery system to targeting moiety is conjugated or associated with an endosomal release agent.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketyals and/or orthoesters.

In one aspect, the drug delivery system is based on liposomal, surfactant, micelle, membranous formulations, nanoparticles, emulsions, nano- and micro-emulsions, intralipid, soybean based formulations, soybean fatty oil, fatty oil based, fish oil (omega-3), antibody, lipidoids and dry powder formulations.

In preferred embodiments liposomes are cationic, anionic or neutral.

In preferred embodiments surfactants are cationic, anionic or neutral.

The kidney contains a high-affinity folate binding protein (FBP) concentrated in the proximal tubular cells (Int. Rev. Cytol. 180.237-284, 1998), Therefore a nucleic acid therapeutic agent (e.g., siRNA or antagomir) can be targeted to the kidney, by targeted delivery of nucleic acid therapeutics using the targeted delivery approach of the present invention.

Drug in the present invention is a nucleic acid therapeutic or an iRNA agent such as siRNA, antagomir, microRNA, antisense, aptamer, plasmids, decoy RNA, immunostimulatory oligonucleotides, antisense microRNAs, splice modulating oligonucleotides, RNA activating oligonucleotides etc. The drug is either conjugated or formulated with the delivery system. In some embodiments, the drug is conjugated with the tether/linker that links the targeting moiety to the delivery system.

In a further aspect, this invention provides a method of modulating expression of a target gene, the method includes administering a drug as defined herein formulated or conjugated with the drug delivery system described herein.

In one aspect, this invention features a pharmaceutical composition having a nucleic acid formulated or conjugated with the drug delivery system described herein and a pharmaceutically acceptable carrier.

In further related embodiments, the present invention includes a lipid particle comprising one or more of the above lipids of the present invention. In certain embodiments, the particle further comprises a targeting lipid described in this application, a cationic lipid, a neutral lipid and a lipid capable of reducing particle aggregation. In one particular embodiment, the lipid particle consists essentially of: (i) a targeting lipid (ii) an amino lipid (iii) a neutral lipid selected from DSPC, POPC, DOPE, and SM; (iv) cholesterol; and (v) PEG-DMG, PEG-C-DOMG or PEG-DMA, in a molar ratio of about 0.5-50% targeting lipid:20-60% cationic lipid:5-25% neutral lipid:25-55% Chol:0.5-15% PEG-DMG or PEG-DMA.

Folate

As used herein, the term "folate" is meant to refer to folate and folate derivatives, including pteroic acid derivatives and analogs. The analogs and derivatives of folic acid suitable for use in the present invention include, but are not limited to, antifolates, dihydrofloates, tetrahydrofolates, tetrahydrorpterins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acid derivatives. Additional folate analogs are described in published US publication US2004/0,242,582 (published Dec. 2, 2004).

Lipid/Lipophile

The terms "lipid" and "lipophile" refer to any fat-soluble molecule such as fats, oils, waxes, terpenes, sterols, fat-soluble vitamins (e.g., A, D, E and K), monoglycerides, diglycerides, triglycerides, fatty acids, hopanoids and phospholipids. Exemplary lipophilic molecules include, but are not limited to, cholesterol, progestesrone, testosterone, estradiol, norethindfrone, cortisone, cholic acid, O3-(oleoyl) lithocholic acid, cholenic acid, O3-(oleoyl)cholenic acid, chenodecoxy cholic acid, glycocholic acid, taurocholic acid, dexoycholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, dimethoxytrityl, phenoxazine, polycyclic aromatic hydrocarbons (e.g., phenazine, dihydrophenazine), lauric acid, stearic acid, arachidic acid, palmitoleic acid, oleic acid, linoleic acid, linolenic acid, archidonic acid, leukotriene A, myrcene, geraniol, carvone, chrysanthemic acid, nepetalactone, menthofuran, alpha-pinene, camphor, farnesol, humulene, nagione, caryophyllene, abieticv acid, lanosterol, and squalene, campesterol, sitosterol, stigmasterol, ergosterol, brassinsterol, distearyl-lithocholamide, borneol, menthol, heptadecyl group, dialkylglycerides, diacylglyceride, and bile acids. When used herein, terms to describe the lipophilic moiety such as a free acid (such as a free fatty acid, e.g., palmitic acid) are used interchangeably with the radical term (e.g., palmitoyl).

Carbohydrate

As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The term "monosaccharide" embraces radicals of allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnosamine, rhamnose, ribose, ribulose, sedoheptulose, sorbose, tagatose, talose, tartaric acid, threose, xylose and xylulose. The monosaccharide can be in D- or L-configuration. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or $C=O$ replaced by $C=S$, or a ring oxygen of cyclic form replaced by sulfur), a seleno sugar, a telluro sugar, an aza sugar (ring carbon replaced by nitrogen), an sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a ironic acid, an aldaric acid, and so forth. Amino sugars include amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide" and "polysaccharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructooligosaccharide, gentianose, gentiobiose, glucan, glucogen, glycogen, hamamelose, heparin, inulin, isolevoglucosenone, isomaltose, isomaltotriose, isopanose, kojibiose, lactose. lactosamine, lactosediamine, laminarabiose, levoglucosan, levoglucosenone, β-maltose, maltriose, mannan-oligosaccharide, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, xylobiose, umbelliferose and the like. Further, it is understood that the "disaccharide", "trisaccharide" and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

Ligands

A wide variety of entities can be used as ligands for conjugation according to the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in Table 2.

TABLE 2

List of peptides with endosomolytic activity.

| Name | Sequence (N to C) | Ref. |
|---|---|---|
| GALA | AALEALAEALAEALAEALEALAEAAAAGGC | 1 |
| EALA | AALAEALAEALAEALAEALAEALAAAAGGC ALEALAEALEALAEA | 2 3 |
| INF-7 | GLFEAIEGFIENGWEGMIWDYG | 4 |

TABLE 2-continued

List of peptides with endosomolytic activity.

| Name | Sequence (N to C) | Ref. |
|---|---|---|
| Inf HA-2 | GLFGAIAGFIENGWEGMIDGWYG | 5 |
| diINF-7 | GLF EAI EGFI ENGW EGMI DGWYGC GLF EAI EGFI ENGW EGMI DGWYGC | 5 |
| diINF3 | GLF EAI EGFI ENGW EGMI DGGC GLF EAI EGFI ENGW EGMI DGGC | 6 |
| GLF | GLFGALAEALAEALAEHLAEALAEALEALAAGGSC | 6 |
| GALA-INF3 | GLFEAIEGFIENGWEGLAEALAEALEALAAGGSC | 6 |
| INF-5 | GLF EAI EGFI ENGW EGnI DG K GLF EAI EGFI ENGW EGnI DG | 4 | n, norleucine

References
1. Subbarao et al., Biochemistry, 1987, 26: 2964-2972.
2. Vogel et al., J. Am. Chem. Soc., 1996, 118: 1581-1586
3. Turk, M. J., Reddy, J. A. et al. (2002). Characterization of a novel pH-sensitive peptide that enhances drug release from folate-targeted liposomes at endosomal pHs. Biochim. Biophys. Acta 1559, 56-68.
4. Plank, C. Oberhauser, B. Mechtler, K. Koch, C. Wagner, E. (1994). The influence of endosome-disruptive peptides on gene transfer using synthetic virus-like gene transfer systems, J. Biol. Chem. 269 12918-12924.
5. Mastrobattista, E., Koning, G. A. et al. (2002). Functional characterization of an endosome-disruptive peptide and its application in cytosolic delivery of immunoliposome-entrapped proteins. J. Biol. Chem. 277, 27135-43.
6. Oberhauser, B., Plank, C. et al. (1995). Enhancing endosomal exit of nucleic acids using pH-sensitive viral fusion peptides. Deliv. Strategies Antisense Oligonucleotide Ther. 247-66.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 3 shows some examples of targeting ligands and their associated receptors.

TABLE 3

Targeting Ligands and their associated receptors

| Liver Cells | Ligand | Receptor |
|---|---|---|
| 1) Parenchymal Cell (PC) (Hepatocytes) | Galactose | ASGP-R (Asiologlycoprotein receptor) |
| | Gal NAc (n-acetyl-galactosamine) | ASPG-R Gal NAc Receptor |
| | Lactose | |
| | Asialofetuin | ASPG-r |
| 2) Sinusoidal Endothelial Cell (SEC) | Hyaluronan | Hyaluronan receptor |
| | Procollagen | Procollagen receptor |
| | Negatively charged molecules | Scavenger receptors |
| | Mannose | Mannose receptors |
| | N-acetyl Glucosamine | Scavenger receptors |
| | Immunoglobulins | Fc Receptor |
| | LPS | CD14 Receptor |
| | Insulin | Receptor mediated transcytosis |
| | Transferrin | Receptor mediated transcytosis |
| | Albumins | Non-specific |
| | Sugar-Albumin conjugates | |
| | Mannose-6-phosphate | Mannose-6-phosphate receptor |
| 3) Kupffer Cell (KC) | Mannose | Mannose receptors |
| | Fucose | Fucose receptors |
| | Albumins | Non-specific |
| | Mannose-albumin conjugates | |

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the conjugate into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the conjugate into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long (see Table 4, for example).

delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-

TABLE 4

Exemplary Cell Permeation Peptides.

| Cell Permeation Peptide | Amino acid Sequence | Reference |
|---|---|---|
| Penetratin | RQIKIWFQNRRMKWKK | Derossi et al., J. Biol. Chem. 269:10444, 1994 |
| Tat fragment (48-60) | GRKKRRQRRRPPQC | Vives et al., J. Biol. Chem., 272:16010, 1997 |
| Signal Sequence-based peptide | GALFLGWLGAAGSTMGAWSQPKKKRKV | Chaloin et al., Biochem. Biophys. Res. Commun., 243:601, 1998 |
| PVEC | LLIILRRRIRKQAHAHSK | Elmquist et al., Exp. Cell Res., 269:237, 2001 |
| Transportan | GWTLNSAGYLLKINLKALAALAKKIL | Pooga et al., FASEB J., 12:67, 1998 |
| Amphiphilic model peptide | KLALKLALKALKAALKLA | Oehlke et al., Mol. Ther., 2:339, 2000 |
| Arg$_9$ | RRRRRRRRR | Mitchell et al., J. Pept. Res., 56:318, 2000 |
| Bacterial cell wall permeating | KFFKFFKFFK | |
| LL-37 | LLGDFFRKSKEKIGKEFKRIVQRIKDFLRNLVPRTES | |
| Cecropin P1 | SWLSKTAKKLENSAKKRISEGIAIAIQGGPR | |
| α-defensin | ACYCRIPACIAGERRYGTCIYQGRLWAFCC | |
| β-defensin | DHYNCVSSGGQCLYSACPIFTKIQGTCYRGKAKCCK | |
| Bactenecin | RKCRIVVIRVCR | |
| PR-39 | RRRPRPPYLPRPRPPPFFPPRLPPRIPPGFPPRFPPRFPGKR-NH2 | |
| Indolicidin | ILPWKWPWWPWRR-NH2 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP. An RFGF analogue (e.g., amino acid sequence AALLPVLLAAP) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) and the Drosophila Antennapedia protein (RQIKIWFQNRRMKWKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_v\sigma_3$ integrin. Thus, one could use RGD peptides, cyclic peptides containing RGD, RGD peptides that include D-amino acids, as well as synthetic RGD mimics. In addition to RGD, one can use other moieties that target the $I_v\text{-}\sigma_3$ integrin ligand. Generally, such ligands can be used to control proliferating cells and angiogeneis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligands amenable to the invention are described in copending applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Linkers/Tethers

The terms "linker" and "tether" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In one embodiment, the linker/tether (underlined) include —(CH$_2$)$_n$NH—; —C(O)(CH$_2$)$_n$NH—; —NR''''(CH$_2$)$_n$NH—, —C(O)—(CH$_2$)$_n$—C(O)—; —C(O)—(CH$_2$)$_n$—C(O)O—; —C(O)—O—; —C(O)—(CH$_2$)$_n$—NH—C(O)—; —C(O)—(CH$_2$)$_n$—; —C(O)—NH—; —C(O)—; —(CH$_2$)$_n$—C(O)—; —(CH$_2$)$_n$—C(O)O—; —(CH$_2$)$_n$—; —(CH$_2$)$_n$—NH—C(O)—; —C(O)—(CH$_2$)$_n$—NH—C(O)—(CH$_2$)$_n$CH—; —(R''')—NH—C(O)—(CH$_2$)$_n$—NH—C(O)—; —(CH$_2$)$_n$C(R')(R'')—SS—(CH$_2$)$_n$—NH—; —C(O)—(CH$_2$)$_n$CH(R''')NH—; —C(O)—(CH$_2$)$_n$—NH—; —C(O)—(CH$_2$)$_n$—SS—(CH$_2$)$_n$CH(R''')—NH—C(O)—(CH$_2$)$_n$CH(R''')NH—; —(CH$_2$)$_n$—NH—C(O)—(CH$_2$)$_n$C(R')(R'')—SS—(CH$_2$)$_n$—; in which each n is independently 1-20 (e.g., 1, 2, 3, 4, 5, 6, 7, 8, 9, 10, 11, 12, 13, 14, 15, 16, 17, 18, 19, or 20), R' and R'' are each independently H, CH3, OH, SH, NH2, NH(Alkyl=Me, Et, Pr, isoPr, Bu, Bn) or N(diAlkyl=Me$_2$, Et$_2$, Bn$_2$); R''' is H, COOH, CONH2, CONHMe, CONMe$_2$, CONH(CH$_2$)$_j$NH$_2$, CONH(CH$_2$)$_j$OH, CONH(CH$_2$)$_j$COOH, CONH(CH$_2$)$_j$SH, CONH(CH$_2$)$_j$CONH$_2$, CONH(CH$_2$)$_j$CONHMe, CONH(CH$_2$)$_j$CONH(CH$_2$CH$_2$O)$_k$H, CONH(CH$_2$)$_j$CONH(CH$_2$CH$_2$O)$_k$NH$_2$, CONH(CH$_2$)$_j$CONH(CH$_2$CH$_2$O)$_k$CH$_3$, CONH(CH$_2$)$_j$CONH(CH$_2$CH$_2$O)$_k$COOH, or CONH(CH$_2$)$_j$CONH(CH$_2$CH$_2$O)$_k$SH; and R'''' is C$_1$-C$_6$ alkyl, j and k are each independently 0-20. Preferably, n is 2, 5, 6, or 11. In other embodiments, the nitrogen may form part of a terminal oxyamino group, e.g., —ONH$_2$, or hydrazino group, —NHNH$_2$. The linker/tether may optionally be substituted, e.g., with hydroxy, alkoxy, perhaloalkyl, and/or optionally inserted with one or more additional heteroatoms, e.g., N, O, or S.

In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —C, —CH, —C(CH$_2$—)(CH$_2$—)CH$_2$—, —C(H)(CH$_2$—)CH$_2$— —N, —N(Q)—C, —O—C, —S—C, —SS—C, —C(O)N(Q)—C, —OC(O)N(Q)—C, —N(Q)C(O)—C, or —N(Q)C(O)O—C; wherein Q is independently for each occurrence H or optionally substituted alkyl. In other embodiment, the branchpoint is glycerol or glycerol derivative.

Lipid Particles

The present invention also provides lipid particles comprising one or more of the targeting lipids described above. Lipid particles include, but are not limited to, liposomes. As used herein, a liposome is a structure having lipid-containing membranes enclosing an aqueous interior. Liposomes may have one or more lipid membranes. The invention contemplates both single-layered liposomes, which are referred to as unilamellar, and multi-layered liposomes, which are referred to as multilamellar. When complexed with nucleic acids, lipid particles may also be lipoplexes, which are composed of cationic lipid bilayers sandwiched between DNA layers, as described, e.g., in Feigner, *Scientific American*.

The lipid particles of the present invention may further comprise one or more additional lipids and/or other components such as cholesterol. Other lipids may be included in the liposome compositions of the present invention for a variety of purposes, such as to prevent lipid oxidation or to attach ligands onto the liposome surface. Any of a number of lipids may be present in liposomes of the present invention, including amphipathic, neutral, cationic, and anionic lipids. Such lipids can be used alone or in combination. Specific examples of additional lipid components that may be present are described below.

Additional components that may be present in a lipid particle of the present invention include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, U.S. Pat. No. 5,885,613).

In particular embodiments, the lipid particles include one or more of an amino lipid or cationic lipid, a neutral lipid, a sterol, and a lipid selected to reduce aggregation of lipid particles during formation, which may result from steric stabilization of particles which prevents charge-induced aggregation during formation.

Examples of lipids that reduce aggregation of particles during formation include polyethylene glycol (PEG)-modified lipids, monosialoganglioside Gm1, and polyamide oligomers ("PAO") such as (described in U.S. Pat. No. 6,320,017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the present invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mePEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a T$_{112}$ less than 60 mins. in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications it may be preferable for the PEG-modified lipid to be rapidly lost from the nucleic acid-lipid particle in vivo and hence the PEG-modified lipid will possess relatively short lipid anchors. In other therapeutic applications it may be preferable for the nucleic acid-lipid particle to exhibit a longer plasma circulation lifetime and hence the PEG-modified lipid will possess relatively longer lipid anchors.

Other exemplary PEG-lipids include, without limitation PEG coupled to dialkyloxypropyls (PEG-DAA) as described in, e.g., WO 05/026372, PEG coupled to diacylglycerol (PEG-DAG) as described in, e.g., U.S. Patent Publication Nos. 20030077829 and 2005008689, PEG coupled to phosphatidylethanolamine (PE) (PEG-PE), or PEG conjugated to ceramides, or a mixture thereof (see, U.S. Pat. No. 5,885,613).

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{10}$ to $C_{20}$ are preferred. In another group of embodiments, lipids with mono or diunsaturated fatty acids with carbon chain lengths in the range of $C_{10}$ to $C_{20}$ are used. Additionally, lipids having mixtures of saturated and unsaturated fatty acid chains can be used. Preferably, the neutral lipids used in the present invention are DOPE, DSPC, POPC, or any related phosphatidylcholine. The neutral lipids useful in the present invention may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Cationic lipids suitable for use in lipid particles of the present invention include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-$N^2$-(sperminecarboxamido)ethyl)-N,N-dimethylammonium trifluoroacetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

Other cationic lipids amenable to the present invention are disclosed in PCT patent application PCT/US2007/080331 filed Oct. 3, 2007.

Anionic lipids suitable for use in lipid particles of the present invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In numerous embodiments, amphipathic lipids are included in lipid particles of the present invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the lipid particles of the present invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. By the time the lipid particle is suitably distributed in the body, it has lost sufficient cloaking agent so as to be fusogenic. With other signal events, it is desirable to choose a signal that is associated with the disease site or target cell, such as increased temperature at a site of inflammation.

In one exemplary embodiment, the lipid particle comprises a mixture of a targeting lipid of the present invention, a cationic lipid, neutral lipids (other than an amino lipid), a sterol (e.g., cholesterol) and a PEG-modified lipid (e.g., a PEG-DMG, PEG-C-DOMG or PEG-DMA). In certain embodiments, the lipid mixture consists of or consists essentially of a targeting lipid of the present invention, a cationic lipid, a neutral lipid, cholesterol, and a PEG-modified lipid. In further preferred embodiments, the lipid particle consists of or consists essentially of the above lipid mixture in molar ratios of about 20-50% targeting lipid:20-70% cationic lipid:5-45% neutral lipid:20-55% cholesterol:0.5-15% PEG-modified lipid.

In a preferred embodiment, all components of the lipid particle are optically pure.

Therapeutic Agent-Lipid Particle Compositions and Formulations

The present invention includes compositions comprising a lipid particle of the present invention and an active agent, wherein the active agent is associated with the lipid particle. In particular embodiments, the active agent is a therapeutic agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade free DNA. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

Active agents, as used herein, include any molecule or compound capable of exerting a desired effect on a cell, tissue, organ, or subject. Such effects may be biological, physiological, or cosmetic, for example. Active agents may be any type of molecule or compound, including e.g., nucleic acids, peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include any therapeutically effective agent or drug, such as anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids.

In certain embodiments, the therapeutic agent is an oncology drug, which may also be referred to as an anti-tumor drug, an anti-cancer drug, a tumor drug, an antineoplastic agent, or the like. Examples of oncology drugs that may be used according to the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litertinoid, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used according to the invention are ellipticin and ellipticin analogs or derivatives, epothilones, intracellular kinase inhibitors and camptothecins.

Nucleic Acid-Lipid Particles

In certain embodiments, lipid particles of the present invention are associated with a nucleic acid, resulting in a nucleic acid-lipid particle. In particular embodiments, the nucleic acid is fully encapsulated in the lipid particle. As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucletoides of the present invention are 20-50 nucleotides in length.

In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, antagomirs and triplex-forming oligonucleotides.

Nucleic acids of the present invention may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, both single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

In particular embodiments, an oligonucleotide (or a strand thereof) of the present invention specifically hybridizes to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions as compared to the region of a gene or mRNA sequence that it is targeting or to which it specifically hybridizes.

RNA Interference Nucleic Acids

In particular embodiments, nucleic acid-lipid particles of the present invention are associated with RNA interference (RNAi) molecules. RNA interference methods using RNAi molecules may be used to disrupt the expression of a gene or polynucleotide of interest. These RNAi molecules are also referred to as iRNA agents and described below.

The iRNA agent should include a region of sufficient homology to the target gene, and be of sufficient length in terms of nucleotides, such that the iRNA agent, or a fragment thereof, can mediate downregulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in one embodiment fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired one embodiment can include, particularly in the antisense strand, one or more, or for example, 6, 5, 4, 3, 2, or fewer mismatches (with respect to the target RNA). The mismatches, particularly in the antisense strand, are most tolerated in the terminal regions and if present may be in a terminal region or regions, e.g., within 6, 5, 4, or 3 nucleotides of the 5' and/or 3' termini. The sense strand need only be sufficiently complementary with the antisense strand to maintain the over all double stranded character of the molecule.

As discussed elsewhere herein, and in the material incorporated by reference in its entirety, an iRNA agent will often be modified or include nucleoside surrogates. Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-termini of an iRNA agent, e.g., against exonucleases, or to favor the antisense siRNA agent to enter into RISC are also envisioned. Modifications can include C3 (or C6, C7, C12) amino linkers, thiol linkers, carboxyl linkers, non-nucleotide spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

iRNA agents include: molecules that are long enough to trigger the interferon response (which can be cleaved by Dicer (Bernstein et al. 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA agents herein. "siRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60, 50, 40, or 30 nucleotide pairs. The siRNA agent, or a cleavage product thereof, can down regulate a target gene, e.g., by inducing RNAi with respect to a target RNA, wherein the target may comprise an endogenous or pathogen target RNA.

Each strand of a siRNA agent can be equal to or less than 30, 25, 24, 23, 22, 21, or 20 nucleotides in length. The strand may be at least 19 nucleotides in length. For example, each strand can be between 21 and 25 nucleotides in length. siRNA agents may have a duplex region of 17, 18, 19, 29, 21, 22, 23, 24, or 25 nucleotide pairs, and one or more overhangs, or one or two 3' overhangs, of 2-3 nucleotides.

In addition to homology to target RNA and the ability to down regulate a target gene, an iRNA agent may have one or more of the following properties:

A single strand iRNA agent may be sufficiently long that it can enter the RISC and participate in RISC mediated cleavage of a target mRNA. A single strand iRNA agent is at least 14, and in other embodiments at least 15, 20, 25, 29, 35, 40, or 50 nucleotides in length. In certain embodiments, it is less than 200, 100, or 60 nucleotides in length.

Hairpin iRNA agents will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region, in one embodiment at the 3', and in certain embodiments on the antisense side of the hairpin. In one embodiment, the overhangs are 2-3 nucleotides in length.

A "double stranded (ds) iRNA agent" as used herein, is an iRNA agent which includes more than one, and in some cases two, strands in which interchain hybridization can form a region of duplex structure.

The antisense strand of a double stranded iRNA agent may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The sense strand of a double stranded iRNA agent may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded iRNA agent may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the ds iRNA agent is sufficiently large that it can be cleaved by an endogenous molecule, e.g., by Dicer, to produce smaller ds iRNA agents, e.g., siRNAs agents It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active siRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional siRNA 5'-end. Antisense strand modifications include 5' phosphorylation as well as any of the other 5' modifications discussed herein, particularly the 5' modifications discussed above in the section on single stranded iRNA molecules.

The sense and antisense strands may be chosen such that the ds iRNA agent includes a single strand or unpaired region at one or both ends of the molecule. Thus, a ds iRNA agent may contain sense and antisense strands, paired to contain an overhang, e.g., one or two 5' or 3' overhangs, or a 3' overhang of 2-3 nucleotides. Many embodiments will have a 3' overhang. Certain siRNA agents will have single-stranded overhangs, in one embodiment 3' overhangs, of 1 or 2 or 3 nucleotides in length at each end. The overhangs can be the result of one strand being longer than the other, or the result of two strands of the same length being staggered. 5' ends may be phosphorylated.

In one embodiment, the length for the duplexed region is between 15 and 30, or 18, 19, 20, 21, 22, and 23 nucleotides in length, e.g., in the siRNA agent range discussed above. siRNA agents can resemble in length and structure the natural Dicer processed products from long dsiRNAs. Embodiments in which the two strands of the siRNA agent are linked, e.g., covalently linked are also included. Hairpin, or other single strand structures which provide the required double stranded region, and a 3' overhang are also within the invention.

The isolated iRNA agents described herein, including ds iRNA agents and siRNA agents can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In one embodiment, an iRNA agent is "sufficiently complementary" to a target RNA, e.g., a target mRNA, such that the iRNA agent silences production of protein encoded by the target mRNA. In another embodiment, the iRNA agent is "exactly complementary" to a target RNA, e.g., the target RNA and the iRNA agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in one embodiment, the iRNA agent specifically discriminates a single-nucleotide difference. In this case, the iRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

RNA agents discussed herein include unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The art has often referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA refers to a molecule in which one or more of the components of the nucleic acid, namely sugars, bases, and phosphate moieties, are different from that which occur in nature, for example, different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

MicroRNAs

Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "The microRNA Registry" Griffiths-Jones S, NAR, 2004, 32, Database Issue, D109-D111; and also at http://microrna.sanger.ac.uk/sequences/.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence. In the case of antisense RNA, they prevent translation of complementary RNA strands by binding to it. Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4): 225-32; Penis et al., Brain Res Mol Brain Res. 1998 Jun. 15; 57(2):310-20; U.S. Pat. No. 5,801,154; U.S. Pat. No. 5,789,573; U.S. Pat. No. 5,718,709 and U.S. Pat. No. 5,610,288). Furthermore, antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Ribozymes

According to another embodiment of the invention, nucleic acid-lipid particles are associated with ribozymes. Ribozymes are RNA-protein complexes having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or *Neurospora* VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; *Neurospora* VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto S., et al. (1992) J. Immunol. 148: 4072-4076), or CpG motifs, as well as other known ISS features (such as multi-G domains, see WO 96/11266).

The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

In particular embodiments, an immunostimulatory nucleic acid is only immunostimulatory when administered in combination with a lipid particle, and is not immunostimulatory when administered in its "free form." According to the present invention, such an oligonucleotide is considered to be immunostimulatory.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein, in its entirety.

Decoy Oligonucleotides

Because transcription factors can recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

Nucleic Acid Modifications

Much of the discussion below refers to single strand molecules. In many embodiments of the invention a double stranded iRNA agent, e.g., a partially double stranded iRNA agent, is envisioned. Thus, it is understood that that double stranded structures (e.g., where two separate molecules are contacted to form the double stranded region or where the double stranded region is formed by intramolecular pairing (e.g., a hairpin structure)) made of the single stranded structures described below are within the invention. Lengths are described elsewhere herein.

As nucleic acids are polymers of subunits, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many cases it will not. By way of example, a modification may only occur at a 3' or 5' terminal position, may only occur in a terminal regions, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In one embodiment it is possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In one embodiment all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases.

Specific modifications are discussed in more detail below.

The Phosphate Group

The phosphate group is a negatively charged species. The charge is distributed equally over the two non-linking oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in one embodiment to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, oxygens of the phosphodiester linkage can be replaced by any one of S, Se, B, C, H, N, or OR(R is alkyl or aryl).

The phosphate linker can also be modified by replacement of a linking oxygen with nitrogen (bridged phosphoroamidates), sulfur (bridged phosphorothioates) and carbon (bridged methylenephosphonates).

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to one embodiment to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diarylamino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)$—$CH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thioalkyl; thioalkoxy; and alkyl, cycloalkyl, aryl, alkenyl and alkynyl, which may be optionally substituted with e.g., an amino functionality. Other substitutents of certain embodiments include 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNA's can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g., nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. In certain embodiments, PNA surrogates may be used.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., $-(CH_2)_n-$, $-(CH_2)_nN-$, $-(CH_2)_nO-$, $-(CH_2)_nS-$, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g., acridines), cross-linkers (e.g., psoralen, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in certain embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)2(O)P—O—(HO)(O)P—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH2-), 5'-alkyletherphosphonates (R=alkylether=methoxymethyl (MeOCH2-), ethoxymethyl, etc., e.g., RP(OH)(O)—O-5'-).

Terminal modifications can also be useful for monitoring distribution, and in such cases the groups to be added may include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N$^4$-acetyl cytosine, 2-thiocytosine, N6-methyladenine, N6-isopentyladenine, 2-methylthio-N-6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are not used for promoting stability, but they can be useful for other reasons, e.g., some, e.g., 2,6-diaminopurine and 2 amino purine, are fluorescent.

Modified bases can reduce target specificity. This may be taken into consideration in the design of iRNA agents.

REFERENCES

The disclosure of all publications, patents, and published patent applications listed herein are hereby incorporated by reference.

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-0-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein. Modification described in WO 00/44895, WO01/75164, or WO02/44321 can be used herein.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 21-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489, 677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. *Nucleic Acids Res.* 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Base References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

The nucleic acid that is used in a lipid-nucleic acid particle according to this invention includes any form of nucleic acid that is known. Thus, the nucleic acid may be a modified nucleic acid of the type used previously to enhance nuclease resistance and serum stability. Surprisingly, however, acceptable therapeutic products can also be prepared using the method of the invention to formulate lipid-nucleic acid particles from nucleic acids that have no modification to the phosphodiester linkages of natural nucleic acid polymers, and the use of unmodified phosphodiester nucleic acids (i.e., nucleic acids in which all of the linkages are phosphodiester linkages) is a preferred embodiment of the invention.

Chimeric Oligonucleotides

It is not necessary for all positions in a given compound to be uniformly modified, and in fact more than one of the aforementioned modifications may be incorporated in a single compound or even at a single nucleoside within an oligonucleotide. Certain preferred oligonucleotides of this invention are chimeric oligonucleotides. "Chimeric oligonucleotides" or "chimeras," in the context of this invention, are oligonucleotides that contain two or more chemically distinct regions, each made up of at least one nucleotide. These oligonucleotides typically contain at least one region of modified nucleotides that confers one or more beneficial properties (such as, e.g., increased nuclease resistance, increased uptake into cells, increased binding affinity for the RNA target) and a region that is a substrate for RNase H cleavage.

In one embodiment, a chimeric oligonucleotide comprises at least one region modified to increase target binding affinity. Affinity of an oligonucleotide for its target is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In one embodiment, the region of the oligonucleotide which is modified to increase target mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance oligonucleotide inhibition of target gene expression.

In another embodiment, a chimeric oligonucletoide comprises a region that acts as a substrate for RNAse H. Of course, it is understood that oligonucleotides may include any combination of the various modifications described herein.

Another modification of the oligonucleotides of the invention involves chemically linking to the oligonucleotide one or more moieties or conjugates which enhance the activity, cellular distribution or cellular uptake of the oligonucleotide. Such conjugates and methods of preparing the same are known in the art.

Those skilled in the art will realize that for in vivo utility, such as therapeutic efficacy, a reasonable rule of thumb is that if a thioated version of the sequence works in the free form, that encapsulated particles of the same sequence, of any chemistry, will also be efficacious. Encapsulated particles may also have a broader range of in vivo utilities, showing efficacy in conditions and models not known to be otherwise responsive to antisense therapy. Those skilled in the art know that applying this invention they may find old models which now respond to antisense therapy. Further, they may revisit discarded antisense sequences or chemistries and find efficacy by employing the invention.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives.

Characteristic of Nucleic Acid-Lipid Particles

In certain embodiments, the present invention relates to methods and compositions for producing lipid-encapsulated nucleic acid particles in which nucleic acids are encapsulated within a lipid layer. Such nucleic acid-lipid particles, incorporating siRNA oligonucleotides, are characterized using a variety of biophysical parameters including: (1) drug to lipid ratio; (2) encapsulation efficiency; and (3) particle size. High drug to lipid rations, high encapsulation efficiency, good nuclease resistance and serum stability and controllable particle size, generally less than 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Nucleic acid to lipid ratio is the amount of nucleic acid in a defined volume of preparation divided by the amount of lipid in the same volume. This may be on a mole per mole basis or on a weight per weight basis, or on a weight per mole basis. For final, administration-ready formulations, the nucleic acid:lipid ratio is calculated after dialysis, chromatography and/or enzyme (e.g., nuclease) digestion has been employed to remove as much of the external nucleic acid as possible;

Encapsulation efficiency refers to the drug to lipid ratio of the starting mixture divided by the drug to lipid ratio of the final, administration competent formulation. This is a measure of relative efficiency. For a measure of absolute efficiency, the total amount of nucleic acid added to the starting mixture that ends up in the administration competent formulation, can also be calculated. The amount of lipid lost during the formulation process may also be calculated. Efficiency is a measure of the wastage and expense of the formulation; and Size indicates the size (diameter) of the particles formed. Size distribution may be determined using quasi-elastic light scattering (QELS) on a Nicomp Model 370 sub-micron particle sizer. Particles under 200 nm are preferred for distribution to neo-vascularized (leaky) tissues, such as neoplasms and sites of inflammation.

Pharmaceutical Compositions

The lipid particles of present invention, particularly when associated with a therapeutic agent, may be formulated as a pharmaceutical composition, e.g., which further comprises a pharmaceutically acceptable diluent, excipient, or carrier, such as physiological saline or phosphate buffer, selected in accordance with the route of administration and standard pharmaceutical practice.

In particular embodiments, pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, globulin, etc. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, the lipid-therapeutic agent (e.g., nucleic acid) particles of the invention may include polyethylene glycol (PEG)-modified phospholipids, PEG-ceramide, or ganglioside $G_{M1}$-modified lipids or other lipids effective to prevent or limit aggregation. Addition of such components does not merely prevent complex aggregation. Rather, it may also provide a means for increasing circulation lifetime and increasing the delivery of the lipid-nucleic acid composition to the target tissues.

The present invention also provides lipid-therapeutic agent compositions in kit form. The kit will typically be comprised of a container that is compartmentalized for holding the various elements of the kit. The kit will contain the particles or pharmaceutical compositions of the present invention, preferably in dehydrated or concentrated form, with instructions for their rehydration or dilution and administration. In certain embodiments, the particles comprise the active agent, while in other embodiments, they do not.

Methods of Manufacture

The methods and compositions of the invention make use of certain targeting lipids, the synthesis, preparation and characterization of which is described in the accompanying Examples. In addition, the present invention provides methods of preparing lipid particles, including those associated with a therapeutic agent, e.g., a nucleic acid. In the methods described herein, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of about 1 wt % to about 30 wt %, preferably 3 to 25 wt %, even more preferably 5 to 15 wt %. The intermediate mixture may optionally be sized to obtain lipid-encapsulated nucleic acid particles wherein the lipid portions are unilamellar vesicles, preferably having a diameter of 20 to 200 nm, more preferably 30 to 150 nm, even more preferably about 40 to 90 nm. The pH is then raised to neutralize at least a portion of the surface charges on the lipid-nucleic acid particles, thus providing an at least partially surface-neutralized lipid-encapsulated nucleic acid composition.

As described above, several of the cationic lipids are amino lipids that are charged at a pH below the $pK_a$ of the amino group and substantially neutral at a pH above the $pK_a$. These cationic lipids are termed titratable cationic lipids and can be used in the formulations of the invention using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. Additional details concerning these uses of such titratable cationic lipids in the formulation of nucleic acid-lipid particles are provided in U.S. Pat. No. 6,287,591 and U.S. Pat. No. 6,858,225, incorporated herein by reference.

It is further noted that the vesicles formed in this manner provide formulations of uniform vesicle size with high content of nucleic acids. Additionally, the vesicles have a size range of from about 20 to about 200 nm, preferably 30 to about 150 nm, more preferably about 30 to about 90 nm.

Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g. pH 7.5) the surface of the lipid particle or liposome is neutralized, allowing any external nucleic acid to be removed. More detailed information on the formulation process is provided in various publications (e.g., U.S. Pat. No. 6,287,591 and U.S. Pat. No. 6,858,225).

In view of the above, the present invention provides methods of preparing lipid/nucleic acid formulations. In the methods described herein, a mixture of lipids is combined with a buffered aqueous solution of nucleic acid to produce an intermediate mixture containing nucleic acid encapsulated in lipid particles, e.g., wherein the encapsulated nucleic acids are present in a nucleic acid/lipid ratio of about 10 wt % to about 20 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

In preparing the nucleic acid-lipid particles of the invention, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. This method is described in more detail in U.S. Pat. No. 5,976,567).

In one exemplary embodiment, the mixture of lipids is a mixture of targeting lipid, cationic lipids, neutral lipids (other than a cationic lipid), a sterol (e.g., cholesterol) and a PEG-modified lipid (e.g., a PEG-DMG, PEG-C-DOMG or PEG-DMA) in an alcohol solvent. In preferred embodiments, the lipid mixture consists essentially of a targeting lipid, acationic amino lipid, a neutral lipid, cholesterol and a PEG-modified lipid in alcohol, more preferably ethanol. In further preferred embodiments, the first solution consists of the above lipid mixture in molar ratios of about 0.5-50% targeting lipid:20-70% cationic lipid:5-45% neutral lipid:20-55% cholesterol:0.5-15% PEG-modified lipid.

In accordance with the invention, the lipid mixture is combined with a buffered aqueous solution that may contain the nucleic acids. The buffered aqueous solution of is typically a solution in which the buffer has a pH of less than the $pK_a$ of the protonatable lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the nucleic acid being encapsulated, and optimization of buffer concentration may be significant to achieving high loading levels (see, e.g., U.S. Pat. No. 6,287,591 and U.S. Pat. No. 6,858,225). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about 0.01 mg/mL to about 200 mg/mL, more preferably from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In particular embodiments, methods of the present invention further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the pKa of the lipid used.

Optionally the lipid vesicles (i.e., lipid particles) can be formed by hydration in an aqueous buffer and sized using any of the methods described above prior to addition of the nucleic acid. As described above, the aqueous buffer should be of a pH below the pKa of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

Method of Use

The lipid particles of the present invention may be used to deliver a therapeutic agent to a cell, in vitro or in vivo. In particular embodiments, the therapeutic agent is a nucleic acid, which is delivered to a cell using a nucleic acid-lipid particles of the present invention. While the following description o various methods of using the lipid particles and related pharmaceutical compositions of the present invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the present invention provides methods for introducing a nucleic acid into a cell. Preferred nucleic acids for introduction into cells are siRNA, immune-stimulating oligonucleotides, plasmids, antisense and ribozymes. These methods may be carried out by contacting the particles or compositions of the present invention with the cells for a period of time sufficient for intracellular delivery to occur.

The compositions of the present invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 mmol and about 10 mmol. In certain embodiments, treatment of the cells with the lipid-nucleic acid compositions will generally be carried out at physiological temperatures (about 37° C.) for periods of time from about 1 to 24 hours, preferably from about 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2\times10^4$ cells/mL. The concentration of the suspension added to the cells is preferably of from about 0.01 to 20 μg/mL, more preferably about 1 μg/mL.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions of the present invention include introduction of antisense oligonucleotides in cells (see, Bennett, et al., *Mol. Pharm.* 41:1023-1033 (1992)).

Alternatively, the compositions of the present invention can also be used for deliver of nucleic acids to cells in vivo, using methods which are known to those of skill in the art. With respect to application of the invention for delivery of DNA or mRNA sequences, Zhu, et al., *Science* 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), incorporated herein by reference, describes the in vivo transfection of lungs of mice with a functioning prokaryotic gene encoding the intracellular enzyme, chloramphenicol acetyltransferase (CAT). Thus, the compositions of the invention can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., *Am. J. Sci.* 298(4):278-281 (1989)) or by direct injection at the site of disease (Culver, Human Gene Therapy, Mary-Ann Liebert, Inc., Publishers, New York. pp. 70-71 (1994)).

The methods of the present invention may be practiced in a variety of hosts. Preferred hosts include mammalian species, such as humans, non-human primates, dogs, cats, cattle, horses, sheep, and the like.

Dosages for the lipid-therapeutic agent particles of the present invention will depend on the ratio of therapeutic agent to lipid and the administrating physician's opinion based on age, weight, and condition of the patient.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In particular embodiments, the therapeutic agent is selected from an siRNA, a microRNA, an antisense oligonucleotide, an antagomir and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antagomir, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In another related embodiment, the present invention includes a method of treating a disease or disorder characterized by underexpression of a polypeptide in a subject, comprising providing to the subject a pharmaceutical composition of the present invention, wherein the therapeutic agent is a plasmid that encodes the polypeptide or a functional variant or fragment thereof.

In further embodiments, the pharmaceutical composition is provided to the subject in combination with a vaccine or antigen. Thus, the present invention itself provides vaccines comprising a lipid particle of the present invention, which comprises an immunostimulatory oligonucleotide, and is also associated with an antigen to which an immune response is desired. In particular embodiments, the antigen is a tumor antigen or is associated with an infective agent, such as, e.g., a virus, bacteria, or parasite.

A variety of tumor antigens, infections agent antigens, and antigens associated with other disease are well known in the art and examples of these are described in references cited herein. Examples of antigens suitable for use in the present invention include, but are not limited to, polypeptide antigens and DNA antigens. Specific examples of antigens are Hepatitis A, Hepatitis B, small pox, polio, anthrax, influenza, typhus, tetanus, measles, rotavirus, diphtheria, pertussis, tuberculosis, and rubella antigens. In a preferred embodiment, the antigen is a Hepatitis B recombinant antigen. In other aspects, the antigen is a Hepatitis A recombinant antigen. In another aspect, the antigen is a tumor antigen. Examples of such tumor-associated antigens are MUC-1, EBV antigen and antigens associated with Burkitt's lymphoma. In a further aspect, the antigen is a tyrosinase-related protein tumor antigen recombinant antigen. Those of skill in the art will know of other antigens suitable for use in the present invention.

Tumor-associated antigens suitable for use in the subject invention include both mutated and non-mutated molecules that may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Pathogens include, but are not limited to, infectious agents, e.g., viruses, that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Also, gram negative and gram positive bacteria serve as antigens in vertebrate animals. Such gram positive bacteria include, but are not limited to *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borelia burgdorferi, Legionella pneumophilia, Mycobacteria* sps (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus (anaerobic sps.), Streptococcus pneumoniae*, pathogenic *Campylobacter* sp., *Enterococcus* sp., *Haemophilus infuenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli.*

Additional examples of pathogens include, but are not limited to, infectious fungi that infect mammals, and more particularly humans. Examples of infectious fingi include, but are not limited to: *Cryptococcus neoformans, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale,* and *Plasmodium vivax*. Other infectious organisms (i.e., protists) include *Toxoplasma gondii*.

In one aspect the invention provides a method of modulating the expression of a target gene in a cell, comprising providing to said cell a composition of the present invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide including a nucleotide bearing such replacement moiety. For example, without limitation, a nucleotide including inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences including such replacement moieties are embodiments of the invention.

By "Factor VII" as used herein is meant a Factor VII mRNA, protein, peptide, or polypeptide. The term "Factor VII" is also known in the art as AI132620, Cf7, Coagulation factor VII precursor, coagulation factor VII, FVII, Serum prothrombin conversion accelerator, FVII coagulation protein, and eptacog alfa.

As used herein, "target sequence" refers to a contiguous portion of the nucleotide sequence of an mRNA molecule formed during the transcription of the gene, including mRNA that is a product of RNA processing of a primary transcription product.

As used herein, the term "strand including a sequence" refers to an oligonucleotide including a chain of nucleotides that is described by the sequence referred to using the standard nucleotide nomenclature.

As used herein, and unless otherwise indicated, the term "complementary," when used in the context of a nucleotide pair, means a classic Watson-Crick pair, i.e., GC, AT, or AU. It also extends to classic Watson-Crick pairings where one or both of the nucleotides has been modified as described herein, e.g., by a rbose modification or a phosphate backpone modification. It can also include pairing with an inosine or other entity that does not substantially alter the base pairing properties.

As used herein, and unless otherwise indicated, the term "complementary," when used to describe a first nucleotide sequence in relation to a second nucleotide sequence, refers to the ability of an oligonucleotide or polynucleotide including the first nucleotide sequence to hybridize and form a duplex structure under certain conditions with an oligonucleotide or polynucleotide including the second nucleotide sequence, as will be understood by the skilled person. Complementarity can include, full complementarity, substantial complementarity, and sufficient complementarity to allow hybridization under physiological conditions, e.g., under physiologically relevant conditions as may be encountered inside an organism. Full complementarity refers to complementarity, as defined above for an individual pair, at all of the pairs of the first and second sequence. When a sequence is "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. Substantial complementarity can also be defined as hybridization under stringent conditions, where stringent conditions may include: 400 mM NaCl, 40 mM PIPES pH 6.4, 1 mM EDTA, 50° C. or 70° C. for 12-16 hours followed by washing. The skilled person will be able to determine the set of conditions most appropriate for a test of complementarity of two sequences in accordance with the ultimate application of the hybridized nucleotides.

However, where two oligonucleotides are designed to form, upon hybridization, one or more single stranded overhangs, such overhangs shall not be regarded as mismatches with regard to the determination of complementarity. For example, a dsRNA including one oligonucleotide 21 nucleotides in length and another oligonucleotide 23 nucleotides in length, wherein the longer oligonucleotide includes a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary", "substantially complementary" and sufficient complementarity to allow hybridization under physiological conditions, e.g., under physiologically relevant conditions as may be encountered inside an organism, may be used hereinwith respect to the base matching between the sense strand and the antisense strand of a dsRNA, or between the antisense strand of a dsRNA and a target sequence, as will be understood from the context of their use.

As used herein, a polynucleotide which is "complementary, e.g., substantially complementary to at least part of" a messenger RNA (mRNA) refers to a polynucleotide which is complementary, e.g., substantially complementary, to a contiguous portion of the mRNA of interest (e.g., encoding Factor VII). For example, a polynucleotide is complementary to at least a part of a Factor VII mRNA if the sequence is substantially complementary to a non-interrupted portion of an mRNA encoding Factor VII.

The term "double-stranded RNA" or "dsRNA", as used herein, refers to a ribonucleic acid molecule, or complex of ribonucleic acid molecules, having a duplex structure including two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker" The RNA strands may have the same or a different number of nucleotides. The maximum number of base pairs is the number of nucleotides in the shortest strand of the dsRNA. In addition to the duplex structure, a dsRNA may comprise one or more nucleotide overhangs. A dsRNA as used herein is also referred to as a "small inhibitory RNA," "siRNA," "siRNA agent," "iRNA agent" or "RNAi agent."

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand. The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of," in as far as they refer to the Factor VII gene, herein refer to the at least partial suppression of the expression of the Factor VII gene, as manifested by a reduction of the amount of mRNA transcribed from the Factor VII gene which may be isolated from a first cell or group of cells in which the Factor VII gene is transcribed and which has or have been treated such that the expression of the Factor VII gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Factor VII gene transcription, e.g. the amount of protein encoded by the Factor VII gene which is secreted by a cell, or the number of cells displaying a certain phenotype, e.g. apoptosis. In principle, Factor VII gene silencing may be determined in any cell expressing the target, either constitutively or by genomic engineering, and by any appropriate assay. However, when a reference is needed in order to determine whether a given siRNA inhibits the expression of the Factor VII gene by a certain degree and therefore is encompassed by the instant invention, the assays provided in the Examples below shall serve as such reference.

For example, in certain instances, expression of the Factor VII gene is suppressed by at least about 20%, 25%, 35%, 40% or 50% by administration of the double-stranded oligonucleotide of the invention. In a preferred embodiment, the Factor VII gene is suppressed by at least about 60%, 70%, or 80% by administration of the double-stranded oligonucleotide of the invention. In a more preferred embodiment, the Factor VII gene is suppressed by at least about 85%, 90%, or 95% by administration of the double-stranded oligonucleotide of the invention.

The terms "treat," "treatment," and the like, refer to relief from or alleviation of a disease or disorder. In the context of the present invention insofar as it relates to any of the other conditions recited herein below (e.g., a Factor VII-mediated condition other than a thrombotic disorder), the terms "treat," "treatment," and the like mean to relieve or alleviate at least one symptom associated with such condition, or to slow or reverse the progression of such condition.

A "therapeutically relevant" composition can alleviate a disease or disorder, or a symptom of a disease or disorder when administered at an appropriate dose.

As used herein, the term "Factor VII-mediated condition or disease" and related terms and phrases refer to a condition or disorder characterized by inappropriate, e.g., greater than normal, Factor VII activity. Inappropriate Factor VII functional activity might arise as the result of Factor VII expression in cells which normally do not express Factor VII, or increased Factor VII expression (leading to, e.g., a symptom of a viral hemorrhagic fever, or a thrombus). A Factor VII-mediated condition or disease may be completely or partially mediated by inappropriate Factor VII functional activity. However, a Factor VII-mediated condition or disease is one in which modulation of Factor VII results in some effect on the underlying condition or disorder (e.g., a Factor VII inhibitor results in some improvement in patient well-being in at least some patients).

A "hemorrhagic fever" includes a combination of illnesses caused by a viral infection. Fever and gastrointestinal symptoms are typically followed by capillary hemorrhaging.

A "coagulopathy" is any defect in the blood clotting mechanism of a subject.

As used herein, a "thrombotic disorder" is any disorder, preferably resulting from unwanted FVII expression, including any disorder characterized by unwanted blood coagulation.

As used herein, the phrases "therapeutically effective amount" and "prophylactically effective amount" refer to an amount that provides a therapeutic benefit in the treatment, prevention, or management of a viral hemorrhagic fever, or an overt symptom of such disorder, e.g., hemorraging, fever, weakness, muscle pain, headache, inflammation, or circulatory shock. The specific amount that is therapeutically effective can be readily determined by ordinary medical practitioner, and may vary depending on factors known in the art, such as, e.g. the type of thrombotic disorder, the patient's history and age, the stage of the disease, and the administration of other agents.

As used herein, a "pharmaceutical composition" includes a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR", heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

"Halogen" means fluoro, chloro, bromo and iodo.

In one embodiment, the methods of the invention may require the use of protecting groups. Protecting group methodology is well known to those skilled in the art (see, for example, PROTECTIVE GROUPS IN ORGANIC SYNTHESIS, Green, T. W. et. al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In one embodiment an "alcohol protecting group" is used. An "alcohol protecting group" is any group which decreases or eliminates unwanted reactivity of an alcohol functional group. Protecting groups can be added and removed using techniques well known in the art.

The compounds of the present invention may be prepared by known organic synthesis techniques, including the methods described in more detail in the Examples.

EXAMPLES

The following examples are offered to illustrate, but not to limit the claimed invention.

Example 1. Synthesis of Carbohydrate Building Blocks for Conjugation

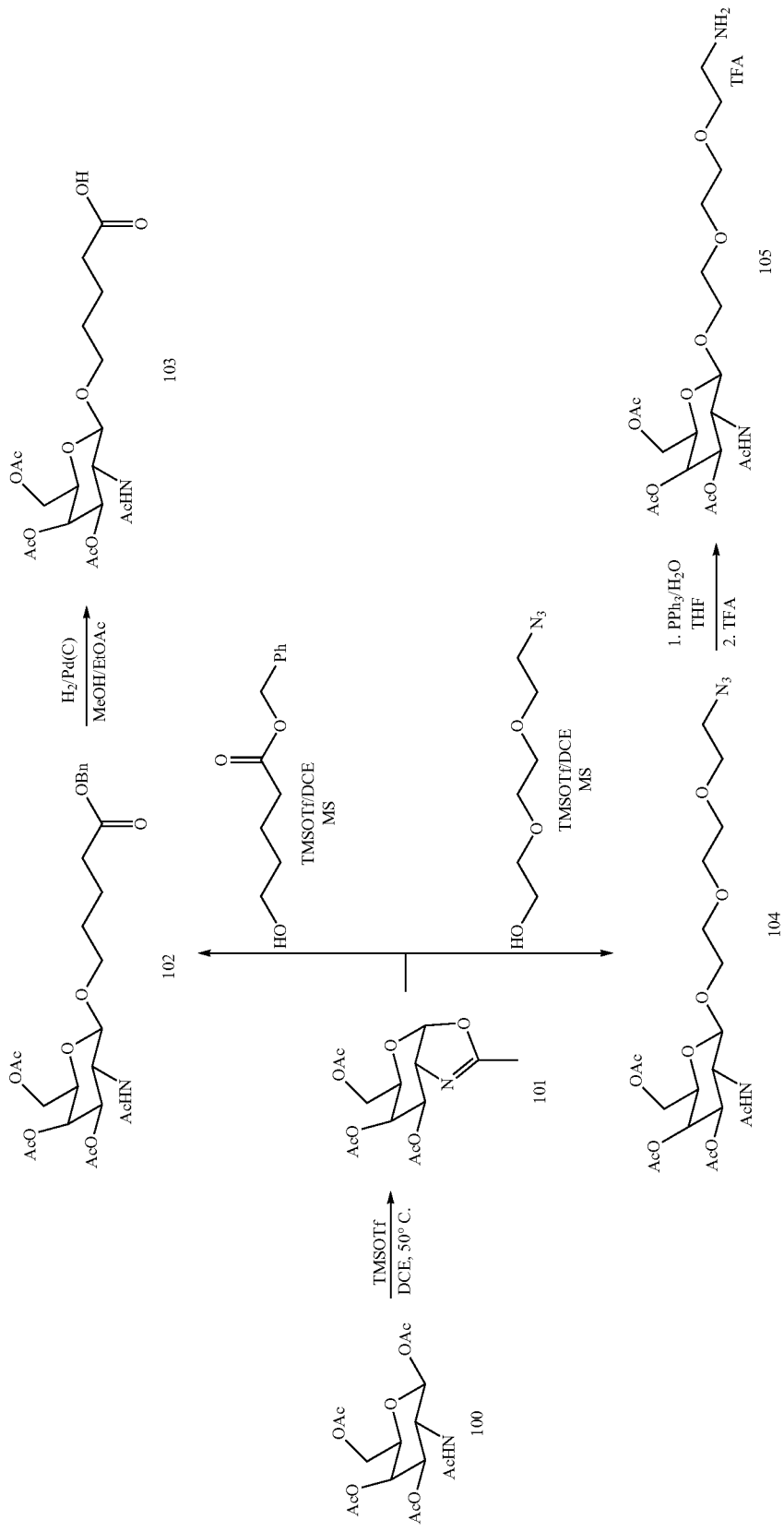

Preparation of 101:

Galactosamine pentaacetate 100 (52.00 g, 133.63 mmol) was taken in dichloroethane (300 mL) at ambient temperature. TMSOTf (44.55 g, 200.44 mmol) was added that and the mixture stirred at 50 C for 90 minutes in a water bath, heating stopped and the mixture stirred overnight at room temperature. It was poured in to an ice cold sodium bicarbonate solution; extracted with dichloromethane, washed with water and dried over sodium sulfate. Solvents were removed the residue dried under high vacuum overnight to get the compound as dark gum (44.50 g, quantitative). It was used for next reaction with out any further purification. $^1$H NMR and MALDI confirmed the product formation. MS: Calculated for $C_{14}H_{19}NO_8$, 329.11. Found 352.1 (M+Na).

Preparation of 102:

Compound 101 (43.70 g, 133.56 mmol) and the benzyl ester (41.71 g, 200.34 mmol) were dissolved in dichloroethane (300 mL), molecular sieves (50 g) was added to that and stirred for 30 minutes. TMSOTf (14.50 g, 66.78 mmol) was added to that and the mixture stirred for overnight at room temperature. It was poured in to an ice cold solution of sodium bicarbonate and extracted with dichloromethane, washed with water and dried over sodium sulfate. Solvents were removed and the residue purified by chromatography (gradient elution: 20-100% ethylacetate/hexanes) to get the required compound as light brown gummy liquid (60.50 g, 86%). 1HNMR, $^{13}$CNMR MS: Calculated for $C_{26}H_{35}NO_{11}$, 537.22. Found 560.21 (M+Na).

Preparation 103:

Compound 102 (60.00 g, 111.68 mmol) was dissolved in a mixture of Methanol/ethylacetate and degassed with argon. Pd/C (6.00 g, 10 wt % Degussa, wet type) was added and hydrogenated under balloon pressure overnight. Filtered through a small pad of celite; washed with methanol and dried under high vacuum overnight to get the product (48.85 g, 98%). 1HNMR, $^{13}$CNMR MS: Calculated for $C_{19}H_{29}NO_{11}$, 447.17. Found 469.9 (M+Na).

Preparation of 104:

Compound 101 (42.30 g, 128.43 mmol) and the azido ethanol (26 g, 192.45 mmol) were dissolved in dichloroethane (300 mL), molecular sieves (50 g) were added to that and stirred for 30 minutes. TMSOTf (14.29 g, 64.21 mmol) was added to that and the mixture stirred for overnight at room temperature. It was poured in to an ice cold solution of sodium bicarbonate and extracted with dichloromethane, washed with water and dried over sodium sulfate. Solvents were removed and the residue purified by chromatography (gradient elution: 20-100% ethyl acetate/hexanes, followed by 5-10% Methanol/ethylacetate) to get the required compound as light brown gummy liquid (59.23 g, 91.00%). $^1$HNMR, $^{13}$CNMR MS: Calculated for $C_{20}H_{32}N_4O_{11}$, 504.21. Found 527.1 (M+Na).

Preparation of 105:

Compound 104 (9.33 g, 18.50 mmol) was dissolved in THF (100 mL) to that PPh$_3$ (5.97 g, 22.2 mmol) was added and the mixture stirred for 48 h. TLC checked to see complete disappearance of starting material. Water (1 mL, 55 mmol) and stirred for another 24 h. TFA (2.85 mL, 23.12 mmol) and toluene (40 mL) were added and the solvents were removed under reduced pressure. The residue was co-evaporated with toluene (2×40 mL) two times and dried under high vacuum. It was used for the next reaction in the same day. MS: Calculated for $C_{20}H_{34}N_2O_{11}$, 478.22. Found 500.8 (M+Na).

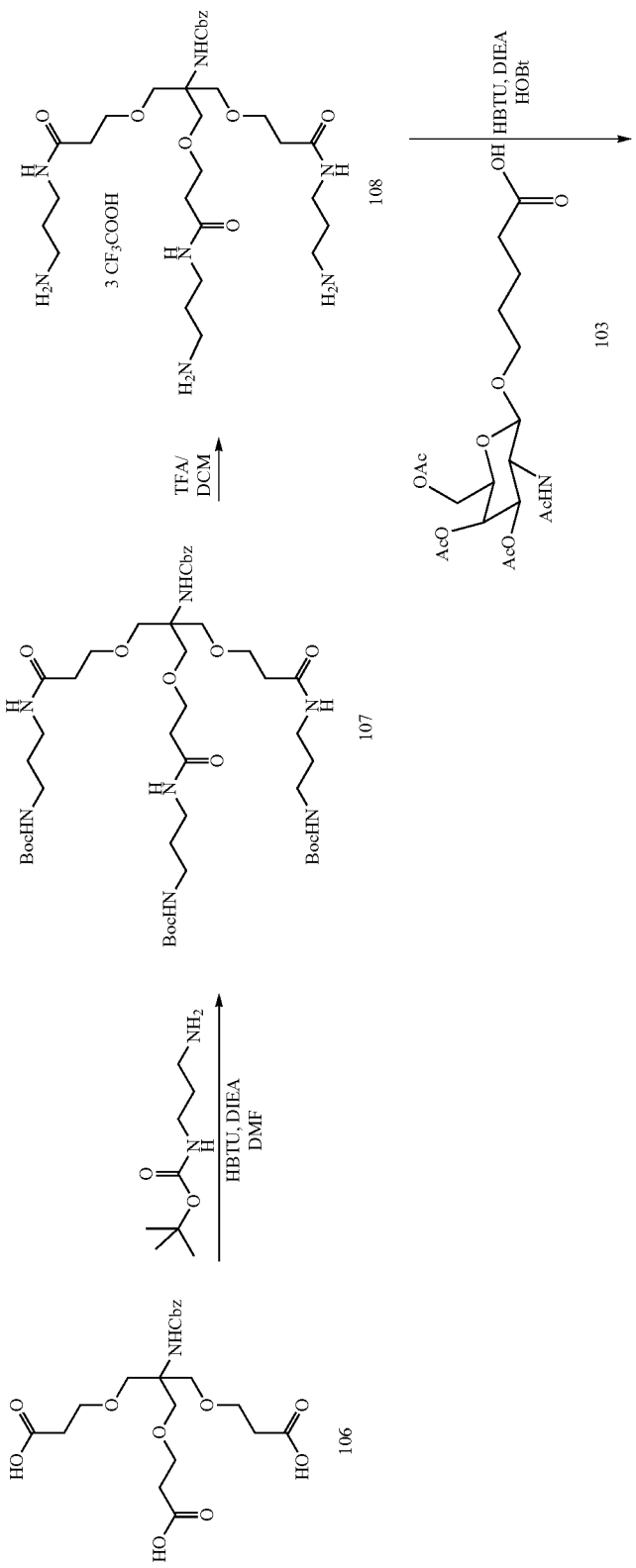

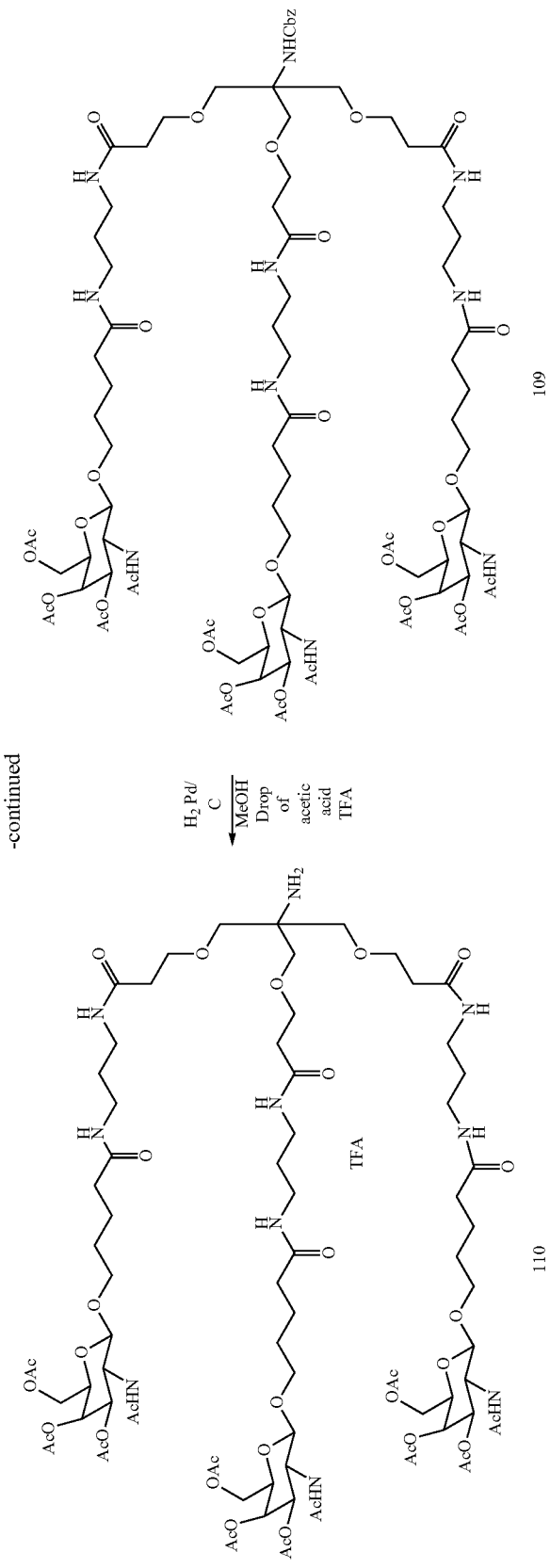

Preparation of 107:

Compound 106 (JOC 2002) (6.94 g, 14.73 mmol) and monoboc propyl amine (10.26 g, 58.89 mmol) were dissolved in DMF (100 mL), to that HBTU (17.26 g, 45.50 mmol) and DIEA (15.36 mL, 88.14 mmol) were added and stirred overnight. Reaction mixture was poured in to ice-water mixture and extracted with dichloromethane, washed with sodium bicarbonate solution, brine and dried over sodium sulfate. Solvents were removed and the residue was purified by chromatography (Ethyl acetate, followed by 2-10% MeOH/DCM) to get the product as white fluffy solid (10.49 g, 76%). MS: Calculated for $C_{45}H_{77}N_7O_{14}$, 939.55. Found 940.53 (M+H).

Preparation of 108:

Compound 107 (2.40 g, 2.56 mmol) was dissolved in dichloromethane (10 mL), to that a mixture of TFA/DCM (1:4, 10 mL) was added and stirred for 30 minutes. Reaction was monitored by mass spectra. 100 mL of toluene was added and removed the solvent under reduced pressure. The residue was co-evaporated two times with toluene (2×100 mL) and dried under high vacuum to get the compound as its TFA salt (white gum, 2.47 g, 99%). It was used for the next reaction with out any further purification. MS: Calculated for $C_{30}H_{53}N_7O_8$, 639.40. Found 640.45 (M+H).

Preparation of 109:

GalNAc acid 103 (4.00 g, 8.99 mmol) was dissolved in DMF (50 mL); HBTU (3.75 g, 9.88 mmol), HOBt (1.34 g, 9.88 mmol) and DIEA (5 mL, 3.2 eq) was added to that and stirred for 3-4 minutes. A solution of 108 (2.47 g, 2.50 mmol) in DMF was added to that and stirred the reaction mixture overnight. TLC was checked, solvents were removed under reduced pressure. The residue was dissolved in dichloromethane, washed with sodium bicarbonate solution (50 mL), water (100 mL) and dried over sodium sulfate. Solvents were removed and the residue was purified by chromatography (ethyl acetate, followed by gradient elution 5-15% MeOH/DCM) to get the product 109 as a white solid (4.20 g, 87%). MS: Calculated for $C_{87}H_{134}N_{10}O_8$, 1926.89. Found 1949.5 (M+Na).

Preparation of 110:

GalNAc derivative 109 (7.50 g, 4.18 mmol) was taken in methanol (50 mL) degassed with argon. Pd/C (0.800 g, 10 wt % Degussa type wet) and couple of drops of acetic acid were added; the mixture was hydrogenated under balloon pressure overnight. Reaction mixture was filtered through a small pad of celite, washed with methanol. TFA (0.465 mL, 5.22 mmol) was added and removed the solvent under reduced pressure. The residue was co-evaporated with toluene (2 times) and dried under high vacuum overnight to get the compound as TFA salt (pale yellow solid, 7.30 g, 99%). MS: Calculated for $C_{79}H_{128}N_{10}O_{36}$, 1792.85. Found 1815.9 (M+Na).

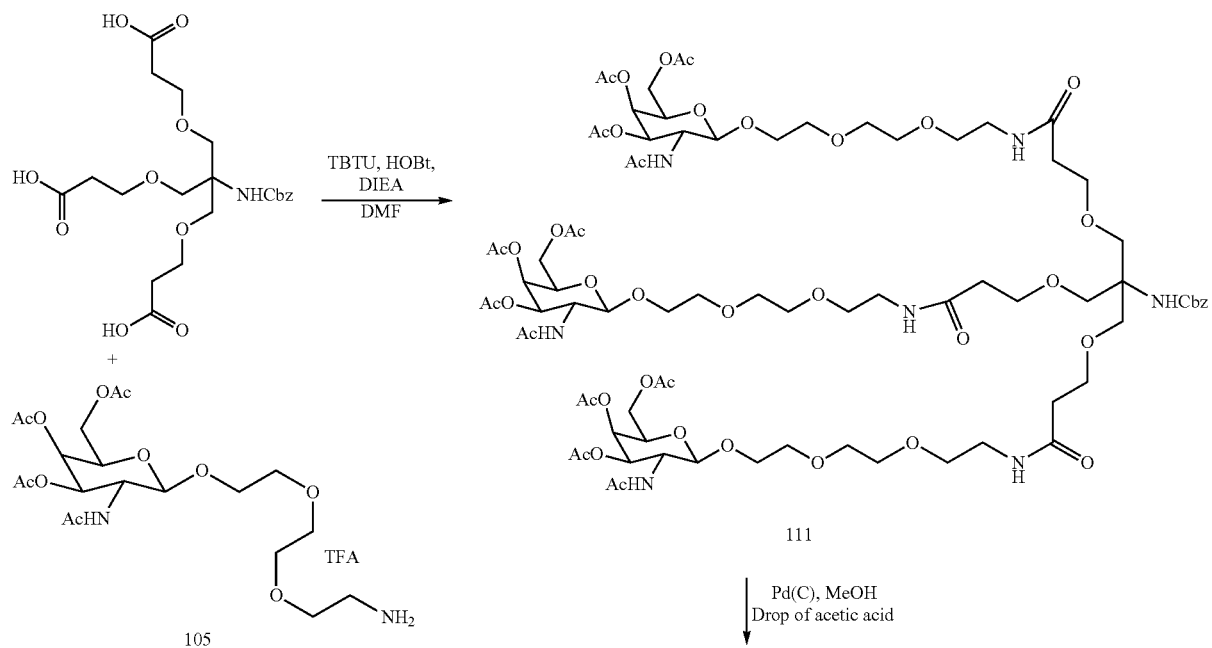

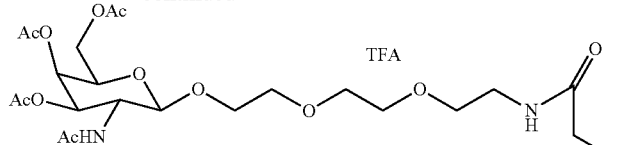

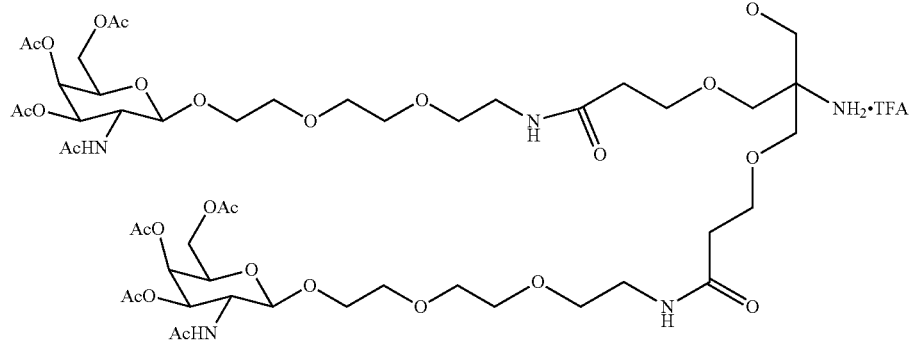

112

Preparation of 111:

The tricarboxylic acid 106 (2.17 g, 4.625 mmol) and amine (18.50 mmol, crude from previous reaction) was dissolved in DMF (100 mL). To that TBTU (5.34 g, 16.63 mmol), HOBt (2.24 g, 16.59 mmol) and DIEA (5.64 mL, 32.36 mmol) was added and stirred the reaction mixture for 24 h. After stirring 24 hrs an additional amount of DIEA (4 mL) was added continued stirring. After 48 hrs solvents were removed under reduced pressure, the residue was dissolved in dichloromethane, washed with 1M phosphoric acid solution, sodium bicarbonate solution, water and dried over sodium sulfate. Solvents were removed and the residue was purified by chromatography (ethyl acetate, followed by 3-15% MeOH/DCM) to get the required compound III as a white solid (5.80 g, 68%) MS: Calculated for $C_{81}H_{125}N_7O_{41}$, 1851.79. Found 1874.20 (M+Na).

Preparation of 112:

GalNAc derivative 111 (5.75 g, 3.09 mmol) was taken in methanol (100 mL) degassed with argon. Pd/C (0.600 g, 10 wt % Degussa type wet) and couple of drops of acetic acid were added; the mixture was hydrogenated under balloon pressure for 36 hrs. Reaction mixture was filtered through a small pad of celite, washed with methanol. TFA (0.354 mL, 1.25 eq) and toluene (30 mL) was added and removed the solvent under reduced pressure. The residue was co-evaporated with toluene (2 times) and dried under high vacuum overnight to get the compound as TFA salt (5.70 g, crude). MS: Calculated for $C_{81}H_{125}N_7O_{41}$, 1717.75. Found 1740.5 (M+Na).

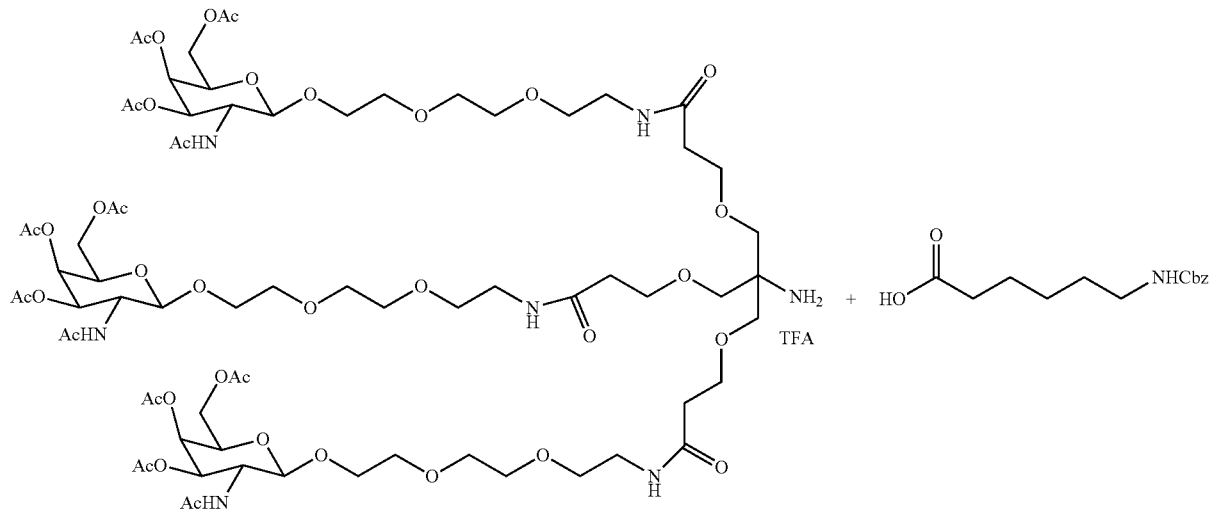

112

HBTU, DIEA
DMF

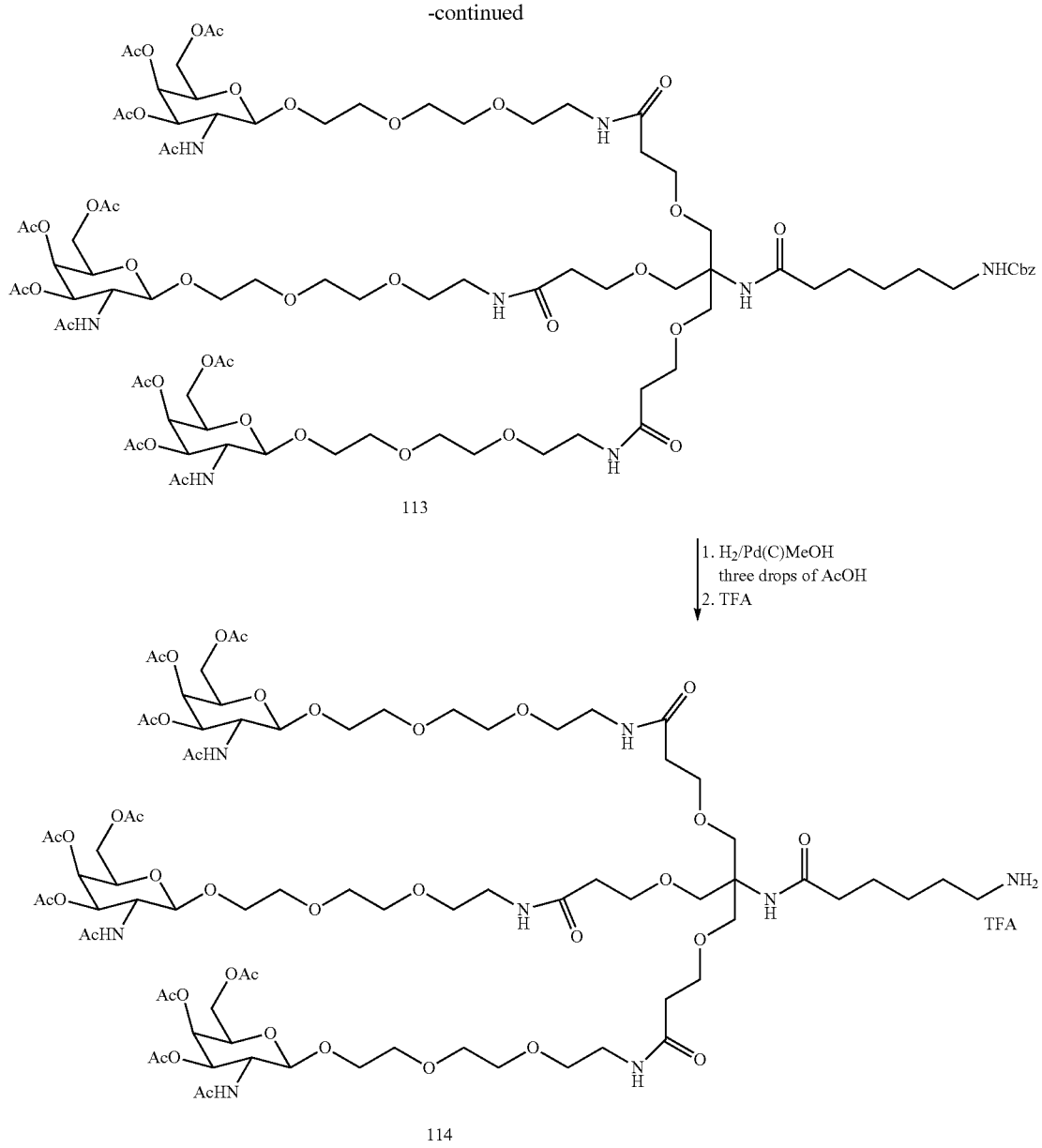

Preparation of 113:

Z-amino caproic acid (2.19 g, 8.25 mmol) was dissolved in DMF (50 mL). To that HBTU (3.13 g, 8.25 mmol) and DIEA (7.19 mL, 5.00 eq.) was added and stirred the mixture for few minutes. GalNAc amine 112 (10.10 g, 5.52 mmol) was dissolved in 50 ml of DMF was added to that and stirred for 48 hrs. TLC and MALDI were checked for product formation. Solvents were removed and the residue was dissolved in DCM, washed with NaHCO$_3$ solution and water. Dried over sodium sulfate and removed the solvents under reduced pressure. Residue was purified by chromatography (eluted with ethyl acetate, followed by gradient elution of 5-15% MeOH/DCM) to get the required compound 113 as off white solid (6.20 g, 57%). MS: Calculated for $C_{87}H_{136}N_8O_{42}$, 1964.88. Found 1987.75 (M+Na).

Preparation of 114:

Compound 113 (6.10 g, 3.10 mmol) was dissolved in Methanol (50 mL), to that 1 mL of acetic acid was added. Degassed the reaction mixture, Pd/C (0.700 g, 10 wt % Degussa wet type) was added to that and hydrogenated under balloon pressure for 36 hrs. Reaction mixture was filtered through a small pad of celite, washed with MeOH. To that 1.25 eq of TFA and toluene (50 mL) were added and removed solvents under reduced pressure. The residue was co-evaporated with toluene two times and dried under high vacuum overnight night to get the required compound as an off white solid (6.10 g, quantitative). This compound used as such for the next reaction with out any further purification. MS: Calculated for $C_{79}H_{130}N_8O_{40}$, 1830.84. Found 1853.81 (M+Na).

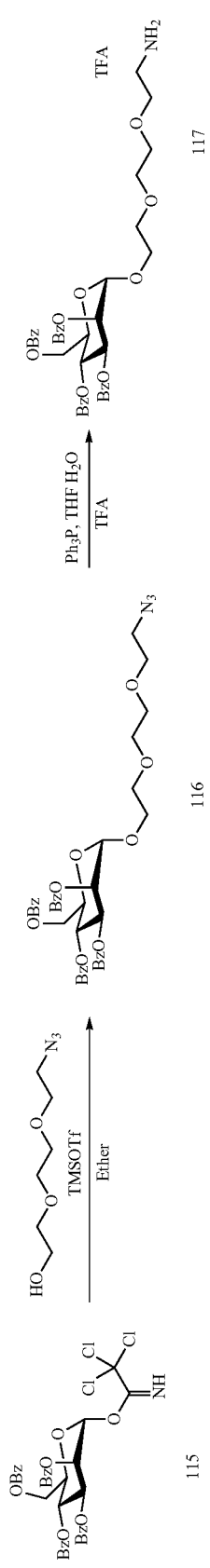
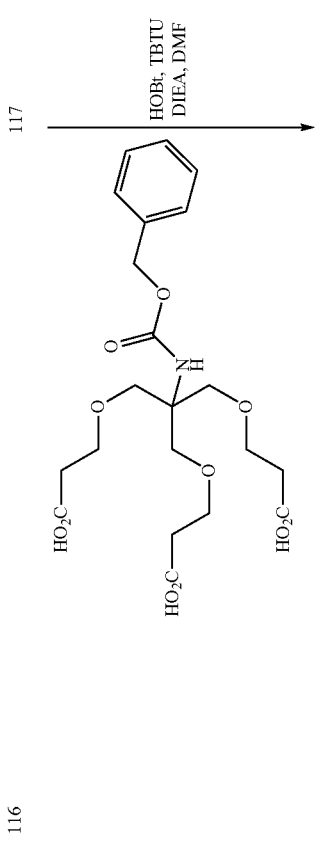
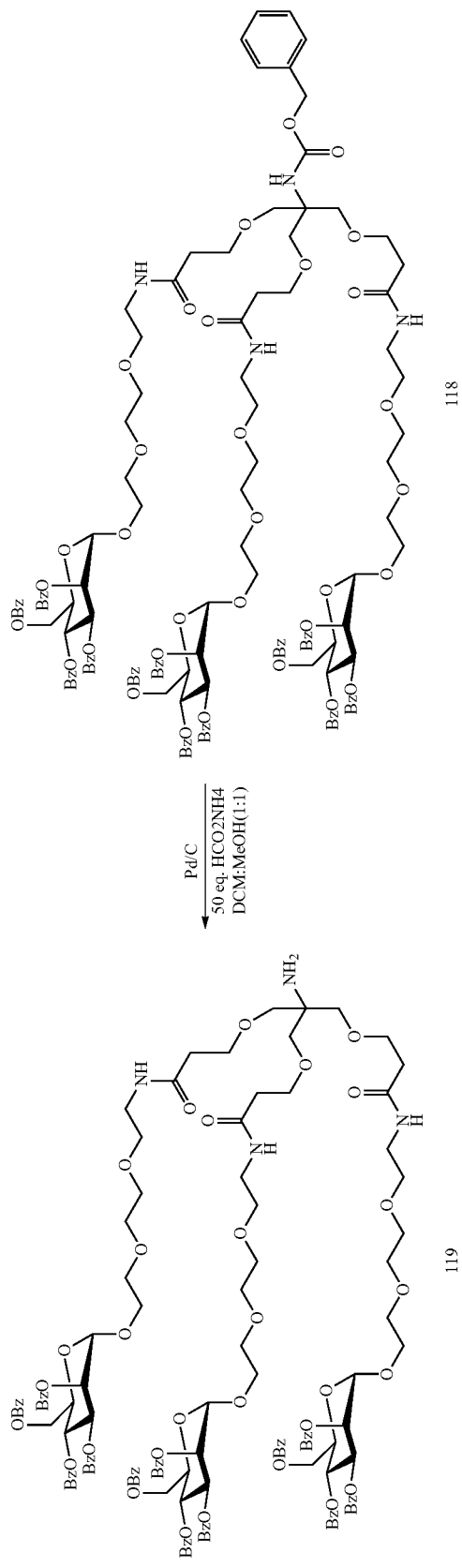

Preparation of 116:

Mannose trichloroacetimidate 115 (15.00 g, 20.24 mmol) and azido alcohol (4.25 g, 1.2 eq) were dissolved in Toluene and aziotroped two times. The residue dried under high vacuum overnight. Anhy. diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (20-50% EtOAc/Hexane) to get compound as colorless liquid (8.36 g, 55%). MS: Calculated for $C_{40}H_{39}N_3O_{12}$, 753.25. Found 776.23 ((M+Na).

purified by chromatography (ethyl acetate, followed by 3-15% MeOH/DCM) to get the required compound 118 as a white solid (41.95 g, 67%) MS: Calculated for $C_{141}H_{146}N_4O_{44}$, 2598.93. Found 2621.89 (M+Na).

Preparation of 119:

Compound 133 (3.05 g, 1.176 mmol) was dissolved in a mixture of DCM/MeOH. To that 50 eq. of ammoniumformate was added followed by 5% Pd/C (1.5 g, 50 wt %) and stirred for 8 hrs at ambient temperature. It was filtered through small pad of celite, washed with MeOH/DCM, solvent was removed and residue dried under high vacuum over night to the compound as a white solid (2.65 g, 92%). MS: Calculated for $C_{133}H_{140}N_4O_{42}$, 2464.89. Found 2487.92 (M+Na).

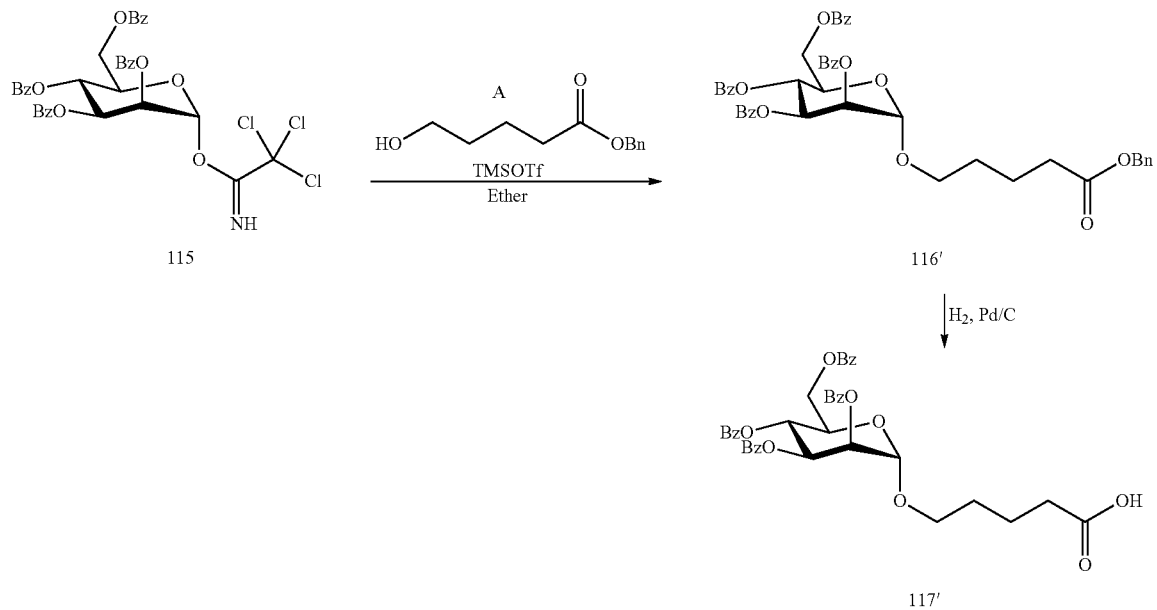

Preparation of 117:

Compound 116 (8.30 g, 11.01 mmol) was dissolved in anhy. THF (70 mL), to that $PPh_3$ (3.46 g, 1.2 eq) was added and the mixture stirred for two days at ambient temperature. Water (1 mL) was added to that and stirred the mixture for another 24 hrs. Reaction was monitored by TLC. Trifluoro acetic acid (1.06 mL, 1.25 eq) and toluene (50 mL) was added to that. Solvents were removed under reduced pressure and residue was co-evaporated toluene two times and dried under high vacuum. This used as such for the next reaction without further purification. MS: Calculated for $C_{40}H_{41}NO_{12}$, 727.26. Found 750.23 ((M+Na).

Preparation of 118:

Tricarboxylic acid (11.05 g, 23.45 mmol), and amine (68.19 g, 94 mmol, crude from previous reaction) was dissolved in DMF (200 mL). To that TBTU (27.09 g, 84 mmol), HOBt (11.34 g, 84 mmol) and DIEA (28 mL, 160 mmol) was added and stirred the reaction mixture for 24 h. After stirring 24 hrs an additional amount of DIEA (28 mL) was added continued stirring. After 48 hrs solvents were removed under reduced pressure, the residue was dissolved in dichloromethane, washed with 1M phosphoric acid solution, sodium bicarbonate solution, and water and dried over sodium sulfate. Solvents were removed and the residue was Preparation of 116':

Mannose trichloroacetimidate 115 (15.23 g, 20.55 mmol) and A (4.36 g, 1.02 eq.) were dissolved in Toluene and aziotroped two times. The residue dried under high vacuum overnight. Anhy. diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (hexane, 15-25% EtOAc/Hexane) to get compound as colorless liquid (14.52 g, 90%). MS: Calculated for $C_{46}H_{42}O_{12}$, 786.27. Found 809.25 ((M+Na).

Preparation of 117':

Mannose benzyl ester (14.30 g, 18.17 mmol) was dissolved in Ethyl acetate (100 mL) to that two drops of acetic acid was added. Degassed, Pd/C (1.50 g, 10 wt % Degussa wet type) was added and hydrogenated under balloon pressure for 24 hrs. Reaction was monitored by TLC and MALDI. It was filtered through a small pad of celite, washed with ethyl acetate. Solvent was removed and the residue dried under high vacuum to get the compound as color less oil (11.20 g, 90%). MS: Calculated for $C_{39}H_{36}O_{12}$, 696.22. Found 719.18 ((M+Na).

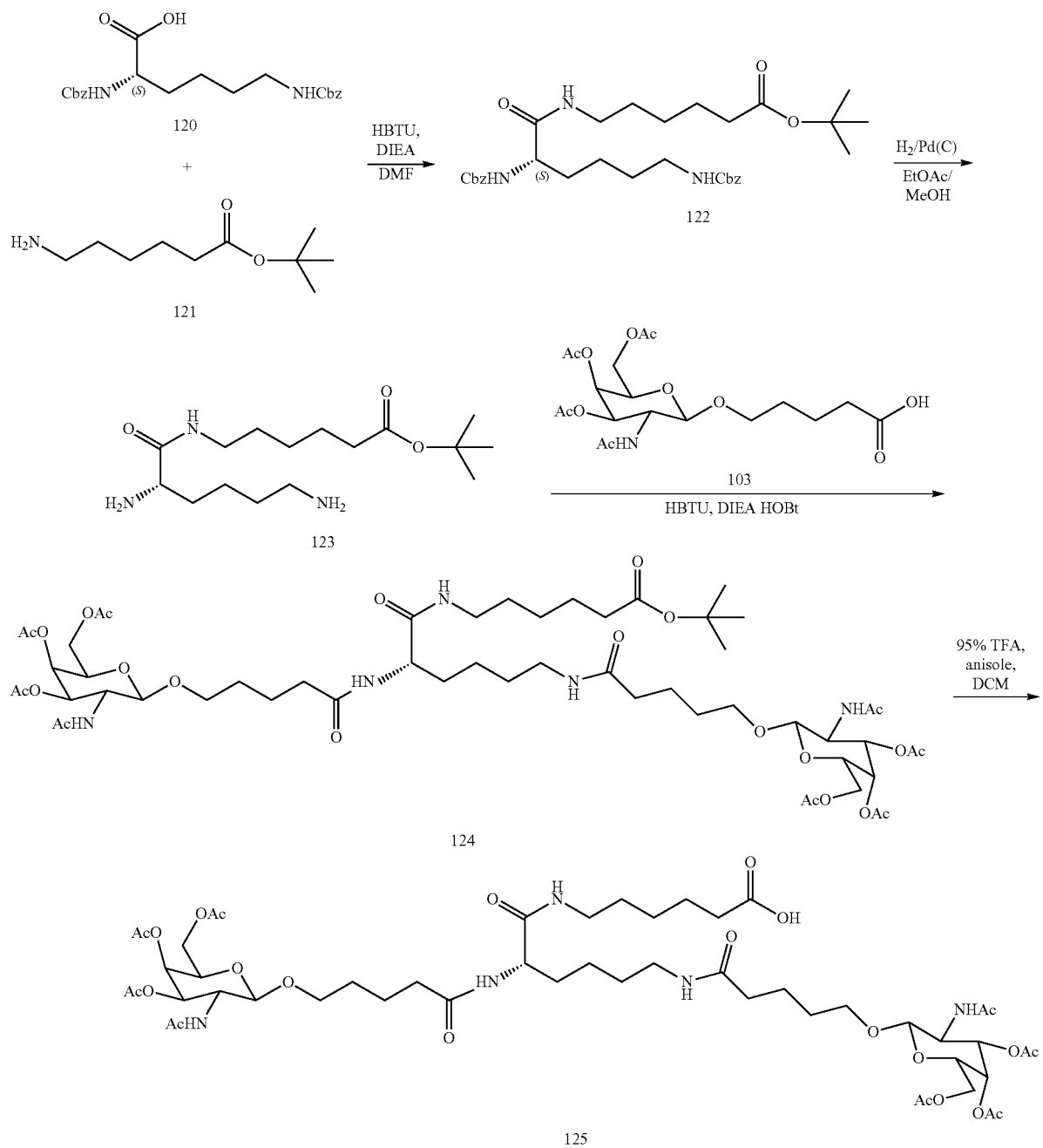

Preparation of 122:

Compound 120 (26.55 g, 64.06 mmol) and 121 (10.00 g, 53.43 mmol) were dissolved in DMF (150 mL). To that HBTU (24.12 g, 64 mmol) and DIEA (46 mL, 5 eq) were added and stirred the reaction mixture overnight. TLC checked and the mixture was added to ice cold water and extracted with a mixture of ether and ethyl acetate dried over sodium sulfate. Solvents were removed and the crude product was purified by chromatography (20-50% ethylacetate/Hexane) to get the required product as an off white solid (23.20 g, 74%). MS. MW calc. for $C_{32}H_{45}N_3O_7$: 583.72. Found 584.73 (M+H).

Preparation of 123:

Compound 122 (3.30 g, 5.65 mmol) was dissolved in a mixture of ethyl acetate/MeOH and hydrogenated under balloon pressure using Pd/C (500 mg) as catalyst overnight. Filtered through a small pad of celite and removed the solvent, this product used for the next reaction without further purification. MS. MW calc. for $C_{16}H_{33}N_3O_3$: 315.25. Found 316.26 (M+H).

Preparation of 124:

Compound 123 (5.65 mmol) and GalNAc acid 103 (5.81 g, 12.99 mmol) were dissolved in DMF (80 mL). To that HBTU (4.97 g, 13.10 mmol) and DIEA (7.00 mL, 3 eq) were added and stirred the reaction mixture overnight. Solvents were removed and the residue dissolved in DCM and washed with water and brine, dried over sodium sulfate. Solvents were removed and the crude product was purified by chromatography (EtOAc, followed by 3-10% MeOH/

DCM) to get the required product as an off white solid (5.25 g, 79%). MS. MW calc. for $C_{54}H_{87}N_5O_{23}$: 1173.58. Found 1196.60 (M+Na).

Preparation of 125:

Biantineary GalNAc derivative 124 (5.15 g, 4.40 mmol) was dissolved in 15 mL of anhydrous DCM, to that 3 mL of anisole and 30 mL of TFA were added and stirred the reaction mixture for 2 hrs at ambient temperature. TLC checked and toluene was added to the reaction mixture, removed the solvents under reduced pressure. Co-evaporated with toluene two times and the residue dissolved in DCM, washed with water, dried over anhydrous sodium sulfate. Crude product was purified by filtration column (10% MeOH/DCM) to get the required product as pale brown solid (4.40 g, 91%). MS. MW calc. for $C_{50}H_{79}N_5O_{23}$: 1117.52. Found 1140.62 (M+Na).

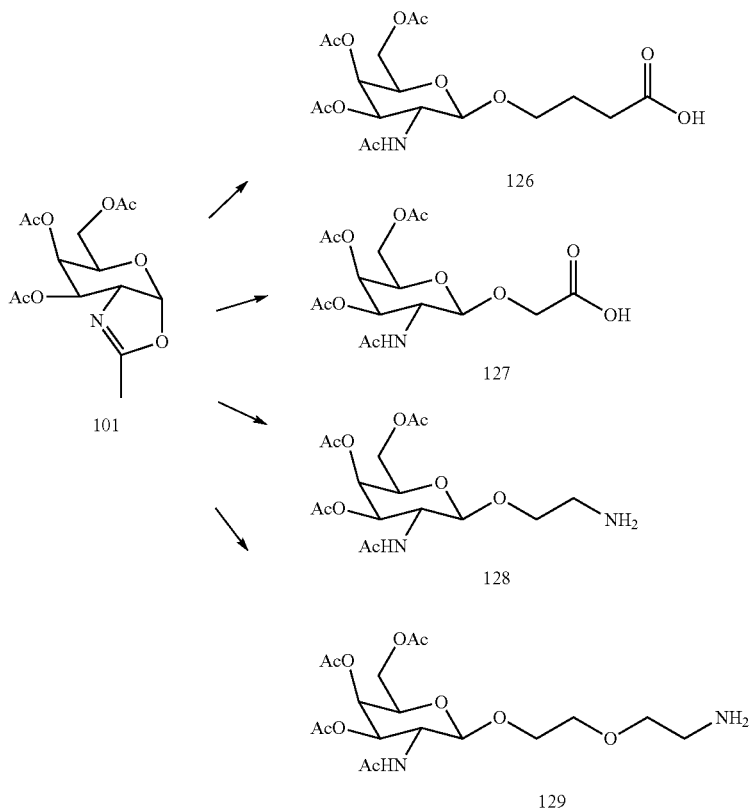 [SMILES: CC(=O)NC1C(OCCCC(=O)O)OC(COC(C)=O)C(OC(C)=O)C1OC(C)=O ; CC(=O)OCC1OC2OC(C)=NC2C(OC(C)=O)C1OC(C)=O ; CC(=O)NC1C(OCC(=O)O)OC(COC(C)=O)C(OC(C)=O)C1OC(C)=O ; CC(=O)NC1C(OCCN)OC(COC(C)=O)C(OC(C)=O)C1OC(C)=O ; CC(=O)NC1C(OCCOCCN)OC(COC(C)=O)C(OC(C)=O)C1OC(C)=O]

Building blocks 126 and 127 are synthesized using a procedure similar to that for synthesis of 103. Building blocks 128 and 129 are synthesized using a procedure similar to that for synthesis of 105.

Scheme 2

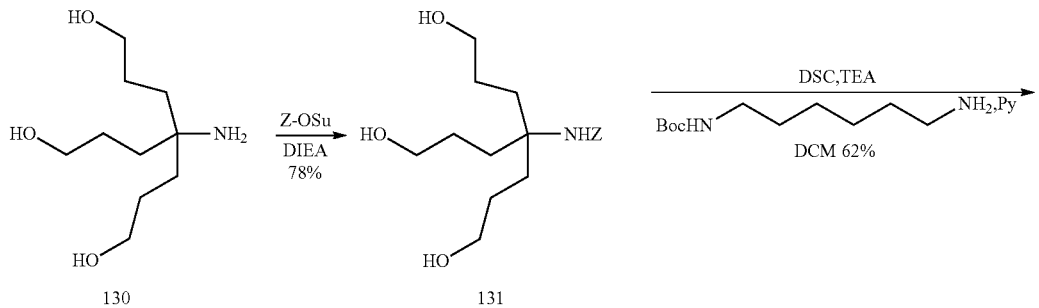

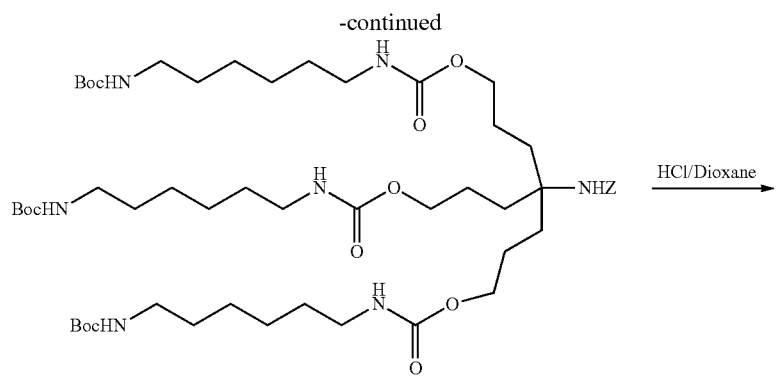
132
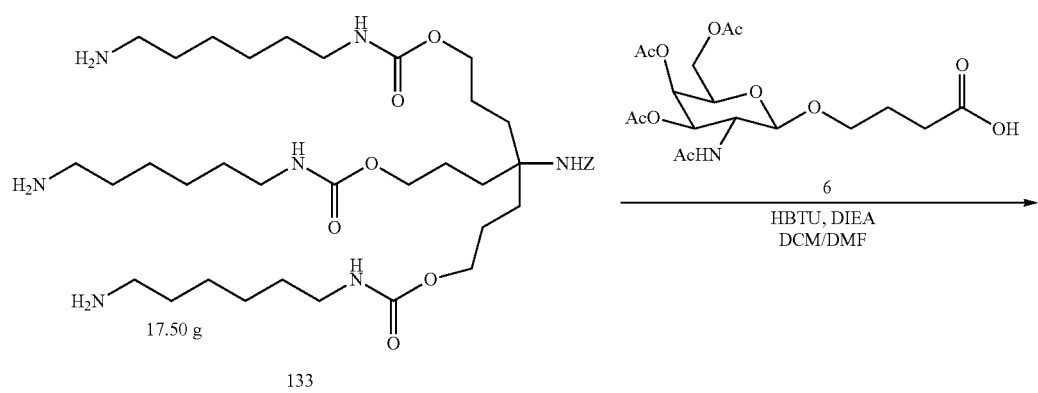
133
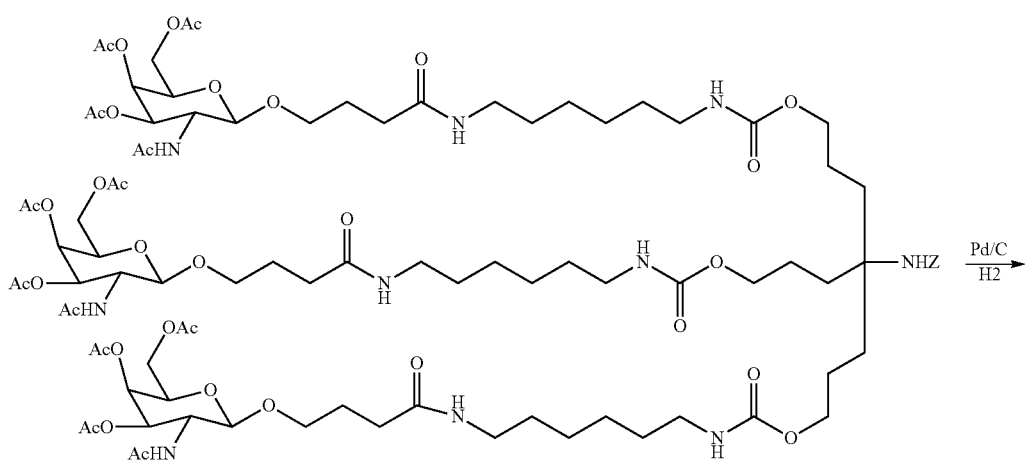
134

-continued
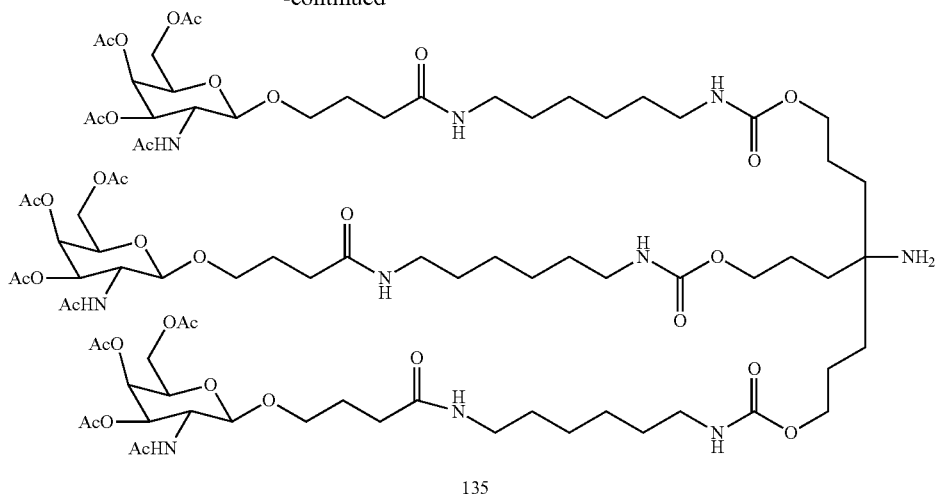
135
Preparation of 135.
Building block 135 is synthesized using a procedure similar to that for synthesis of 110.
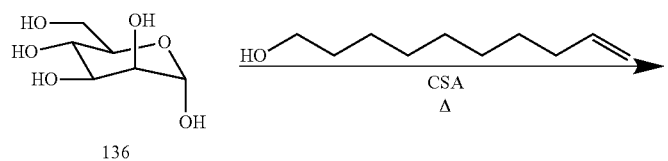
136
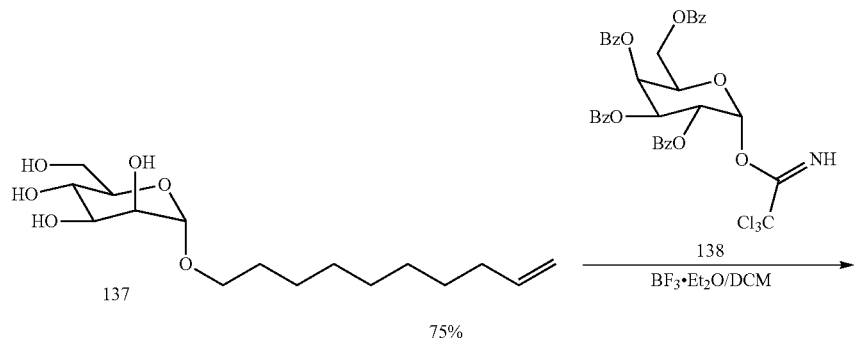
137
138
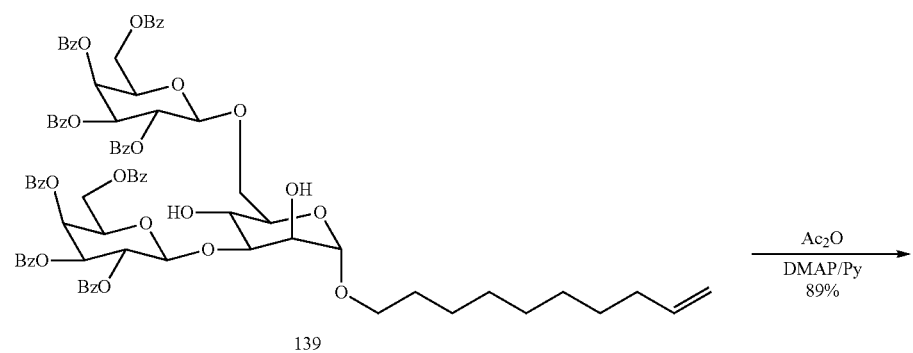
139

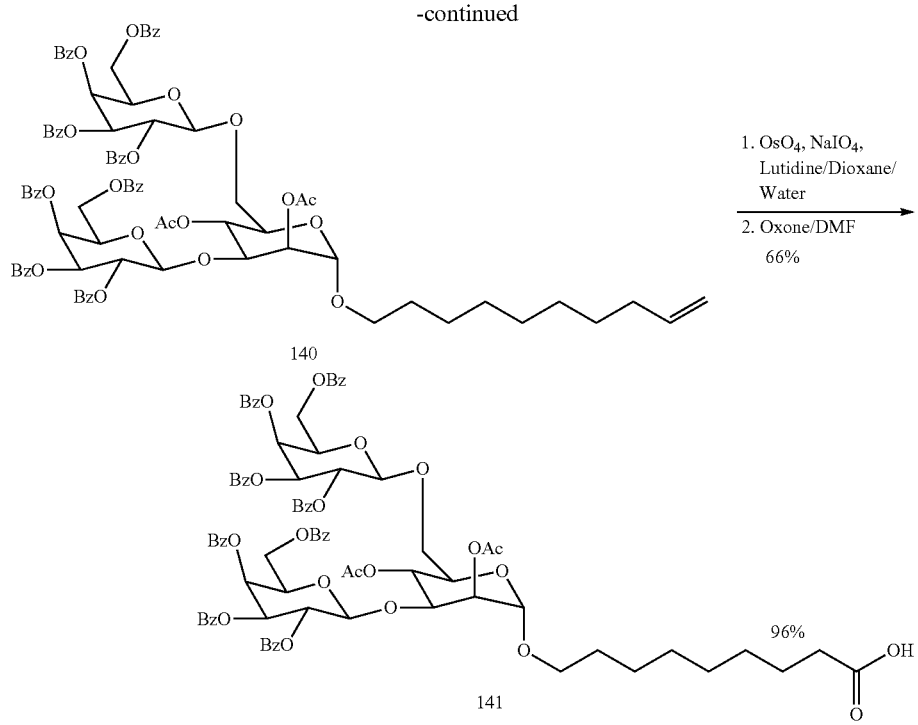

Preparation of 137:

Mannose (10.00 g, 55.53 mmol) and Decinol (100 g, solvent) and CSA (500 mg) were stirred at 110° C. in an oil bath for overnight. The color of the decinol turned to dark brown overnight. Bulk of the decinol was distilled out under reduced pressure. The residue was dissolved in DCM and neutralized with TEA. Extracted the solution with water and dried over sodium sulfate. Solvent was removed and the residue was purified by filtration through a small pad of silica gel, first ethyl acetate followed by 10-15% MeOH/DCM to get the product (7.52 g, 42%). $^1$H NMR (CDCl$_3$, 400 MHz) δ 400 MHz) (7.52 g, 42%). ol) and Decinol (100 g, solvent) and CSA (500 mg) were stirred at 110° C. in an oil bath.

Preparation of 139:

Compound 137 (0.172 g, 0.541 mmol) was dissolved in anhydrous DCM (10 mL) under argon. MS was added to that and cooled the reaction in an ice bath. BF$_3$.Et$_2$O (10μ (10 2 g, 0.541 mmol) was dissolved in anhydrous DCM (10 mL) under argon. MS was ad138 (1.00 g. 1.35 mmol) in 5 mL of DCM was added drop wise over a period of 15 minutes. Reaction was monitored by TLC, once the acceptor was finished the reaction was quenched with TEA and diluted with DCM, filtered off MS and dried. The residue was purified by chromatography (gradient elution 10-40% EtOAc/Hexane) to the compound as a white fluffy solid (0.550 g, 69%). $^1$H NMR (CDCl$_3$, 400 MHz) δ 400 MHz) 35 mmol) in 5 mL of DCM was added drop wise over a period of 15 minutes. Reaction was monitored by TLC, once the acceptor was finished the reaction was quenched with TEA and diluted with DCM, filter $^{13}$C NMR (CDCl$_3$, 100 MHz) δ 100 MHz) 35 mmol) in 5 mL of DCM was added drop wise over a period of 15 minutes. Reaction was monitored by TLC, once the acceptor was finished the reaction was quenched with TEA and 2H), 1.30-0.92 (m, 12H. 63, 128.61, 128.54, 128.47, 128.44, 114.37, 102.74, 102.68, 98.81, 85.27, 72.43, 71.96, 71.37, 71.31, 71.01, 70.30, 70.26, 70.05, 68.31, 68.23, 67.41, 66.11, 62.63, 62.08, 33.96, 29.65, 29.58, 29.53, 29.58, 29.08, 26.20. MS. Molecular weight calculated for C$_{84}$H$_{82}$O$_{24}$, Cal. 1474.52. Found 1497.60 (M+Na).

Preparation of 140:

Compound 139 (0.104 g, 0.07 mmol) was dissolved in a mixture of DCM/Py (10 mL, 1:1). Ac$_2$O (0.5 mL, excess) and DMAP (0.050 g) and stirred the reaction overnight. The reaction was quenched with MeOH, solvents were removed and residue was purified by chromatography (gradient elution 10-30% EtOAc/Hexane) to the compound was white fluffy solid (0.108 g, 99%). $^1$H NMR (CDCl$_3$, 400 MHz) δ 400 MHz) excess) and DMAP (0.050 g) and stirred the reaction overnight. The reaction was quenched with MeOH, solvents were remove 07 (m, 13H), 3.90-3.80 (m, 1H), 3.69-3.61 (m, 1H), 3.36-3.28 (m, 1H), 2.98-2.81 (m, 1H), 2.08 (s, 3H), 2.10-2.01 (m, 4H), 1.35 (s, 3H), 1.42-1.20 (m, 12H). $^{13}$C NMR (CDCl$_3$, 100 MHz) δ 100 MHz) excess) and DMAP (0.050 g) and stirred the reaction overnight. The reaction 7.82, 10.43 Hz, 1H), 5.65-5.47 (m, 2H), 5.10-4.07 (m, 13H), 3.90-3.80 (m, 1H), 3.69-3.61 (m, 1H), 3.36-3.28 (m, 1H), 2.98-2.81 (m, 1H), 2.08 (s, 3H), 2.10-2.01 (m, 4H, 128.47, 128.40, 114.35, 102.32, 99.58, 96.64, 74.51, 72.11, 71.91, 71.46, 71.21, 6978, 6972, 69.51, 69.28, 68.19, 68.03, 67.82, 67.12, 61.97, 61.83, 33.94, 29.63, 29.61, 29.55, 29.49, 29.27, 29.20, 29.05, 26.11, 21.06, 20.02. MS: Molecular weight calculated for C$_{88}$H$_{86}$O$_{26}$, Cal. 1558.54. Found 1581.8 (M+Na).

Preparation of 141:

Compound 141 (1.36 g, 0.873 mmol) was dissolved in a mixture of Dioxane: Water (40 mL, 3:1). To the reaction mixture lutidine (0.203 mL, 2 eq), followed by OsO$_4$ solution (1 mL. 0.05M solution in $^t$Butanol) were added. Sodium periodate (0.774 g, 4 eq) was added and stirred for 4 hr's at room temperature. Reaction was monitored by TLC, once the starting material was consumed; the mixture was diluted with water and extracted with DCM (3 times) and dried over sodium sulfate. All the solvents were removed and the residue was directly used next reaction. Residue from the above reaction was dissolved in DMF (20 mL) to that Oxone (0.590 g, 1.05 eq) and stirred at ambient temperature for 3 h. Once the starting material was consumed, 2 mL of 1M HCl was added and diluted with Ethyl acetate. Washed with water, brine and dried over sodium sulfate. Solvents were removed and the residue was purified by chromatography (gradient elution 20-40% EtOAc/hexane) to get the compound as a white solid (1.08 g 79%). $^1$H NMR (DMSO-d$_6$, 400 MHz) δ 400 MHz)-d eq) and stirred at ambient temperature for 3 h. Once the starting material was consumed, 2 mL of 1M HCl was added and diluted with Ethyl acetate. Washed with water, brine and dried 0.15 (d, J=7.8 Hz, 1H), 4.90-4.35 (m, 7H), 4.10-3.55 (m, 4H), 3.30-3.20 (m, 1H), 2.96-2.87 (m, 1H), 2.18-2.10 (m, 2H), 1.96 (s, 3H), 2.01-1.95 (m, 1H), 1.51-1.39 (m, 2H), 1.27 (s, 3H), 1.20-1.01 (m, 12H). $^{13}$C NMR (CDCl$_3$, 100 MHz) δ 100 MHz)-d eq) and stirred at ambient temperature for 3 h. Once the starting material was consumed, 2 mL of 1.60, 133.49, 130.18, 130.08, 128.85, 129.61, 129.52, 129.44, 129.20, 129.13, 128.91, 128.89, 128.81, 128.78, 128.71, 128.51, 128.45, 102.34, 99.67, 96.65, 74.60, 72.17, 71.94, 71.49, 71.21, 69.82, 69.79, 69.59, 69.37, 68.22, 68.11, 67.81, 67.20, 64.55, 61.99, 61.85, 60.59, 44.06, 33.96, 30.79, 29.39, 29.31, 29.24, 29.20, 29.17, 29.08, 26.08, 24.85, 24.79, 22.20, 21.24, 21.11, 20.07. MS: Molecular weight calculated for C$_{87}$H$_{84}$O$_{28}$, Cal. 1576.51. Found 1599.50 (M+Na).

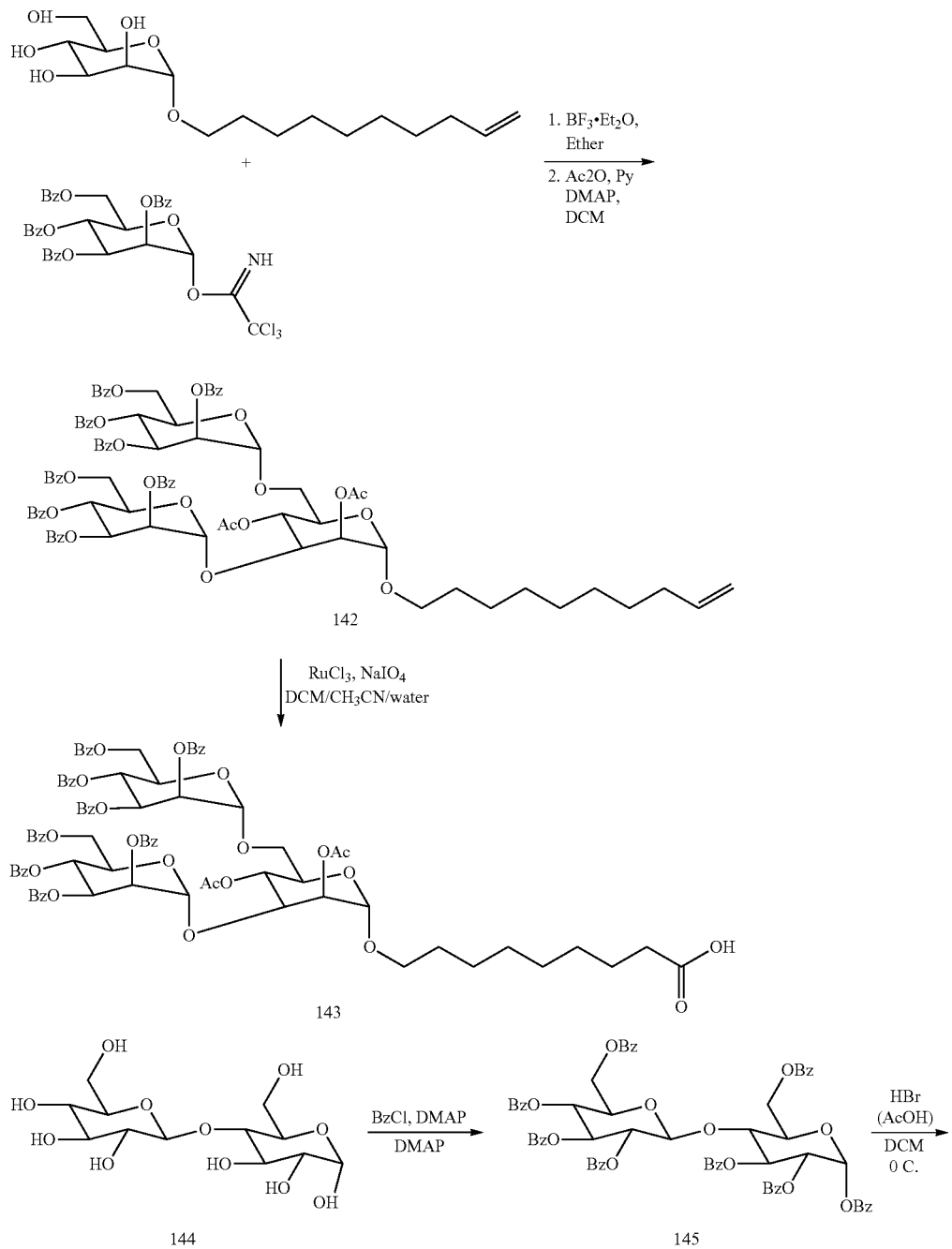

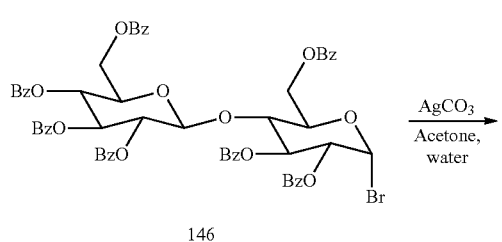
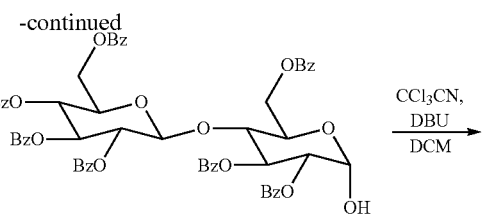

146 → 147

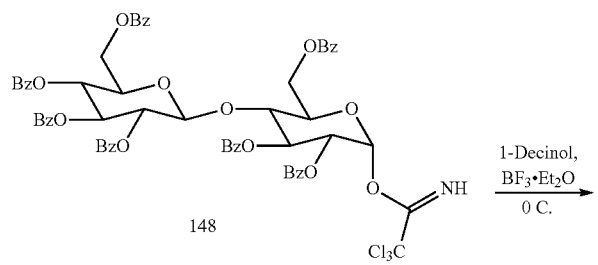

148

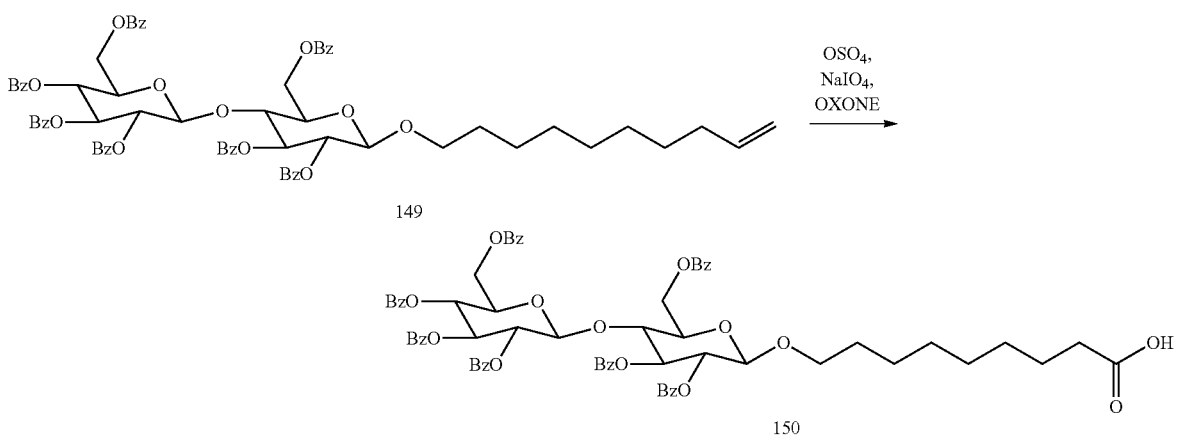

149 → 150

Preparation of 148.

Compound 148 was synthesized according to the reported procedure (Martin, C.; Karen, P.; Laurence, V. Chem. Pharm. Bull. 2004, 52, 965-971.)

Preparation of 149:

1-Decinol (0.300 g, 1.92 mmol) and trichloroacetimidate 148 (2.33 g, 1.2 eq) was dissolved in anhydrous DCM (10 mL) under argon. MS was added to that and cooled the reaction in an ice bath. BF$_3$·Et$_2$O (30μ (30 g, 1.2 eq) was dissolved in anhydrous DCM (10 mL) under argon. MS was added to that and cooled the reaction in an ice bath. BF130.08, 128.85, 129.61, 129.52, 129.44, 129.20, 129.13, 128.91, 128.89, 128.81. 128.78, 128.71, 128.51, 128.45, 102.34, 99.60% EtOAc/Hexane) to the compound as a white fluffy solid (2.01 g, 86%). $^1$H NMR (CDCl$_3$, 400 MHz) δ 400 MHz) 2 eq) was dissolved in anhydrous DCM (10 mL) under argon. MS was added to that and cooled the reaction in an ice bath. BF130.08, 128.85, 129.61, 129.10 (m, 4H), 1.00-1.60 (m, 11H). $^{13}$C NMR (CDCl$_3$, 100 MHz) δ 100 MHz) 2 eq) was dissolved in anhydrous DCM (10 mL) under argon. MS was added to that and cooled the reaction in an ice bath. BF130.08, 128.85, 129.61, 129.10 (m, 4H), 1.00-1.60 (m, 11H). 8.91, 128.81, 130.12, 130.05, 129.98, 129.95, 129.92, 129.88, 129.80, 129.77, 129.73, 129.68, 129.62, 129.55, 129.50, 129.47, 129.41, 129.40, 129.29, 129.14, 129.11, 129.03, 128.96, 128.87, 128.84, 128.83, 128.78, 128.76, 128.63, 128.56, 128.54, 128.48, 128.37, 128.26, 114.33, 114.26, 100.92, 100.84, 97.04, 96.52, 75.36, 75.17, 74.84, 73.37, 72.95, 72.90, 72.81, 72.57, 72.507, 71.94, 71.58, 71.05, 70.37, 70.27, 70.19, 70.06, 69.86, 69.24, 69.19, 69.02, 63.71, 63.56, 63.20, 62.93, 62.69, 33.96, 33.91, 32.93, 29.60, 29.53, 29.50, 29.46, 29.42, 29.33, 29.30, 29.22, 29.14, 29.06, 29.00. MS. Molecular weight calculated for $C_{71}H_{68}O_{18}$, Cal. 1208.44. Found 1231.4 (M+Na).

Preparation of 150:

Compound 149 (7.26 g, 6 mmol) was dissolved in a mixture of Dioxane: Water (100 mL, 3:1). To the reaction mixture lutidine (0.7 mL, 2 eq), followed by OsO$_4$ solution (5 mL. 0.05M solution in $^t$Butanol) were added. Sodium periodate (5.11 g, 4 eq) was added and stirred for 4 hr's at room temperature. Reaction was monitored by TLC, once the starting material was consumed; the mixture was diluted with water and extracted with DCM (3 times) and dried over sodium sulfate. All the solvents were removed and the residue was directly used next reaction. Residue from the above reaction was dissolved in DMF (60 mL) to that Oxone (3.86 g, 1.05 eq) and stirred at ambient temperature for 3 h.

Once the starting material was consumed, 10 mL of 1M HCl was added and diluted with Ethyl acetate. Washed with water, brine and dried over sodium sulfate. Solvents were removed and the residue was purified by chromatography (gradient elution 20-40% EtOAc/hexane) to get the compound 150 as a white solid (5.50 g 75%). $^1$H NMR (DMSO-$d_6$, 400 MHz) δ 400 MHz)-dolid (5.50 g 75%). iodate (5.11 g, 4 eq) was added and stirred for 4 hr's at room temperature. Re$^{13}$C NMR (DMSO-$d_6$, 100 MHz) δ 100 MHz)-dolid (5.50 g 75%). iodate (5.11 g, 4 eq) was added and stirred for 4 hr's at room temperature. Reaction was monitored by TLC, once the starting material was consumed; the mixture was dilut99, 164.88, 164.75, 164.70, 164.60, 164.54, 164.50, 133.80, 133.71, 133.58, 133.42, 133.29, 133.15, 129.88, 129.42, 129.36, 129.29, 129.23, 129.20, 129.12, 129.07, 129.05, 129.03, 128.91, 128.88, 128.72, 128.59, 128.48, 128.38, 99.96, 99.29, 99.22, 95.96, 95.64, 95.22, 93.10, 75.61, 74.86, 74.57, 74.37, 74.15, 73.59, 73.14, 72.58, 71.46, 71.15, 70.48, 70.31, 70.09, 69.97, 69.00, 68.87, 68.22, 67.81, 63.65, 62.49, 60.73, 59.76, 43.01, 33.68, 33.62, 32.54, 28.84, 28.82, 28.61, 28.55, 28.47, 28.40, 25.47, 25.21, 24.52, 24.43, 20.45. MS. Molecular weight calculated for $C_{70}H_{66}O_{20}$, Cal. 1226.41. Found 1249.4 (M+Na).

Example 2. Synthesis of Pteroic Acid Precursors for Conjugation

Appropriately substituted pteroic acid precursor 110 was prepared as follows.

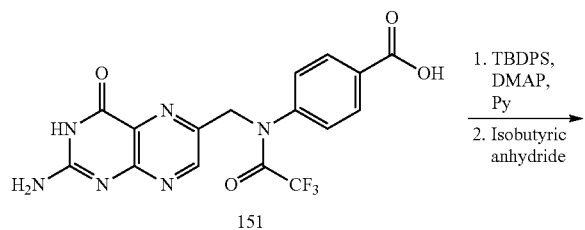

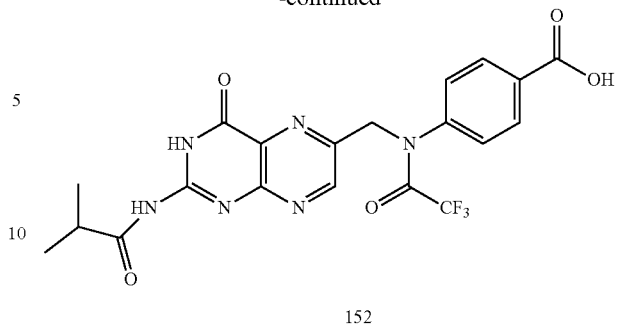

152

Synthesis of 4-[(2-isobutyrylamino-4-oxo-3,4-dihydro-pteridin-6-ylmethyl)-(2,2,2-trifluoroacetyl)-amino]benzoic acid 152

To a suspension of pteroic acid (25 g, 61.2 mmol) and DMAP (11.25 g, 92 mmol) in anhydrous pyridine (400 mL), TBDPS chloride (42 g, 153 mmol) was added. The reaction mixture was stirred at room temperature for 30 h after which isobutric anhydride (14.6 g, 92 mmol) was added and the mixture was slightly warmed. An additional 60 mL of pyridine was also added and the reaction mixture was stirred at room temperature overnight. The reaction mixture became homogenous after which pyridine and other volatiles were concentrated in a rotary evaporator. The residue was stirred with EtOAc (1 L) and acetic acid (100 mL) and water (500 mL) for 24 h. The thus obtained slurry was filtered, the residue was washed with water (500 mL), EtOAc (1 L) and dried to obtain the pure product as a white solid (26.1 g, 89%). $^1$H NMR (DMSO-$d_6$, 400 MHz) δ=8.87 (s, 1H), 7.95 (d, J=8.6 Hz, 2H), 7.67 (d, J=8.6 Hz, 2H), 5.21 (s, 2H), 2.79-2.74 (m, 1H), 1.12 (d, J=6.83 Hz, 6H), $^{13}$C NMR (DMSO-$d_6$) δ=180.72, 166.49, 159.25, 149.87, 147.68, 142.69, 136.34, 134.45, 130.54, 129.16, 128.86, 127.49, 34.96, 33.09, 26.52, 18.88, 18.74. $^{19}$F NMR (DMSO-$d_6$) δ −64.32. MS. Molecular weight calculated for $C_{20}H_{17}F_3N_6O_5$, Cal. 478.12. Found 479.12 (MH$^+$).

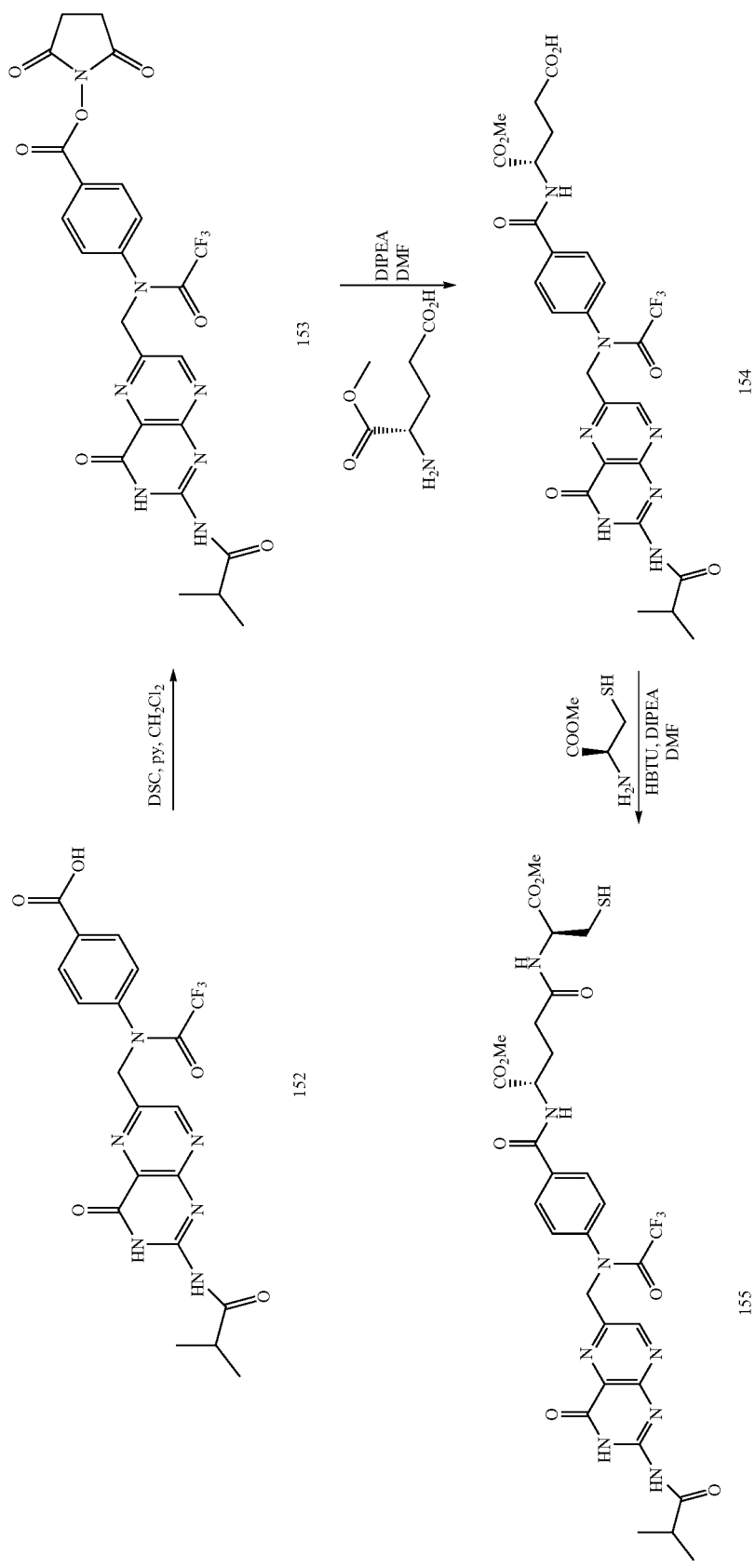

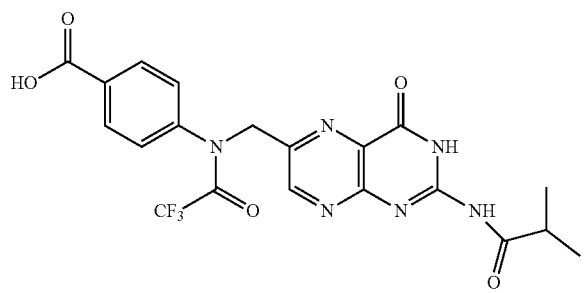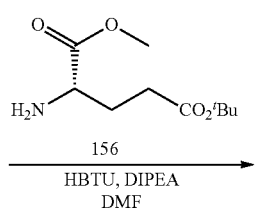

152

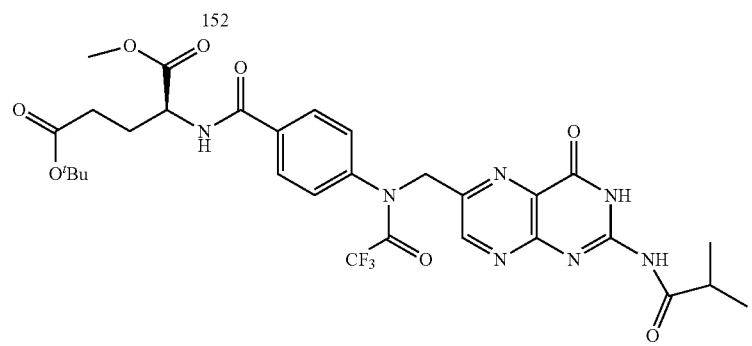

157

|TFA
CH₂Cl₂

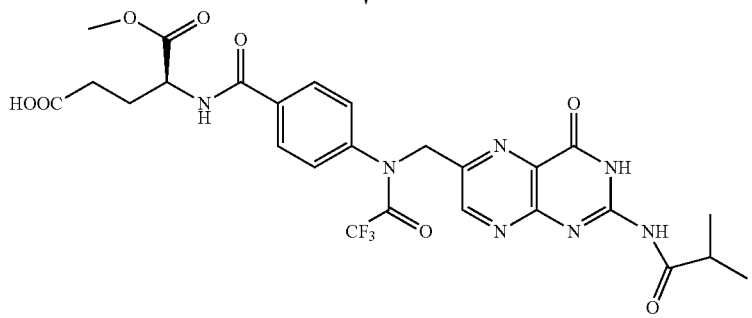

158

In order to synthesize an appropriately substituted more versatile precursor of Folic acid amenable for RNA synthesis, the following strategy was used. In this method the protected Folic acid 152 was treated with the γ-tert-butyl, α-Me ester of glutamic acid, 156 to obtain the ester 157 which on treatment with TFA/CH₂Cl₂ provided the precursor 158.

Synthesis of 2-{4-[(2-isobutyrylamino-4-oxo-3,4-dihydro-pteridin-6-ylmethyl)-(2,2,2-trifluoroacetyl)-amino}-pentanedioic acid 5-tert-butyl ester 1-methyl ester 157

In a representative procedure, the pteroic acid precursor 152 (2.4 g, 5 mmol) was dissolved in anhydrous DMF (20 mL), HBTU (1.9 g, 1 eq.) followed by DIEA (1 mL, 5 eq.) were added and stirred for 20 minutes. To this reaction mixture the amine hydrochloride 156 (1.2 g, 1 eq) was added as a solution in DMF (6 mL). Reaction was monitored by TLC (8% MeOH/DCM, PMA stain). TLC of the reaction mixture showed completion of the reaction. The reaction mixture was slowly poured in ice with vigorous stirring. The precipitated product was filtered to get the product 157 as a white solid (Yield=2.85 g, 86%). $^1$H NMR (DMSO-d₆, 400 MHz) δ=12.33 (s, 1H), 11.94 (s, 1H), 8.88 (s, 1H), 8.82 (d, J=7.3 Hz, 1H), 7.90 (d, J=8.6 Hz, 2H), 7.68 (d, J=8.4 Hz, 2H), 5.22 (s, 2H), 4.46-4.40 (m, 1H), 3.62 (s, 3H), 2.86-2.73 (m, 1H), 2.32 (t, J=7.4 Hz, 2H) 2.05-1.90 (m, 2H), 1.35 (m, 9H), 1.12 (d, J=6.8 Hz, 6H). $^{13}$C NMR DMSO-d₆) δ=180.75, 172.13, 171.45, 165.64, 159.10, 154.80, 149.97, 149.79, 147.72, 141.75, 134.15, 130.53, 128.70, 128.49, 117.50, 114.64, 79.79, 51.96, 51.91, 34.96, 31.22, 27.68, 25.71, 18.72. MS. Molecular weight calculated for $C_{30}H_{34}F_3N_7O_8$, Cal. 677.63. Found 676.72 (M−H⁻).

Synthesis of 2-{4-[(2-isobutyrylamino-4-oxo-3,4-dihydro-pteridin-6-ylmethyl)-(2,2,2-trifluoroacetyl)-amino}-pentanedioic acid 1-methyl ester 158

The ester 157 (2 g, 2.9 mmol) was dissolved in 20 mL of 50% TFA in dichloromethane and the solution was stirred at room temperature for 30 min. after which the TLC showed the complete disappearance of the starting ester. The reaction mixture was concentrated and the residue was crystallized from $CH_2Cl_2$:Hexanes (2:3) and crystallized product was filtered off and dried to obtain the pure product 158 (1.76 g, 96%) as off white powder. $^1$H NMR (DMSO-$d_6$, 400 MHz) δ=12.32 (bs, 1H), 11.94 (s, 1H), 8.88 (s, 1H), 8.84 (d, J=7.4 Hz, 1H), 7.90 (d, J=8.3 Hz, 2H), 7.69 (d, J=8.3 Hz, 2H), 5.22 (s, 2H), 4.45-4.41 (m, 1H), 3.62 (s, 3H), 2.78-2.75 (m, 1H), 2.35 (t, J=7.4 Hz, 2H) 2.07-1.92 (m, 2H), 1.12 (d, J=6.8 Hz, 6H). $^{13}$C NMR DMSO-$d_6$) δ=180.77, 173.70, 172.19, 165.70, 159.21, 155.54, 149.93, 149.84, 147.75, 141.78, 134.18, 130.53, 128.71, 128.49, 117.51, 114.64, 53.98, 52.06, 51.93, 34.97, 30.11, 25.68, 18.73. MS. Molecular weight calculated for $C_{26}H_{26}F_3N_7O_8$, Cal. 621.18. Found 620.18 (M−H$^−$).

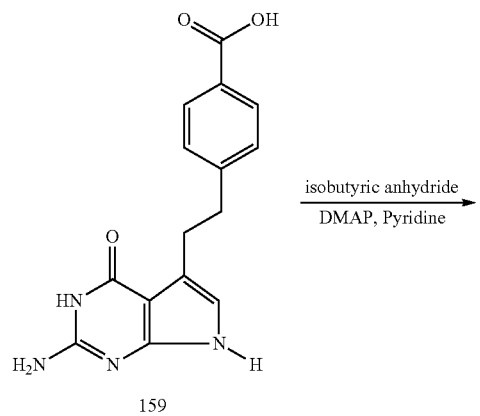

159

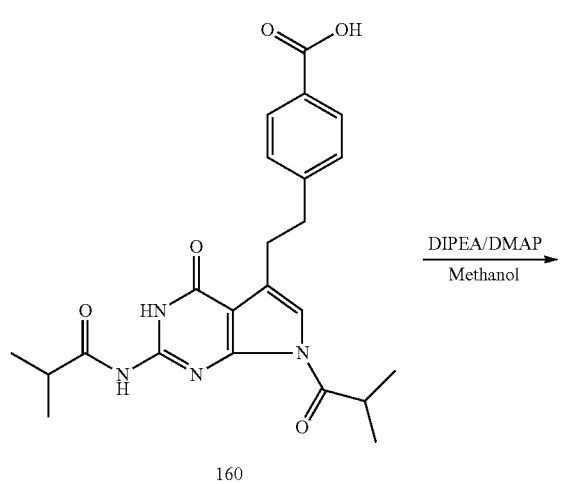

160

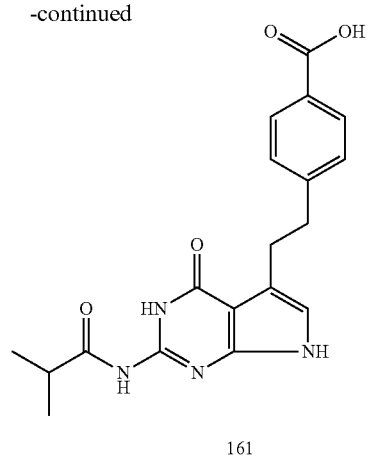

161

Synthesis of 160.

To suspension of Compound 159 (0.2 g, 0.000671 moles) in anhydrous pyridine (5 mL) was added DMAP (0.13 g, 0.0010 moles), followed by isobuytric anhydride (0.6 mL, 0.0040 moles) at room temperature. The resulting mixture was then refluxed for 4 hr. After completion of reaction (by TLC), the mixture was poured onto ice-HCl/hexane and stirred well. The resulting solid was filtered, washed with haxane and used directly for further reactions. Yield (0.1 g, 34%). $^1$H NMR (DMSO, 400 MHz): δ=12.08 (s, 1H), 11.48 (s, 1H), 7.85 (d, 2H), 7.35 (d, 2H), 7.22 (s, 1H), 4.33 (m, 1H), 2.98 (m, 2H), 2.96 (m, 2H), 2.81 (m, 1H), 1.19 (d, 6H), 1.14 (d, 6H). $^{13}$C NMR (DMSO): δ=179.85, 175.21, 167.00, 156.64, 147.81, 147.34, 146.73, 129.08, 128.32, 128.14, 121.27, 116.00, 106.07, 35.02, 34.51, 33.37, 26.90, 18.72, 18.64. MS (MH)$^+$: 439.40.

Synthesis of 197.

To a stirring solution of 160 (0.4 g, 0.00091 moles) in 5 ml MeOH, DIPEA (0.036 mL, 0.00278 moles), was added at room temperature. (Note: After addition of DIPEA reaction mixture becomes clear). After 10 minutes DMAP (catalytic) was added to the mixture. The completion of reaction was monitored by TLC (& LCMS). MeOH was then concentrated and the residue was diluted with water (5 mL). Acidification with dilute HCl was followed by extraction with ethyl acetate. Organic layer was separated, dried over $Na_2SO_4$ and concentrated. The crude mixture was pure enough and was used directly for further reactions. Yield: 260 mg (54%). $^1$H NMR (DMSO, 400 MHz), δ=12.77 (bs, 1H), 11.68 (s, 1H), 11.34 (s, 2H), 7.84 (d, 2H), 7.32 (d, 2H), 6.64 (s, 1H), 3.01 (m, 2H), 2.94 (m, 2H), 2.74 (m, 1H), 1.09 (d, 6H). MS (MH)$^+$: 369.10.

In order to synthesize azido functional group containing folate conjugates the following strategy was used. The azido amine tether 165 was synthesized starting from the commercially available diamine 162 as shown below.

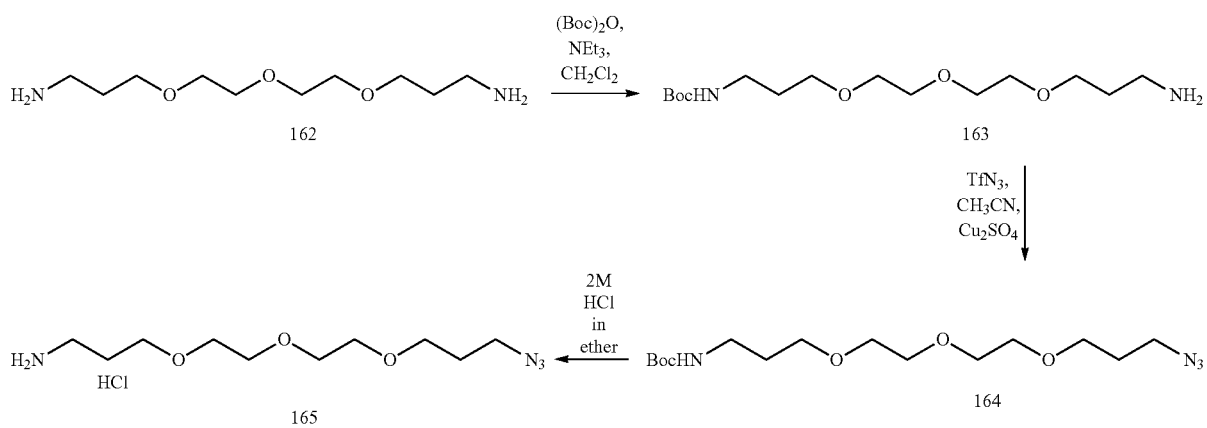 [SMILES: NCCCOCCOCCOCCCN ; CC(C)(C)OC(=O)NCCCOCCOCCOCCCN ; [N-]=[N+]=NCCCOCCOCCOCCCN ; CC(C)(C)OC(=O)NCCCOCCOCCOCCCN=[N+]=[N-] ; Cl]

Synthesis of Amine 163.

To a solution of the diamine (22 g, 0.1 mol) in dichloromethane (300 mL), triethylamine (15 mL) was added and the mixture was cooled in ice bath. To this cold solution a solution of (Boc)$_2$O in CH$_2$Cl$_2$ (100 mL) was added dropwise and the mixture was stirred overnight. The reaction mixture was washed with satd. NaHCO$_3$ (200 mL), water (300 mL), brine (300 mL) and dried (Na$_2$SO$_4$). Concentration of this organic layer followed by column purification provided the pure mono Boc amine 202 in 55% yield. MS: MW Calc. for C$_{15}$H$_{32}$N$_2$O$_5$: 320.42. Found 321.41 (MH$^+$).

Synthesis of Azide 164.

The triflic azide stock solution was prepared as reported in *Tetrahedron Letters* 47 (2006) 2382-2385. The amine (0.96 g, 3 mmol), sodium bicarbonate (0.85 mg, 10 mmol) and copper (II) sulfate pentahydrate (22 mg, 0.1 mmol) were dissolved in water (3 mL). Triflic azide stock solution (5 mL) was added, followed by the addition of methanol (20 mL) to yield a homogeneous system. The blue mixture was stirred for 30 min after which the TLC and MS showed the complete disappearance of starting amine. The reaction mixture was concentrated in a rotary evaporator and the residue was purified by chromatography on silica gel (eluent: dichloromethane-methanol) to obtain the pure azide 164 (1 g, 96%) as an oil. MS: MW Calc. for C$_{15}$H$_{30}$N$_4$O$_5$: 346.42. Found 347.41 (MH$^+$). $^1$HNMR (CDCl$_3$, 400 MHz) δ=4.68 (bs, 1H), 3.40-3.30 (m, 12H), 3.16 (t, J=6.4 Hz, 2H), 3.00-2.95 (m, 2H), 1.68-1.54 (m, 4H), 1.04 (s, 9H).

Synthesis of 165.

The azide 203 (1 g, 2.88 mmol) was dissolved in ethanol (10 mL) and to this a 2M solution of HCl in ether was added and the mixture was stirred at room temperature overnight. The MS showed the absence of starting material. The reaction mixture was concentrated and the thus obtained oil was used as such for the next reaction without further purification. MS: MW Calc. for C$_{10}$H$_{23}$ClN$_4$O$_3$: 246.17. Found 247.17 (MH$^+$). $^1$HNMR (DMSO-d$_6$, 400 MHz) δ=8.96 (bs, 1H), 7.92 (bs, 2H), 3.52-3.40 (m, 12H), 3.37 (t, J=6.8 Hz, 2H), 2.85-2.77 (m, 2H), 1.81-1.70 (m, 4H).

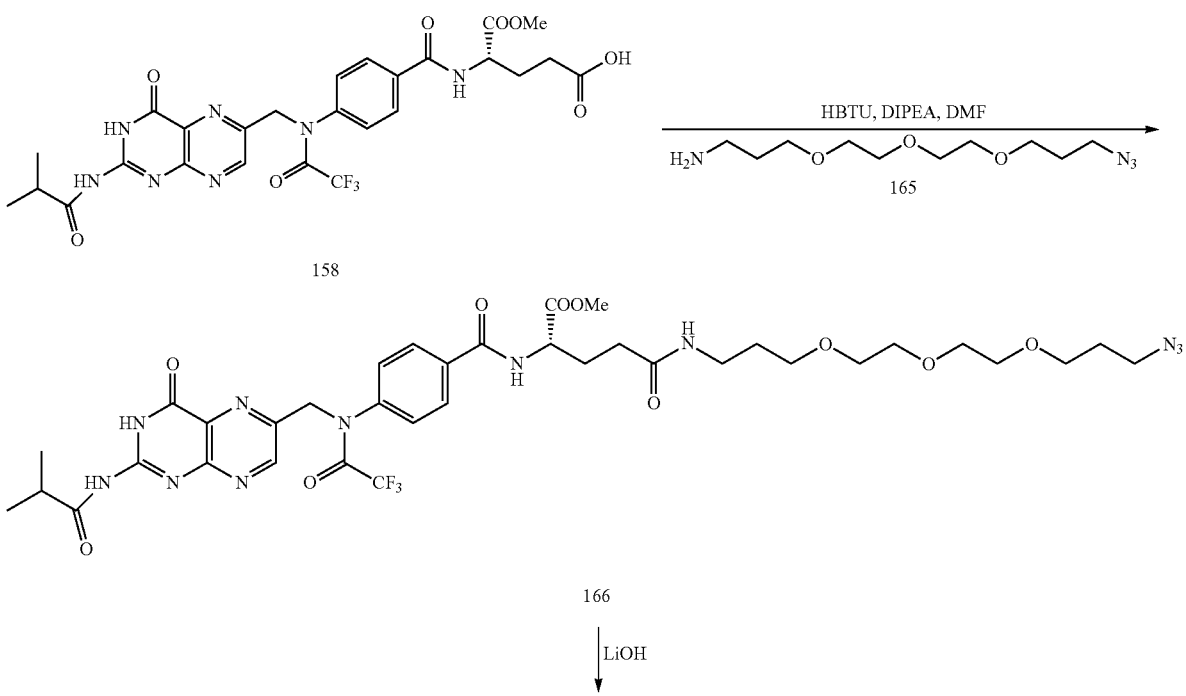

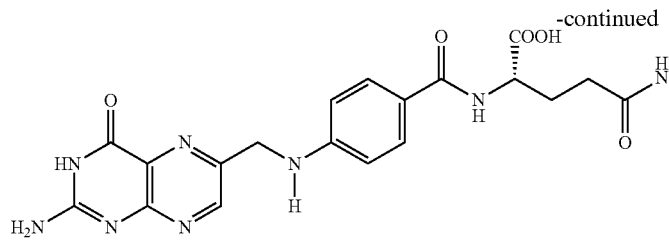

167

Coupling of the amine 165 (0.6 g) with the acid 158 (1.2 g) provided the coupled azide 166 (1.68 g, 93%) as a light yellow foam. $^1$H NMR (DMSO-d$_6$, 400 MHz) □=12.34 (s, 1H), 11.95 (s, 1H), 8.89 (s, 2H), 7.92 (d, J=8.4 Hz, 2H), 7.81 (m, 1H), 7.70 (d, J=8.4 Hz, 2H), 5.22 (s, 2H), 4.40-4.34 (m, 1H), 3.62 (s, 3H), 3.50-3.31 (m, 15H), 3.09-3.00 (m, 2H), 2.80-2.72 (m, 1H), 2.20 (t, J=7.4 Hz, 2H) 2.10-1.89 (m, 2H), 1.76-1.54 (m, 4H), 1.12 (d, J=6.8 Hz, 6H). MS. Molecular weight calculated for C$_{36}$H$_{46}$F$_3$N$_{11}$O$_{10}$, Cal. 849.81. Found 850.2 (MH$^+$).

Synthesis of 167:

The azide 166 (1 g) was dissolved in THF (20 mL) and to it an aqueous solution of lithium hydroxide (100 mg in 2 mL of water) was added and the solution was stirred at room temperature for 4 h after which the MS showed the complete disappearance of SM. The reaction mixture was acidified to pH 5 using acetic acid and the RM was diluted with ethyl acetate (100 mL). The precipitated product was filtered off and washed with water and ethyl acetate and dried under vacuo at 40° C. overnight to get the pure azide 167 (0.455 g 55%) as an orange solid. $^1$H NMR (DMSO-d$_6$, 400 MHz) δ=8.59 (s, 1H), 7.85 (bs, 1H), 7.72 (bs, 1H), 7.56 (d, J=8.4 Hz, 2H), 6.88 (bs, 1H), 6.65 (d, J=8.4 Hz, 2H), 4.45 (s, 2H), 4.00-4.02 (m, 1H), 3.50-3.33 (m, 14H), 3.04-3.00 (m, 2H), 2.07-1.83 (m, 4H), 1.76-1.54 (m, 4H). MS. Molecular weight calculated for C$_{29}$H$_{39}$N$_{11}$O$_8$, Cal. 669.69. Found 668.2 (M–H$^-$).

In another embodiment, the alkyne containing folic acid is synthesized as follows. In this case the protected pteroic acid 158 was coupled with the protected lysine 168 to get the coupled product 169 which on Cbz deprotection provided the amine 170. Coupling of the amine 170 with the acid 171 provided the coupled product 172 which after purification and deprotection provided the product 173 as described below.

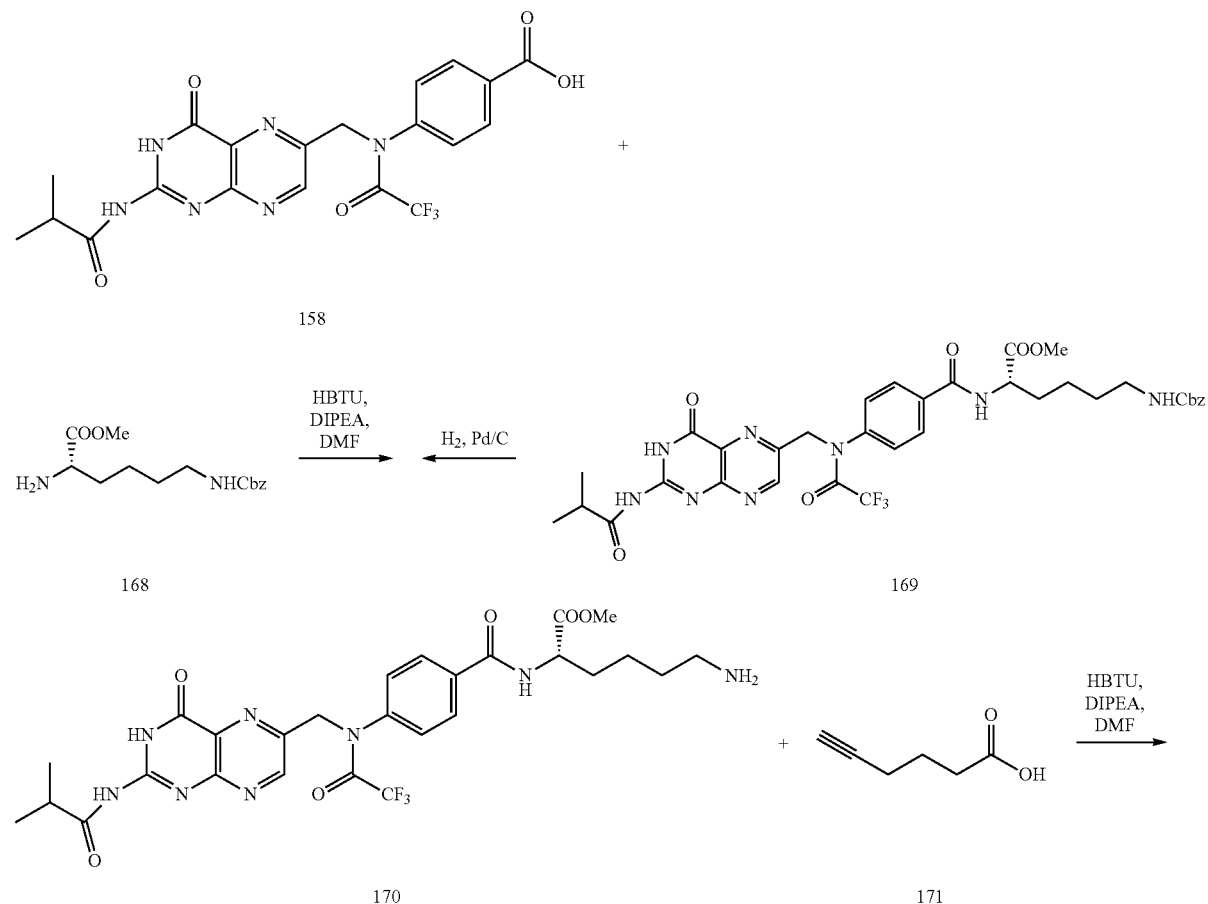

-continued

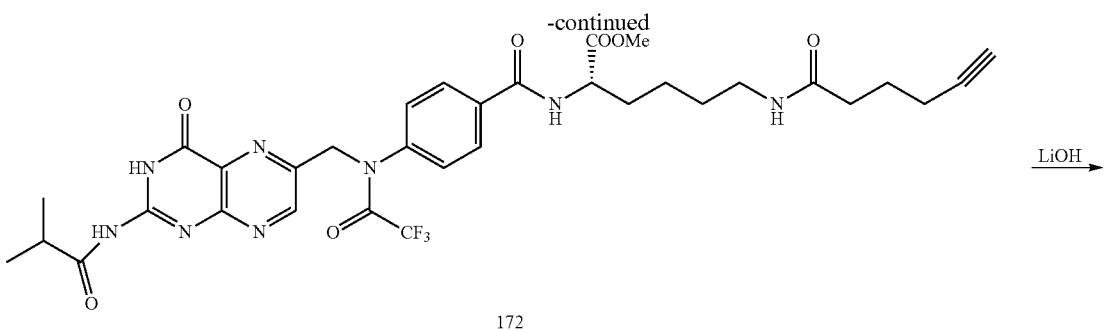

172

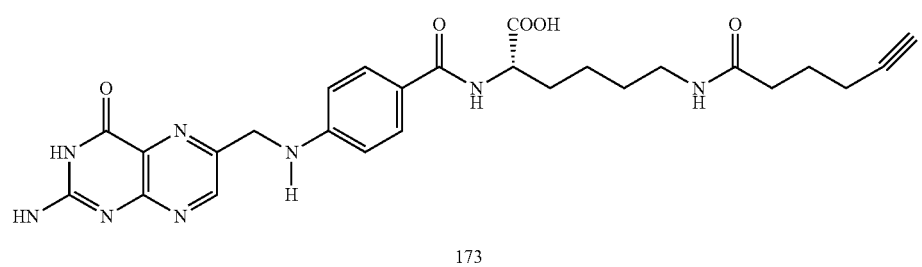

173

Synthesis of 169:
Using a similar procedure to that used for the synthesis of 166, coupling of the acid 158 with the lysine derivative 168 provided the coupling product 169 as a white solid in 95% yield.

Synthesis of 170:
The compound 169 on hydrogenation with Pd/C provided the deprotected amine 170 as a yellow solid.

Synthesis of 172:
Coupling of the amine 170 with the acid 171 using a procedure to that used for the synthesis of 166 provided the couple product 172 in high yields.

Synthesis of 173:
The deprotection of the protecting groups is achieved using a similar procedure as described for the synthesis of 167 to isolate the fully deprotected alkyne 173.

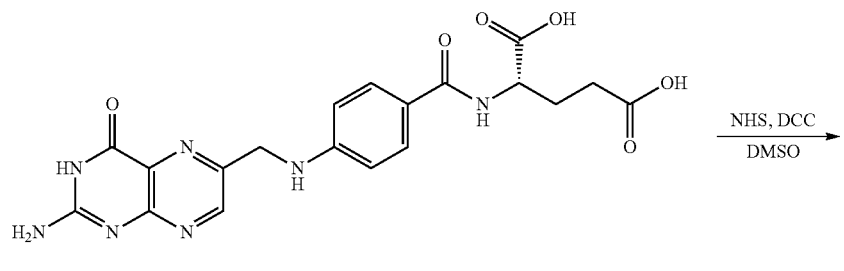

174

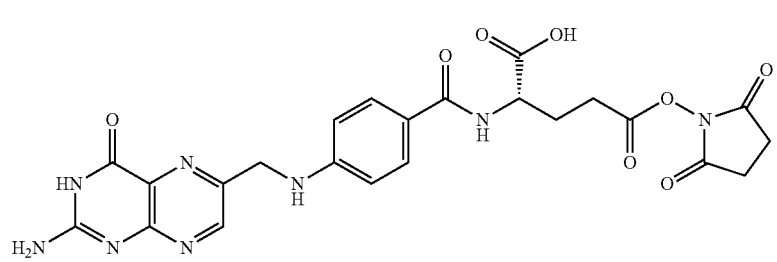

175

Preparation of 175.

Treatment of folic acid 174 with DCC followed by N-hydroxysuccinimide provided the activated ester 175 in 80% yield. In a typical procedure, folic acid (5 g, 11.33 mmol) was dissolved in anhydrous DMSO (100 mL) and to this solution was added, triethylamine (2.5 mL), DCC (4.7 g, 22.6 mmol) and N-hydroxysuccinimide (2.6 g, 22.6 mmol) and the solution was stirred at room temperature in dark for 18 h. The reaction mixture was filtered and to the filtrate EtOAc (1 L) was added and the precipitated product was filtered, washed with ethyl acetate (500 mL), ether (200 mL) and dried under vacuum to isolate the product as a yellow powder. The purity of the product was found to be 83% by HPLC. This product was used as such for the coupling steps without further purification.

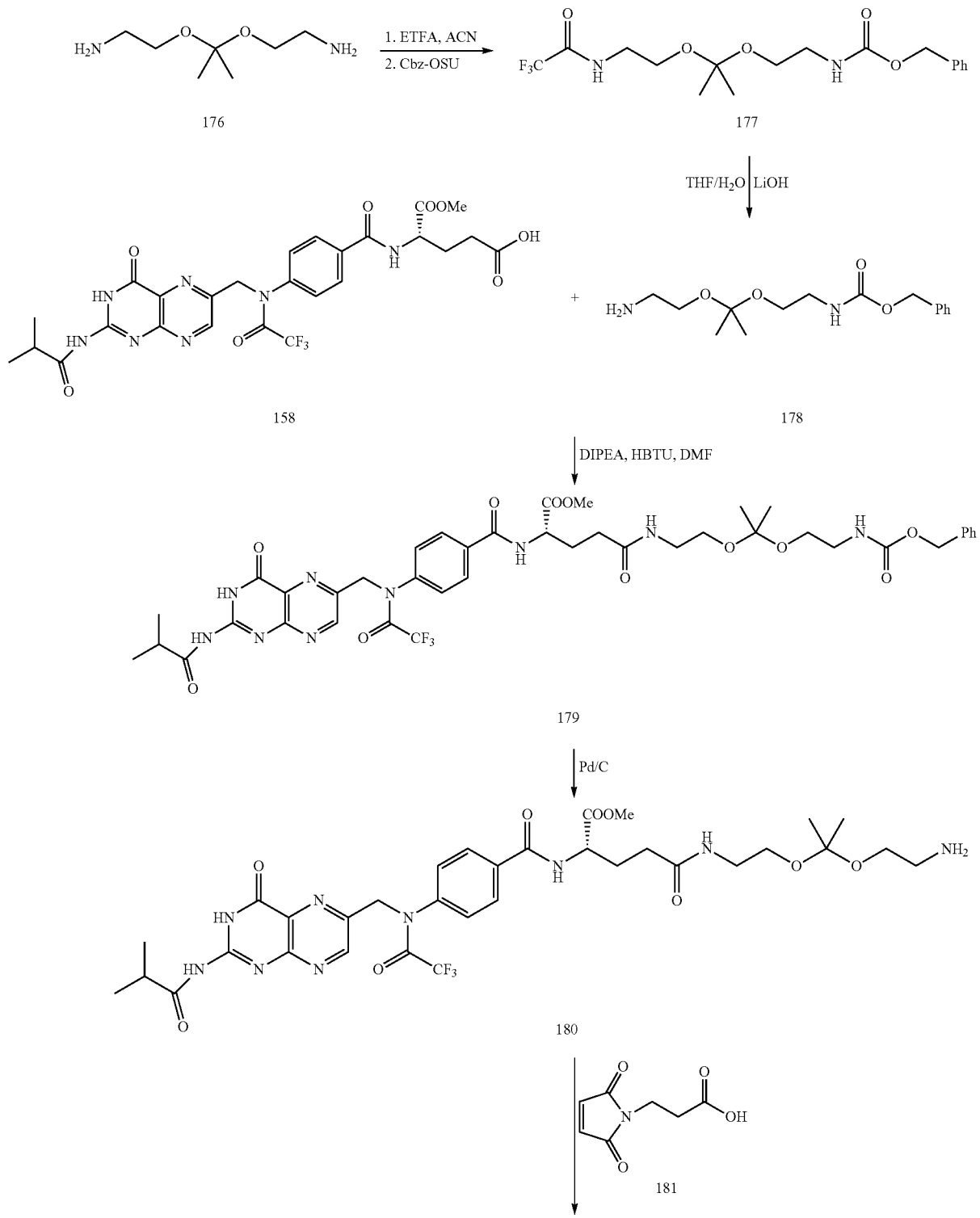

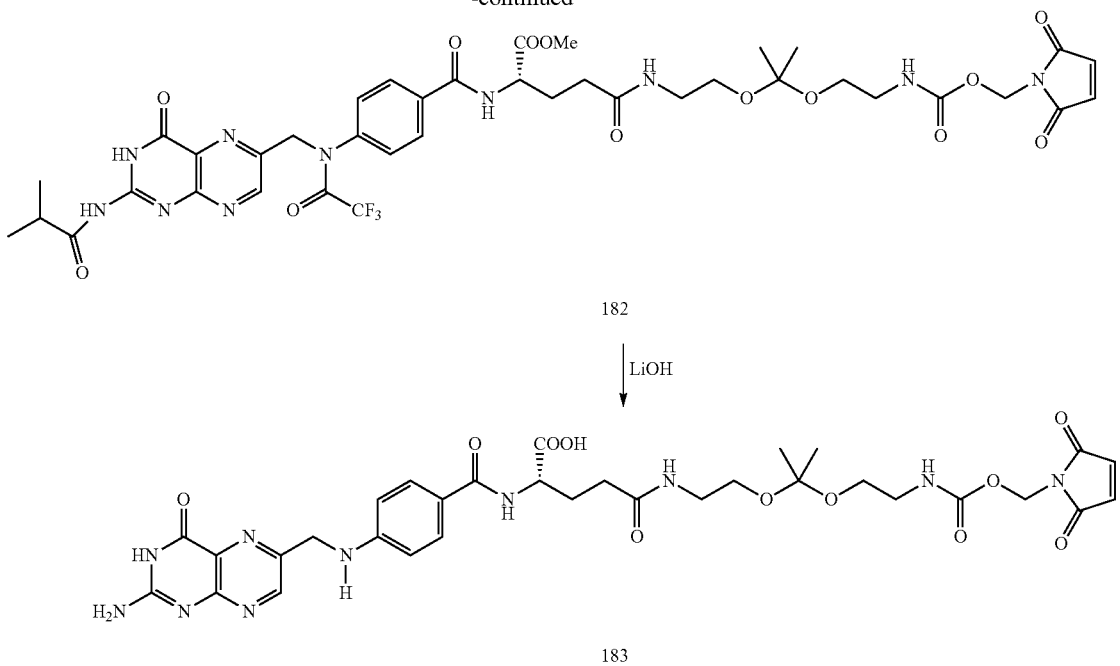

182

183

Preparation of 183.

The ketal 176 was synthesized using a reported procedure (Paramonov, S. E.; Bachelder, E. M.; Beaudette, T. T.; Standley, S. M.; Lee, C. C.; Dashe, J.; Frechet, Jean M. J. Fully Acid-Degradable Biocompatible Polyacetal Microparticles for Drug Delivery. *Bioconjugate Chemistry* (2008), 19 (4), 911-919). The transient protection of the ketal was carried out in two steps in one pot first by treating the diamine with one equivalent of ethyltrifluoroacetate followed by one equivalent of Cbz-OSu to provide the di protected derivative 177 in 80% yield after column purification. The protected amine 177 on treatment with aqueous LiOH provided the amine 178 in quantitative yield. Coupling of this amine 178 (0.5 g) with the protected folic acid 158 (1 g) provided the coupled product 179 (1.1 g) which on hydrogenation provided the amine 180 in quantitative yield. Coupling of amine 180 was carried out with the maleimidopropionic acid 181 to give the coupled product 182 in good yields. The final deprotection of all the protecting group in 182 is carried out using ice-cold aqueous LiOH in THF to afford the precursor 183 as an orange solid.

Example 3. Synthesis of Lipid Conjugates

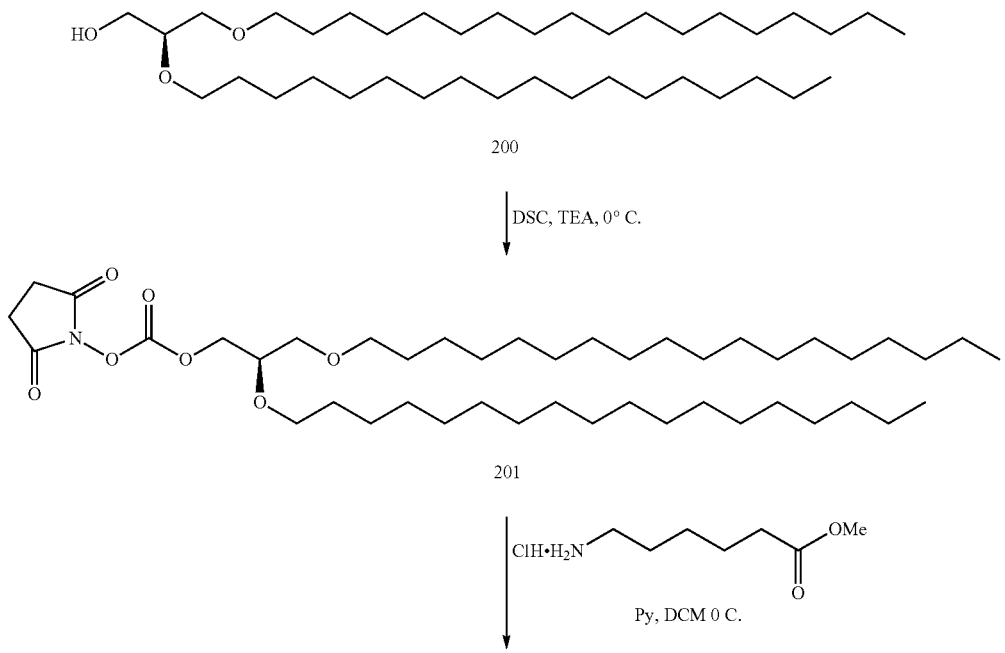

-continued

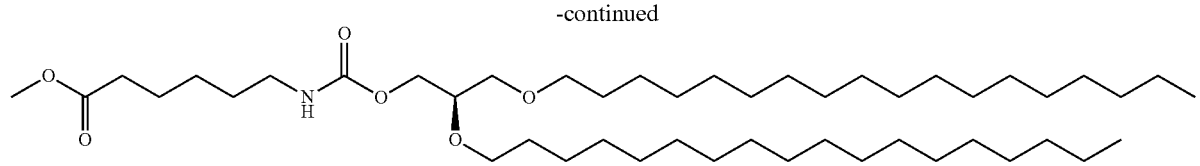

202

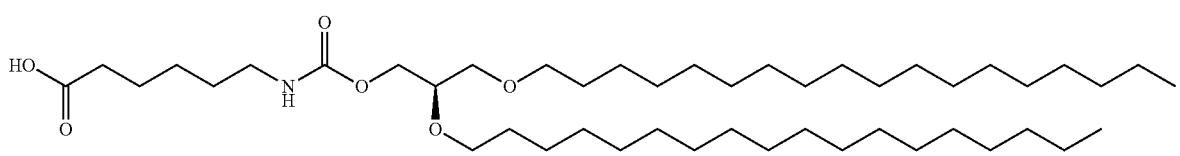

203

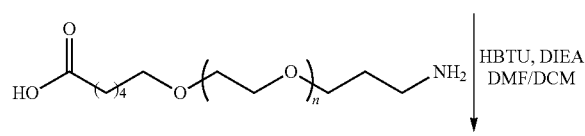

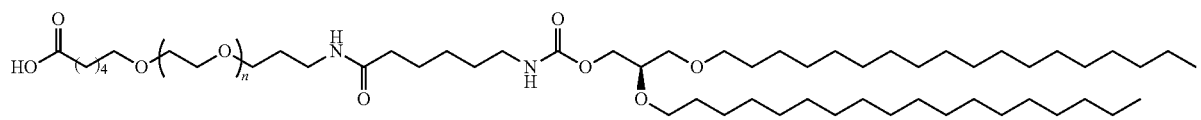

204

Preparation of 201:

1,2-Dioctadecyl sn glycerol (8.50 g, 14.23 mmol) and DSC (5.47 g, 1.5 eq.) were dissolved in DCM (100 mL) and cooled in an ice-water bath. Triethylamine (6.00 mL, 44 mmol) was added and stirred the mixture overnight. The mixture was transferred to a separatory funnel diluted with DCM, washed with bicarbonate solution and water. DCM layer separated and dried over sodium sulfate. Solvents were removed and the residue dried under high vacuum overnight. It was used for the next reaction with out further purification (Yield, 11.50 g).

Preparation of 202:

Compound 201 (4.00 g, 5.42 mmol) and 6-aminohexanoate hydrochloride (1.477 g, 1.5 eq.) were dissolved in DCM and cooled in an ice bath. Pyridine (5 mL) was added to the mixture and stirred overnight. Solvents were removed and the residue dried under high vacuum. The residue extracted with dichloromethane, washed with bicarbonate and water. Crude product was purified by chromatography (Gradient elution of EtOAc/Haxane) to get the required product 202 (Yield-3.80 g, 91%). MS: Calculated for $C_{47}H_{93}NO_6$, 767.70. Found 768.68 (M+H).

Preparation of 203:

Compound 202 (4.50 g, 5.86 mmol) was dissolved in a mixture of THF/MeOH/Water (2:2:1) and cooled in an ice bath. LiOH (1.23 g, Seq.) was added and the mixture stirred overnight. TLC checked and the mixture neutralized with AcOH. Solvents were removed and the residue extracted with dichloromethane, washed with water. Solvents were removed and the residue purified by chromatography to get the required compound as a white solid (Yield, 4.32 g, 97%). MS: Calculated for $C_{46}H_{91}NO_6$, 753.68. Found 752.70 (M−H).

Preparation of 204:

Compound 203 (0.832 g, 1.10 mmol) and HBTU (0.461 g, 1.21 mmol) were dissolved in a mixture of DCM/DMF to that DIEA (0.573 mL) was added and stirred the mixture for 5 minutes. PEG amino acid (2.00 g, 0.921 mmol) was added and stirred the mixture overnight. Solvent was removed and the residue purified by chromatography (Ethyl acetate, then 5-10% MeOH/DCM) to get the required product (2.58 g, 95%). MS calculated Average MWt. 2700-2900. Found 2720-2960.

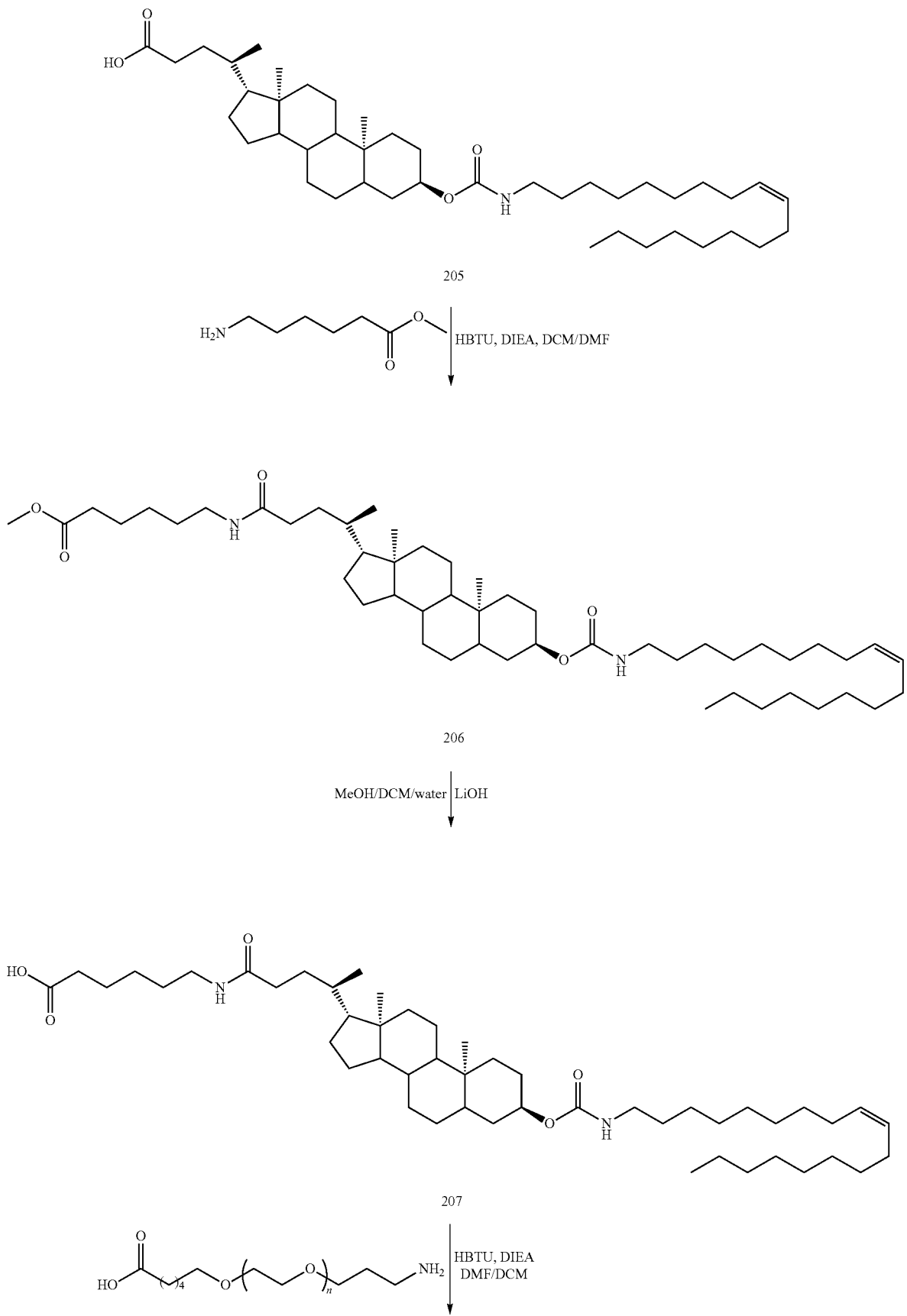

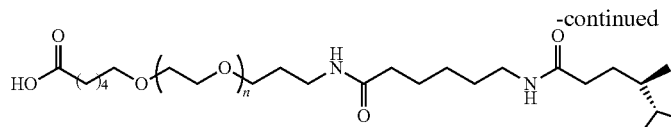

-continued

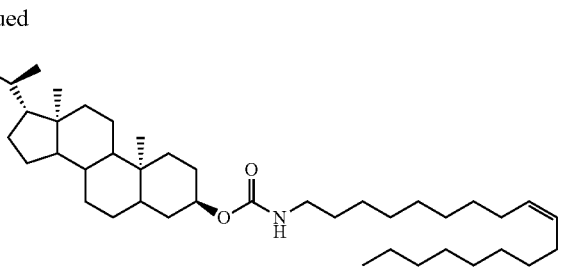

208

Preparation of 206:

Compound 205 (2.11 g, 3.15 mmol) and methylamino hexanoate (0.688 g, 1.2 eq.) were dissolved in a mixture of DMF/DCM (50 mL). To that HBTU (1.31 g, 1.05 eq) and DIEA (2 mL, excess) were added. The mixture stirred overnight at ambient temperature overnight. The mixture was poured into ice-water mixture and extracted with ether. Ether layer separated and dried over sodium sulfate. Solvents were removed and the residue purified by chromatography to get the required product 206 (yield –2.27 g, 90%).

Preparation of 207:

Compound 206 (2.25 g, 2.925 mmol) was dissolved in a mixture of THF/MeOH/Water (50 mL, 2:2:1) and cooled in an ice bath. LiOH (0.614 g, Seq.) was added and the mixture stirred overnight. TLC checked and the mixture neutralized with AcOH. Solvents were removed and the residue extracted with dichloromethane, washed with water. Solvents were removed and the residue purified by chromatography to get the required compound as a white solid (Yield, 2.12 g, 96%). MS: Calculated for $C_{49}H_{86}N_2O_5$, 782.65. Found 781.70 (M–H).

Preparation of 208:

Compound 207 (0.865 g, 1.10 mmol) and HBTU (0.461 g, 1.21 mmol) were dissolved in a mixture of DCM/DMF to that DIEA (0.573 mL) was added and stirred the mixture for 5 minutes. PEG amino acid (2.00 g, 0.921 mmol) was added and stirred the mixture overnight. Solvent was removed and the residue purified by chromatography (Ethyl acetate, then 5-12% MeOH/DCM) to get the required product (1.60 g, 59%). MS calculated Average MWt. 2750-2950. Found 2730-2970.

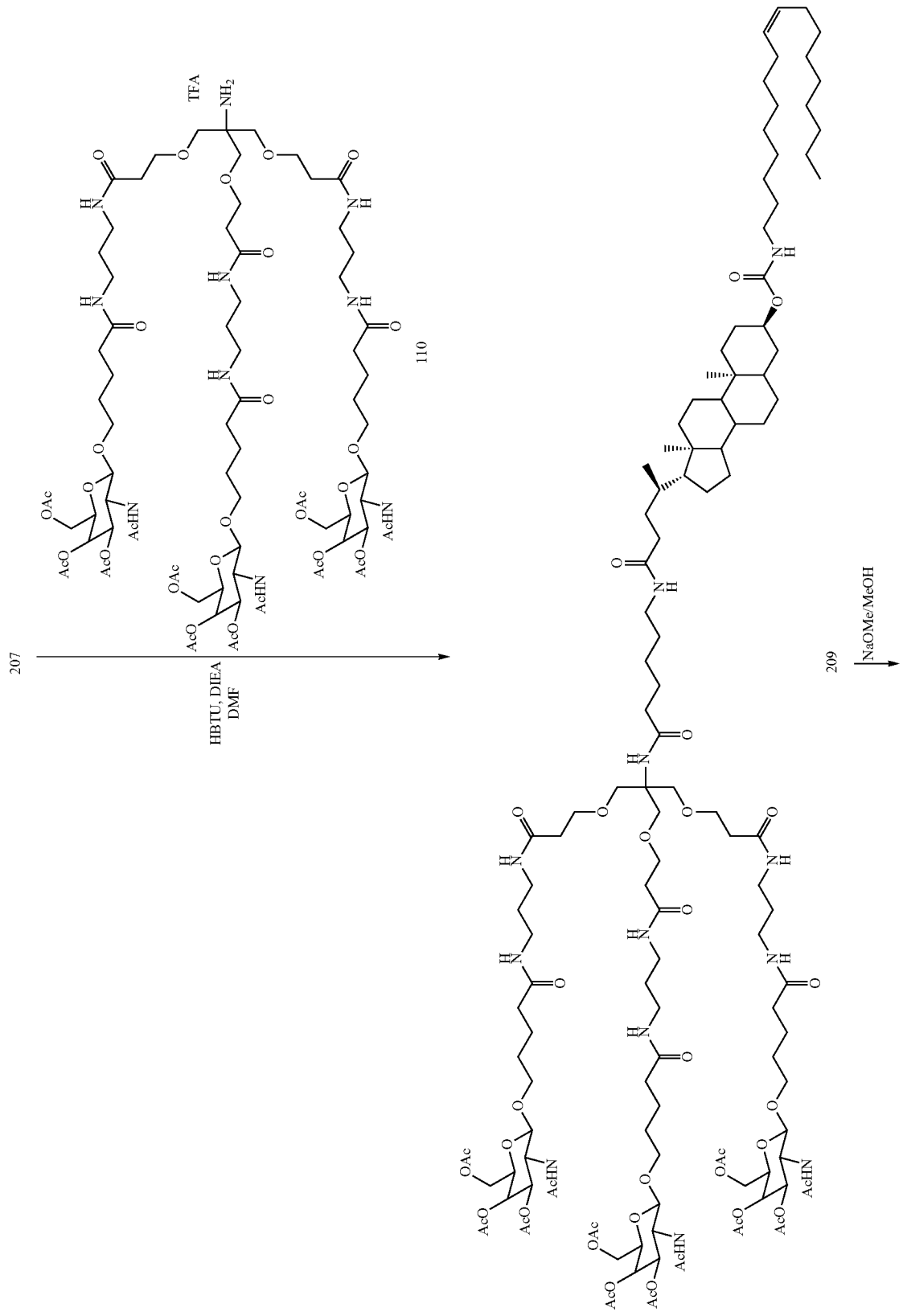

-continued
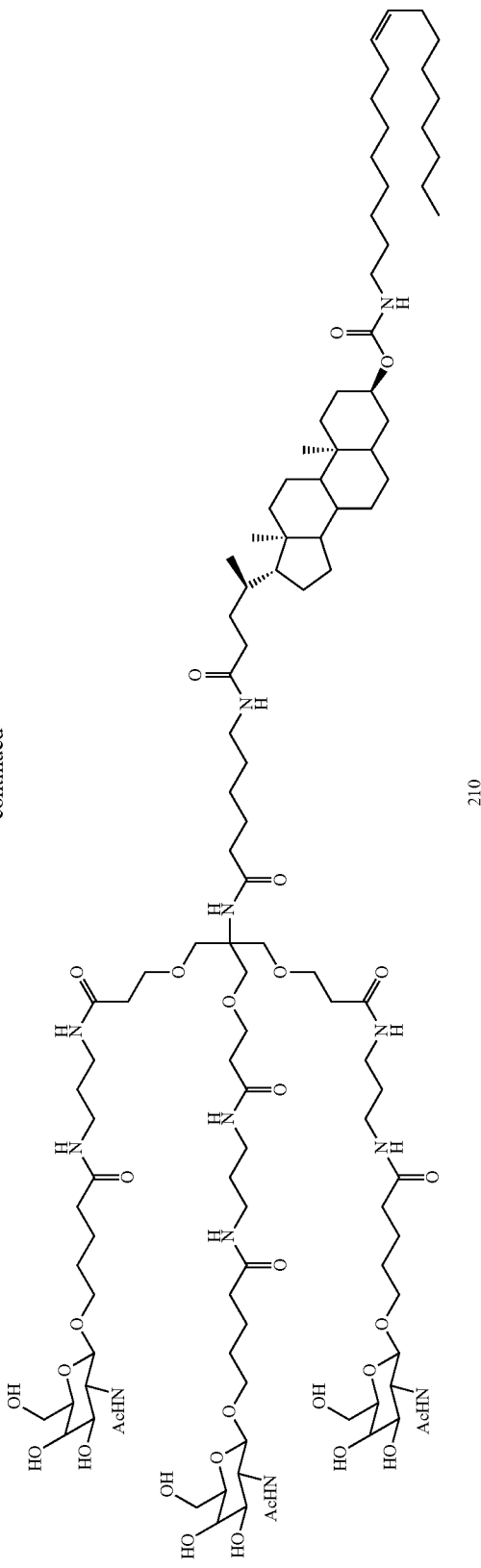
210

Preparation of 209:

Compound 207 (0.994 g, 1.269 mmol) and HBTU (0.505 g, 1.05 eq.) were dissolved in a mixture of DCM/DMF to that DIEA (0.660 mL) was added and stirred the mixture for 5 minutes. A solution of GalNAc amine (2.00 g, 1.057 mmol) was added and stirred the mixture overnight. TLC checked and solvents were removed and the residue purified by chromatography (DCM, Ethyl acetate, then 5-20% MeOH/DCM) to get the required product (1.83 g, 68%). MS: Calculated for $C_{128}H_{212}N_{12}O_{40}$, 2557.49. Found 2579.94 (M+Na).

Preparation of 210:

Compound 209 (0.506 g, 0.1978 mmol) was dissolved in a mixture of MeOH/DCM (10 mL, 2:1) to that NaOMe (4 mL, 0.5 M solution in MeOH) was added and stirred the mixture overnight. Reaction was monitored by TLC. pH was adjusted to 5-6 using acetic acid. Solvents were removed and the residue dissolved in MeOH and passed through cation exchange resin. Solvents were removed and the residue dissolved in EtOH and filtered through 0.2 μm filter. The residue was dried under high vacuum at 40° C. for two days to get the required compound as a gummy liquid (0.407 g, 92%). MS: Calculated for $C_{110}H_{194}N_{12}O_{31}$, 2179.40. Found 2202.32 (M+Na).

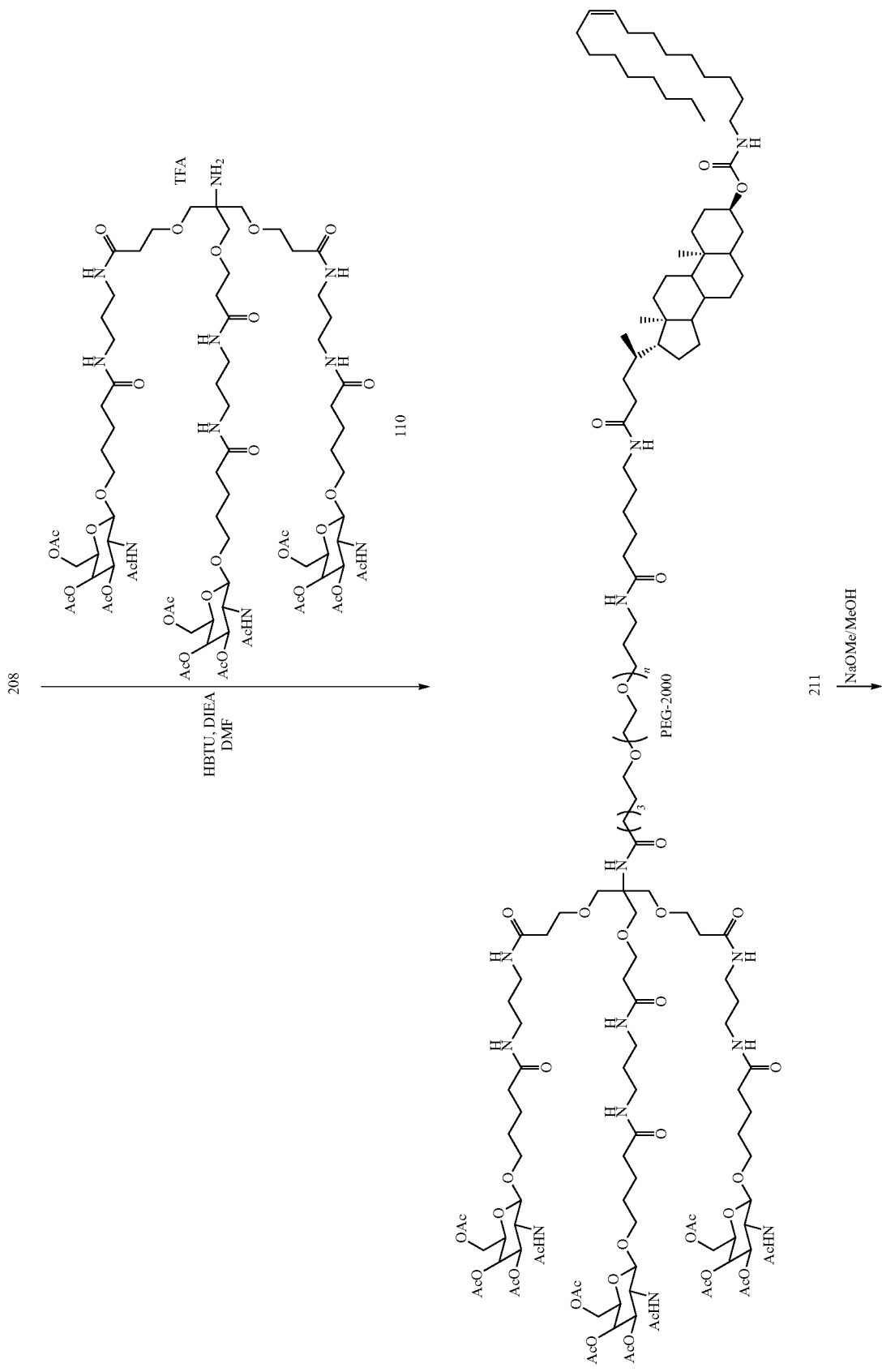

-continued
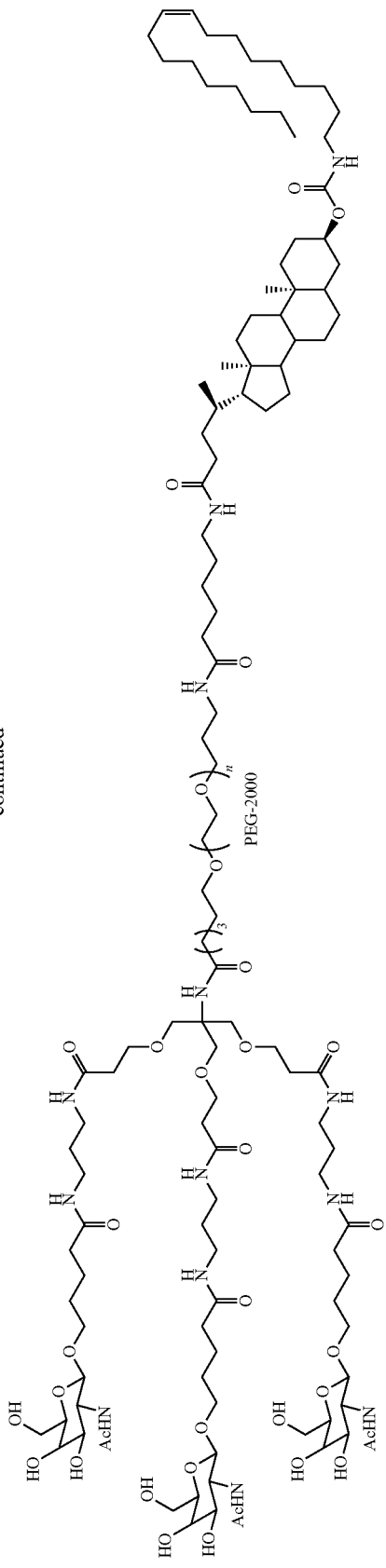
212

Preparation of 211:

Compound 208 (1.51 g, 0.514 mmol) and HBTU (0.195 g, 0.514 eq.) were dissolved in a mixture of DCM/DMF to that DIEA (0.268 mL) was added and stirred the mixture for 5 minutes. A solution of GalNAc amine (0.971 g, 0.514 mmol) was added and stirred the mixture overnight. TLC checked and solvents were removed and the residue purified by chromatography (DCM, Ethyl acetate, then 5-20% MeOH/DCM) to get the required product (1.92 g, 78%). MS calculated Average MWt. 4600-4900. found 4600-4900.

Preparation of 210:

Compound 209 (0.503 g, 0.106 mmol) was dissolved in a mixture of MeOH/DCM (10 mL, 2:1) to that NaOMe (2 mL, 0.5 M solution in MeOH) was added and stirred the mixture overnight. Reaction was monitored by TLC. pH was adjusted to 5-6 using acetic acid. Solvents were removed and the residue dissolved in MeOH and passed through cation exchange resin. Solvents were removed and the residue dissolved in EtOH and filtered through 0.2 μm filter. The residue was dried under high vacuum at 40° C. for two days to get the required compound as a white solid (0.420 g, 92%). MS calculated Average MWt. 4200-4500. found 4200-4500.

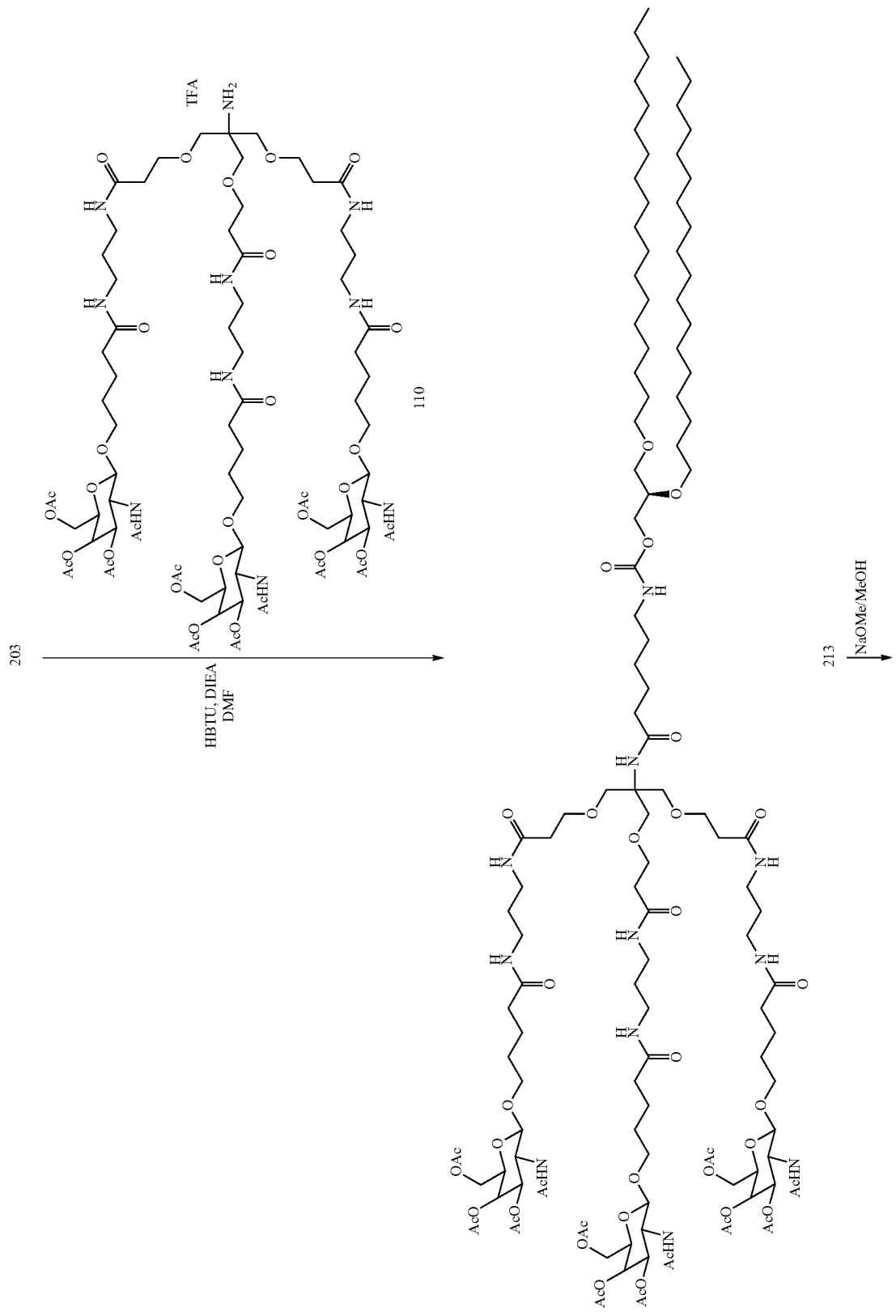

-continued
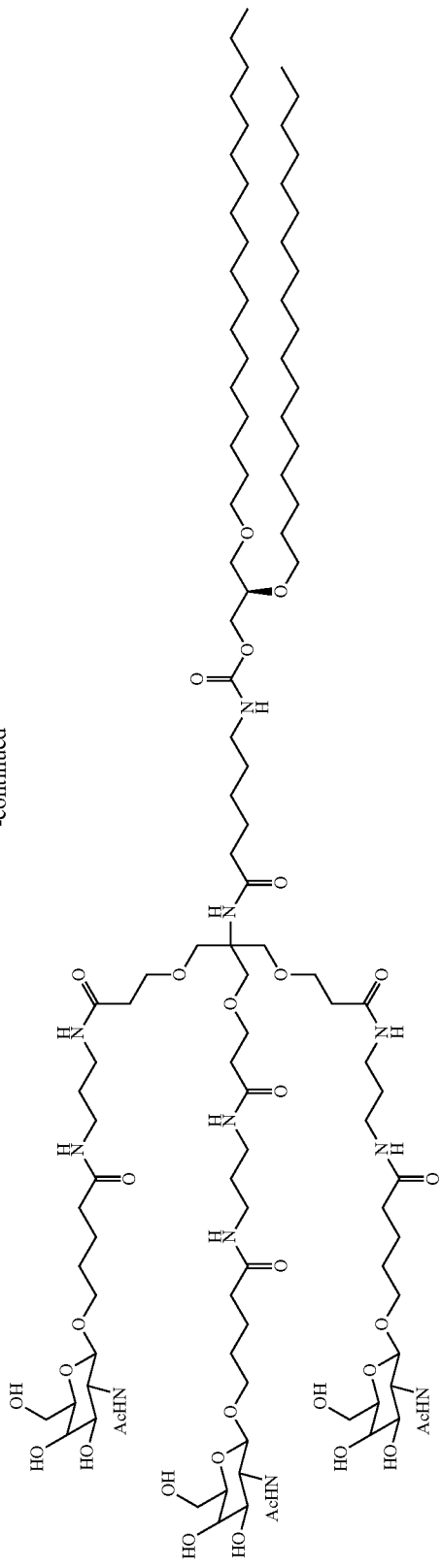
214

Preparation of 213:

Compound 203 (0.956 g, 1.268 mmol) and HBTU (0.505 g, 1.33 mmol) were dissolved in a mixture of DCM/DMF to that DIEA (0.661 mL) was added and stirred the mixture for 5 minutes. A solution of GalNAc amine (2.00 g, 1.057 mmol) was added and stirred the mixture overnight. TLC checked and solvents were removed and the residue purified by chromatography (DCM, Ethyl acetate, then 5-20% MeOH/DCM) to get the required product (1.78 g, 67%). MS: Calculated for $C_{125}H_{217}N_{11}O_{41}$, 2528.52. Found 2551.48 (M+Na).

Preparation of 214:

Compound 213 (0.518 g, 0.205 mmol) was dissolved in a mixture of MeOH/DCM (10 mL, 2:1) to that NaOMe (4 mL, 0.5 M solution in MeOH) was added and stirred the mixture overnight. Reaction was monitored by TLC. pH was adjusted to 5-6 using acetic acid. Solvents were removed and the residue dissolved in MeOH and passed through cation exchange resin. Solvents were removed and the residue dissolved in EtOH and filtered through 0.2 μm filter. The residue was dried under high vacuum at 40° C. for two days to get the required compound as a white solid (0.360 g, 86%). MS: Calculated for $C_{107}H_{199}N_{11}O_{32}$, 2150.43. Found 2173.31 (M+Na).

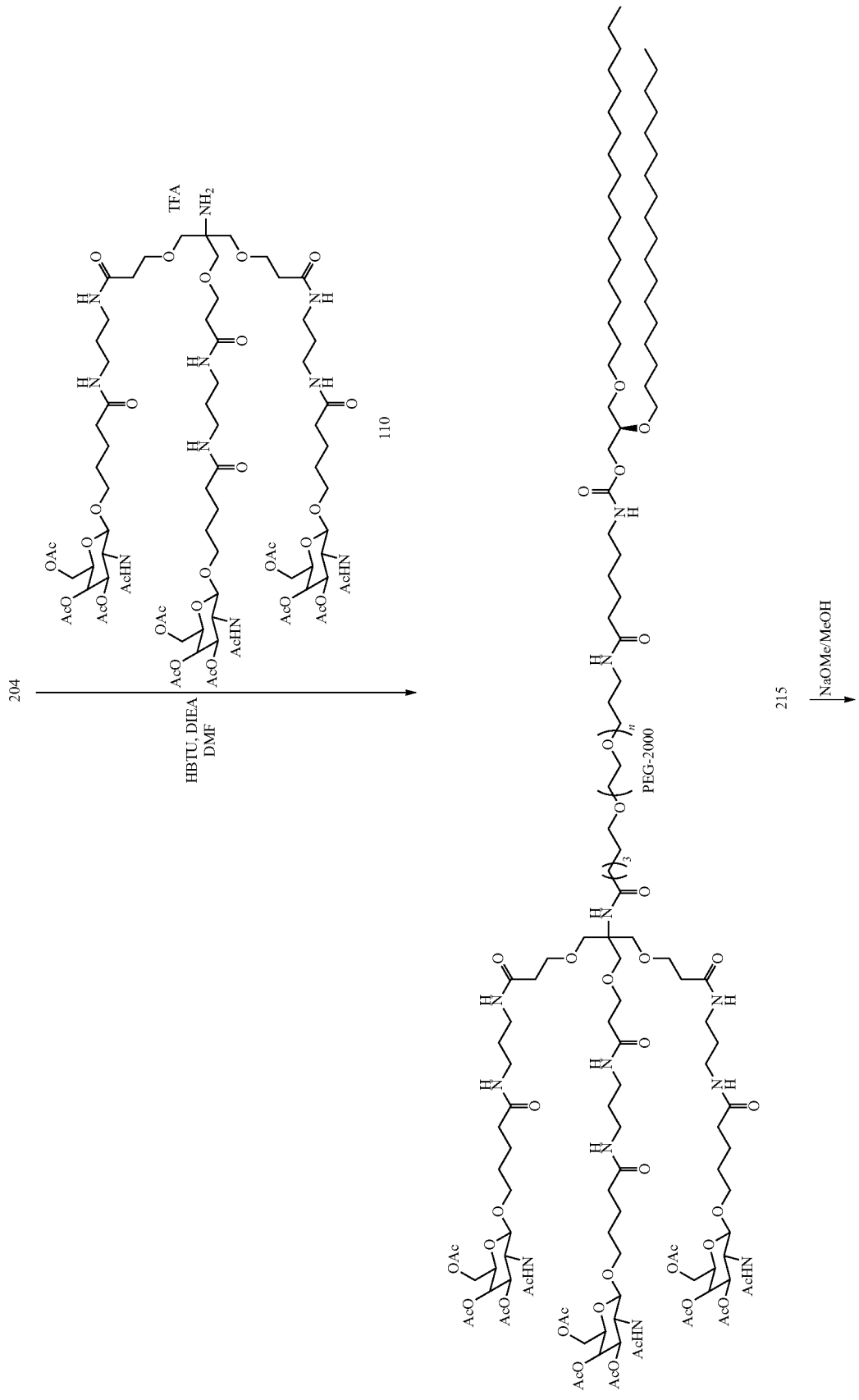

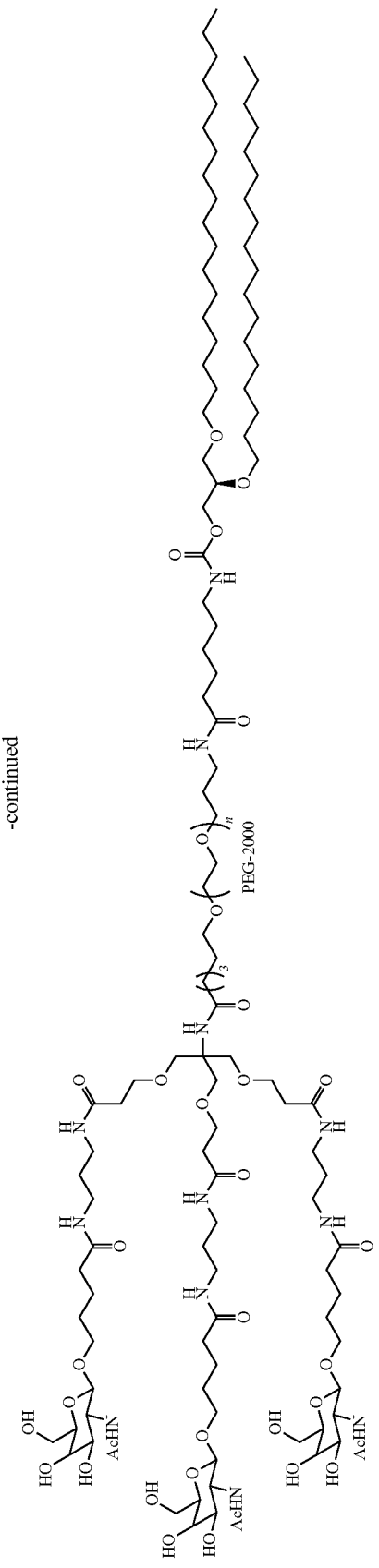
216

Preparation of 215:

Compound 204 (2.58 g, 0.880 mmol) and HBTU (0.333 g, 0.880 mmol) were dissolved in a mixture of DCM/DMF to that DIEA (0.463 mL) was added and stirred the mixture for 5 minutes. A solution of GalNAc amine (1.679 g, 0.514 mmol) was added and stirred the mixture overnight. TLC checked and solvents were removed and the residue purified by chromatography (DCM, Ethyl acetate, then 5-20% MeOH/DCM) to get the required product (2.30 g, 55%). MS calculated Average MWt. 4500-4800. found 4500-4800.

Preparation of 216:

Compound 215 (0.545 g, 0.115 mmol) was dissolved in a mixture of MeOH/DCM (10 mL, 2:1) to that NaOMe (2 mL, 0.5 M solution in MeOH) was added and stirred the mixture overnight. Reaction was monitored by TLC. pH was adjusted to 5-6 using acetic acid. Solvents were removed and the residue dissolved in MeOH and passed through cation exchange resin. Solvents were removed and the residue dissolved in EtOH and filtered through 0.2 µm filter. The residue was dried under high vacuum at 40° C. for two days to get the required compound as a white solid (0.339 g, 68%). MS calculated Average MWt. 4200-4500. found 4200-4500.

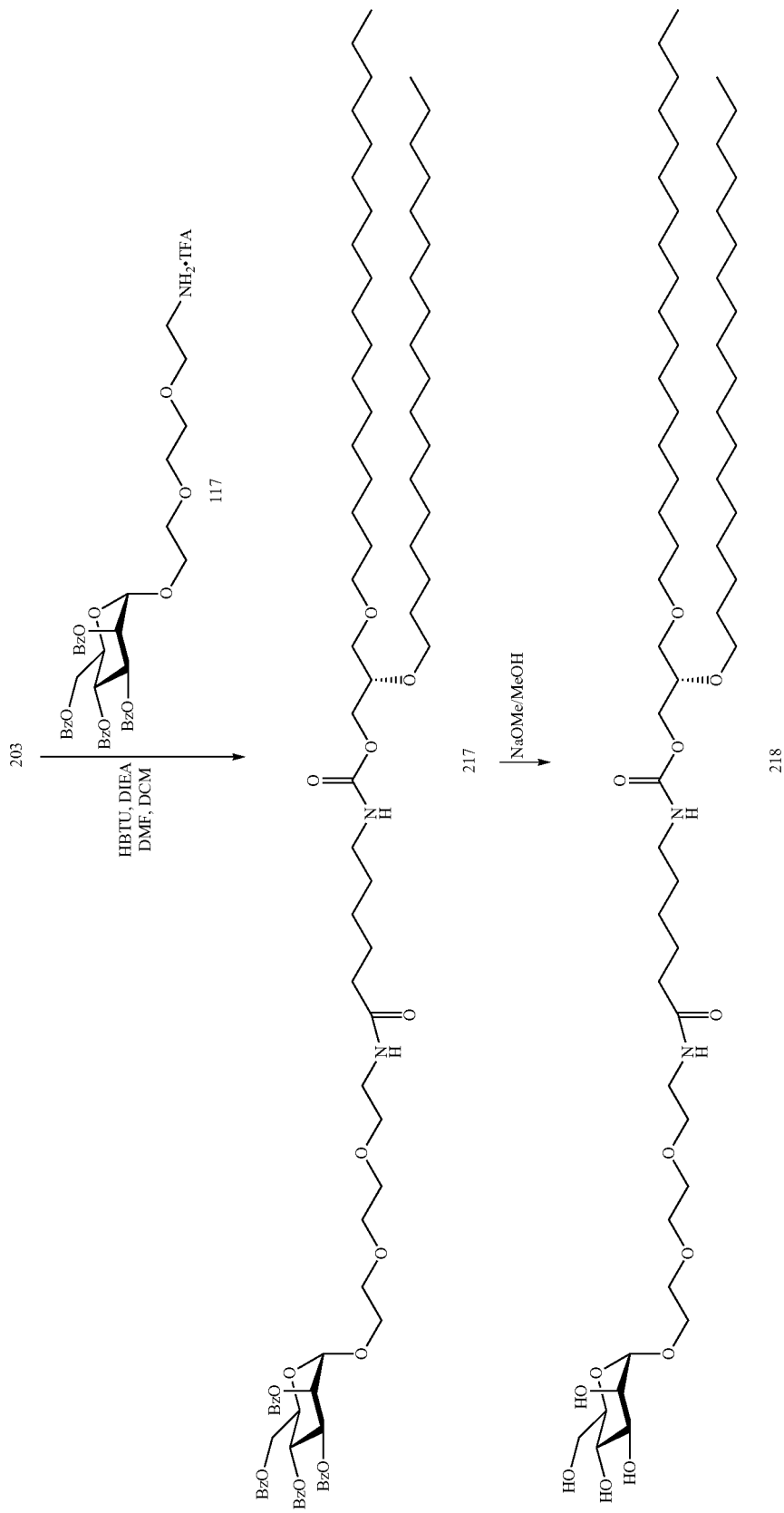

Preparation of 217:

Compound 203 (1.099 g, 1.45 mmol) and HBTU (0.550 g, 1.45 mmol) were dissolved in a mixture of DCM/DMF to that DIEA (1.26 mL) was added and stirred the mixture for 5 minutes. A solution of Mannose amine (1.47 g, 1.2 eq) was added and stirred the mixture overnight. TLC checked and solvents were removed and the residue purified by chromatography (50-80% Ethyl acetate/hexane, then ethylacetate) to get the required product (1.90 g, 89%). MS: Calculated for $C_{86}H_{130}N_2O_{17}$, 1462.94. Found 1463.95 (M+H).

Preparation of 218:

Compound 217 (1.87 g, 1.27 mmol) was dissolved in a mixture of MeOH/DCM (10 mL, 2:1) to that NaOMe (12 mL, 0.5 M solution in MeOH) was added and stirred the mixture overnight. Reaction was monitored by TLC; 5 mL of NaOMe solution was again added and continued the stirring for another 24 hrs. Solvents were removed and the residue dissolved in MeOH/DCM and passed through cation exchange resin. Solvent was removed and the residue purified by chromatography (5-10% MeOH/DCM). The residue was dried under high vacuum at 40° C. for two days to get the required compound as a white solid (0.567 g, 42%). MS: Calculated for $C_{58}H_{114}N_2O_{13}$, 1046.83. Found 1069.80 (M+Na).

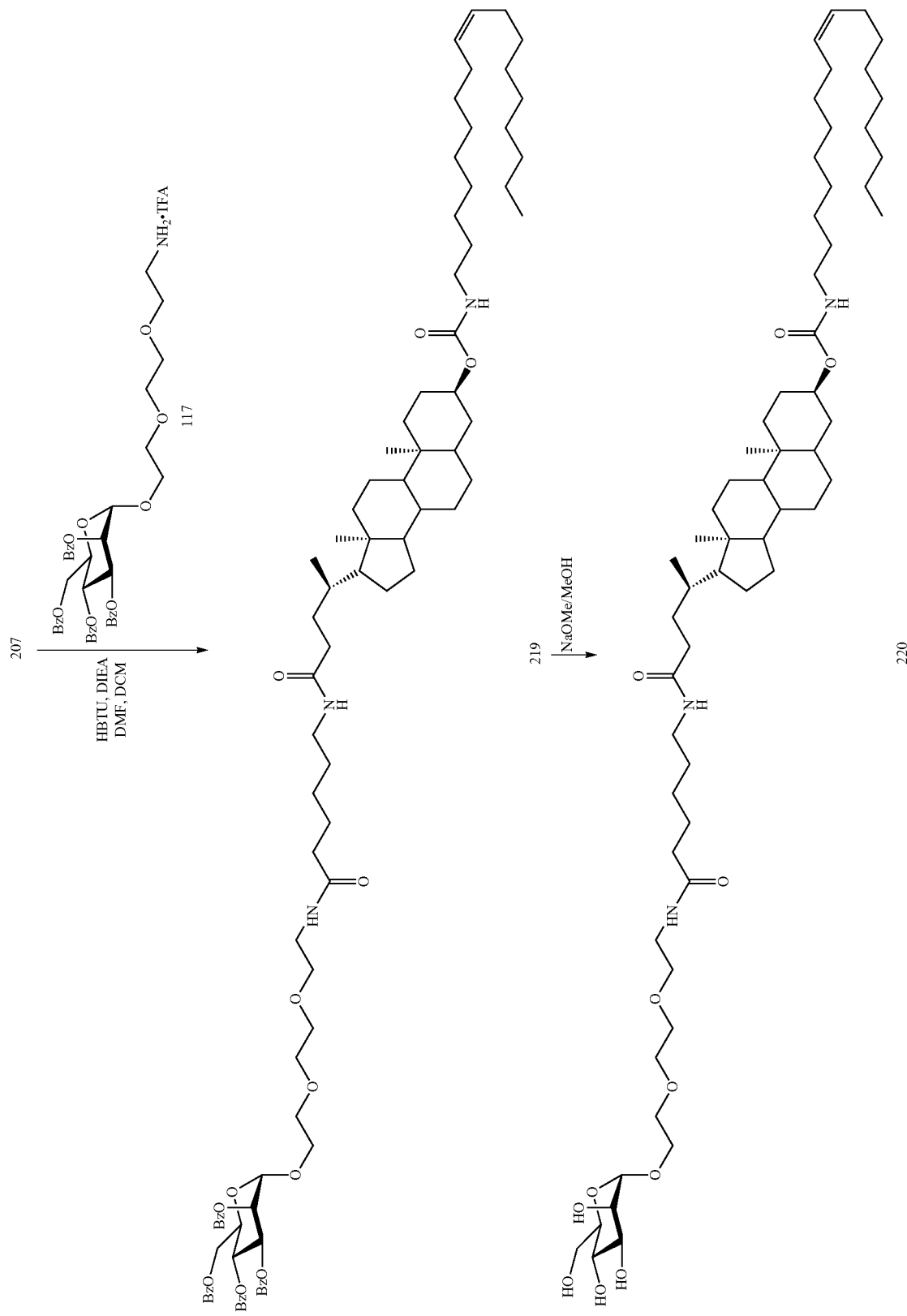

Preparation of 219:

Compound 207 (1.039 g, 1.32 mmol) and HBTU (0.510 g, 1.339 mmol) were dissolved in a mixture of DCM/DMF to that DIEA (1.15 mL) was added and stirred the mixture for 5 minutes. A solution of Mannose amine (1.338 g, 1.2 eq) was added and stirred the mixture overnight. TLC checked and solvents were removed and the residue purified by chromatography (50% Ethyl acetate/hexane, then ethyl acetate followed by 5% MeOH/DCM) to get the required product (1.63 g, 83%). MS: Calculated for $C_{89}H_{125}N_3O_{16}$, 1491.91. Found 1515.01 (M+Na).

Preparation of 220:

Compound 219 (1.55 g, 1.038 mmol) was dissolved in a mixture of MeOH/DCM (10 mL, 2:1) to that NaOMe (10 mL, 0.5 M solution in MeOH) was added and stirred the mixture overnight. Reaction was monitored by TLC; 5 mL of NaOMe solution was again added and continued the stirring for another 24 hrs. Solvents were removed and the residue dissolved in MeOH/DCM and passed through cation exchange resin. Solvent was removed and the residue purified by chromatography (First eluted with 50% EtOAc/Hexane, EtOAc, followed by 5-10% MeOH/DCM). The residue was dried under high vacuum at 40° C. for two days to get the required compound as a white solid (0.616 g, 55%). MS: Calculated for $C_{61}H_{109}N_3O_{12}$, 1075.80. Found 1098.81 (M+Na).

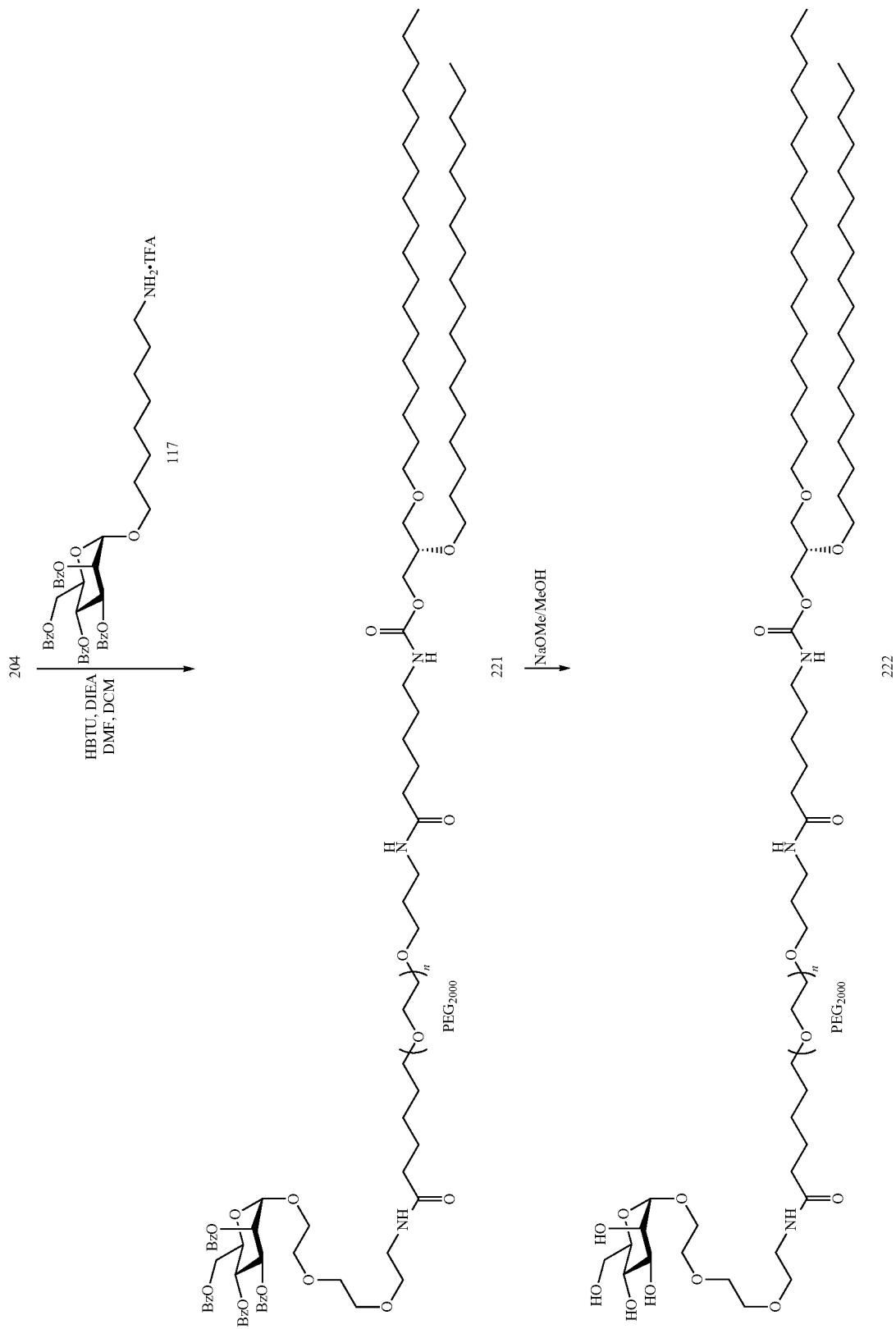

Preparation of 221:

Compound 204 (1.17 g, 0.402 mmol) and HBTU (0.168 g, 0.442 mmol) were dissolved in a mixture of DCM/DMF to that DIEA (0.420 mL) was added and stirred the mixture for 5 minutes. A solution of Mannose amine (0.406 g, 0.482 mmol) was added and stirred the mixture overnight. TLC checked and solvents were removed and the residue purified by chromatography (Ethyl acetate, then 3-10% MeOH/DCM) to get the required product (1.10 g, 75%). MS calculated Average MWt. 3400-3800. found 3400-3800.

Preparation of 222:

Compound 221 (0.952 g, 0.263 mmol) was dissolved in a mixture of MeOH/DCM (10 mL, 2:1) to that NaOMe (3 mL, 0.5 M solution in MeOH) was added and stirred the mixture overnight. Reaction was monitored by TLC; 2 mL of NaOMe solution was again added and continued the stirring for another 24 hrs. Solvents were removed and the residue dissolved in MeOH/DCM and passed through cation exchange resin. Solvent was removed and the residue purified by chromatography (First eluted with EtOAc, followed by 5-20% MeOH/DCM). The residue was dried under high vacuum at 40° C. for two days to get the required compound as a white solid (0.50 g, 59%). MS calculated Average MWt. 3100-3400. found 3100-3400.

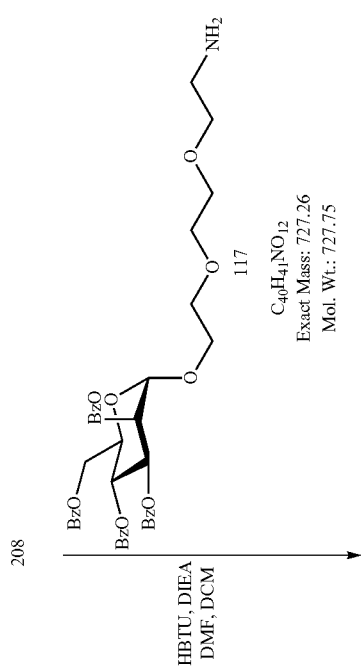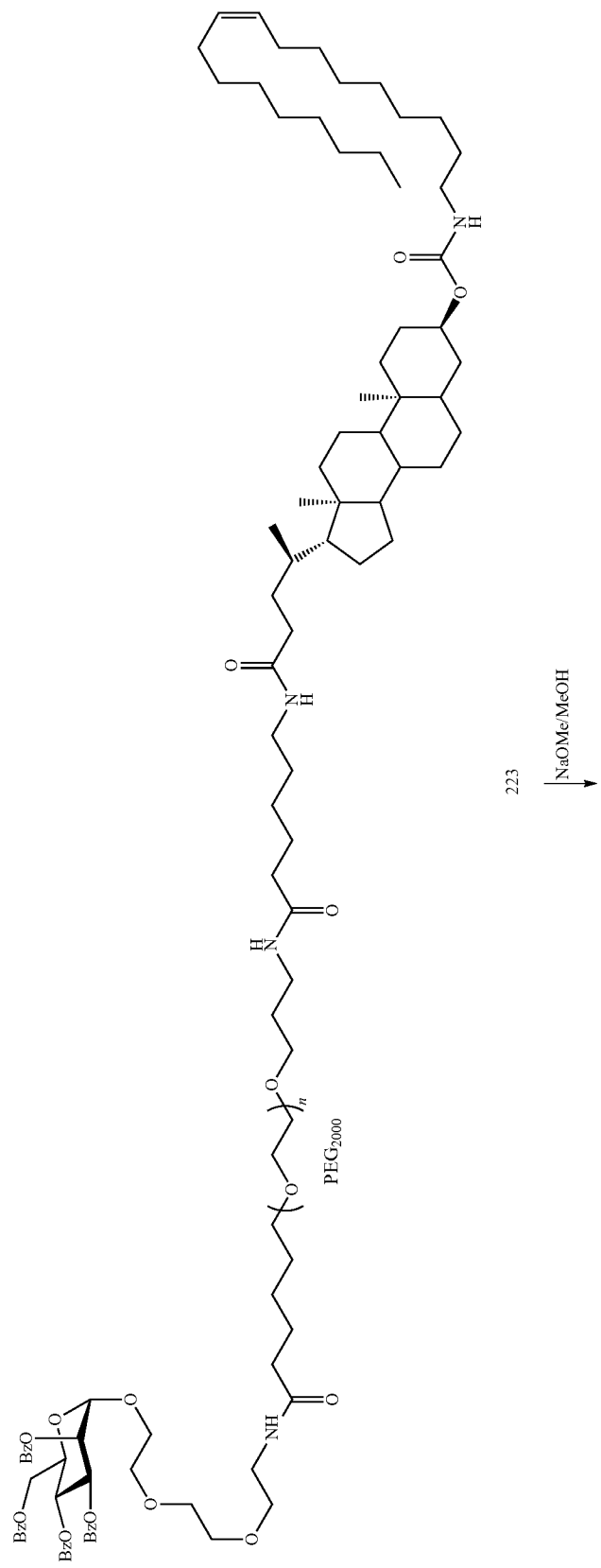

-continued
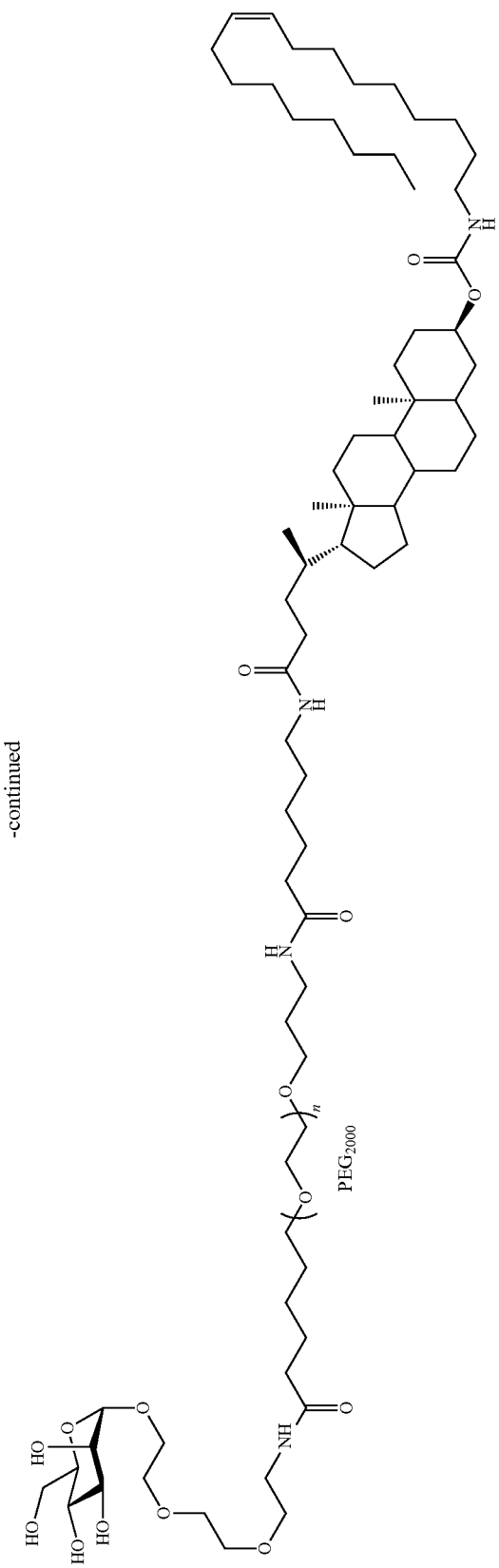
224

Preparation of 223:

Compound 208 (1.14 g, 0.388 mmol) and HBTU (0.162 g, 0.426 mmol) were dissolved in a mixture of DCM/DMF to that DIEA (0.405 mL) was added and stirred the mixture for 5 minutes. A solution of Mannose amine (0.392 g, 0.466 mmol) was added and stirred the mixture overnight. TLC checked and solvents were removed and the residue purified by chromatography (Ethyl acetate, then 3-10% MeOH/DCM) to get the required product (1.30 g, 92%). MS calculated Average MWt. 3400-3800. found 3400-3800.

as a white solid (0.456 g, 40%). MS calculated Average MWt. 3100-3400. found 3100-3400.

Example 4. Synthesis of mPEG2000-1,2-Di-O-alkyl-sn3-carbomoylglyceride (PEG-DMG)

The PEG-lipids, such as mPEG2000-1,2-Di-O-alkyl-sn3-carbomoylglyceride (PEG-DMG) were synthesized using the following procedures:

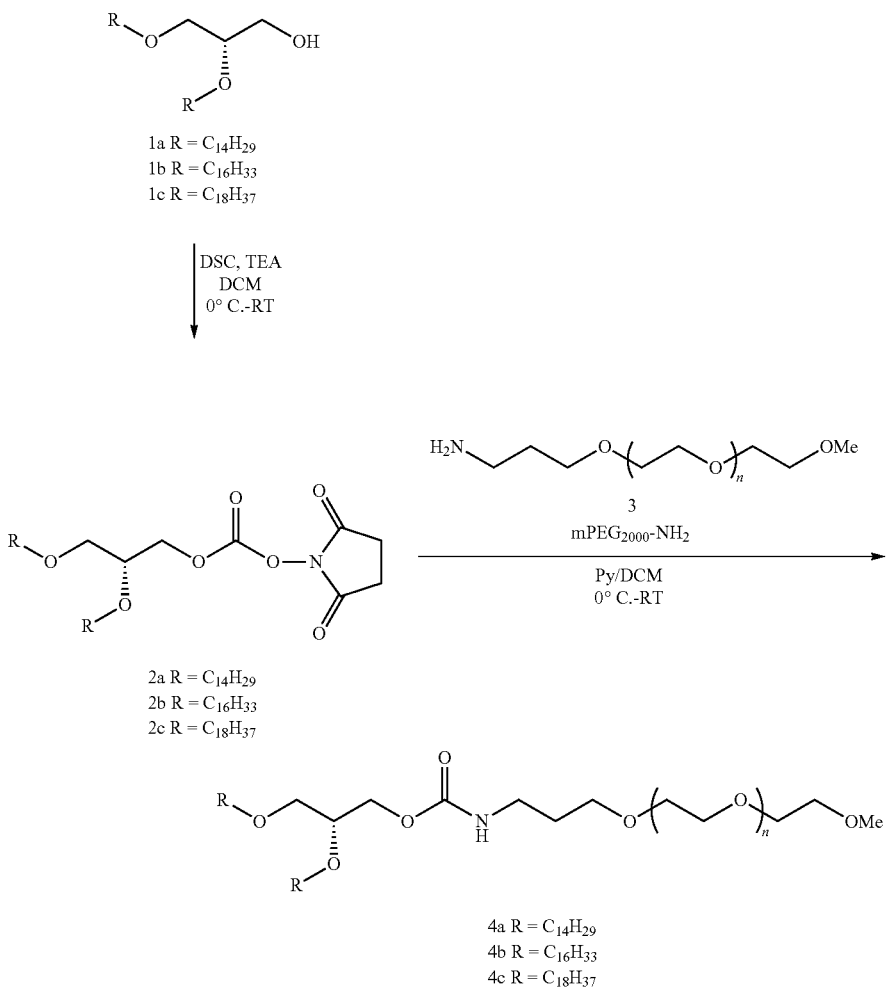

$^a$Scheme 1: mPEG2000-1,2-Di-O-alkyl-sn3-carbomoylglyceride

1a R = $C_{14}H_{29}$
1b R = $C_{16}H_{33}$
1c R = $C_{18}H_{37}$

DSC, TEA
DCM
0° C.-RT

2a R = $C_{14}H_{29}$
2b R = $C_{16}H_{33}$
2c R = $C_{18}H_{37}$ mPEG$_{2000}$-NH$_2$

Py/DCM
0° C.-RT

4a R = $C_{14}H_{29}$
4b R = $C_{16}H_{33}$
4c R = $C_{18}H_{37}$

Preparation of 224:

Compound 223 (1.303 g, 0.357 mmol) was dissolved in a mixture of MeOH/DCM (10 mL, 2:1) to that NaOMe (3.5 mL, 0.5 M solution in MeOH) was added and stirred the mixture overnight. Reaction was monitored by TLC; 2 mL of NaOMe solution was again added and continued the stirring for another 24 hrs. Solvents were removed and the residue dissolved in MeOH/DCM and passed through cation exchange resin. Solvent was removed and the residue purified by chromatography (First eluted with EtOAc, followed by 5-20% MeOH/DCM). The residue was dried under high vacuum at 40° C. for two days to get the required compound Preparation of Compound 228a:

1,2-Di-O-tetradecyl-sn-glyceride 225a (30 g, 61.80 mmol) and N,N'-succinimidylcarboante (DSC, 23.76 g, 1.5 eq) were taken in dichloromethane (DCM, 500 mL) and stirred over an ice water mixture. Triethylamine (25.30 mL, 3 eq) was added to stirring solution and subsequently the reaction mixture was allowed to stir overnight at ambient temperature. Progress of the reaction was monitored by TLC. The reaction mixture was diluted with DCM (400 mL) and the organic layer was washed with water (2×500 mL), aqueous NaHCO$_3$ solution (500 mL) followed by standard work-up. Residue obtained was dried at ambient temperature under high vacuum overnight. After drying the crude carbonate 226a thus obtained was dissolved in dichloromethane (500 mL) and stirred over an ice bath. To the stirring solution mPEG$_{2000}$-NH$_2$ (227, 103.00 g, 47.20 mmol, purchased from NOF Corporation, Japan) and anhydrous pyridine (80 mL, excess) were added under argon. In one embodiment, the methoxy-(PEG)x-amine has an x=from 45-49, preferably 47-49, and more preferably 49. The reaction mixture was then allowed stir at ambient temperature overnight. Solvents and volatiles were removed under vacuum and the residue was dissolved in DCM (200 mL) and charged on a column of silica gel packed in ethyl acetate. The column was initially eluted with ethyl acetate and subsequently with gradient of 5-10% methanol in dichloromethane to afford the desired PEG-Lipid 228a as a white solid (105.30 g, 83%). $^1$H NMR (CDCl$_3$, 400 MHz) δ=5.20-5.12 (m, 1H), 4.18-4.01 (m, 2H), 3.80-3.70 (m, 2H), 3.70-3.20 (m, —O—CH$_2$—CH$_2$—O—, PEG-CH$_2$), 2.10-2.01 (m, 2H), 1.70-1.60 (m, 2H), 1.56-1.45 (m, 4H), 1.31-1.15 (m, 48H), 0.84 (t, J=6.5 Hz, 6H). MS range found: 2660-2836.

Preparation of 228b:

1,2-Di-O-hexadecyl-sn-glyceride 225b (1.00 g, 1.848 mmol) and DSC (0.710 g, 1.5 eq) were taken together in dichloromethane (20 mL) and cooled down to 0° C. in an ice water mixture. Triethylamine (1.00 mL, 3 eq) was added to that and stirred overnight. The reaction was followed by TLC, diluted with DCM, washed with water (2 times), NaHCO$_3$ solution and dried over sodium sulfate. Solvents were removed under reduced pressure and the residue 226b under high vacuum overnight. This compound was directly used for the next reaction without further purification. MPEG$_{2000}$-NH$_2$ 227 (1.50 g, 0.687 mmol, purchased from NOF Corporation, Japan) and compound from previous step 226b (0.702 g, 1.5 eq) were dissolved in dichloromethane (20 mL) under argon. The reaction was cooled to 0° C. Pyridine (1 mL, excess) was added to that and stirred overnight. The reaction was monitored by TLC. Solvents and volatiles were removed under vacuum and the residue was purified by chromatography (first Ethyl acetate then 5-10% MeOH/DCM as a gradient elution) to get the required compound 228b as white solid (1.46 g, 76%). $^1$H NMR (CDCl$_3$, 400 MHz) δ=5.17 (t, J=5.5 Hz, 1H), 4.13 (dd, J=4.00 Hz, 11.00 Hz, 1H), 4.05 (dd, J=5.00 Hz, 11.00 Hz, 1H), 3.82-3.75 (m, 2H), 3.70-3.20 (m, —O—CH$_2$—CH$_2$—O—, PEG-CH$_2$), 2.05-1.90 (m, 2H), 1.80-1.70 (m, 2H), 1.61-1.45 (m, 6H), 1.35-1.17 (m, 56H), 0.85 (t, J=6.5 Hz, 6H). MS range found: 2716-2892.

Preparation of 228c:

1,2-Di-O-octadecyl-sn-glyceride 225c (4.00 g, 6.70 mmol) and DSC (2.58 g, 1.5 eq) were taken together in dichloromethane (60 mL) and cooled down to 0° C. in an ice water mixture. Triethylamine (2.75 mL, 3 eq) was added to that and stirred overnight. The reaction was followed by TLC, diluted with DCM, washed with water (2 times), NaHCO$_3$ solution and dried over sodium sulfate. Solvents were removed under reduced pressure and the residue under high vacuum overnight. This compound was directly used for the next reaction with further purification. MPEG$_{2000}$-NH$_2$ 227 (1.50 g, 0.687 mmol, purchased from NOF Corporation, Japan) and compound from previous step 226c (0.760 g, 1.5 eq) were dissolved in dichloromethane (20 mL) under argon. The reaction was cooled to 0° C. Pyridine (1 mL, excess) was added to that and stirred overnight. The reaction was monitored by TLC. Solvents and volatiles were removed under vacuum and the residue was purified by chromatography (first Ethyl acetate then 5-10% MeOH/DCM as a gradient elution) to get the required compound 228c as white solid (0.92 g, 48%). $^1$H NMR (CDCl$_3$, 400 MHz) δ=5.22-5.15 (m, 1H), 4.16 (dd, J=4.00 Hz, 11.00 Hz, 1H), 4.06 (dd, J=5.00 Hz, 11.00 Hz, 1H), 3.81-3.75 (m, 2H), 3.70-3.20 (m, —O—CH$_2$—CH$_2$—O—, PEG-CH$_2$), 1.80-1.70 (m, 2H), 1.60-1.48 (m, 4H), 1.31-1.15 (m, 64H), 0.85 (t, J=6.5 Hz, 6H). MS range found: 2774-2948.

Example 5. Factor VII (FVII) In Vitro Assay

Cell Seeding for Transfection.

Cells are seeded into 96-well plates one day prior to siRNA transfection at a density of 15,000 cells per well in media without antibiotics (150,000 cells/ml media, 100 μl per well).

Standard Transfection Conditions for FVII Stable Cell Line

- Lipofectamine 2000 at a concentration of 0.5 μL/well is used for transfection in a 96 well plate set-up
- FVII-targeting siRNA or control siRNA is diluted to a concentration of 6 nM in OptiMEM
- siRNA and transfection agent (lipofectamine 2000) are mixed and complex allowed to form by incubating 20 minutes at room temperature
- After 20 minutes, 50 μL of complexes (out of total 60 μl volume) added to a single well containing cells that were seeded on the previous day (well already contains 100 μL of growth medium), sample is mixed by gently pipetting up and down; well now contains 150 μL total volume, 1 nM siRNA, 0.5 μL LF 2000 reagent
- Plate is returned to 37° C. incubator.
- After 24 h, media is removed and replaced with fresh media (100 μL/well)
- 24 hours after media exchange, media supernatant is collected for FVII activity assay
- Levels of Factor VII protein in the supernatant are determined in samples using a chromogenic assay (Coaset Factor VII, DiaPharma Group, OH or Biophen FVII, Aniara Corporation, OH) according to manufacturer's protocols Example 6. FVII and apoB In Vivo Assay C57BL/6 mice (Charles River Labs, MA) and Sprague-Dawley rats (Charles River Labs, MA) receive either saline or siRNA in desired formulations via tail vein injection at a volume of 0.01 mL/g. At various time points post-administration, animals are anesthesized by isofluorane inhalation and blood is collected into serum separator tubes by retroorbital bleed. Serum levels of Factor VII protein are determined in samples using a chromogenic assay (Coaset Factor VII, DiaPharma Group, OH or Biophen FVII, Aniara Corporation, OH) according to manufacturer's protocols. A standard curve is generated using serum collected from saline treated animals. In experiments where liver mRNA levels are assessed at various time points post-administration, animals are sacrificed and livers are harvested and snap frozen in liquid nitrogen. Frozen liver tissue is ground into powder. Tissue lysates are prepared and liver mRNA levels of Factor VII and apoB are determined using a branched DNA assay (QuantiGene Assay, Panomics, CA).

Example 7. Targeting Lipid-Mediated Delivery in Rodent Hepatic Gene Silencing Models The liver represents an attractive organ for therapeutic intervention, both because of the number of potential hepatic targets as well as the highly-perfused nature of the organ, which may render it more amenable to delivery of exogenous siRNAs. A liver-directed in vivo screen is used to identify targeting lipid/siRNA complexes that facilitate high levels of siRNA-mediated gene silencing in hepatocytes, the cells comprising the liver parenchyma. Factor VII, a blood clotting factor, is an ideal target gene for assaying functional siRNA delivery to liver. It is produced specifically in hepatocytes; therefore, gene silencing indicates successful delivery to parenchyma, as opposed to delivery solely to the cells of the reticulo-endothelial system (e.g., Kupffer cells). Furthermore, Factor VII is a secreted protein that can be readily measured in serum, obviating the need to sacrifice animals. Finally, owing to its short half-life (2-5 hours), silencing at the mRNA level is manifest as silencing at the protein level with minimal lag.

All procedures used in animal studies conducted at Alnylam are approved by the Institutional Animal Care and Use Committee (IACUC) and are consistent with local, state, and federal regulations as applicable. Mice will receive two daily i.v. injections of different lipid formulations of siRNA at a dose of 2.5 mg/kg. Factor VII protein levels are quantified 24 h after the second administration. Alternatively, rats are injected with cationic lipid/siRNA at 1.25, 2.5, 5, and 10 mg/kg. Animals are bled at various time points and sacrificed 48 h after administration. Evaluated are liver factor VII mRNA levels, serum Factor VII protein levels, and prothrombin time.

Example 8. Specificity of Liposome-Mediated siRNA Delivery in Rodent Hepatic Gene Silencing Models All procedures used in animal studies conducted at Alnylam are approved by the Institutional Animal Care and Use Committee (IACUC) and are consistent with local, state, and federal regulations as applicable. To verify the specificity of gene silencing, liver mRNA levels are measured for both Factor VII and another hepatocyte-expressed gene, apolipoprotein B (apoB). Animals will be treated with formulations containing only siFVII or only siapoB and levels of mRNAs transcribed from both genes will be measured. Further, administration of a cationic lipid formulation of a mixture of the two siRNAs will be evaluated as will the effect of a mismatched Factor VII siRNA. These data will show that the observed gene silencing is a direct result of the specific effects of lipid/siRNA on mRNA levels in the liver and that these effects are applicable to multiple hepatocyte-expressed genes.

Example 9. In Vivo Rodent Factor VII and apoB Silencing Experiments

All procedures used in animal studies conducted at Alnylam are approved by the Institutional Animal Care and Use Committee (IACUC) and are consistent with local, state, and federal regulations as applicable. C57BL/6 mice (Charles River Labs, MA) and Sprague-Dawley rats (Charles River Labs, MA) receive either saline or siRNA in lipid formulations via tail vein injection at a volume of 0.01 mL/g. At various time points post-administration, animals are anesthesized by isofluorane inhalation and blood is collected into serum separator tubes by retroorbital bleed. Serum levels of Factor VII protein are determined in samples using a chromogenic assay (Coaset Factor VII, DiaPharma Group, OH or Biophen FVII, Aniara Corporation, OH) according to manufacturer's protocols. A standard curve is generated using serum collected from saline-treated animals. In experiments where liver mRNA levels are assessed, at various time points post-administration, animals are sacrificed and livers are harvested and snap frozen in liquid nitrogen. Frozen liver tissue is ground into powder. Tissue lysates are prepared and liver mRNA levels of Factor VII and apoB are determined using a branched DNA assay (QuantiGene Assay, Panomics, CA).

Example 10. In Vivo Mouse RSV Silencing Experiments

All procedures used in animal studies conducted at Alnylam are approved by the Institutional Animal Care and Use Committee (IACUC) and are consistent with local, state, and federal regulations as applicable. BALB/c mice (Harlan Sprague-Dawley Laboratories, Indianapolis, Ind.) are anesthetized by intraperitoneal (i.p.) administration of 2,2,2-tribromoethanol (Avertin) and instilled intranasally (i.n.) with lipid/siRNA formulations in a total volume of 50 μL. At 4 h post siRNA instillation, the mice are anesthetized and infected intranasally with $10^6$ PFU of RSV/A2 or RSV/B1. Prior to removal of lungs at day 4 post-infection, anesthetized mice are exsanguinated by severing the right caudal artery. Lung tissue will be collected on ice in phosphate-buffered saline (PBS, Invitrogen) to determine virus titers. RSV titers from lungs are measured by immunostaining plaque assay. Lungs are homogenized with a hand-held Tissumiser homogenizer (Fisher Scientific, Pittsburgh, Pa.). The lung homogenates are placed on ice for 5-10 minutes to allow debris to settle. Clarified lung lysates are diluted 10-fold in serum-free D-MEM, added to 95% confluent Vero E6 cells cultured in D-MEM in 24-well plates, and incubated for 1 h at 37° C., followed by 2% methylcellulose overlay. At 5 days post-infection, the media is removed and the cells were fixed with acetone:methanol (60:40) and immunostained. Plaques are counted and log (10) pfu/g lung versus PBS or siRNA mismatch control is determined Example 11. Silencing in Peritoneal Macrophages All procedures used in animal studies conducted at Alnylam are approved by the Institutional Animal Care and Use Committee (IACUC) and are consistent with local, state, and federal regulations as applicable. C57B1/6J mice (Jackson Labs) are injected intraperitoneally with 1 mL of 4% Brewers Thioglycollate medium (Difco) 3 days prior to injecting 10 mg/kg of lipid/siRNA i.p (4 mice per group). Peritoneal lavage is collected 4 days later and stained with appropriate fluorophore conjugated antibodies (BD Biosciences). Flow cytometry samples are analyzed on the LSRII flowcytometer (BD Bioscience) and FlowJo software (Treestar) is used to identify the $CD11b^{high}Gr1^{low}$ macrophage population and quantify expression of surface proteins of interest.

Example 12. In Vivo miRNA Silencing Experiments

All procedures used in animal studies conducted at Alnylam are approved by the Institutional Animal Care and Use Committee (IACUC) and are consistent with local, state, and federal regulations as applicable. C57BL/6NCRL mice (Charles River, Sulzfeld, Germany) will receive lipid formulations of antagomir or anti-miR via tail vein injection at 5 mg/kg (0.5 mg/mL) on three consecutive days. Livers are taken at day 4 and expression levels of miRNA of interest are determined. Liver tissue is dissolved in proteinase K-containing cell and tissue lysis buffer (EPICENTRE, Madison, Wis.) and subjected to sonication. Total RNA is extracted with TE-saturated phenol (Roth, Karlsruhe, Germany) and subsequently precipitated using ethanol. Synthetic DNA probes complementary to the mouse miRNA of interest, as well as mouse U6 RNA as a control, are 5'-end labeled using polynucleotide kinase (New England Biolabs) and γ-32P ATP (GE Healthcare).

Total liver RNA is simultaneously hybridized in solution to a miRNA-specific probe and the U6 probe. The hybridization conditions allow detection of U6 RNA and mature miRNA, but not pre-miRNA. Following treatment with 51 nuclease, samples are loaded on denaturing 10% acrylamide gels. Gels are exposed to a phosphoimager screen and analyzed on a Typhoon 9200 instrument (GE Healthcare). Relative signal intensities of miRNA versus U6 are calculated for each sample.

Example 13. Cationic Lipid-mediated Delivery of Single-Stranded Oligoribonucleotides (Antagomirs) In Vivo To examine the utility of cationic lipid materials in the delivery of nucleic acid drugs other than siRNAs, we will tested the potential of cationic lipids to facilitate the delivery of single-stranded 2'-O-Me oligoribonucleotides targeting miRNAs (antagomirs or anti-miRs). In vivo delivery of anti-miR results in specific target miRNA silencing and, consequently, the specific upregulation of genes regulated by the target miRNA. Cationic lipid-formulated anti-miR122 will be given at doses of 5 mg/kg on three consecutive days to mice as described above.

Expression of genes regulated by miR-122 will be analyzed using a branched DNA assay. Briefly, 30-50 mg of frozen liver tissue is lysed in 1 mL Tissue and Cell Lysis Buffer (EPICENTRE, WI) by sonication. Between 10 and 40 µL of lysate is used for the branched DNA assay, depending on signal strength of target gene. Probe sets are designed using QuantiGene ProbeDesigner software. Target gene expression is assayed according to QuantiGene Detection Assay recommendations and normalized to corresponding GAPDH housekeeper expression from same liver tissue lysate.

Example 14. Evaluation of Toxicity

All procedures used in animal studies conducted at Alnylam are approved by the Institutional Animal Care and Use Committee (IACUC) and are consistent with local, state, and federal regulations as applicable. Rats are given four once-per-week i.v. bolus injections of a formulated siRNA at doses as high as 10 mg/kg/week. A control siRNA that should not hybridize with any known mRNA will be used in order to eliminate any potential target silencing-related toxicities. The appearance and weights of all organs will be determined.

Example 15. Targeting Lipid-Mediated Gene Silencing in Non-Human Primates

To determine the effects of cationic lipid-formulated siRNA in a third animal species, studies in non-human primates will be performed. All procedures using cynomolgus monkeys will be conducted by a certified contract research organization using protocols consistent with local, state, and federal regulations as applicable and approved by the Institutional Animal Care and Use Committee (IACUC). Cynomolgus monkeys (n=6 per group) will receive either 5 mL/kg phosphate-buffered saline, 2.5 mg/kg formulated control siRNA (1.25 mL/kg), 2.5 mg/kg (1.25 mL/kg) formulated siApoB, or 6.25 mg/kg (3.125 mL/kg) formulated siApoB as bolus i.v. injections via the brachial vein. For apoB-100 protein measurements, serum will be collected pre-dose and at 0.5, 1, 2, 3, 4, 6, 8, 11, 14, 17, 20, 23, 26, and 30 days post administration. In a subsequent experiment, cynomolgus monkeys (n=3 per group) will receive either 2.5 mg/kg formulated control siRNA or 2.5 or 6.25 mg/kg of formulated siApoB as bolus i.v. injections via the saphenous vein. For apoB-100 protein measurements, serum will be collected pre-dose and at 12, 24, and 48 h post administration. ApoB-100 protein levels will be determined using an ELISA assay. Clinical chemistries are analyzed at pre-dose and 24 and 48 h post administration. Hematology and coagulation parameters are analyzed at pre-dose and 48 h post administration. Animals are sacrificed at 48 h. Liver Apob mRNA levels are determined in liver samples using a branched DNA assay (QuantiGene Assay, Panomics, CA The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:
1. A pharmaceutical formulation, comprising:
(i) a targeting lipid having a structure shown in formula (I)

$$L^A[\text{-P-Q-R-}]_q\text{T-}L^B \qquad \text{Formula (I)}$$

wherein:
$L^A$ has the structure shown in formula V:

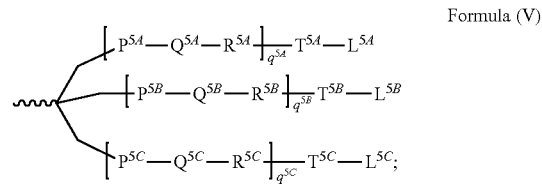

Formula (V)

$q^{5A}$, $q^{5B}$ and $q^{5C}$ represent independently for each occurrence 0-20; $P^{5A}$, $P^{5B}$, $P^{5C}$, $T^{5A}$, $T^{5B}$ and $T^{5C}$ are each independently for each occurrence absent, NR', O, C(O), NHC(O), or C(O)NH $Q^{5A}$, $Q^{5B}$ and $Q^{5C}$ are independently for each occurrence —$(CH_2)_n$—

$R^{5A}$, $R^{5B}$ and $R^{5C}$ are each independently for each occurrence absent, CO, NH, O, NHC(O), or C(O)NH;

$L^{5A}$, $L^{5B}$ and $L^{5C}$ are each N-acetyl-galactosamine, q represents 0-20;

P is each independently for each occurrence absent, NR', O, C(O), NHC(O), or C(O)NH Q is independently for each occurrence, —(CH$_2$)$_n$—, or —(CH$_2$CH$_2$O)$_P$CH$_2$CH$_2$—;

R is each independently for each occurrence absent, CO, NH, O, NHC(O), or C(O)NH;

T is NHC(O);

L$^B$ has the structure of formula (VI):

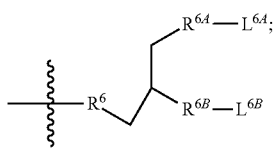

R$^6$, R$^{6A}$ and R$^{6B}$ are O,

R' is H;

L$^{6A}$ and L$^{6B}$ are each independently C$_6$-C$_{28}$ alkyl:

n represent independently for each occurrence 1-20; and p represent independently for each occurrence 0-50;

(ii) a cationic lipid;

(iii) a neutral lipid selected from DSPC, POPC, DOPE, and SM;

(iv) cholesterol; and (v) PEG-DMG, or PEG-DMA, wherein the components are in a molar ratio of about 0.5-50% targeting lipid: 20-60% cationic lipid:5-25% neutral lipid:25-55% Chol:0.5-15% PEG-DMG or PEG-DMA.

2. The pharmaceutical formulation of claim 1, wherein L$^A$ is

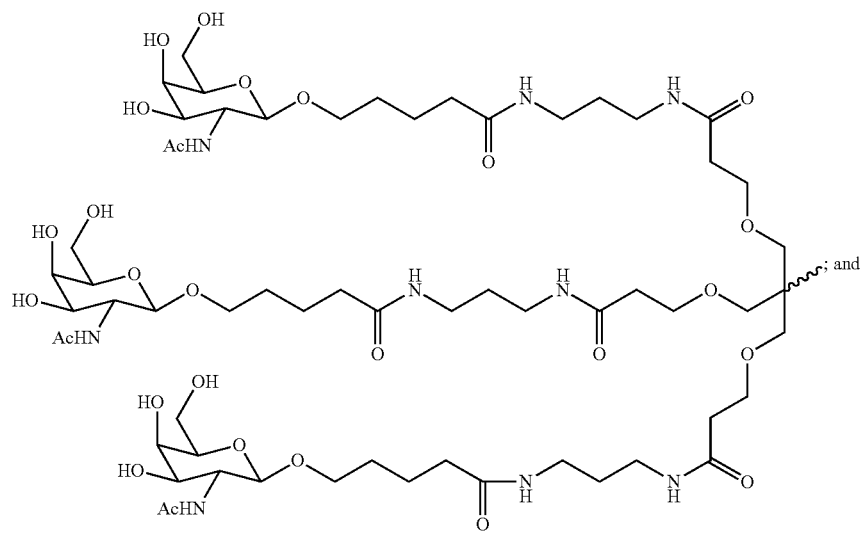 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

L$^B$ is

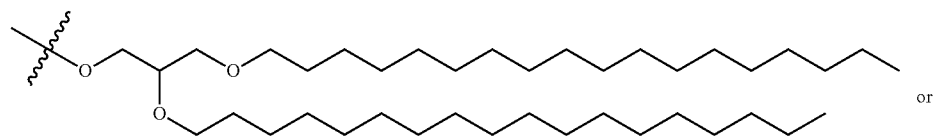 [SMILES: *OCC(COCCCCCCCCCCCCCCCCCC)OCCCCCCCCCCCCCCCCCC]

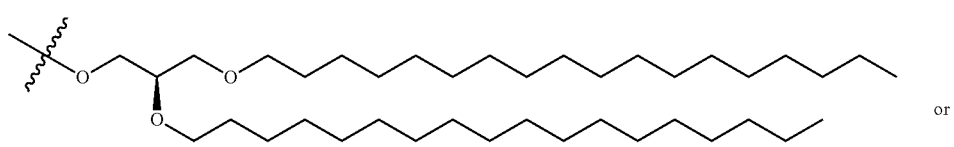 [SMILES: *OC[C@@H](COCCCCCCCCCCCCCCCCCC)OCCCCCCCCCCCCCCCCCC]

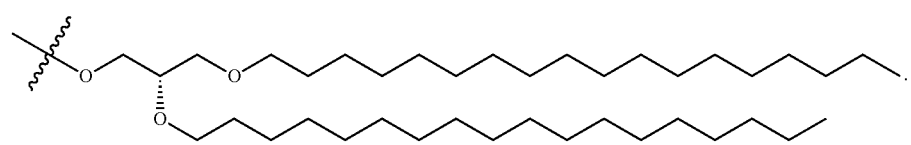 [SMILES: *OC[C@H](COCCCCCCCCCCCCCCCCCC)OCCCCCCCCCCCCCCCCCC]

3. A pharmaceutical formulation, comprising:
(i) a targeting lipid having a structure shown in formula 214 or 216

203 204
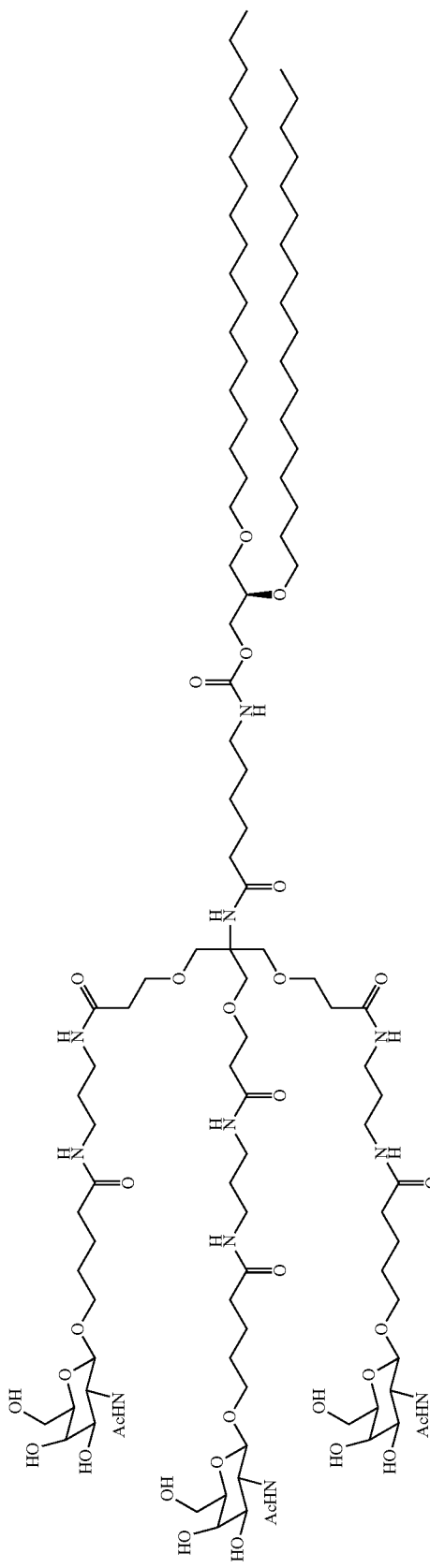
214
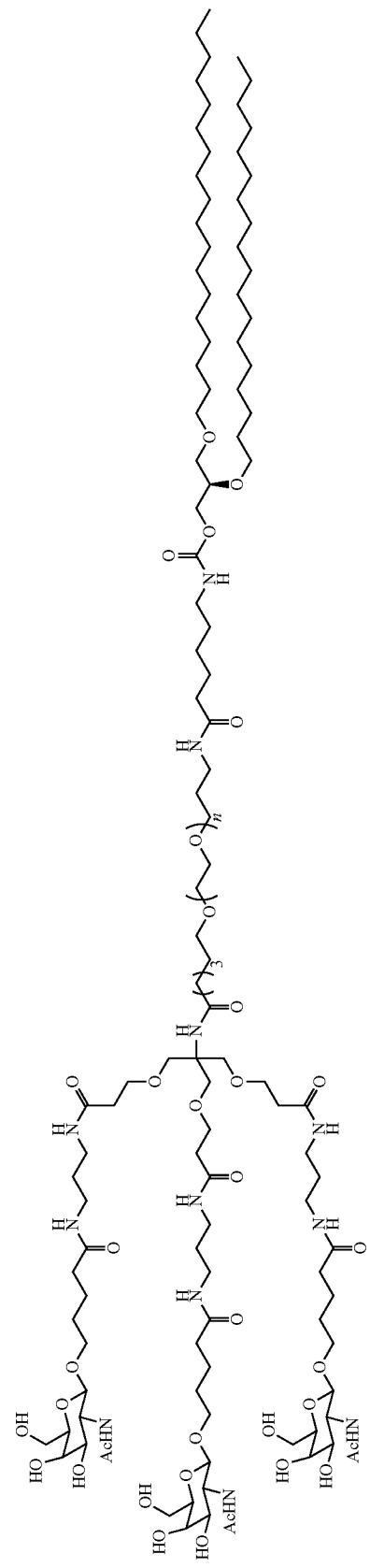
216 PEG-2000

(ii) a cationic lipid;
(iii) a neutral lipid selected from DSPC, POPC, DOPE, and SM;
(iv) cholesterol; and
(v) PEG-DMG, or PEG-DMA, wherein the components are in a molar ratio of about 0.5-50% targeting lipid: 20-60% cationic lipid:5-25% neutral lipid:25-55% cholesterol:0.5-15% PEG-DMG or PEG-DMA.

4. The pharmaceutical formulation of claim 1, further comprising an oligonucleotide.

5. The pharmaceutical formulation of claim 4, wherein said oligonucleotide is single stranded.

6. The pharmaceutical formulation of claim 4, wherein said oligonucleotide is double stranded.

7. The pharmaceutical formulation of claim 4, wherein said oligonucleotide is a iRNA agent.

8. The pharmaceutical formulation of claim 4, wherein said oligonucleotide is an siRNA agent.

9. The pharmaceutical formulation of claim 4, wherein said oligonucleotide is modified to resist degradation.

10. The pharmaceutical formulation of claim 4, wherein said oligonucleotide comprises a conjugated ligand.

11. A compound having a structure shown in formula 214 or 216

207 208
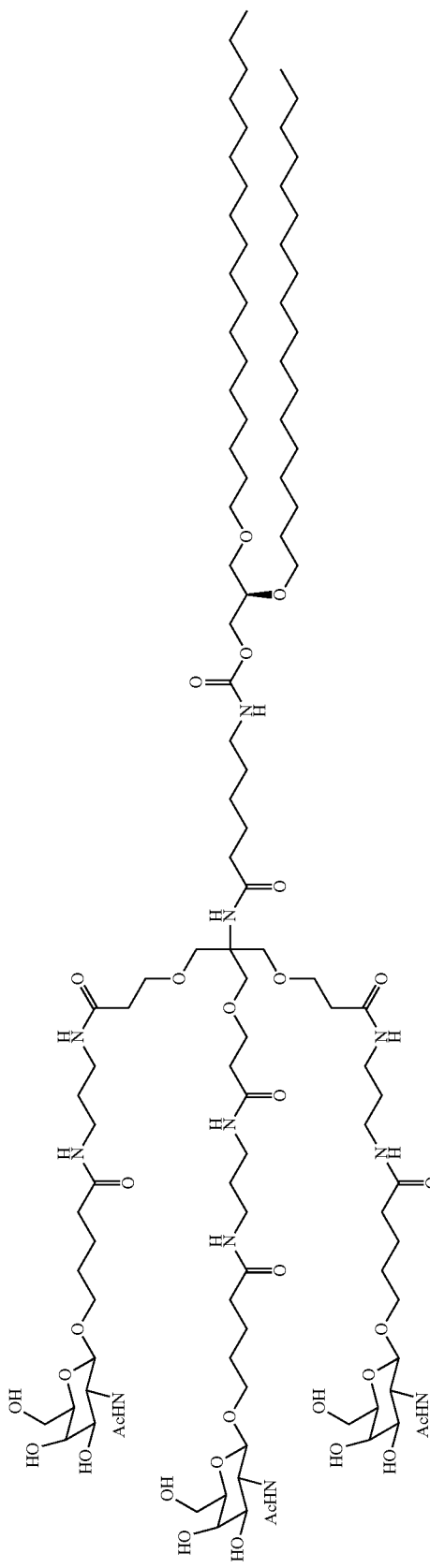
214
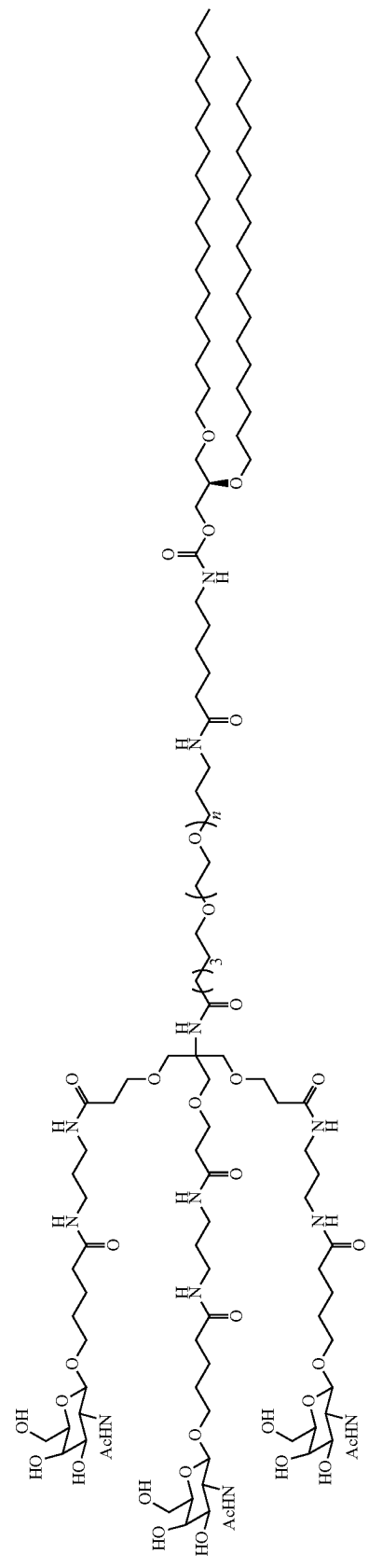
216
or
PEG-2000

* * * * *